(12) United States Patent
Harkin et al.

(10) Patent No.: US 10,260,097 B2
(45) Date of Patent: Apr. 16, 2019

(54) METHOD OF USING A GENE EXPRESSION PROFILE TO DETERMINE CANCER RESPONSIVENESS TO AN ANTI-ANGIOGENIC AGENT

(75) Inventors: Denis Paul Harkin, Dromore (GB); Fionnuala Patterson, Greenisland (GB); Claire Trinder, Stratford-upon-Avon (GB); Eamonn J. O'Brien, Hillsborough (GB); Caroline Michie, Nr Kirkcaldy (GB); Charlie Gourley, Dumfermline (GB); Laura A. Hill, Lisburn (GB); Katherine E. Keating, Magherafelt (GB); Jude O'Donnell, Galbally (GB); Max Bylesjo, Glasgow (GB); Steve Deharo, Hillsborough (GB); Vitali Proutski, Oxford (GB); Richard Kennedy, Belfast (GB); Timothy Davison, Hillsborough (GB); Andreas Winter, Gersthofen (DE); Andrena McCavigan, Derryadd Lurgan (IE)

(73) Assignee: Almac Diagnostics Limited, Craigavon (GB)

( * ) Notice: Subject to any disclaimer, the term of this patent is extended or adjusted under 35 U.S.C. 154(b) by 647 days.

(21) Appl. No.: 14/123,406

(22) PCT Filed: Jun. 4, 2012

(86) PCT No.: PCT/US2012/040805
§ 371 (c)(1),
(2), (4) Date: Feb. 24, 2014

(87) PCT Pub. No.: WO2012/167278
PCT Pub. Date: Dec. 6, 2012

(65) Prior Publication Data
US 2014/0342924 A1    Nov. 20, 2014

Related U.S. Application Data

(60) Provisional application No. 61/492,488, filed on Jun. 2, 2011.

(51) Int. Cl.
*C12Q 1/6881* (2018.01)
*C12Q 1/6886* (2018.01)
*G01N 33/574* (2006.01)

(52) U.S. Cl.
CPC ......... *C12Q 1/6881* (2013.01); *C12Q 1/6886* (2013.01); *G01N 33/57407* (2013.01); *G01N 33/57415* (2013.01); *G01N 33/57449* (2013.01); *G01N 33/57492* (2013.01); *C12Q 2600/106* (2013.01); *C12Q 2600/158* (2013.01); *G01N 2800/50* (2013.01); *G01N 2800/52* (2013.01); *G01N 2800/7014* (2013.01)

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. | |
| 5,288,644 A | 2/1994 | Beavis et al. | |
| 5,324,633 A | 6/1994 | Fodor et al. | |
| 5,432,049 A | 7/1995 | Fischer et al. | |
| 5,470,710 A | 11/1995 | Weiss et al. | |
| 5,492,806 A | 2/1996 | Drmanac et al. | |
| 5,503,980 A | 4/1996 | Cantor | |
| 5,510,270 A | 4/1996 | Fodor et al. | |
| 5,525,464 A | 6/1996 | Drmanac et al. | |
| 5,547,839 A | 8/1996 | Dower et al. | |
| 5,580,732 A | 12/1996 | Grossman et al. | |
| 5,661,028 A | 8/1997 | Foote | |
| 5,800,992 A | 9/1998 | Fodor et al. | |
| 2002/0123044 A1 | 9/2002 | Blashuk et al. | |
| 2002/0137680 A1 | 9/2002 | Ahmed | |
| 2003/0215424 A1 | 11/2003 | Seul et al. | |
| 2005/0186208 A1* | 8/2005 | Fyfe .................. | A61K 39/3955 424/145.1 |
| 2006/0127928 A1 | 6/2006 | Bacus et al. | |
| 2006/0134663 A1 | 6/2006 | Harkin et al. | |
| 2006/0211060 A1 | 9/2006 | Haley et al. | |
| 2007/0065858 A1 | 3/2007 | Haley | |

(Continued)

FOREIGN PATENT DOCUMENTS

| | | |
|---|---|---|
| CA | 2 726 811 A1 | 12/2009 |
| CA | 2 730 614 A1 | 1/2010 |

(Continued)

OTHER PUBLICATIONS

Li, J. et al. Possible angiogenic roles for claudin-4 in ovarian cancer. Cancer Biology and Therapy 8, 1806-1814 (2009).*

(Continued)

*Primary Examiner* — Soren Harward
(74) *Attorney, Agent, or Firm* — Finnegan, Henderson, Farabow, Garrett & Dunner, LLP

(57) ABSTRACT

Methods and compositions are provided for the identification of a molecular diagnostic test for cancer. The test identifies cancer subtypes that are responsive to anti-angiogenesis therapeutics and enables classification of a patient within this subtype. The present invention can be used to determine whether patients with cancer are clinically responsive or non-responsive to a therapeutic regimen prior to administration of any anti-angiogenic agent. This test may be used in different cancer types and with different drugs that directly or indirectly affect angiogenesis or angiogenesis signalling. In addition, the present invention may be used as a prognostic indicator for certain cancer types. In particular, the present invention is directed to the use of certain combinations of predictive markers, wherein the expression of the predictive markers correlates with responsiveness or non-responsiveness to a therapeutic regimen.

21 Claims, 15 Drawing Sheets
(15 of 15 Drawing Sheet(s) Filed in Color)
Specification includes a Sequence Listing.

(56) References Cited

U.S. PATENT DOCUMENTS

| | | | | |
|---|---|---|---|---|
| 2008/0199855 A1* | 8/2008 | Nister | ............... | C12Q 1/6886 435/6.16 |
| 2008/0286771 A1* | 11/2008 | Hudson | ............... | C12Q 1/6886 435/6.12 |
| 2008/0305962 A1* | 12/2008 | Wirtz | ............... | C12Q 1/6886 506/9 |
| 2009/0023149 A1* | 1/2009 | Knudsen | ............... | C12Q 1/6886 435/6.14 |
| 2009/0082218 A1 | 3/2009 | Harkin et al. | | |
| 2009/0232814 A1 | 9/2009 | Goldberg et al. | | |
| 2009/0304594 A1 | 12/2009 | Fantin et al. | | |
| 2010/0196366 A1* | 8/2010 | Bunn | ............... | C12Q 1/6886 424/133.1 |
| 2010/0304989 A1* | 12/2010 | Von Hoff | ............... | G16H 50/20 506/9 |
| 2016/0002732 A1 | 1/2016 | Harkin et al. | | |

FOREIGN PATENT DOCUMENTS

| | | |
|---|---|---|
| CA | 2 747 937 A1 | 7/2010 |
| EP | 0 373 203 B2 | 6/1990 |
| EP | 0 785 280 B1 | 7/1997 |
| JP | 2007-517058 A | 6/2007 |
| JP | 2007-532113 A | 11/2007 |
| JP | 2009-524438 A | 7/2009 |
| JP | A-2010-504530 | 2/2010 |
| JP | A-2012-513422 | 6/2012 |
| JP | A-2012-525159 | 10/2012 |
| WO | WO 95/21265 | 8/1995 |
| WO | WO 96/31622 | 10/1996 |
| WO | WO 97/10365 | 3/1997 |
| WO | WO 97/27317 | 7/1997 |
| WO | WO 2003/095977 A2 | 11/2003 |
| WO | WO 2004/005883 A2 | 1/2004 |
| WO | WO 2004/108896 A2 | 12/2004 |
| WO | WO 2005/066371 A2 | 7/2005 |
| WO | WO 2005/100606 A2 | 10/2005 |
| WO | WO 2007/067500 A2 | 6/2007 |
| WO | WO 2007/090076 A2 | 8/2007 |
| WO | WO 2007/122369 A2 | 11/2007 |
| WO | WO 2008/082730 A2 | 7/2008 |
| WO | WO 2009/022129 A1 | 2/2009 |
| WO | WO 2009/042814 A1 | 4/2009 |
| WO | WO 2009/045115 A1 | 4/2009 |
| WO | WO 2009/061800 A2 | 5/2009 |
| WO | WO 2009/076229 A2 | 6/2009 |
| WO | WO 2009/149297 A1 | 12/2009 |
| WO | WO 2010/009337 A2 | 1/2010 |
| WO | WO 2010/010153 A1 | 1/2010 |
| WO | WO 2010/072348 A1 | 7/2010 |
| WO | WO 2010/088688 A2 | 8/2010 |
| WO | WO 2010/127322 A1 | 11/2010 |
| WO | WO 2011/005273 A1 | 1/2011 |
| WO | WO 2011/033006 A1 | 3/2011 |
| WO | WO 2012/037378 A2 | 3/2012 |
| WO | WO 2012/052757 A1 | 4/2012 |
| WO | WO 2012/092336 A2 | 7/2012 |
| WO | WO 2012/167278 A1 | 12/2012 |
| WO | WO 2013/106765 A1 | 7/2013 |
| WO | WO 2013/175429 A1 | 11/2013 |
| WO | WO 2014/087156 A1 | 6/2014 |

OTHER PUBLICATIONS

Yang, S. X. et al. Gene expression profile and angiogenic marker correlates with response to neoadjuvant bevacizumab followed by bevacizumab plus chemotherapy in breast cancer. Clinical Cancer Research 14, 5893-5899 (2008).*

Gerger, A., LaBonte, M. & Lenz, H.-J. Molecular Predictors of Response to Antiangiogenesis Therapies. The Cancer Journal 17, 134-141 (2011).*

Jubb, A. M. & Harris, A. L. Biomarkers to predict the clinical efficacy of bevacizumab in cancer. Lancet Oncol. 11, 1172-1183 (2010).*

Tothill, R. W. et al. Novel molecular subtypes of serous and endometrioid ovarian cancer linked to clinical outcome. Clinical Cancer Research 14, 5198-5208 (2008).*

Jain, R. K. et al. Biomarkers of response and resistance to antiangiogenic therapy. Nature Reviews Clinical Oncology 6, 327-338 (2009).*

Lambrechts, D., Lenz, H. J., De Haas, S., Carmeliet, P. & Scherer, S. J. Markers of response for the antiangiogenic agent bevacizumab. Journal of Clinical Oncology 31, 1219-1230 (2013).*

Shojaei, F. Anti-angiogenesis therapy in cancer: Current challenges and future perspectives. Cancer Letters 320, 130-137 (2012).*

Chinese First Office Action for co-pending Chinese Patent Application No. 201280037298.2, dated Feb. 2, 2015, 7 pages, English translation included.

New Zealand Office Action dated Aug. 28, 2014 in co-pending New Zealand Patent Application No. 618191, pp. 1-3.

International Search Report and Written Opinion dated Apr. 24, 2014 in co-pending PCT International Application No. PCT/GB2013/053202.

Database Geneseq [Online], "Human Expression Signature Biomarker DNA, Seq ID: 853.", retrieved from EBI Accession No. GSN: BAH85778, Database Accession No. BAH85778 Sequence.

Lu et al., "Insulin-Like Growth Factor-I Receptor Signaling and Resistance to Trastuzumab (Herceptin)," Journal of the National Cancer Institute, Dec. 19, 2001, vol. 93, No. 24, pp. 1852-1857.

Italiano et al., "Patterns of Deregulation of Insuling Growth Factor Signalling Pathway in Paediatric and Adult Gastrointenstinal Stromal Tumours," European Journal of Cancer, Nov. 1, 2012, vol. 48, No. 17, pp. 3215-3222.

International Search Report and Written Opinion dated Oct. 5, 2012 for PCT/US2012/040805, pp. 1-13.

Aghajanian et al., "OCEANS: A Randomized, Double-Blind, Placebo-Controlled Phase III Trial of Chemotherapy With or Without Bevacizumab in Patients With Platinum-Sensitive Recurrent Epithelial Ovarian, Primary Peritoneal, or Fallopian Tube Cancer," Journal of Clinical Oncology, Jun. 10, 2012; vol. 30, No. 17: pp. 2039-2045.

Ahdesmäki and Strimmer, "Feature Selection in Omics Prediction Problems Using Cat Scores and False Nondiscovery Rate Control," The Annals of Applied Statistics, 2010; vol. 4, No. 1: pp. 503-519.

Aresu et al, "Matrix metalloproteinases and their inhibitors in canine mammary tumors," BMC Veterinary Research, Jul. 4, 2011, vol. 7: 33.

Bauerschlag et al., "Evaluation of Potentially Predictive Markers for Anti-Angiogenic Therapy with Sunitinib in Recurrent Ovarian Cancer Patients", Translational Oncology, 6:305-310, (2013).

Benjamini et al., "Controlling the False Discovery Rate: A Practical and Powerful Approach to Multiple Testing," Journal of the Royal Statistical Society. Series B (Methodological), 1995; vol. 57, No. 1: 289-300.

Bredel et al, "A Network Model of a Cooperative Genetic Landscape in Brain Tumors," JAMA, Jul. 15, 2009, vol. 302, No. 3: 261-275.

Breiman, "Random Forests," Machine Learning, 2001; vol. 45: pp. 5-32.

Brieger et al, "Recurrence of pleomorphic adenoma of the parotid gland-predictive value of cadherin-11 and fascin," APMIS, Dec. 1, 2008 vol. 116, No. 12: pp. 1050-1057.

Burger, "Phase II Trial of Bevacizumab in Persistent or Recurrent Epithelial Ovarian Cancer or Primary Peritoneal Cancer: A Gynecologic Oncology Group Study," Journal of Clinical Oncology, Nov. 20, 2007; vol. 25, No. 33: pp. 5165-5171.

Burlingame et al., "Mass Spectrometry," Anal. Chem., Jun. 15, 1988; vol. 60, No. 12: pp. 294R-342R.

Collinson et al., "Predicting response to bevacizumab in ovarian cancer: a panel of potential biomarkers informing treatment selection", Clin Cancer Res, 19(18):5227-5239, (2013).

Costa et al., "Reversing HOXA9 Oncogene Activation by PI3K Inhibition: Epigenetic Mechanism and Prognostic Significance in Human Glioblastoma," Cancer Research, 2010; vol. 70, No. 2: pp. 453-4786 (Published OnlineFirst Jan. 12, 2010).

(56) References Cited

OTHER PUBLICATIONS

Davies et al, "Effects of bevacizumab in mouse model of endometrial cancer: Defining the molecular basis for resistance," Oncology Reports, Jan. 14, 2011, vol. 25, No. 3: pp. 855-862.
Dudoit et al., "Comparison of Discrimination Methods for the Classification of Tumors Using Gene Expression Data," Journal of the American Statistical Association, Mar. 2002, vol. 97, No. 457: pp. 77-87.
Elgaaen et al, "POLD2 and KSP37 (FGFBP2) Correlate Strongly with Histology, Stage and Outcome in Ovarian Carcinomas," PLoS One, Nov. 4, 2010; vol. 5, No. 11: p. e13837.
Escudier et al., Phase III Trial of Bevacizumab Plus Interferon Alfa-2a in Patients With Metastatic Renal Cell Carcinoma (AVOREN): Final Analysis of Overall Survival, Journal of Clinical Oncology, May 1, 2010; vol. 28, No. 13: pp. 2144-2150.
Faber et al, "Alteration of MMP-2 and -14 expression by imatinib in HPV-positive and -negative squamous cell carcinoma," Oncology Reports, Apr. 20, 2012; vol. 28, No. 1: pp. 172-178.
Friedman et al., Bevacizumab Alone and in Combination With Irinotecan in Recurrent Glioblastoma, Journal of Clinical Oncology, Oct. 1, 2009; vol. 27, No. 28: pp. 4733-4740.
Hassan et al., "Prognostic molecular biomarkers in GISTs," Gastroenterology, Apr. 1, 2004; vol. 126, No. 4, Suppl. 2: pp. A392-A393, Abstract No. M2077.
Hu et al, "Expression of matrix metalloproteinases-9,2,7 and tissue inhibitor of metalloproteinases-1,2,3 mRNA in ovarian tumors and their clinical significance," Ai Zheng (Chinese Journal of Cancer), Oct. 1, 2004, vol. 23, No. 10, pp. 1194-1198.
Hurwitz et al., "Bevacizumab plus Irinotecan, Fluorouracil, and Leucovorin for Metastatic Colorectal Cancer," The New England Journal of Medicine, Jun. 3, 2004, vol. 350 No. 23, pp. 2335-2342.
Jang et al, "Suppression of hepatic tumor growth and metastasis by metronomic therapy in a rat model of hepatocellular carcinoma," Experimental and Molecular Medicine, May 31, 2011; vol. 43, No. 5: pp. 305-312.
Kikuchi et al, "Frequent Inactivation of a Putative Tumor Suppressor, Angiopoietin-Like Protein 2, in Ovarian Cancer," Cancer Research, Jul. 1, 2008, vol. 68, No. 13; pp. 5067-5075.
Liu et al. "Vascular gene expression patterns are conserved in primary and metastatic brain tumors," Journal of Neuro-Oncology, 2010; vol. 99, No. 1: pp. 13-24.
Llovet and Bruix, "Molecular targeted therapies in hepatocellular carcinoma," Hepatology, Oct. 1, 2008; vol. 48, No. 4, , pp. 1312-1327.
Lopez et al., "The disparate nature of "intergenic" polyadenylation sites," RNA, 2006; vol. 12: pp. 1794-1801.
Mannelqvist et al, "Gene Expression Patterns Related to Vascular Invasion and Aggressive Features in Endometrial Cancer," The American Journal of Pathology, Feb. 1, 2011; vol. 178, No. 2: pp. 861-871.
McCluggage, "Morphological subtypes of ovarian carcinoma: a review with emphasis on new developments and pathogenesis," Pathology, Aug. 2011; vol. 43, No. 5: pp. 420-432.
Review of "Molecular Biology and Biotechnology A Comprehensive Desk Reference," VCH, Weinheim Germany, 1995, Meyers (Ed.), in Biochemical Education, 1996; vol. 24, No. 1; p. 66.
Miller et al., "Randomized Phase III Trial of Capecitabine Compared With Bevacizumab Plus Capecitabine in Patients With Previously Treated Metastatic Breast Cancer," Journal of Clinical Oncology, Feb. 1, 2005; vol. 23, No. 4: pp. 792-799.
Miller et al., "Paclitaxel plus Bevacizumab versus Paclitaxel Alone for Metastatic Breast Cancer," The New England Journal of Medicine, Dec. 27, 2007; vol. 357: pp. 2666-2676.
Morimoto et al "Gene expression profiling of human colon xenograft tumors following treatment with SU11248, a multitargeted tyrosine kinase inhibitor," Oncogene, Feb. 26, 2004, vol. 23, No. 8: pp. 1618-1626.
Nakajima et al, "CDH11 expression is associated with survival in patients with osteosarcoma," Cancer Genomics & Proteomics, Jan. 1, 2008; vol. 5, No. 1: pp. 37-42.

Nakamura et al., "KRN951, a Highly Potent Inhibitor of Vascular Endothelial Growth Factor Receptor Tyrosine Kinases, Has Antitumor Activities and Affects Functional Vascular Properties," Cancer Res, Sep. 15, 2006; vol. 66, No. 18, pp. 9134-9142.
Nguyen and Rocke., "Tumor classification by partial least squares using microarray gene expression data," Bioinformatics, 2002; vol. 18, No. 1: pp. 39-50.
O'Shaughnessy et al., "A meta-analysis of overall survival data from three randomized trials of bevacizumab (BV) and first-line chemotherapy as treatment for patients with metastatic breast cancer (MBC)," Journal of Clinical Oncology, 2010 ASCO Annual Meeting Abstracts, 2010; vol. 28, No. 15_suppl (May 20 Supplement): Abstract 1005.
Pal et al, "Breaking through a Plateau in Renal Cell Carcinoma Therapeutics: Development and Incorporation of Biomarkers," Molecular Cancer Therapeutics, Dec. 1, 2010; vol. 9, No. 12; pp. 3115-3125.
Perren et al., "A Phase 3 Trial of Bevacizumab in Ovarian Cancer," The New England Journal of Medicine, Dec. 29, 2011; vol. 365, No. 26:2484-96.
Phillips et al., "Molecular subclasses of high-grade glioma predict prognosis, delineate a pattern of disease progression, and resemble stages in neurogenesis," Cancer Cell, Mar. 2006; vol. 9: 157-173.
Quackenbush, "Microarray analysis and tumor classification," New England Journal of Medicine. 2006 354(23): 2463-2472.
Reck et al., "Phase III Trial of Cisplatin Plus Gemcitabine With Either Placebo or Bevacizumab as First-Line Therapy for Nonsquamous Non-Small-Cell Lung Cancer: AVAiL," Journal of Clinical Oncology, Mar. 10, 2009; vol. 27, No. 8: pp. 1227-1234.
Reinmuth et al., "Current data on predictive markers for anti-angiogenic therapy in thoracic tumours", Eur Reinmuth J, 36:915-924, (2010).
Rini et al., "Bevacizumab Plus Interferon Alfa Compared With Interferon Alfa Monotherapy in Patients With Metastatic Renal Cell Carcinoma: CALGB 90206," Journal of Clinical Oncology, Nov. 20, 2008; vol. 26, No. 33: pp. 5422-5428.
Ripley et al, "Expression of matrix metalloproteinase-26 and tissue inhibitors of metalloproteinase-3 and -4 in normal ovary and ovarian carcinoma," International Journal of Gynecological Cancer, Sep. 1, 2006; vol. 16, No. 5: pp. 1794-1800.
Sandler et al., "Paclitaxel-Carboplatin Alone or with Bevacizumab for Non-Small-Cell Lung Cancer," The New England Journal of Medicine, Dec. 14, 2006; vol. 355, No. 24: pp. 2542-2550.
Schena et al., "Parallel human genome analysis: Microarray-based expression monitoring of 1000 genes," Proc. Natl. Acad. Sci. USA, Oct. 1996; vol. 93: pp. 10614-10619.
Stadlmann et al, "Cytokine-regulated expression of collagenase-2 (MMP-8) is involved in the progression of ovarian cancer," European Journal of Cancer, Nov. 1, 2003; vol. 39, No. 17: pp. 2499-2505.
Ståhle et al., "Partial Least Squares Analysis With Cross-Validation for the Two-Class Problem: A Monte Carlo Study," Journal of Chemometrics, 1987; vol. 1: pp. 185-196.
Tanney et al., "Generation of a non-small cell lung cancer transcriptome microarray," BMC Medical Genomics, May 30, 2008, 1:20.
Tibshirani et al., "Estimating the Number of clusters in a data set via the gap statistic," J. R. Statist. Soc. B, 2001; vol. 63, Part 2: pp. 411-423.
Tibshirani et al., "Diagnosis of multiple cancer types by shrunken centroids of gene expression," PNAS, May 14, 2002; vol. 99, No. 10: pp. 6567-6572.
Tothill et al., "Novel Molecular Subtypes of Serous and Endometrioid Ovarian Cancer Linked to Clinical Outcome," Clin Cancer Res Aug. 15, 2008; vol. 14, No1. 16; pp. 5198-5208.
Wang et al., "Identification of candidate predictive and surrogate molecular markers for dasatinib in prostate cancer: rationale for patient selection and efficacy monitoring," Nov. 29, 2007; Genome Biology vol. 8, No. 11: R255.
Watanabe et al, "Gene expression of vascular endothelial growth factor A, thymidylate synthase, and tissue inhibitor of metalloproteinase 3 in prediction of response to bevacizumab treatment in colorectal cancer patients", Diseases of the Colon & Rectum, Aug. 1, 2011; vol. 54, No. 8: pp. 1026-1035.

(56) References Cited

OTHER PUBLICATIONS

Willett et al., "Direct evidence that the VEGF-specific antibody bevacizumab has antivascular effects in human rectal cancer," Nat Med, Feb. 2004; vol. 10, No. 2: pp. 145-147.
Wold, "Pattern Recognition by Means of Disjoint Principal Components Models," Pattern Recognition, Pergamon Press 1976, vol. 8, pp. 127-139.
Wolmark, A phase III trial comparing mFOLFOX6 to mFOLFOX6 plus bevacizumab in stage II or III carcinoma of the colon: Results of NSABP Protocol C-08, Journal of Clinical Oncology, 2009 ASCO Annual Meeting Proceedings (Post-Meeting Edition). 2009; vol. 27, No. 18S, 2009: Abstract LBA4.
Wray et al., "The Genetic Interpretation of Area under the ROC Curve in Genomic Profiling," PLoS Genetics, Feb. 2010, vol. 6, No. 2: e1000864.
Yang et al., "A Randomized Trial of Bevacizumab, an Anti-Vascular Endothelial Growth Factor Antibody, for Metastatic Renal Cancer," The New England Journal of Medicine, Jul. 31, 2003; vol. 349, No. 5: pp. 427-434.
Australian Patent Examination Report No. 1 for co-pending Australian Patent Application No. 2012261820, dated Apr. 13, 2016. 6 pages.
Chinese Notification of the Second Office Action for corresponding Chinese Patent Application No. 201280037298.2, dated Nov. 18, 2015. 7 pages. English excerpt included.
Chinese Notification of the Third Office Action for corresponding Chinese Patent Application No. 201280037298.2, dated Jun. 12, 2016. 4 pages. English excerpt included.
Communication Pursuant to Rules 161(1) and 162 EPC for Application No. 15705693.8-1403, dated Sep. 16, 2016.
Eurasian Office Action for co-pending Eurasian Patent Application No. 201391805, dated Jun. 26, 2015. 1 page. English excerpt included.
Indonesian Patent Examination Stage I for co-pending Indonesian Patent Application No. W00201305928, dated Oct. 27, 2016. 1 page. English excerpt included.
International Search Report for International Application No. PCT/GB2015/050352, dated Jul. 5, 2015. (U.S. Appl. No. 15/116,641).
International Search Report for International Application No. PCT/GB2015/051557, dated Sep. 9, 2015. (U.S. Appl. No. 15/311,618).
Japanese Notice of Reasons for Rejection for co-pending Japanese Patent Application No. 2014-513800, dated Apr. 12, 2016. 4 pages. English excerpt included.
Mexican Patent Office Action for co-pending Mexican Patent Application No. MX/a/2013/014065, dated Apr. 13, 2016. 3 pages. English excerpt included.
Mexican Patent Office Action for co-pending Mexican Patent Application No. MX/a/2013/014065, dated Oct. 24, 2016. 4 pages. English excerpt included.
Written Opinion of the International Searching Authority for International Application No. PCT/GB2015/050352, dated Jul. 5, 2015. (U.S. Appl. No. 15/116,641).
Written Opinion of the International Searching Authority for International Application No. PCT/GB2015/051557, dated Sep. 9, 2015. (U.S. Appl. No. 15/311,618).
Co-pending U.S. Appl. No. 14/649,421.
Co-pending U.S. Appl. No. 15/116,641.
Co-pending U.S. Appl. No. 15/311,618.
Azad et al., "Correlative studies of a phase I trial of combination anti-vascular endothelial growth factor (VEGF) therapy with sorafenib and bevacizumab," Developmental Therapeutics: Molecular Therapeutics, Abstract 3545, (2008).
Garcia et al., "Phase II clinical trial of bevacizumab and low-dose metronomic oral cyclophosphamide in recurrent ovarian cancer: a trial of the California, Chicago, and Princess Margaret Hospital phase II consortia," J Clin Oncol, 26(1):76-82, (2008).
Jubb et al., "Impact of vascular endothelial growth factor-A expression, thrombospondin-2 expression, and microvessel density on the treatment effect of bevacizumab in metastatic colorectal cancer," J Clin Oncol, 24(2):217-227, (2006).
Yang et al., "A randomized trial of bevacizumab, an anti-vascular endothelial growth factor antibody, for metastatic renal cancer," N Engl J Med, 349(5):427-434, (2003).
Chinese Notification of the Fourth Office Action for corresponding Chinese Patent Application No. 201280037298.2, dated Mar. 2, 2017. 9 pages. English excerpt included.
Mexican Patent Office Action for co-pending Mexican Patent Application No. MX/a/2013/014065, dated Apr. 6, 2017. 9 pages. English excerpt included.
Communication pursuant to Article 94(3) EPC for EP Application No. 12 793 609.4-1405, dated Aug. 18, 2017, 8 pages.
Burgess et al., "Possible disassociation of the heparin-binding and mitogenic activities of heparin-binding (acidic fibroblast) growth factor-1 from its receptor-binding activities by site-directed mutagenesis of a single lysine residue," J Cell Biol 111(5 Pt 1):2129-2138, (1990).
Dean et al., "Identification of candidate angiogenic inhibitors processed by matrix metalloproteinase 2 (MMP-2) in cell-based proteomic screens: disruption of vascular endothelial growth factor (VEGF)/heparin affin regulatory peptide (pleiotrophin) and VEGF/Connective tissue growth factor angiogenic inhibitory complexes by MMP-2 proteolysis," Mol Cell Biol 27(24):8454-8465, (2007).
Huang et al., "Stat1 negatively regulates angiogenesis, tumorigenicity and metastasis of tumor cells," Oncogene 21(16):2504-2512, (2002).
Lazar et al., "Transforming growth factor alpha: mutation of aspartic acid 47 and leucine 48 results in different biological activities," Mol Cell Biol 8(3):1247-1252, (1988).

\* cited by examiner

METHOD OF USING A GENE EXPRESSION PROFILE TO DETERMINE CANCER RESPONSIVENESS TO AN ANTI-ANGIOGENIC AGENT

CROSS-REFERENCE TO RELATED APPLICATIONS

The present invention claims the priority benefit of U.S. Provisional Patent Application 61/492,488 filed Jun. 2, 2011, which is incorporated herein by reference.

FIELD OF THE INVENTION

The present invention relates to a molecular diagnostic test useful for diagnosing cancers from different anatomical sites that includes the use of a common subtype related to angiogenesis. The invention includes the derivation of a gene classification model from gene expression levels. One application is the stratification of response to, and selection of patients for cancer therapeutic drug classes and thus guide patient treatment selection. Another application is the stratification of cancer patients into those that respond and those that do not respond to anti-angiogenic therapeutics. The present invention provides a test that can guide therapy selection as well as selecting patient groups for enrichment strategies during clinical trial evaluation of novel therapeutics. The invention can be used as a prognostic indicator for certain cancers including ovarian cancer, breast cancer, and glioblastoma. The angiogenesis subtype can be identified from fresh/frozen (FF) or formalin fixed paraffin embedded FFPE patient samples.

BACKGROUND

The pharmaceutical industry continuously pursues new drug treatment options that are more effective, more specific or have fewer adverse side effects than currently administered drugs. Drug therapy alternatives are constantly being developed because genetic variability within the human population results in substantial differences in the effectiveness of many established drugs. Therefore, although a wide variety of drug therapy options are currently available, more therapies are always needed in the event that a patient fails to respond.

Traditionally, the treatment paradigm used by physicians has been to prescribe a first-line drug therapy that results in the highest success rate possible for treating a disease. Alternative drug therapies are then prescribed if the first is ineffective. This paradigm is clearly not the best treatment method for certain diseases. For example, in diseases such as cancer, the first treatment is often the most important and offers the best opportunity for successful therapy, so there exists a heightened need to choose an initial drug that will be the most effective against that particular patient's disease.

Ovarian cancer is the leading cause of death among all gynecological cancers in western countries. This high death rate is due to the diagnosis at an advanced stage in most patients. Epithelial ovarian cancer (EOC) constitutes 90% of ovarian malignancies and is classified into distinct histologic categories including serous, mucinous, endometrioid, clear cell, transitional, mixed, and undifferentiated subtypes. There is increasing evidence that these differed histologies arise from different aetiologies. There have been recent advances in the methodology used to classify epithelial ovarian cancer (McCluggage, W. G. "Morphological subtypes of ovarian carcinoma: a review with emphasis on new developments and pathogenesis," PATHOLOGY 2011 August; 43(5):420-32). One of the consequences of this is that many tumors that would previously been classified as endometrioid are now being classified as serous.

The current standard treatment for ovarian cancer is debulking surgery and standard platinum taxane based cytotoxic chemotherapy. However, not all patients respond to this, and of those that do, approximately 70% will experience a recurrence. Specific targeted therapies for ovarian cancer based on histological or molecular classification have not yet reached the marketplace. Similarly for other types of cancer, there is still no accurate way of selecting appropriate cytotoxic chemotherapeutic agents.

The advent of microarrays and molecular genomics has the potential for a significant impact on the diagnostic capability and prognostic classification of disease, which may aid in the prediction of the response of an individual patient to a defined therapeutic regimen. Microarrays provide for the analysis of large amounts of genetic information, thereby providing a genetic fingerprint of an individual. There is much enthusiasm that this technology will ultimately provide the necessary tools for custom-made drug treatment regimens.

Currently, healthcare professionals have few mechanisms to help them identify cancer patients who will benefit from chemotherapeutic agents. Identification of the optimal first-line drug has been difficult because methods are not available for accurately predicting which drug treatment would be the most effective for a particular cancer's physiology. This deficiency results in relatively poor single agent response rates and increased cancer morbidity and death. Furthermore, patients often needlessly undergo ineffective, toxic drug therapy.

Angiogenesis is a key component of neo-vascularisation of tumors and essential to tumorigenesis and metastasis. As such, it is a key area for therapeutic intervention and has been correlated to poor prognosis and reduced survival. This has promoted the development of a number of agents that target angiogenesis related processes and pathways, including the market leader and first FDA-approved anti-angiogenic, bevacizumab (Avastin), produced by Genentech/Roche.

Treatment regimens that include bevacizumab have demonstrated broad clinical activity[1-10]. However, no overall survival (OS) benefit has been shown after the addition of bevacizumab to cytotoxic chemotherapy in most cancers[8, 12-13]. This suggests that a substantial proportion of tumours are either initially resistant or quickly develop resistance to VEGF blockade (the mechanism of action of bevacizumab). In fact, 21% of ovarian, 10% of renal and 33% of rectal cancer patients show partial regression when receiving bevacizumab monotherapy, suggesting that bevacizumab may be active in small subgroups of patients, but that such incremental benefits do not reach significance in unselected patients. As such, the use of a biomarker of response to bevacizumab would improve assessment of treatment outcomes and thus enable the identification of patient subgroups that would receive the most clinical benefit from bevacizumab treatment. This would be particularly relevant in the case of metastatic breast cancer, where the absence of a clinically beneficial biomarker has undermined the use of bevacizumab. Thus far, no such biomarker has been clinically validated to predict bevacizumab efficacy. Hypertension and VEGF polymorphisms are so far the only biomarkers to show potential, but important questions remain about their use in a clinical setting.

Another approach to anti-angiogenic therapy is simulataneous targeting of multiple angiogenic pathways rather than selective targeting of the VEGF pathway. Theoretically, multitargeted anti-angiogenic agents should more completely inhibit angiogenesis than agents such as bevacizumab and thus may produce greater therapeutic benefit. It has been postulated that in some tumors, angiogenesis may require VEGF only in the early stages of disease but is driven by additional angiogenic pathways as the disease progresses. Therefore, by targeting multiple pathways, it may be possible to counteract compensatory escape mechanisms that could lead to resistance to VEGF inhibition.

As for other types of cancer there is still no accurate way of selecting which patients will or will not respond to standard of care with an anti-angiogenic therapeutic or single agent anti-angiogenic therapy.

What is therefore needed is a molecular diagnostic test that would facilitate the stratification of patients based upon their predicted response to anti-angiogenic therapeutics, either in combination with standard of care or as a single-agent therapeutic. This would allow for the rapid identification of those patients who should receive alternative therapies. Such a molecular diagnostic test should be predictive of therapeutic responsiveness across different cancer types with sufficient accuracy.

SUMMARY OF THE INVENTION

Disclosed are methods of using a collection of biomarkers expressed in cancer such that when some or all of the transcripts are over or under-expressed, they identify a subtype of cancer that has an up-regulation in molecular signaling relating to angiogenesis. The invention also provides methods for indicating responsiveness or non-responsiveness to anti-angiogenic agents. In different aspects, this collection of biomarkers may form the basis of a single parameter or multiparametric predictive test that could be delivered using methods known in the art such as microarray, Q-PCR, immunohistochemistry, ELISA or other technologies that can quantify mRNA or protein expression.

In addition, the cancer sub-type described herein is common to many types of cancer and is not limited to a single cancer disease type. Therefore, the expression signatures disclosed herein may be used to predict responsiveness or non-responsiveness of cancer therapeutics across different cancer types in different tissues. In one embodiment of the invention, these biomarkers are useful for evaluating a cancer tumor's responsiveness to anti-angiogenic therapeutics. In one exemplary embodiment, the cancer is ovarian cancer. In another exemplary embodiment, the cancer is glioblastoma. In another exemplary embodiment, the cancer is breast cancer.

The invention described herein is not limited to any one drug; it can be used to identify responders and non responders to any of a range of drugs currently in use, under development and novel that directly or indirectly affect or target angiogeneic processes. In one embodiment, the present invention may be used to evaluate adjuvant or neoadjuvant bevacizumab or dasatanib, either as single agents, or in combination with standard of care therapy. In another embodiment, the present invention may be used to evaluate Avastin, VEGF-TRAP, treatment in ovarian cancer.

The present invention relates to prediction of response to drugs using at least or up to different 10 classifications of response, such as overall survival, progression free survival, radiological response, as defined by RECIST, complete response, partial response, stable disease and serological markers such as, but not limited to, PSA, CEA, CA125, CA15-3 and CA19-9. In certain embodiments this invention can be used to evaluate survival in ovarian, breast, and glioblastoma.

In another aspect, the present invention relates to the identification of an angiogenesis sub-type in cancers. The sub-type can be detected by determining the expression levels of certain biomarkers. An expression signature defines a set of biomarkers whose expression is predictive of cancer types that are responsive or non-responsive to anti-angiogenic agents. In certain exemplary embodiments, the expression signature comprises two or more biomarkers selected from the biomarkers listed in Table 1A and 1B. In another exemplary embodiment, the expression signature comprises two or more biomarkers selected from the sequences of SEQ ID NOs: 632-801 (Group I) or SEQ ID NOs: 802-974 (Group II). In another exemplary embodiment, the expression signature comprises two or more biomarkers selected from the biomarkers listed in Table 2A and 2B. In another exemplary embodiment, the expression signature comprises the biomarkers listed in Table 2A and 2B and their corresponding weights as determined using a PLS classifier.

In another aspect, the present invention relates to kits for conventional diagnostic uses listed above such as qPCR, microarray, and immunoassays such as immunohistochemistry, ELISA, Western blot and the like. Such kits include appropriate reagents and directions to assay the expression of the genes or gene products and quantify mRNA or protein expression.

Also disclosed are methods for identifying human tumors with or without the angiogenesis phenotype. In certain exemplary embodiments, such methods may be used to identify patients that are sensitive to and respond to drugs that inhibit, either directly or indirectly, processes relating to angiogenesis. In certain other exemplary embodiments, such methods may be used to identify patients that are resistant to or do not respond to drugs that inhibit, either directly or indirectly, processes relating to angiogenesis.

In another aspect, the invention can be used as a prognostic indicator in certain cancer types. In one exemplary embodiment, the cancer is ovarian cancer. In another exemplary embodiment, the cancer is breast cancer. In yet another exemplary embodiment, the cancer is glioblastoma.

This invention also relates to guiding effective treatment of patients. Further, methods relating to selection of patient treatment regimens and selecting patients for clinical trials of current, or developmental stage drugs that directly or indirectly affect angiogenesis are provided.

In addition, methods that accommodate the use of archived formalin fixed paraffin-embedded (FFPE) biopsy material, as well as fresh/frozen (FF) tissue, for assay of all transcripts, and are therefore compatible with the most widely available type of biopsy material, are described herein. A biomarker expression level may be determined using RNA obtained from FFPE tissue, fresh frozen tissue or fresh tissue that has been stored in solutions such as RNAlater®.

BRIEF DESCRIPTION OF DRAWINGS

The patent or application file contains at least one drawing executed in color. Copies of this patent or patent application publication with color drawing(s) will be provided by the United States Patent and Trademark Office upon request and payment of the necessary fee.

FIG. 2A shows a histogram representing the significance of the top 10 enriched Gene Ontology Biological processes. Red bars indicate significance of a process at a p-value of 0.05 after false discovery rate correction. FIG. 2B represents the subset of the Gene Ontology Biological processes tree where processes include one or more genes encoded by the probe sets in cluster 3. Red coloured processes indicate significance of that process at a p-value of 0.05 after false discovery rate correction. Black coloured processes include one or more genes encoded by the probe sets in cluster 3, but are not significant.

FIG. 7A shows a histogram representing the significance of the top 10 enriched Gene Ontology biological processes. Red bars indicate significance of a process at a p-value of 0.05 after False Discovery Rate correction. FIG. 7B represents the subset of the Gene Ontology Biological processes tree where processes include one or more genes encoded by the probe sets in cluster 2 (angiogenesis). Red coloured processes indicate significance of that process at a p-value of 0.05 after false discovery rate correction. Black coloured processes include one or more genes encoded by the probe sets in the angiogenesis cluster, but are not significant.

SEQUENCE LISTING

Figure 1:
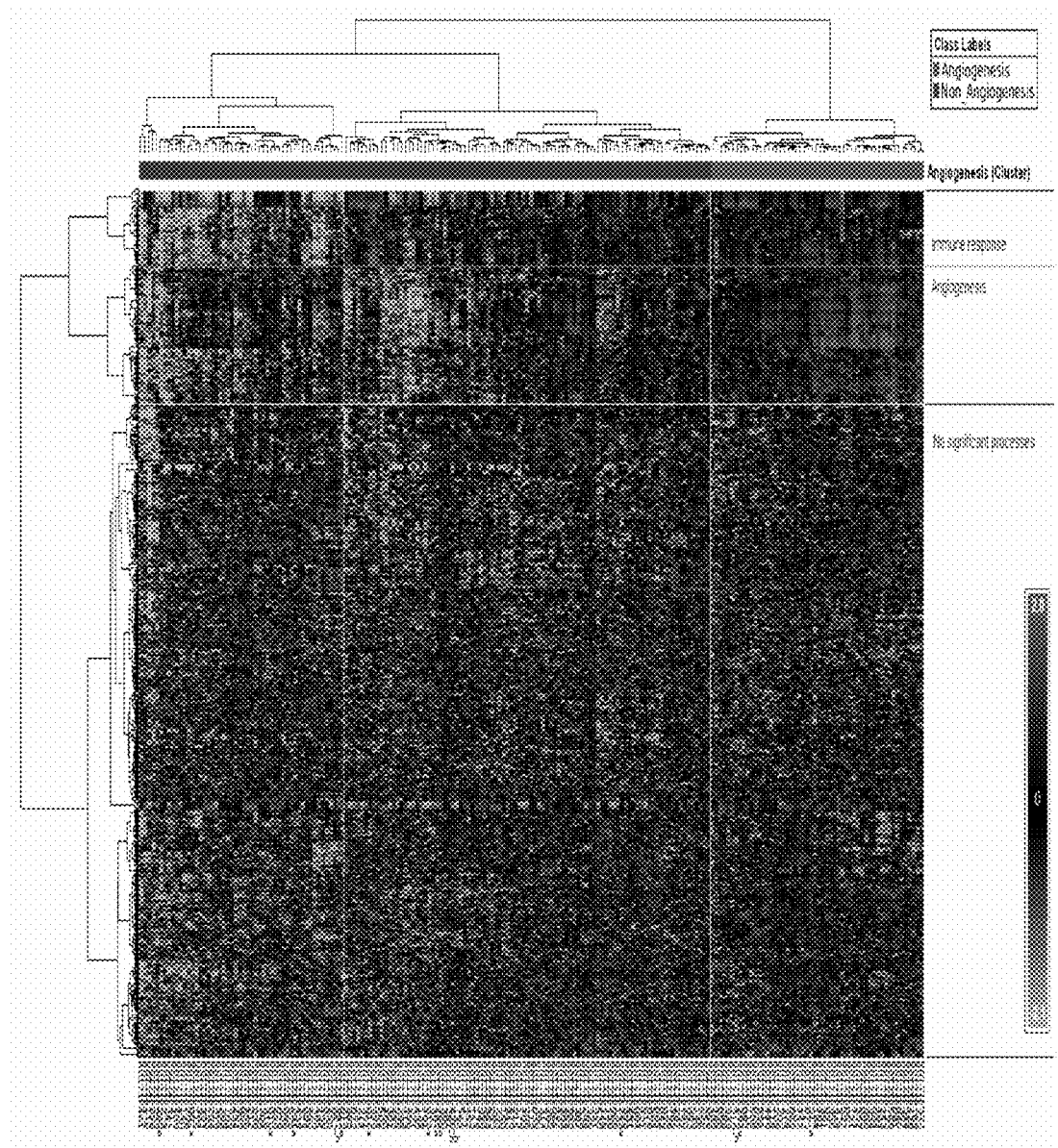
FIG. 1 provides a heatmap representing the hierarchical agglomerative clustering analysis of the most variable genes across 199 serous samples of the Almac Diagnostics' epithelial ovarian cancer sample set. The functional analysis of the probeset clusters is summarized on the right hand side of the image. The legend across the top of the image indicates the classifier group each sample was assigned to for classifier generation (i.e. Class labels).

The nucleic and amino acid sequences listed in the accompanying sequence listing are shown using standard letter abbreviations for nucleotide bases, as defined in 37 C.F.R. § 1.822. Only one strand of each nucleic acid sequence is shown, but the complementary strand is understood as included by any reference to the displayed strand.

The Sequence Listing is submitted as an ASCII text file in the form of the file named ADL_0801WP_ST25.txt, which was created on Jun. 4, 2012 and is 352,839 bytes, which is incorporated by reference herein.

DETAILED DESCRIPTION OF THE INVENTION

Unless defined otherwise, technical and scientific terms used herein have the same meaning as commonly understood by one of ordinary skill in the art to which this disclosure belongs. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

As used herein terms "marker panel," "expression classifier," "classifier," "expression signature," or "signature" may be used interchangeably.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

A major goal of current research efforts in cancer is to increase the efficacy of perioperative systemic therapy in patients by incorporating molecular parameters into clinical therapeutic decisions. Pharmacogenetics/genomics is the study of genetic/genomic factors involved in an individuals' response to a foreign compound or drug. Agents or modulators which have a stimulatory or inhibitory effect on expression of a biomarker of the invention can be administered to individuals to treat (prophylactically or therapeutically) cancer in the patient. It is ideal to also consider the pharmacogenomics of the individual in conjunction with such treatment. Differences in metabolism of therapeutics may possibly lead to severe toxicity or therapeutic failure by altering the relationship between dose and blood concentration of the pharmacologically active drug. Thus, understanding the pharmacogenomics of an individual permits the selection of effective agents (e.g., drugs) for prophylactic or therapeutic treatments. Such pharmacogenomics can further be used to determine appropriate dosages and therapeutic regimens. Accordingly, the level of expression of a biomarker of the invention in an individual can be determined to thereby select appropriate agent(s) for therapeutic or prophylactic treatment of the individual.

The present invention relates to a molecular diagnostic tests useful for diagnosing cancers from different anatomical sites that includes the use of a common subtype related to angiogenesis. The invention includes expression signatures that identify a subject as responsive or non-responsive to anti-angiogenic therapeutics. The expression signature is derived by obtaining the expression profiles of samples from a sample set of known pathology and/or clinical outcome. The samples may originate from the same sample tissue type or different tissue types. As used herein an "expression profile" comprises a set of values representing the expression level for each biomarker analyzed from a given sample.

The expression profiles from the sample set are then analyzed using a mathematical model. Different mathematical models may be applied and include, but are not limited to, models from the fields of pattern recognition (Duda et al. Pattern Classification, $2^{nd}$ ed., John Wiley, New York 2001), machine learning (Schölkopf et al. Learning with Kernels, MIT Press, Cambridge 2002, Bishop, Neural Networks for Pattern Recognition, Clarendon Press, Oxford 1995), statistics (Hastie et al. The Elements of Statistical Learning, Springer, New York 2001), bioinformatics (Dudoit et al., 2002, J. Am. Statist. Assoc. 97:77-87, Tibshirani et al., 2002, Proc. Natl. Acad. Sci. USA 99:6567-6572) or chemometrics (Vandeginste, et al., Handbook of Chemometrics and Qualimetrics, Part B, Elsevier, Amsterdam 1998). The mathematical model identifies one or more biomarkers expressed in the sample set that are most predictive of a given disease phenotype. These one ore more biomarkers define an expression signature. Accordingly, an expression signature includes the biomarkers identified as most predictive of a given disease phenotype. In certain exemplary embodiments, the mathematical model defines a variable, such as a weight, for each identified biomarker. In certain exemplary embodiments, the mathematical model defines a decision function. The decision function may further define a threshold score which separates the sample set into two disease phenotypes such as, but not limited to, samples that are responsive and non-responsive to anti-angiogenic therapeutics. In one exemplary embodiment, the decision function and expression signature are defined using a linear classifier.

To classify new samples using a defined expression signature, the biomarkers defined by the expression signature are isolated and an expression profile of the biomarker(s) determined. The new sample biomarker expression profile is analyzed with the same mathematical model used to define the expression signature. In certain exemplary embodiments, the mathematical model defines an expression score for the new sample. The expression score may be determined by combining the expression values of the biomarkers with corresponding scalar weights using non-linear, algebraic, trigonometric or correlative means to derive a single scalar value. The expression score is compared to the threshold score and the sample classified as responsive or non-responsive to anti-angiogenic therapeutics. In one exemplary embodiment, a sample expression value greater than the reference expression value indicates a patient will be responsive to an anti-angiogenic therapeutic. In another exemplary embodiment, a sample expression score below the threshold score indicates the patient will not be responsive to an anti-angiogenic therapeutic. In another exemplary embodiment, a sample expression score below the threshold expression score indicates the patient has a cancer type, or is at risk of developing a cancer type, that is not responsive to an anti-angiogenic therapeutic. In another exemplary embodiment, a sample expression score above the reference expression score indicates the patient has a cancer type, or is at risk of developing a cancer type, that is responsive to an anti-angiogenic therapeutic. Where an expression signature is derived from a tissue sample set comprising one type of cancer tissue, the expression signature is not limited to identifying the same cancer sub-type only in tissues of the same cancer type, but may be used with other cancer types that share the same cancer sub-type. For example, where an expression signature is derived from ovarian cancer samples, the expression signature may be used to identify a similar angiogenesis sub-type in different cancers such as glioblastoma or breast cancer.

One application of the expression signatures disclosed herein is the stratification of response to, and selection of patients for therapeutic drug classes that encompass anti-angiogenic therapies. By examining the expression of a collection of the identified biomarkers in a tumor, it is possible to determine which therapeutic agent or combination of agents will be most likely to reduce the growth rate of a cancer. It is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued. The present invention provides a test that can guide therapy selection as well as selecting patient groups for enrichment strategies during clinical trial evaluation of novel therapeutics. For example, when evaluating a putative anti-angiogeneic agent or treatment regime, the expression signatures and methods disclosed herein may be used to select individuals for clinical trials that have cancer types that are responsive to anti-angiogenic agents. The angiogenesis subtype can be identified from a fresh/frozen (FF) or formalin fixed paraffin embedded (FFPE) patient sample. In one exemplary embodiment, the cancer type is ovarian cancer. In another exemplary embodiment, the cancer type is a glioblastoma. In a further exemplary embodiment, the cancer type is breast cancer.

A cancer is "responsive" to a therapeutic agent if its rate of growth is inhibited as a result of contact with the therapeutic agent, compared to its growth in the absence of contact with the therapeutic agent. Growth of a cancer can be measured in a variety of ways. For instance, the size of a tumor or measuring the expression of tumor markers appropriate for that tumor type.

A cancer is "non-responsive" to a therapeutic agent if its rate of growth is not inhibited, or inhibited to a very low degree, as a result of contact with the therapeutic agent when compared to its growth in the absence of contact with the therapeutic agent. As stated above, growth of a cancer can be measured in a variety of ways, for instance, the size of a tumor or measuring the expression of tumor markers appropriate for that tumor type. The quality of being non-responsive to a therapeutic agent is a highly variable one, with different cancers exhibiting different levels of "non-responsiveness" to a given therapeutic agent, under different conditions. Still further, measures of non-responsiveness can be assessed using additional criteria beyond growth size of a tumor such as, but not limited to, patient quality of life, and degree of metastases.

Identifying Expression Signatures

The expression signatures of the present invention are identified by analyzing the expression profiles of certain biomarkers in a patient sample set. Biomarkers suitable for use in the present invention include DNA, RNA, and proteins. The biomarkers are isolated from a patient sample and their expression levels determined to derive a set of expression profiles for each sample analyzed in the patient sample set.

a. Expression Profiles

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic or prognostic methods is one that is a nucleic acid sample. The nucleic acid sample includes a population of nucleic acids that includes the expression information of the phenotype determinative biomarkers of the cell or tissue being analyzed. In some embodiments, the nucleic acid may include RNA or DNA nucleic acids, e.g., mRNA, cRNA, cDNA etc., so long as the sample retains the expression information of the host cell or tissue from which it is obtained. The sample may be prepared in a number of different ways, as is known in the art, e.g., by mRNA isolation from a cell, where the isolated mRNA is used as isolated, amplified, or employed to prepare cDNA, cRNA, etc., as is known in the field of differential gene expression. Accordingly, determining the level of mRNA in a sample includes preparing cDNA or cRNA from the mRNA and subsequently measuring the cDNA or cRNA. The sample is typically prepared from a cell or tissue harvested from a subject in need of treatment, e.g., via biopsy of tissue, using standard protocols, where cell types or tissues from which such nucleic acids may be generated include any tissue in which the expression pattern of the to be determined phenotype exists, including, but not limited to, disease cells or tissue, body fluids, etc.

The expression profile may be generated from the initial nucleic acid sample using any convenient protocol. While a variety of different manners of generating expression profiles are known, such as those employed in the field of differential gene expression/biomarker analysis, one representative and convenient type of protocol for generating expression profiles is array-based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

b. Diseases and Sample Tissue Sources

In certain exemplary embodiments, the patient sample set comprises cancer tissue samples, such as archived samples. The patient sample set is preferably derived from cancer tissue samples having been characterized by prognosis, likelihood of recurrence, long term survival, clinical outcome, treatment response, diagnosis, cancer classification, or personalized genomics profile. As used herein cancer includes, but is not limited to, leukemia, brain cancer, prostate cancer, liver cancer, ovarian cancer, stomach cancer, colorectal cancer, throat cancer, breast cancer, skin cancer, melanoma, lung cancer, sarcoma, cervical cancer, testicular cancer, bladder cancer, endocrine cancer, endometrial cancer, esophageal cancer, glioma, lymphoma, neuroblastoma, osteosarcoma, pancreatic cancer, pituitary cancer, renal cancer, and the like. In one embodiment, the methods described herein refer to cancers that are treated with anti-angiogenic agents, anti-angiogenic targeted therapies, inhibitors of angiogenesis signaling, but not limited to these classes. These cancers also include subclasses and subtypes of these cancers at various stages of pathogenesis. In certain exemplary embodiments the patient sample set comprises ovarian cancer samples. In another exemplary embodiment, the patient sample set comprises, breast cancer samples. In yet another exemplary embodiment, the patient sample set comprises glioblastoma samples.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, ascites, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual, for example, fresh frozen or formalin fixed and/or paraffin embedded.

As used herein, the term "patient" includes human and non-human animals. The preferred patient for treatment is a human. "Patient" and "subject" are used interchangeably herein.

c. Biomarkers

As used herein, the term "biomarker" can refer to a gene, an mRNA, cDNA, an antisense transcript, a miRNA, a polypeptide, a protein, a protein fragment, or any other nucleic acid sequence or polypeptide sequence that indicates either gene expression levels or protein production levels. When a biomarker indicates or is a sign of an abnormal process, disease or other condition in an individual, that biomarker is generally described as being either over-expressed or under-expressed as compared to an expression level or value of the biomarker that indicates or is a sign of a normal process, an absence of a disease or other condition in an individual. "Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The terms "differential biomarker expression" and "differential expression" are used interchangeably to refer to a biomarker whose expression is activated to a higher or lower level in a subject suffering from a specific disease, relative to its expression in a normal subject, or relative to its expression in a patient that responds differently to a particular therapy or has a different prognosis. The terms also include biomarkers whose expression is activated to a higher or lower level at different stages of the same disease. It is also understood that a differentially expressed biomarker may be either activated or inhibited at the nucleic acid level or protein level, or may be subject to alternative splicing to result in a different polypeptide product. Such differences may be evidenced by a variety of changes including mRNA levels, miRNA levels, antisense transcript levels, or protein surface expression, secretion or other partitioning of a polypeptide. Differential biomarker expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a biomarker among, for example, normal and diseased cells, or among cells which have undergone different disease events or disease stages.

In certain exemplary embodiments, the biomarker is an RNA transcript. As used herein "RNA transcript" refers to both coding and non-coding RNA, including messenger RNAs (mRNA), alternatively spliced mRNAs, ribosomal RNA (rRNA), transfer RNA (tRNA), small nuclear RNAs (snRNA), and antisense RNA. Measuring mRNA in a biological sample may be used as a surrogate for detection of the level of the corresponding protein and gene in the biological sample. Thus, any of the biomarkers or biomarker panels described herein can also be detected by detecting the appropriate RNA. Methods of biomarker expression profiling include, but are not limited to quantitative PCR, NGS, northern blots, southern blots, microarrays, SAGE, immunoassays (ELISA, EIA, agglutination, nephelometry, turbidimetry, Western blot, immunoprecipitation, immunocytochemistry, flow cytometry, Luminex assay), and mass spectrometry. The overall expression data for a given sample may be normalized using methods known to those skilled in the art in order to correct for differing amounts of starting material, varying efficiencies of the extraction and amplification reactions.

In certain exemplary embodiments, biomarkers useful for distinguishing between cancer types that are responsive and non-responsive to anti-angiogenic therapeutics can be determined by identifying biomarkers exhibiting the highest degree of variability between samples in the patient data set as determined using the expression detection methods and patient sample sets discussed above. Standard statistical methods known in the art for identifying highly variable data points in expression data may be used to identify the highly variable biomarkers. For example, a combined background and variance filter to the patient data set. The background filter is based on the selection of probe sets with expression E and expression variance $var_E$ above the thresholds defined by background standard deviation $\sigma Bg$ (from the Expression Console software) and quantile of the standard normal distribution $z_\alpha$ at a specified significance a probesets were kept if:

$$E > \log_2((z_a \sigma_{Bg})); \log_2((var_E) > 2[\log_2(\sigma_{Bg}) - E - \log_2(\log(2))]$$

where a defines a significance threshold. In certain exemplary embodiment, the significance threshold is $6.3 \cdot 10^{-5}$. In another exemplary embodiment, the significance threshold may be between $1.0 \cdot 10^{-7}$ to $1.0 \cdot 10^{-3}$.

In certain exemplary embodiments, the highly variable biomarkers may be further analyzed to group samples in the patient data set into sub-types or clusters based on similar gene expression profiles. For examples, biomarkers may be clustered based on how highly correlated the up-regulation or down-regulation of their expression is to one another. Various clustering analysis techniques known in the art may be used. In one exemplary embodiment, hierarchical agglomerative clustering is used to identify the cancer sub-types. To determine the biological relevance of each sub-type, the biomarkers within each cluster may be further mapped to their corresponding genes and annotated by cross-reference to one or more gene ontology databases containing information on biological activity and biological pathways associated with the gene. In one exemplary embodiment, biomarker in clusters enriched for angiogenesis, vasculature development and immune response general functional terms are grouped into a putative angiogenesis sample group and used for expression signature generation. In another exemplary embodiment, biomarkers in clusters that are up regulated and enriched for angiogeneis, vasculature development and immune response general functional terms are grouped into a putative angiongenesis sample group and used for expression signature generation. In another exemplary embodiment, biomarkers in clusters that are down regulated and enriched for angiogenesis, vasculature development and immune response general functional terms are grouped into a putative angiongenesis sample group and used for expression signature generation. Further details for conducting functional analysis of biomarker clusters is provided in the Examples section below.

In one exemplary embodiment, the biomarkers useful in deriving an expression signature for distinguishing cancer sub-types that are, or are not, responsive to anti-angiogenic therapeutics include those biomarkers listed in Table 1A, Table 1B, or both. In another exemplary embodiment, the biomarkers useful in deriving an expression signature for distinguishing cancer sub-types that are, or are not, responsive to anti-angiogenic therapeutics include those biomarkers listed in Group I (comprising SEQ ID NOs: 632-801) or Group II (comprising SEQ ID NOs: 802-974), or both. These biomarkers are identified as having predictive value to determine a patient response to a therapeutic agent. Their expression correlates with the response, or lack thereof, to an agent, and more specifically, an anti-angiogenic therapeutic agent. By examining the expression of a collection of the identified biomarkers in a tumor, it is possible to determine which therapeutic agent or combination of agents will be most likely to reduce the growth rate of a cancer. By examining a collection of identified biomarkers in a tumor, it is also possible to determine which therapeutic agent or combination of agents will be the least likely to reduce the growth rate of a cancer. By examining the expression of a collection of biomarkers, it is therefore possible to eliminate ineffective or inappropriate therapeutic agents. Importantly, in certain embodiments, these determinations can be made on a patient-by-patient basis or on an agent-by-agent basis. Thus, one can determine whether or not a particular therapeutic regimen is likely to benefit a particular patient or type of patient, and/or whether a particular regimen should be continued.

TABLE 1A

Angiogenesis and immune response cluster genes of FIG. 1

| SEQ NO: | Orientation | Gene Symbol |
| --- | --- | --- |
| 1 | Sense | STAT1 |
| 2 | Sense | PDGFC |
| 3 | Sense | TGFB3 |
| 4 | Sense | RAC2 |
| 5 | Sense | MARCKS |
| 6 | Sense | ALOX5 |
| 7 | Sense | COL8A1 |
| 8 | Sense | CTSS |
| 9 | Sense | HAVCR2 |
| 10 | Sense | RAB31 |
| 11 | Sense | KCNAB2 |
| 12 | Sense | THBS1 |
| 13 | Sense | SH3BP4 |
| 14 | Sense | CTGF |
| 15 | Sense | CTGF |
| 16 | Sense | VCAN |
| 17 | Sense | IGKC |
| 18 | Sense | IGKC |
| 19 | Sense | IGKC |
| 20 | Sense | SGK1 |
| 21 | Sense | NFATC1 |
| 22 | Sense | HMHA1 |
| 23 | Sense | FCGR1C /// FCGR1A /// FCGR1B |
| 24 | Sense | EDA2R |
| 25 | Sense | COL8A1 |
| 26 | Sense | COL12A1 |
| 27 | Sense | HLA-B |
| 28 | Sense | HLA-F |
| 29 | Sense | HLA-C |
| 30 | Sense | SPP1 |
| 31 | Sense | MYO1F |
| 32 | Sense | SPARC |
| 33 | Sense | SPARC |

TABLE 1A-continued

Angiogenesis and immune response cluster genes of FIG. 1

| SEQ NO: | Orientation | Gene Symbol |
|---|---|---|
| 34 | Sense | UBD /// GABBR1 |
| 35 | Sense | CCND1 |
| 36 | Sense | COL1A1 |
| 37 | Sense | EGR1 |
| 38 | Sense | EGR1 |
| 39 | Sense | TNFSF10 |
| 40 | Sense | SULF2 |
| 41 | Sense | CERCAM |
| 42 | Sense | ATF3 |
| 43 | Sense | MIR21 |
| 44 | Sense | BASP1 |
| 45 | Sense | IFIT2 |
| 46 | Sense | SULF1 |
| 47 | Sense | IGLC2 /// IGLC3 |
| 48 | Sense | IGLC2 /// IGLC3 |
| 49 | Sense (Fully0Exonic) | IGLC2 /// IGLC3 |
| 50 | Sense | IGLC2 /// IGLC3 |
| 51 | Sense | IGLC2 /// IGLC3 |
| 52 | Sense | IGLC1 |
| 53 | Sense | IGLC1 |
| 54 | Sense | IGLC2 /// IGLC3 |
| 55 | Sense | ANGPTL2 |
| 56 | Sense | COL5A2 |
| 57 | Sense | IGJ |
| 58 | Sense | THY1 |
| 59 | Sense | NDN |
| 60 | Sense | RGS2 |
| 61 | Sense | MEIS3P1 /// MEIS3P2 |
| 62 | Sense | GBP2 |
| 63 | Sense | CSF1R |
| 64 | Sense | C1R |
| 65 | Sense | FAT1 |
| 66 | Sense | COL1A1 |
| 67 | Sense | RHOB |
| 68 | Sense | MMP11 |
| 69 | Sense | GADD45B |
| 70 | Sense | MMP14 |
| 71 | Sense | MMP14 |
| 72 | Sense | IGHG4 |
| 73 | Sense | DDX60L |
| 74 | Sense | SPP1 |
| 75 | Sense | ROR2 |
| 76 | Sense | CTSK |
| 77 | Sense | FCGR2B |
| 78 | Sense | PTAFR |
| 79 | Sense | ICAM1 |
| 80 | Sense | HCLS1 |
| 81 | No Transcript Match | — |
| 82 | Sense | SLFN11 |
| 83 | No Transcript Match | — |
| 84 | Sense | JAM3 |
| 85 | Sense | TMEM49 |
| 86 | Sense | TMEM49 |
| 87 | Sense | LTBP2 |
| 88 | Sense | IRS1 |
| 89 | Sense | COL5A2 |
| 90 | Sense | C17orf91 |
| 91 | Sense | GPNMB |
| 92 | Sense | FAM198B |
| 93 | Sense | MICAL2 |
| 94 | Sense | TMEM2 |
| 95 | Sense | CHST15 |
| 96 | Sense | SECTM1 |
| 97 | Sense | DCN |
| 98 | Sense | VCAM1 |
| 99 | Sense | TNFAIP3 |
| 100 | Sense | C1QA |
| 101 | Sense | C1QA |
| 102 | Sense | FBXO32 |
| 103 | Sense | COL12A1 |
| 104 | Sense | CPE |
| 105 | Sense | CIITA |
| 106 | Sense | GAS7 |
| 107 | Sense | COL3A1 |
| 108 | Sense | FN1 |
| 109 | Sense | IFI30 |
| 110 | Sense | ITGB2 |
| 111 | Sense | ELN |
| 112 | Sense | CMTM3 |
| 113 | Sense | ANTXR1 |
| 114 | Sense | ARHGDIB |
| 115 | Sense | LAPTM5 |
| 116 | Sense | SOX4 |
| 117 | Sense | IFI44L |
| 118 | Sense | IL4I1 |
| 119 | Sense | ANTXR2 |
| 120 | Sense | IGLC2 /// IGLC3 |
| 121 | Sense | EPSTI1 |
| 122 | Sense | BIRC3 |
| 123 | Sense | IGLC2 /// IGLC3 |
| 124 | Sense | BST2 |
| 125 | Sense | TNFSF10 |
| 126 | Sense | COL10A1 |
| 127 | Sense | IGLC2 /// IGLC3 |
| 128 | Sense | FBP1 |
| 129 | Sense | RHOBTB3 |
| 130 | Sense | CDK6 |
| 131 | Sense | CD74 |
| 132 | Sense | ISM1 |
| 133 | Sense | C1QC |
| 134 | Sense | BIN2 |
| 135 | Sense | CSRNP1 |
| 136 | Sense | TYROBP |
| 137 | Sense | C1QTNF3 |
| 138 | Sense | DCN |
| 139 | Sense | IGFBP4 |
| 140 | Sense | AOAH |
| 141 | Sense | SIRPA |
| 142 | Sense | FOSB |
| 143 | Sense | CCDC80 |
| 144 | Sense | IGLC1 |
| 145 | Sense | HCST |
| 146 | Sense | IFI35 |
| 147 | Sense | BIRC3 |
| 148 | Sense | COL3A1 |
| 149 | Sense | IFITM2 |
| 150 | Sense | ZFP36 |
| 151 | Sense | MMP11 |
| 152 | Sense | COL1A2 |
| 153 | Sense | HLA-DPA1 |
| 154 | Sense | TWIST1 |
| 155 | Sense | ZNF154 |
| 156 | Sense | EGR1 |
| 157 | Sense | IGLC2 /// IGLC3 |
| 158 | Sense | TNFSF10 |
| 159 | Sense | IGKC |
| 160 | Sense | IGHG1 /// IGHG4 |
| 161 | Sense | GBP5 |
| 162 | Sense | COL1A2 |
| 163 | Sense | APOC1 |
| 164 | No Transcript Match | — |
| 165 | Sense | COL3A1 |
| 166 | AntiSense | PXDN |
| 167 | AntiSense | EGR1 |
| 168 | Sense | GBP3 |
| 169 | Sense | ISG15 |
| 170 | Sense | — |
| 171 | Sense | KIAA0146 |
| 172 | Sense | CMAH |
| 173 | Sense | APBB2 |
| 174 | Sense | TPM1 |
| 175 | No Transcript Match | — |
| 176 | Sense | DMD |
| 177 | No Genome Match | — |
| 178 | Sense | IL10RA |
| 179 | Sense | — |
| 180 | No Transcript Match | — |
| 181 | Sense | DUSP1 |
| 182 | Sense | GBP1 |
| 183 | Sense | PARVG |
| 184 | Sense | MAFF |
| 185 | Sense | PDGFC |

TABLE 1A-continued

Angiogenesis and immune response cluster genes of FIG. 1

| SEQ NO: | Orientation | Gene Symbol |
|---|---|---|
| 186 | Sense | MSN |
| 187 | Sense | RSAD2 |
| 188 | Sense | TPM1 |
| 189 | Sense | EMB |
| 190 | Sense | C6orf155 |
| 191 | Sense | FOS |
| 192 | Sense | DEXI |
| 193 | Sense | RNF19A |
| 194 | Sense | FBXO32 |
| 195 | Sense | DPYSL3 |
| 196 | Sense | PRICKLE1 |
| 197 | AntiSense | EGR1 |
| 198 | AntiSense | NRP2 |
| 199 | Sense | B2M |
| 200 | AntiSense | MIR21 |
| 201 | Sense | MMP2 |
| 202 | Sense | CDR1 |
| 203 | Sense | HLA-B |
| 204 | Sense | CTGF |
| 205 | Sense | DCN |
| 206 | Sense | SOD2 |
| 207 | Sense | FN1 |
| 208 | Sense | COL8A2 |
| 209 | Sense | SGK1 |
| 210 | Sense | TIMP3 |
| 211 | Sense | ACTA2 |
| 212 | Sense | SRGN |
| 213 | Sense | LOXL1 |
| 214 | Sense | CCR1 |
| 215 | Sense | GBP1 |
| 216 | Sense | CDH11 |
| 217 | Sense | FCGR3A |
| 218 | Sense | LUM |
| 219 | Sense | NNMT |
| 220 | Sense | COL1A2 |
| 221 | Sense | RGS1 |
| 222 | Sense | GJA1 |
| 223 | Sense | SPARCL1 |
| 224 | Sense | DAB2 |
| 225 | AntiSense | CTHRC1 |
| 226 | Sense | RGS16 |
| 227 | Sense | FBLN1 |
| 228 | Sense | SPP1 |
| 229 | Sense | CTSB |
| 230 | Sense | SPP1 |
| 231 | Sense | SDC1 |
| 232 | Sense | PLAU |
| 233 | Sense | PDGFRA |
| 234 | Sense | SERPINF1 |
| 235 | Sense | BGN |
| 236 | Sense | COL6A3 |
| 237 | AntiSense | C3 |
| 238 | AntiSense | C3 |
| 239 | AntiSense | SPP1 |
| 240 | AntiSense | HLA-DQA1 |
| 241 | AntiSense | GAS1 |
| 242 | Sense | VCAN |
| 243 | AntiSense | — |
| 244 | Sense | IGHG4 /// IGHG2 /// IGHG1 /// IGHGP |
| 245 | Sense | IGHG2 |
| 246 | Sense | C3orf26 |
| 247 | AntiSense | ATF3 |
| 248 | AntiSense | ATF3 |
| 249 | AntiSense | SULF1 |
| 250 | Sense | FN1 |
| 251 | AntiSense | CALD1 |
| 252 | AntiSense | CALD1 |
| 253 | Sense | TMEM49 |
| 254 | Sense | TMEM49 |
| 255 | Sense | CHD5 |
| 256 | AntiSense | EGR1 |
| 257 | AntiSense | SNAI2 |
| 258 | AntiSense | ITPRIPL2 |

TABLE 1A-continued

Angiogenesis and immune response cluster genes of FIG. 1

| SEQ NO: | Orientation | Gene Symbol |
|---|---|---|
| 259 | AntiSense | GABBR1 /// UBD |
| 260 | AntiSense | GABBR1 /// UBD |
| 261 | AntiSense | TWIST1 |
| 262 | AntiSense | TWIST1 |
| 263 | AntiSense | BATF2 |
| 264 | AntiSense | NFKBIZ |
| 265 | Sense | C3orf26 |
| 266 | AntiSense | LOXL1 |
| 267 | Sense | — |
| 268 | AntiSense | TIMP2 |
| 269 | AntiSense | FN1 |
| 270 | AntiSense | COL1A1 |
| 271 | AntiSense | DCN |
| 272 | Sense | TREH |
| 273 | AntiSense | UBE2L6 |
| 274 | AntiSense | APOL1 |
| 275 | AntiSense | BIRC3 |
| 276 | AntiSense | BIRC3 |
| 277 | Sense | LILRB4 |
| 278 | Sense | FGD2 |
| 279 | Sense | TMEM49 |
| 280 | Sense | NCF4 |
| 281 | Sense | COL10A1 |
| 282 | Sense | GAL3ST4 |
| 283 | Sense | HCK |
| 284 | Sense | TAGLN |
| 285 | Sense | TWIST1 |
| 286 | Sense | HCLS1 |
| 287 | Sense | LPAR6 |
| 288 | Sense | ITGB2 |
| 289 | Sense | LST1 |
| 290 | Sense | HLA-B |
| 291 | Sense | C17orf91 |
| 292 | Sense | ZC3H12A |
| 293 | Sense | KLF10 |
| 294 | Sense | BASP1 |
| 295 | Sense | BASP1 |

TABLE 1B

Figure 6:
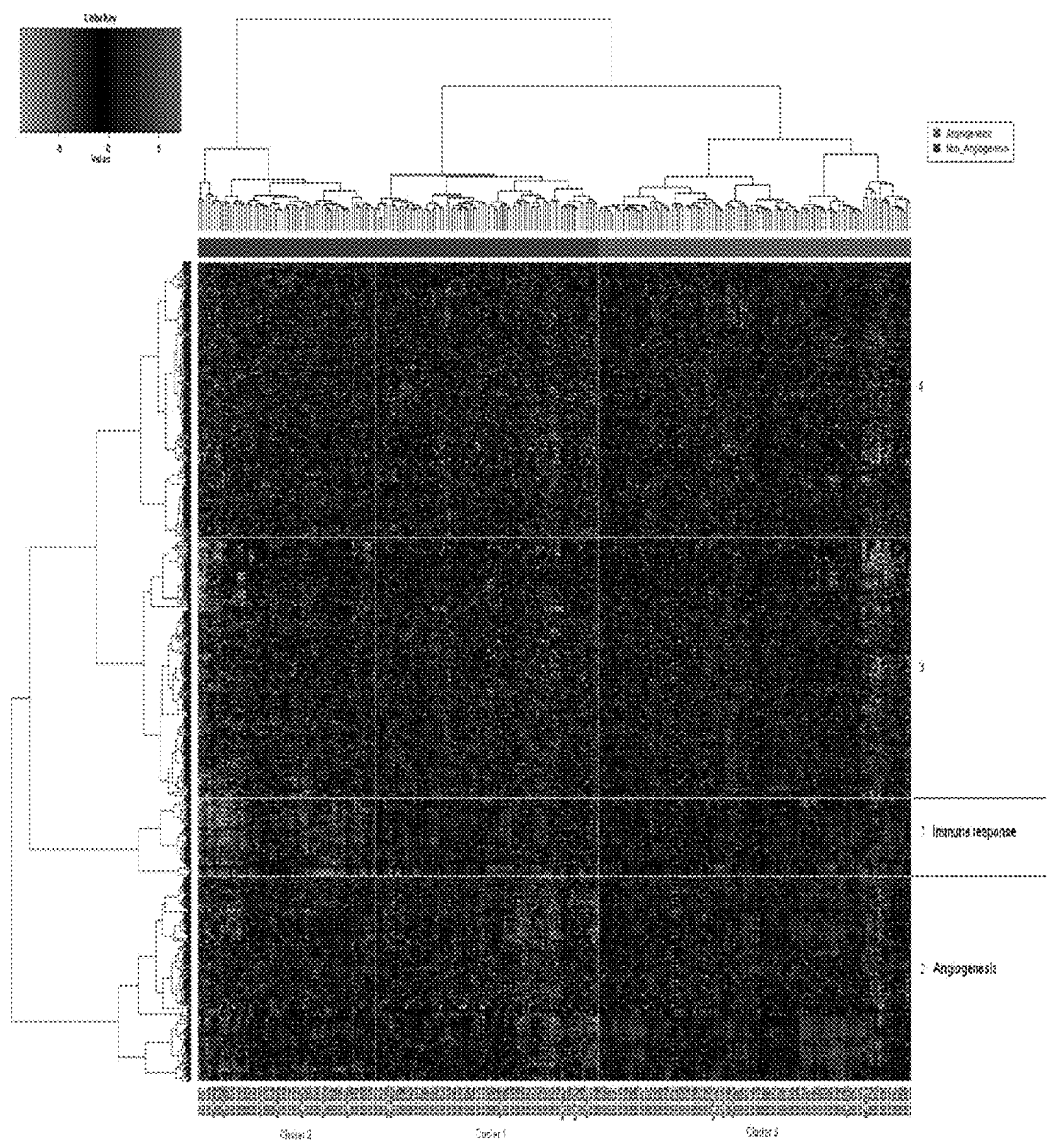
FIG. 6 provides a heatmap representing the hierarchical agglomerative clustering analysis of the most variable genes across 265 serous samples of an epithelial ovarian cancer sample set reclassified according to updated pathological classification criteria. The functional analysis of the probeset clusters is summarized on the right hand side of the image. The legend across the top of the image indicates the classifier group each sample was assigned to for classifier generation (i.e. Class labels).
Figure 7A:
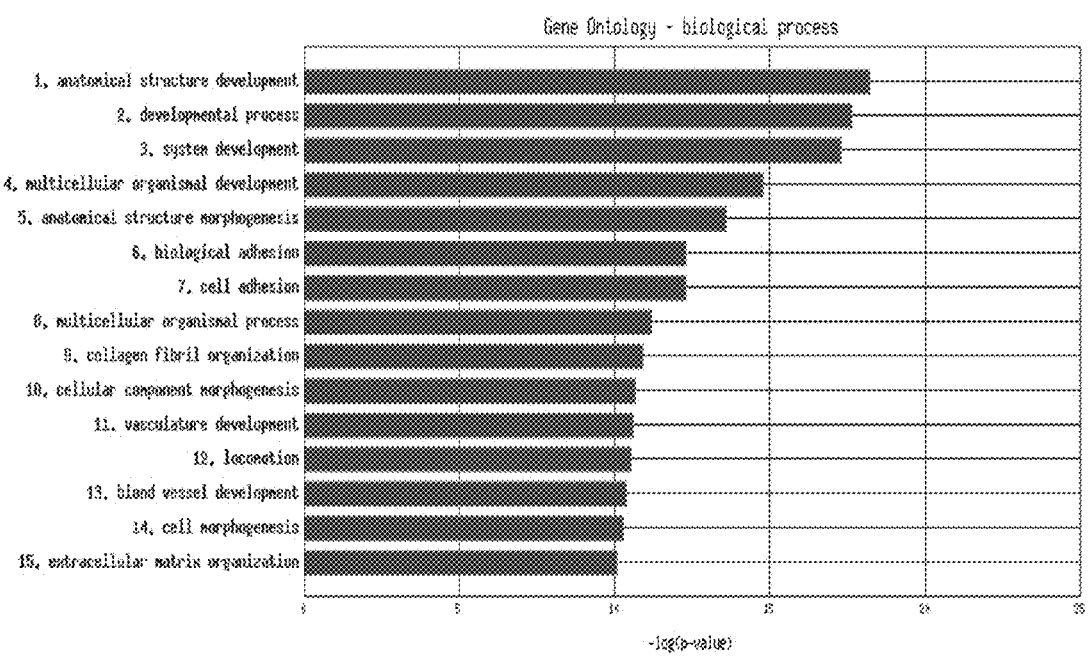
FIG. 7A and FIG. 7B represent the functional analysis results of the angiogenesis probeset of the 265 serous only samples in an epithelial ovarian cancer training set using a functional enrichment tool (FET) algorithm.
Figure 7B:
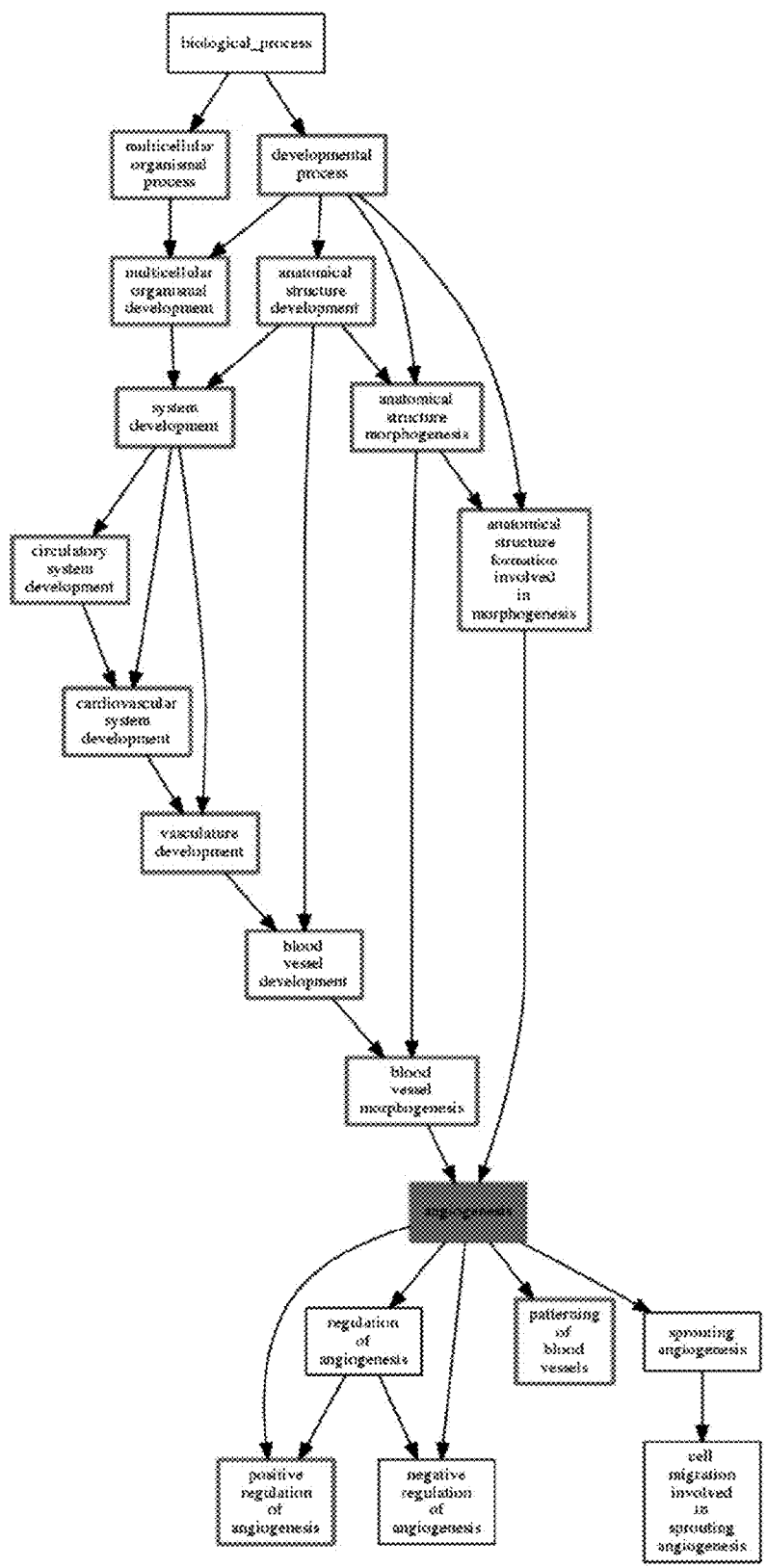

Angiogenesis and immune response cluster genes of FIG. 6

| SEQ NO: | Orientation | Gene Symbol |
|---|---|---|
| 2 | Sense (Fully Exonic) | PDGFC |
| 3 | Sense (Fully Exonic) | TGFB3 |
| 4 | Sense (Fully Exonic) | RAC2 |
| 5 | Sense (Fully Exonic) | MARCKS |
| 6 | Sense (Fully Exonic) | ALOX5 |
| 7 | Sense (Fully Exonic) | COL8A1 |
| 11 | Sense (Fully Exonic) | KCNAB2 |
| 12 | Sense (Fully Exonic) | THBS1 |
| 14 | Sense (Fully Exonic) | CTGF |
| 15 | Sense (Fully Exonic) | CTGF |
| 16 | Sense (Fully Exonic) | VCAN |
| 18 | Sense (Fully Exonic) | IGKC |
| 19 | Sense (Fully Exonic) | IGKC |
| 21 | Sense (includes Intronic) | NFATC1 |
| 22 | Sense (Fully Exonic) | HMHA1 |
| 23 | Sense (Fully Exonic) | FCGR1B |
| 24 | Sense (Fully Exonic) | EDA2R |
| 25 | Sense (Fully Exonic) | COL8A1 |
| 26 | Sense (Fully Exonic) | COL12A1 |
| 27 | Sense (Fully Exonic) | HLA-B |
| 28 | Sense | HLA-F |
| 37 | Sense (Fully Exonic) | EGR1 |
| 40 | Sense (Fully Exonic) | SULF2 |
| 41 | Sense (Fully Exonic) | CERCAM |
| 42 | Sense (Fully Exonic) | ATF3 |
| 43 | Sense (Fully Exonic) | MIR21 |
| 45 | Sense (Fully Exonic) | IFIT2 |
| 47 | Sense (Fully Exonic) | IGLC3 |
| 48 | Sense (Fully Exonic) | IGLC3 |

TABLE 1B-continued

Angiogenesis and immune response cluster genes of FIG. 6

| SEQ NO: | Orientation | Gene Symbol |
|---|---|---|
| 49 | Sense (Fully Exonic) | IGLC3 |
| 50 | Sense (Fully Exonic) | IGLC3 |
| 51 | Sense (Fully Exonic) | IGLC3 |
| 54 | Sense (Fully Exonic) | IGLC3 |
| 55 | Sense (Fully Exonic) | ANGPTL2 |
| 56 | Sense (Fully Exonic) | COL5A2 |
| 58 | Sense (Fully Exonic) | THY1 |
| 59 | Sense (Fully Exonic) | NDN |
| 60 | Sense (Fully Exonic) | RGS2 |
| 61 | Sense (Fully Exonic) | MEIS3P2 |
| 62 | Sense (Fully Exonic) | GBP2 |
| 65 | Sense (Fully Exonic) | FAT1 |
| 66 | Sense (Fully Exonic) | COL1A1 |
| 68 | Sense (Fully Exonic) | MMP11 |
| 69 | Sense (Fully Exonic) | GADD45B |
| 71 | Sense (Fully Exonic) | MMP14 |
| 72 | Sense (Fully Exonic) | IGHG4 |
| 80 | Sense (Fully Exonic) | HCLS1 |
| 83 | No Transcript match | |
| 84 | Sense (Fully Exonic) | JAM3 |
| 86 | Sense (Fully Exonic) | TMEM49 |
| 87 | Sense (Fully Exonic) | LTBP2 |
| 88 | Sense (Fully Exonic) | IRS1 |
| 90 | Sense (Fully Exonic) | C17orf91 |
| 91 | Sense (Fully Exonic) | GPNMB |
| 92 | Sense (Fully Exonic) | FAM198B |
| 95 | Sense (Fully Exonic) | CHST15 |
| 97 | Sense (Fully Exonic) | DCN |
| 98 | Sense (Fully Exonic) | VCAM1 |
| 105 | Sense (Fully Exonic) | CIITA |
| 106 | Sense (Fully Exonic) | GAS7 |
| 107 | Sense (Fully Exonic) | COL3A1 |
| 110 | Sense (Fully Exonic) | ITGB2 |
| 111 | Sense (Fully Exonic) | ELN |
| 112 | Sense (Fully Exonic) | CMTM3 |
| 113 | Sense (Fully Exonic) | ANTXR1 |
| 118 | Sense (Fully Exonic) | IL4I1 |
| 119 | Sense (Fully Exonic) | ANTXR2 |
| 120 | Sense (Fully Exonic) | IGLC2 /// IGLC3 |
| 123 | Sense (Fully Exonic) | IGLC3 |
| 124 | Sense (Fully Exonic) | BST2 |
| 126 | Sense (Fully Exonic) | COL10A1 |
| 127 | Sense (Fully Exonic) | IGLC3 |
| 128 | Sense (Fully Exonic) | FBP1 |
| 129 | Sense (Fully Exonic) | RHOBTB3 |
| 131 | Sense (Fully Exonic) | CD74 |
| 132 | Sense (Fully Exonic) | ISM1 |
| 135 | Sense (Fully Exonic) | CSRNP1 |
| 138 | Sense (Fully Exonic) | DCN |
| 139 | Sense (Fully Exonic) | IGFBP4 |
| 143 | Sense (Fully Exonic) | CCDC80 |
| 148 | Sense (Fully Exonic) | COL3A1 |
| 150 | Sense (Fully Exonic) | ZFP36 |
| 151 | Sense (Fully Exonic) | MMP11 |
| 152 | Sense (Fully Exonic) | COL1A2 |
| 153 | Sense (Fully Exonic) | HLA-DPA1 |
| 154 | Sense (Fully Exonic) | TWIST1 |
| 155 | Sense (Fully Exonic) | ZNF154 |
| 157 | Sense (Fully Exonic) | IGLC3 |
| 159 | Sense (Fully Exonic) | IGKC |
| 160 | Sense (Fully Exonic) | IGHG1 |
| 162 | Sense (Fully Exonic) | COL1A2 |
| 163 | Sense (Fully Exonic) | APOC1 |
| 167 | AntiSense | EGR1 |
| 171 | Sense (Fully Exonic) | KIAA0146 |
| 174 | Sense (Fully Exonic) | TPM1 |
| 176 | Sense (includes Intronic) | DMD |
| 180 | No Transcript match | |
| 181 | Sense (Fully Exonic) | DUSP1 |
| 182 | Sense (Fully Exonic) | GBP1 |
| 185 | Sense (includes Intronic) | PDGFC |
| 186 | Sense (includes Intronic) | MSN |
| 188 | Sense (includes Intronic) | TPM1 |
| 189 | Sense (Fully Exonic) | EMB |
| 191 | Sense (Fully Exonic) | FOS |
| 195 | Sense (includes Intronic) | DPYSL3 |
| 197 | AntiSense | EGR1 |
| 198 | AntiSense | NRP2 |
| 201 | Sense (Fully Exonic) | MMP2 |
| 204 | Sense (Fully Exonic) | CTGF |
| 211 | Sense (Fully Exonic) | ACTA2 |
| 213 | Sense (Fully Exonic) | LOXL1 |
| 216 | Sense (Fully Exonic) | CDH11 |
| 218 | Sense (Fully Exonic) | LUM |
| 219 | Sense (Fully Exonic) | NNMT |
| 222 | Sense (Fully Exonic) | GJA1 |
| 225 | AntiSense | CTHRC1 |
| 229 | Sense (Fully Exonic) | CTSB |
| 232 | Sense (Fully Exonic) | PLAU |
| 233 | Sense (Fully Exonic) | PDGFRA |
| 242 | Sense (Fully Exonic) | VCAN |
| 243 | AntiSense | — |
| 244 | Sense (Fully Exonic) | IGHG4 /// IGHG2 /// IGHG1 /// IGHGP |
| 245 | Sense (Fully Exonic) | IGHG2 |
| 246 | Sense (includes Intronic) | C3orf26 |
| 247 | AntiSense | ATF3 |
| 248 | AntiSense | ATF3 |
| 250 | Sense (Fully Exonic) | FN1 |
| 251 | AntiSense | CALD1 |
| 252 | AntiSense | CALD1 |
| 256 | AntiSense | EGR1 |
| 261 | AntiSense | TWIST1 |
| 262 | AntiSense | TWIST1 |
| 263 | AntiSense | BATF2 |
| 264 | AntiSense | NFKBIZ |
| 265 | Sense (includes Intronic) | C3orf26 |
| 266 | AntiSense | LOXL1 |
| 267 | Sense (includes Intronic) | — |
| 269 | AntiSense | FN1 |
| 270 | AntiSense | COL1A1 |
| 272 | Sense (Fully Exonic) | TREH |
| 274 | AntiSense | APOL1 |
| 281 | Sense (Fully Exonic) | COL10A1 |
| 282 | Sense (Fully Exonic) | GAL3ST4 |
| 284 | Sense (Fully Exonic) | TAGLN |
| 285 | Sense (Fully Exonic) | TWIST1 |
| 286 | Sense (Fully Exonic) | HCLS1 |
| 288 | Sense (Fully Exonic) | ITGB2 |
| 290 | Sense (Fully Exonic) | HLA-B |
| 291 | Sense (Fully Exonic) | C17orf91 |
| 296 | Sense (Fully Exonic) | FBLIM1 |
| 297 | Sense (Fully Exonic) | COL15A1 |
| 298 | Sense (Fully Exonic) | AQP7P3 |
| 299 | AntiSense | IGFBP5 |
| 300 | Sense (Fully Exonic) | FANK1 |
| 301 | AntiSense | INS |
| 302 | Sense (Fully Exonic) | COL27A1 |
| 303 | Sense (Fully Exonic) | COL5A1 |
| 304 | Sense (Fully Exonic) | PRICKLE2 |
| 305 | Sense (Fully Exonic) | N/A |
| 306 | Sense (Fully Exonic) | GXYLT2 |
| 307 | Sense (includes Intronic) | KLF12 |
| 308 | No Transcript match | |
| 309 | Sense (Fully Exonic) | FBXO32 |
| 310 | No Transcript match | |
| 311 | Sense (Fully Exonic) | ASAH2B |
| 312 | AntiSense | PPFIBP1 |
| 313 | AntiSense | XIST |
| 314 | Sense (Fully Exonic) | IGFBP6 |
| 315 | Sense (Fully Exonic) | ROBO1 |
| 316 | Sense (Fully Exonic) | TPM1 |
| 317 | AntiSense | N/A |
| 318 | AntiSense | PLEKHG1 |
| 319 | Sense (Fully Exonic) | NR2F1 |
| 320 | Sense (Fully Exonic) | NPDC1 |
| 321 | AntiSense | INS |
| 322 | Sense (Fully Exonic) | TRAF5 |
| 323 | Sense (Fully Exonic) | CALD1 |
| 324 | Sense (includes Intronic) | CHRM3 |

TABLE 1B-continued

Angiogenesis and immune response cluster genes of FIG. 6

| SEQ NO: | Orientation | Gene Symbol |
|---|---|---|
| 325 | Sense (Fully Exonic) | AMOTL1 |
| 326 | Sense (includes Intronic) | COL12A1 |
| 327 | Sense (Fully Exonic) | PLXNA4 |
| 328 | Sense (includes Intronic) | TMEM43 |
| 329 | Sense (includes Intronic) | RORA |
| 330 | AntiSense | INS |
| 331 | Sense (Fully Exonic) | TSPAN18 |
| 332 | No Transcript match | |
| 333 | Sense (Fully Exonic) | TNC |
| 334 | Sense (Fully Exonic) | TYRO3 |
| 335 | AntiSense | EFNA5 |
| 336 | Sense (Fully Exonic) | MYL9 |
| 337 | Sense (Fully Exonic) | MIR198 |
| 338 | Sense (includes Intronic) | N/A |
| 339 | Sense (includes Intronic) | PLA2R1 |
| 340 | Sense (Fully Exonic) | COL14A1 |
| 341 | Sense (Fully Exonic) | NRP1 |
| 342 | Sense (Fully Exonic) | FSCN1 |
| 343 | Sense (includes Intronic) | PDGFD |
| 344 | No Transcript match | |
| 345 | Sense (includes Intronic) | DOCK4 |
| 346 | Sense (Fully Exonic) | TRIM13 |
| 347 | Sense (Fully Exonic) | IGFBP5 |
| 348 | Sense (Fully Exonic) | C19orf63 |
| 349 | AntiSense | KLF6 |
| 350 | AntiSense | TRIO |
| 351 | Sense (Fully Exonic) | COL4A1 |
| 352 | Sense (Fully Exonic) | EPDR1 |
| 353 | Sense (Fully Exonic) | FNDC1 |
| 354 | Sense (Fully Exonic) | IL1R1 |
| 355 | Sense (Fully Exonic) | CES4 |
| 356 | Sense (Fully Exonic) | GPR176 |
| 357 | Sense (includes Intronic) | GXYLT2 |
| 358 | AntiSense | WHSC1L1 |
| 359 | Sense (Fully Exonic) | N/A |
| 360 | Sense (Fully Exonic) | RGN |
| 361 | Sense (includes Intronic) | CA3 |
| 362 | Sense (Fully Exonic) | TIMP3 |
| 363 | Sense (Fully Exonic) | EFNA5 |
| 364 | Sense (Fully Exonic) | RASGRF2 |
| 365 | Sense (includes Intronic) | RELL1 |
| 366 | AntiSense | ACSS3 |
| 367 | Sense (Fully Exonic) | STMN3 |
| 368 | Sense (Fully Exonic) | N/A |
| 369 | AntiSense | C7orf29 |
| 370 | Sense (Fully Exonic) | HOXC6 |
| 371 | Sense (Fully Exonic) | KLF8 |
| 372 | Sense (includes Intronic) | SERINC5 |
| 373 | Sense (Fully Exonic) | AKT3 |
| 374 | Sense (Fully Exonic) | TGFB2 |
| 375 | AntiSense | WNT5A |
| 376 | No Transcript match | |
| 377 | No Transcript match | |
| 378 | AntiSense | IGFBP7 |
| 379 | No Transcript match | |
| 380 | Sense (includes Intronic) | SULT1C4 |
| 381 | Sense (Fully Exonic) | AASS |
| 382 | Sense (Fully Exonic) | HEPH |
| 383 | Sense (Fully Exonic) | ADH5 |
| 384 | Sense (Fully Exonic) | TIMP2 |
| 385 | Sense (Fully Exonic) | EMP1 |
| 386 | Sense (Fully Exonic) | CXCL14 |
| 387 | Sense (Fully Exonic) | ZNF548 |
| 388 | Sense (Fully Exonic) | SGCB |
| 389 | Sense (includes Intronic) | ASH2L |
| 390 | Sense (includes Intronic) | SERINC5 |
| 391 | No Genome match | |
| 392 | Sense (Fully Exonic) | TMEM159 |
| 393 | Sense (includes Intronic) | RBMS3 |
| 394 | Sense (Fully Exonic) | TMEM49 |
| 395 | Sense (includes Intronic) | RORA |
| 396 | No Transcript match | |
| 397 | AntiSense | ZNF608 |
| 398 | No Genome match | |
| 399 | Sense (Fully Exonic) | ADAMTS2 |
| 400 | Sense (Fully Exonic) | APCDD1 |
| 401 | AntiSense | GXYLT2 |
| 402 | Sense (Fully Exonic) | XIST |
| 403 | Sense (Fully Exonic) | MBNL2 |
| 404 | Sense (Fully Exonic) | SHF |
| 405 | Sense (includes Intronic) | APBB2 |
| 406 | No Transcript match | |
| 407 | Sense (Fully Exonic) | COL14A1 |
| 408 | Sense (Fully Exonic) | IGFBP5 |
| 409 | Sense (Fully Exonic) | CREB5 |
| 410 | AntiSense | INS |
| 411 | Sense (Fully Exonic) | BAHCC1 |
| 412 | Sense (Fully Exonic) | RFXAP |
| 413 | Sense (Fully Exonic) | INS |
| 414 | Sense (Fully Exonic) | DDR2 |
| 415 | Sense (Fully Exonic) | CA12 |
| 416 | Sense (Fully Exonic) | RHOB |
| 417 | Sense (Fully Exonic) | N/A |
| 418 | Sense (Fully Exonic) | SNORD116-4 |
| 419 | Sense (Fully Exonic) | MEG3 |
| 420 | Sense (Fully Exonic) | WNT4 |
| 421 | Sense (Fully Exonic) | FBLN2 |
| 422 | AntiSense | DAAM1 |
| 423 | No Transcript match | |
| 424 | Sense (Fully Exonic) | CHN1 |
| 425 | Sense (includes Intronic) | APBB2 |
| 426 | Sense (Fully Exonic) | PTRF |
| 427 | AntiSense | IGF1 |
| 428 | Sense (Fully Exonic) | UST |
| 429 | Sense (Fully Exonic) | SMARCA1 |
| 430 | Sense (includes Intronic) | N/A |
| 431 | Sense (Fully Exonic) | IGLC3 |
| 432 | AntiSense | INS |
| 433 | Sense (Fully Exonic) | KANK4 |
| 434 | AntiSense | IGF1 |
| 435 | Sense (Fully Exonic) | CYP27A1 |
| 436 | AntiSense | EIF2B5 |
| 437 | No Transcript match | |
| 438 | Sense (Fully Exonic) | SNRNP25 |
| 439 | Sense (Fully Exonic) | SETD7 |
| 440 | Sense (Fully Exonic) | MSX1 |
| 441 | Sense (Fully Exonic) | HOPX |
| 442 | Sense (Fully Exonic) | NID2 |
| 443 | Sense (Fully Exonic) | IGF1 |
| 444 | Sense (Fully Exonic) | PSD3 |
| 445 | Sense (Fully Exonic) | FGFR1 |
| 446 | Sense (Fully Exonic) | ETV1 |
| 447 | Sense (Fully Exonic) | ZNF655 |
| 448 | No Genome match | |
| 449 | AntiSense | INS |
| 450 | Sense (Fully Exonic) | SFRP2 |
| 451 | Sense (Fully Exonic) | SPAG16 |
| 452 | AntiSense | NR2F2 |
| 453 | Sense (includes Intronic) | SYNPO2 |
| 454 | Sense (Fully Exonic) | FAM101B |
| 455 | AntiSense | IGF2 |
| 456 | Sense (Fully Exonic) | CA3 |
| 457 | Sense (Fully Exonic) | XIST |
| 458 | No Transcript match | |
| 459 | Sense (Fully Exonic) | WNT7A |
| 460 | Sense (includes Intronic) | N/A |
| 461 | Sense (Fully Exonic) | FGFR1 |
| 462 | AntiSense | FXYD6 |
| 463 | Sense (Fully Exonic) | FGFR1 |
| 464 | Sense (includes Intronic) | IGFBP7 |
| 465 | Sense (Fully Exonic) | TIMP2 |
| 466 | Sense (Fully Exonic) | DUSP1 |
| 467 | Sense (includes Intronic) | SERINC5 |
| 468 | No Transcript match | |
| 469 | Sense (Fully Exonic) | ABLIM1 |
| 470 | Sense (Fully Exonic) | ARL4A |
| 471 | AntiSense | SH3TC2 |
| 472 | AntiSense | NR2F2 |
| 473 | Sense (Fully Exonic) | ENG |
| 474 | Sense (Fully Exonic) | MGP |
| 475 | Sense (Fully Exonic) | MEG3 |
| 476 | AntiSense | FAM115A |

TABLE 1B-continued

Angiogenesis and immune response cluster genes of FIG. 6

| SEQ NO: | Orientation | Gene Symbol |
|---|---|---|
| 477 | Sense (Fully Exonic) | EGR1 |
| 478 | Sense (Fully Exonic) | SNORD116-3 |
| 479 | Sense (Fully Exonic) | AEBP1 |
| 480 | Sense (includes Intronic) | SDK1 |
| 481 | Sense (Fully Exonic) | ENC1 |
| 482 | Sense (Fully Exonic) | SNORD116-7 |
| 483 | Sense (Fully Exonic) | N/A |
| 484 | Sense (Fully Exonic) | APOD |
| 485 | AntiSense | N/A |
| 486 | AntiSense | GAS1 |
| 487 | Sense (Fully Exonic) | VPS36 |
| 488 | No Transcript match | |
| 489 | Sense (Fully Exonic) | SPHK2 |
| 490 | Sense (Fully Exonic) | SNORD116-8 |
| 491 | Sense (Fully Exonic) | MYO10 |
| 492 | Sense (Fully Exonic) | HOXC6 |
| 493 | Sense (Fully Exonic) | RNF149 |
| 494 | Sense (Fully Exonic) | BTG2 |
| 495 | Sense (includes Intronic) | MAP3K1 |
| 496 | Sense (Fully Exonic) | SNORD116-23 |
| 497 | Sense (includes Intronic) | ACSL4 |
| 498 | Sense (Fully Exonic) | CYP27C1 |
| 499 | Sense (includes Intronic) | COL12A1 |
| 500 | Sense (Fully Exonic) | IGFBP5 |
| 501 | Sense (Fully Exonic) | DUSP4 |
| 502 | Sense (Fully Exonic) | PFKFB3 |
| 503 | Sense (Fully Exonic) | SDC2 |
| 504 | AntiSense | FXYD6 |
| 505 | Sense (Fully Exonic) | COL5A1 |
| 506 | Sense (Fully Exonic) | MARCKS |
| 507 | Sense (Fully Exonic) | IRS2 |
| 508 | Sense (Fully Exonic) | N/A |
| 509 | AntiSense | FSCN1 |
| 510 | Sense (Fully Exonic) | FYN |
| 511 | Sense (Fully Exonic) | IGFBP5 |
| 512 | Sense (Fully Exonic) | NUDT4P1 |
| 513 | Sense (Fully Exonic) | NFKBIZ |
| 514 | Sense (Fully Exonic) | N/A |
| 515 | Sense (Fully Exonic) | C7orf41 |
| 516 | Sense (Fully Exonic) | MEG3 |
| 517 | Sense (Fully Exonic) | N/A |
| 518 | Sense (Fully Exonic) | PLEKHG1 |
| 519 | Sense (Fully Exonic) | ZNF827 |
| 520 | Sense (Fully Exonic) | ZNF175 |
| 521 | Sense (Fully Exonic) | XIST |
| 522 | Sense (includes Intronic) | GSN |
| 523 | Sense (includes Intronic) | RORA |
| 524 | Sense (Fully Exonic) | CA13 |
| 525 | AntiSense | TMX4 |
| 526 | Sense (Fully Exonic) | KIT |
| 527 | Sense (includes Intronic) | WDR78 |
| 528 | Sense (Fully Exonic) | ECEL1 |
| 529 | Sense (Fully Exonic) | XIST |
| 530 | Sense (Fully Exonic) | PROCR |
| 531 | Sense (Fully Exonic) | C9orf167 |
| 532 | Sense (Fully Exonic) | MUC6 |
| 533 | Sense (includes Intronic) | P4HA2 |
| 534 | Sense (Fully Exonic) | FAM69C |
| 535 | Sense (Fully Exonic) | NOX4 |
| 536 | Sense (includes Intronic) | N/A |
| 537 | No Transcript match | |
| 538 | Sense (Fully Exonic) | SMOX |
| 539 | Sense (Fully Exonic) | KIAA0922 |
| 540 | No Transcript match | |
| 541 | Sense (Fully Exonic) | XIST |
| 542 | Sense (Fully Exonic) | NPAS2 |
| 543 | Sense (Fully Exonic) | NAV1 |
| 544 | Sense (includes Intronic) | N/A |
| 545 | Sense (Fully Exonic) | HLA-A |
| 546 | Sense (Fully Exonic) | FAM46C |
| 547 | Sense (Fully Exonic) | N/A |
| 548 | Sense (Fully Exonic) | SLAMF7 |
| 549 | Sense (Fully Exonic) | FCER1G |
| 550 | Sense (Fully Exonic) | C1S |
| 551 | Sense (Fully Exonic) | NUPR1 |
| 552 | AntiSense | C1QC |
| 553 | AntiSense | SAT1 |
| 554 | Sense (Fully Exonic) | SOD2 |
| 555 | Sense (Fully Exonic) | IRF1 |
| 556 | Sense (Fully Exonic) | SFN |
| 557 | AntiSense | LTB |
| 558 | Sense (Fully Exonic) | ARID5A |
| 559 | Sense (Fully Exonic) | BST2 |
| 560 | Sense (Fully Exonic) | HLA-F |
| 561 | Sense (Fully Exonic) | XAF1 |
| 562 | Sense (Fully Exonic) | TCOF1 |
| 563 | Sense (Fully Exonic) | RPL23AP1 |
| 564 | Sense (Fully Exonic) | IL1RN |
| 565 | Sense (Fully Exonic) | IFIT5 |
| 566 | Sense (Fully Exonic) | B2M |
| 567 | AntiSense | GBP1 |
| 568 | Sense (Fully Exonic) | HLA-F |
| 569 | Sense (Fully Exonic) | DGKA |
| 570 | Sense (Fully Exonic) | XBP1 |
| 571 | Sense (Fully Exonic) | PLCG2 |
| 572 | Sense (Fully Exonic) | FAM46C |
| 573 | No Genome match | |
| 574 | Sense (Fully Exonic) | TREM2 |
| 575 | Sense (Fully Exonic) | LGALS9 |
| 576 | Sense (Fully Exonic) | HLA-DPB1 |
| 577 | AntiSense | ODF3B |
| 578 | Sense (Fully Exonic) | MX1 |
| 579 | Sense (Fully Exonic) | STAT1 |
| 580 | Sense (Fully Exonic) | CTSB |
| 581 | Sense (Fully Exonic) | FAM26F |
| 582 | Sense (includes Intronic) | PARP14 |
| 583 | AntiSense | SAT1 |
| 584 | Sense (Fully Exonic) | CTSS |
| 585 | No Transcript match | |
| 586 | Sense (Fully Exonic) | CTSB |
| 587 | Sense (Fully Exonic) | ADAM8 |
| 588 | Sense (includes Intronic) | B2M |
| 589 | Sense (Fully Exonic) | FLVCR2 |
| 590 | Sense (Fully Exonic) | TYROBP |
| 591 | AntiSense | SAMD9L |
| 592 | Sense (Fully Exonic) | SAMD9L |
| 593 | Sense (Fully Exonic) | SIGLEC1 |
| 594 | Sense (Fully Exonic) | MMP7 |
| 595 | Sense (Fully Exonic) | APOL1 |
| 596 | Sense (Fully Exonic) | CYLD |
| 597 | Sense (Fully Exonic) | HLA-B |
| 598 | Sense (Fully Exonic) | SAT1 |
| 599 | Sense (Fully Exonic) | C1QB |
| 600 | Sense (Fully Exonic) | HLA-DMB |
| 601 | Sense (Fully Exonic) | NLRC5 |
| 602 | Sense (Fully Exonic) | FAM20A |
| 603 | AntiSense | N/A |
| 604 | Sense (Fully Exonic) | STAT1 |
| 605 | Sense (includes Intronic) | STAT1 |
| 606 | Sense (Fully Exonic) | STAT1 |
| 607 | AntiSense | N/A |
| 608 | Sense (Fully Exonic) | DERL3 |
| 609 | Sense (Fully Exonic) | HLA-F |
| 610 | Sense (Fully Exonic) | MAFB |
| 611 | Sense (Fully Exonic) | CD4 |
| 612 | Sense (Fully Exonic) | HLA-A |
| 613 | Sense (Fully Exonic) | UBE2L6 |
| 614 | Sense (Fully Exonic) | C1QC |
| 615 | Sense (Fully Exonic) | CD163 |
| 616 | Sense (Fully Exonic) | LRMP |
| 617 | Sense (Fully Exonic) | C11orf17 |
| 618 | Sense (Fully Exonic) | XAF1 |
| 619 | Sense (Fully Exonic) | GLRX |
| 620 | Sense (Fully Exonic) | IFIH1 |
| 621 | Sense (Fully Exonic) | CD44 |
| 622 | Sense (Fully Exonic) | LITAF |
| 623 | Sense (Fully Exonic) | CCDC69 |
| 624 | Sense (Fully Exonic) | GBP5 |
| 625 | Sense (Fully Exonic) | PML |
| 626 | Sense (Fully Exonic) | SAMD9 |

TABLE 1B-continued

Angiogenesis and immune response cluster genes of FIG. 6

| SEQ NO: | Orientation | Gene Symbol |
|---|---|---|
| 627 | Sense (Fully Exonic) | CBR3 |
| 628 | Sense (Fully Exonic) | RASGRP2 |
| 629 | Sense (Fully Exonic) | FCGR2A |
| 630 | Sense (Fully Exonic) | BST2 |
| 631 | Sense (Fully Exonic) | HLA-A |

In certain exemplary embodiments, all or a portion of the biomarkers recited in Table 1A and Table 1B, may be used in an expression signature. In certain other exemplary embodiments, all or a portion of the biomarkers recited in Group I or Group II may be used in an expression signature. For example, expression signatures comprising the biomarkers in Table 1A, Table 1B, Group I, and Group II, can be generated using the methods provided herein and can comprise between one, and all of the markers set forth in Tables 1A, 1B, Group I, Group II and each and every combination in between (e.g., four selected markers, 16 selected markers, 74 selected markers, etc.). In some embodiments, the expression signature comprises at least 5, 10, 20, 40, 60, 100, 150, 200, or 300 or more markers. In other embodiments, the predictive biomarker panel comprises no more than 5, 10, 20, 40, 60, 100, 150, 200, 300, 400, 500, 600 or 700 markers. In one exemplary embodiment, the expression signature includes a plurality of markers listed in Table 1A. In another exemplary embodiment, the expression signature includes a plurality of biomarkers listing in Table 1B. In yet another exemplary embodiment, the expression signature includes a plurality of biomarkers listed in Table 1A and Table 1B. In another exemplary embodiment, the expression signature includes a plurality of biomarkers listed in Group I. In another exemplary embodiment, the expression signature includes a plurality of biomarkers listed in table Group II. In yet another exemplary embodiment, the expression signature includes a plurality of biomarkers listed in Groups I and II. In some embodiments the expression signature includes at least about 1%, about 5%, about 10%, about 20%, about 30%, about 40%, about 50%, about 60%, about 70%, about 80%, about 90%, about 95%, about 96%, about 97%, about 98%, or about 99% of the markers listed in Table 1A, Table 1B, Group I, Group II, or a combination thereof. Selected expression signatures can be assembled from the biomarkers provided using methods described herein and analogous methods known in the art. In one embodiment, the expression signature contains all 250 genes or gene products in Table 1A. In another exemplary embodiment, the expression signature contains all 486 genes or gene products in Table 1B. In another exemplary embodiment the expression signature comprises SEQ ID NOs: 632-801. In another exemplary embodiment, the expression signature comprises SEQ ID NOs: 802-974.

4. Mathematical Models

The following methods may be used to derive expression signatures for distinguishing between subjects that are responsive or non-responsive to anti-angiogenic therapeutics, or as prognostic indicators of certain cancer types, including expression signatures derived from the biomarkers disclosed above. In certain other exemplary embodiments, the expression signature is derived using a decision tree (Hastie et al. The Elements of Statistical Learning, Springer, New York 2001), a random forest (Breiman, 2001 Random Forests, Machine Learning 45:5), a neural network (Bishop, Neural Networks for Pattern Recognition, Clarendon Press, Oxford 1995), discriminant analysis (Duda et al. Pattern Classification, 2nd ed., John Wiley, New York 2001), including, but not limited to linear, diagonal linear, quadratic and logistic discriminant analysis, a Prediction Analysis for Microarrays (PAM, (Tibshirani et al., 2002, Proc. Natl. Acad. Sci. USA 99:6567-6572)) or a Soft Independent Modeling of Class Analogy analysis. (SIMCA, (Wold, 1976, Pattern Recogn. 8:127-139)).

Biomarker expression values may be defined in combination with corresponding scalar weights on the real scale with varying magnitude, which are further combined through linear or non-linear, algebraic, trigonometric or correlative means into a single scalar value via an algebraic, statistical learning, Bayesian, regression, or similar algorithms which together with a mathematically derived decision function on the scalar value provide a predictive model by which expression profiles from samples may be resolved into discrete classes of responder or non-responder, resistant or non-resistant, to a specified drug, drug class, or treatment regimen. Such predictive models, including biomarker membership, are developed by learning weights and the decision threshold, optimized for sensitivity, specificity, negative and positive predictive values, hazard ratio or any combination thereof, under cross-validation, bootstrapping or similar sampling techniques, from a set of representative expression profiles from historical patient samples with known drug response and/or resistance.

In one embodiment, the biomarkers are used to form a weighted sum of their signals, where individual weights can be positive or negative. The resulting sum ("expression score") is compared with a pre-determined reference point or value. The comparison with the reference point or value may be used to diagnose, or predict a clinical condition or outcome.

As described above, one of ordinary skill in the art will appreciate that the biomarkers included in the classifier provided in Tables 1A, 1B, Group I and Group II will carry unequal weights in a classifier for responsiveness or resistance to a therapeutic agent. Therefore, while as few as one sequence may be used to diagnose or predict an outcome such as responsiveness to therapeutic agent, the specificity and sensitivity or diagnosis or prediction accuracy may increase using more sequences.

As used herein, the term "weight" refers to the relative importance of an item in a statistical calculation. The weight of each biomarker in a gene expression classifier may be determined on a data set of patient samples using analytical methods known in the art.

In certain exemplary embodiments, the expression signature is defined by a decision function. A decision function is a set of weighted expression values derived using a linear classifier. All linear classifiers define the decision function using the following equation:

$$f(x) = w'\cdot x + b = \Sigma w_i \cdot x_i + b \quad (1)$$

All measurement values, such as the microarray gene expression intensities $x_i$, for a certain sample are collected in a vector x. Each intensity is then multiplied with a corresponding weight $w_i$ to obtain the value of the decision function $f(x)$ after adding an offset term b. In deriving the decision function, the linear classifier will further define a threshold value that splits the gene expression data space into two disjoint halves. Exemplary linear classifiers include but are not limited to partial least squares (PLS), (Nguyen et al., Bioinformatics 18 (2002) 39-50), support vector machines (SVM) (Schölkopf et al., Learning with Kernels, MIT Press, Cambridge 2002), and shrinkage discriminant analysis (SDA) (Ahdesmaki et al., Annals of applied statistics 4, 503-519 (2010)). In one exemplary embodiment, the linear classifier is a PLS linear classifier.

The decision function is empirically derived on a large set of training samples, for example from patients showing responsiveness or resistance to a therapeutic agent. The threshold separates a patient group based on different characteristics such as, but not limited to, responsiveness/non-responsiveness to treatment. The interpretation of this quantity, i.e. the cut-off threshold responsiveness or resistance to a therapeutic agent, is derived in the development phase ("training") from a set of patients with known outcome. The corresponding weights and the responsiveness/resistance cut-off threshold for the decision score are fixed a priori from training data by methods known to those skilled in the art. In one exemplary embodiment, Partial Least Squares Discriminant Analysis (PLS-DA) is used for determining the weights. (L. Ståhle, S. Wold, J. Chemom. 1 (1987) 185-196; D. V. Nguyen, D. M. Rocke, Bioinformatics 18 (2002) 39-50).

Effectively, this means that the data space, i.e. the set of all possible combinations of biomarker expression values, is split into two mutually exclusive halves corresponding to different clinical classifications or predictions, for example, one corresponding to responsiveness to a therapeutic agent and the other to non-responsiveness. In the context of the overall classifier, relative over-expression of a certain biomarker can either increase the decision score (positive weight) or reduce it (negative weight) and thus contribute to an overall decision of, for example, responsiveness or resistance to a therapeutic agent.

In certain exemplary embodiments of the invention, the data is transformed non-linearly before applying a weighted sum as described above. This non-linear transformation might include increasing the dimensionality of the data. The non-linear transformation and weighted summation might also be performed implicitly, for example, through the use of a kernel function. (Schölkopf et al. Learning with Kernels, MIT Press, Cambridge 2002).

In certain exemplary embodiments, the patient training set data is derived by isolated RNA from a corresponding cancer tissue sample set and determining expression values by hybridizing the isolated RNA to a microarray. In certain exemplary embodiments, the microarray used in deriving the expression signature is a transcriptome array. As used herein a "transcriptome array" refers to a microarray containing probe sets that are designed to hybridize to sequences that have been verified as expressed in the diseased tissue of interest. Given alternative splicing and variable poly-A tail processing between tissues and biological contexts, it is possible that probes designed against the same gene sequence derived from another tissue source or biological context will not effectively bind to transcripts expressed in the diseased tissue of interest, leading to a loss of potentially relevant biological information. Accordingly, it is beneficial to verify what sequences are expressed in the disease tissue of interest before deriving a microarray probe set. Verification of expressed sequences in a particular disease context may be done, for example, by isolating and sequencing total RNA from a diseased tissue sample set and cross-referencing the isolated sequences with known nucleic acid sequence databases to verify that the probe set on the transcriptome array is designed against the sequences actually expressed in the diseased tissue of interest. Methods for making transcriptome arrays are described in United States Patent Application Publication No. 2006/0134663, which is incorporated herein by reference. In certain exemplary embodiments, the probe set of the transcriptome array is designed to bind within 300 nucleotides of the 3' end of a transcript. Methods for designing transcriptome arrays with probe sets that bind within 300 nucleotides of the 3' end of target transcripts are disclosed in United States Patent Application Publication No. 2009/0082218, which is incorporated by reference herein. In certain exemplary embodiments, the microarray used in deriving the gene expression profiles of the present invention is the Almac Ovarian Cancer DSA™ microarray (Almac Group, Craigavon, United Kingdom).

An optimal linear classifier can be selected by evaluating a linear classifier's performance using such diagnostics as "area under the curve" (AUC). AUC refers to the area under the curve of a receiver operating characteristic (ROC) curve, both of which are well known in the art. AUC measures are useful for comparing the accuracy of a classifier across the complete data range. Linear classifiers with a higher AUC have a greater capacity to classify unknowns correctly between two groups of interest (e.g., ovarian cancer samples and normal or control samples). ROC curves are useful for plotting the performance of a particular feature (e.g., any of the biomarkers described herein and/or any item of additional biomedical information) in distinguishing between two populations (e.g., individuals responding and not responding to a therapeutic agent). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

In one exemplary embodiment the expression signature is directed to the 25 biomarkers detailed in Table 2A with corresponding ranks and weights detailed in the table or alternative rankings and weightings, depending, for example, on the disease setting. In another exemplary embodiment, the expression signature is directed to the 45 biomarkers detailed in Table 2B with corresponding ranks and weights detailed in the table or alternative rankings and weightings, depending, for example, on the disease setting. Tables 2A and 2B rank the biomarkers in order of decreasing weight in the classifier, defined as the rank of the average weight in the compound decision score function measured under cross-validation.

TABLE 2A

Gene symbols and corresponding ranked weights for a 25 gene signature

25 Gene Signature

| Rank | Gene Symbol | Weight |
| --- | --- | --- |
| 1 | CCDC80 | 0.0584 |
| 2 | INHBA | 0.0508 |
| 3 | THBS2 | 0.0504 |
| 4 | SFRP2 | 0.0437 |
| 5 | MMP2 | 0.0367 |
| 6 | PLAU | −0.0323 |
| 7 | FAP | 0.0300 |
| 8 | FN1 | 0.0277 |
| 9 | COL8A1 | −0.0248 |
| 10 | RAB31 | 0.0244 |
| 11 | FAM38B | 0.0242 |
| 12 | VCAN | 0.0230 |
| 13 | GJB2 | 0.0223 |
| 14 | ITGA5 | 0.0216 |
| 15 | CRISPLD2 | 0.0192 |
| 16 | C17orf91 | 0.0167 |
| 17 | BGN | −0.0142 |
| 18 | TIMP3 | 0.0130 |
| 19 | ALPK2 | 0.0123 |
| 20 | LUM | 0.0104 |
| 21 | NKD2 | −0.0098 |
| 22 | LOX | −0.0082 |
| 23 | MIR1245 | 0.0059 |
| 24 | LOXL1 | 0.0052 |
| 25 | CXCL12 | 0.0048 |

TABLE 2B

Gene symbols and corresponding ranked weights for a 45 gene signature

45 Gene Signature

| Rank | Gene Symbol | Weight |
| --- | --- | --- |
| 1 | TMEM200A | 0.0595 |
| 2 | GJB2 | 0.0560 |
| 3 | MMP13 | 0.0383 |
| 4 | GFPT2 | 0.0380 |
| 5 | POSTN | −0.0355 |
| 6 | BICC1 | 0.0304 |
| 7 | CDH11 | 0.0283 |
| 8 | MRVI1 | 0.0256 |
| 9 | PMP22 | 0.0240 |
| 10 | COL11A1 | −0.0237 |
| 11 | IGFL2 | 0.0222 |
| 12 | LUM | −0.0220 |
| 13 | NTM | −0.0218 |
| 14 | BGN | 0.0211 |
| 15 | COL3A1 | −0.0210 |
| 16 | COL10A1 | 0.0197 |
| 17 | RAB31 | 0.0180 |
| 18 | ANGPTL2 | 0.0166 |
| 19 | PLAU | 0.0166 |
| 20 | COL8A1 | 0.0164 |
| 21 | MIR1245 | 0.0153 |
| 22 | POLD2 | 0.0146 |
| 23 | NKD2 | 0.0145 |
| 24 | FZD1 | 0.0143 |
| 25 | COPZ2 | 0.0139 |
| 26 | ITGA5 | 0.0136 |
| 27 | VGLL3 | 0.0125 |
| 28 | INHBA | −0.0118 |
| 29 | MMP14 | 0.0110 |
| 30 | VCAN | 0.0100 |
| 31 | THBS2 | −0.0087 |
| 32 | RUNX2 | 0.0083 |
| 33 | TIMP3 | 0.0081 |
| 34 | SFRP2 | −0.0079 |
| 35 | COL1A2 | 0.0078 |
| 36 | COL5A2 | −0.0072 |
| 37 | SERPINF1 | 0.0068 |
| 38 | KIF26B | −0.0052 |
| 39 | TNFAIP6 | 0.0050 |
| 40 | MMP2 | 0.0040 |
| 41 | FN1 | 0.0031 |
| 42 | ALPK2 | 0.0024 |
| 43 | CTSK | 0.0015 |
| 44 | LOXL1 | −0.0014 |
| 45 | FAP | 0.0000 |

In one exemplary embodiment, the expression signature comprises one or more biomarkers selected from the group consisting of: CCDC80, INHBA, THBS2, SFRP2, MMP2, PLAU, FAP, FN1, COL8A1, RAB31, FAM38B, VCAN, GJB2, ITGA5, CRISPLD2, C17, f91, BGN, TIMP3, ALPK2, LUM, NKD2, LOX, MIR1245, LOXL1, and CXCL12.

In another exemplary embodiment, the expression signature comprises at least CCDC80, INHBA, THBS2 and SFRP2 and at least N additional biomarkers selected from the list of biomarkers in Table 2a, wherein N equals 2, 3, 4, 5, 6, 7, 8, 9, 10, 11, 12, 13, 14, 15, 16, 17, 18, 19, 20, or 21. In a further aspect, therapeutic responsiveness is predicted in an individual by conducting an assay on a biological sample from the individual and detecting biomarker values that each correspond to the biomarkers CCDC80, INHBA, THBS2 and SFRP2 and one of at least N additional biomarkers selected from the list of biomarkers in Table 2a, wherein N equals 2, 3, 4, 5, 6, 7, 8, 9, 10, 11, 12, 13, 14, 15, 16, 17, 18, 19, 20 or 21. In a further aspect, therapeutic responsiveness is predicted in an individual by conducting an assay on a biological sample from the individual and detecting biomarker values that each correspond to the biomarker CCDC80 and one of at least N additional biomarkers selected from the list of biomarkers in Table 2a, wherein N equals 2, 3, 4, 5, 6, 7, 8, 9, 10, 11, 12, 13, 14, 15, 16, 17, 18, 29, 20, 21, 22, 23 or 24. In a further aspect, therapeutic responsiveness is predicted in an individual by conducting an assay on a biological sample from the individual and detecting biomarker values that each correspond to the biomarker INHBA and one of at least N additional biomarkers selected from the list of biomarkers in Table 2a, wherein N equals 2, 3, 4, 5, 6, 7, 8, 9, 10, 11, 12, 13, 14, 15, 16, 17, 18, 29, 20, 21, 22, 23 or 24. In a further aspect, therapeutic responsiveness is predicted in an individual by conducting an assay on a biological sample from the individual and detecting biomarker values that each correspond to the biomarker THBS2 and one of at least N additional biomarkers selected from the list of biomarkers in Table 2a, wherein N equals 2, 3, 4, 5, 6, 7, 8, 9, 10, 11, 12, 13, 14, 15, 16, 17, 18, 29, 20, 21, 22, 23 or 24. In a further aspect, therapeutic responsiveness is predicted in an individual by conducting an assay on a biological sample from the individual and detecting biomarker values that each correspond to the biomarker SFRP2 and one of at least N additional biomarkers selected from the list of biomarkers in Table 2a, wherein N equals 2, 3, 4, 5, 6, 7, 8, 9, 10, 11, 12, 13, 14, 15, 16, 17, 18, 29, 20, 21, 22, 23 or 24.

In another exemplary embodiment, the expression signature comprises one or more biomarkers selected from the group consisting of: TMEM200A, GJB2, MMP13, GFPT2, POSTN, BICC1, CDH11, MRVI1, PMP22, COL11A1, IGFL2, LUM, NTM, BGN, COL3A1, COL10A1, RAB31, ANGPTL2, PLAU, COL8A, MIR1245, POLD2, NKD2, FZD1, COPZ2, ITGA5, VGLL3, INHBA, MMP14, VCAN, THBS2, RUNX2, TIMP3, SFRP2, COL1A2, COL5A2, SERPINF1, KIF26B, TNFAIP6, MMP2, FN1, ALPK2, CTSK, LOXL1 and FAP.

In another exemplary embodiment, the expression signature comprises at least TMEM200A, GJB2, MMP13 and GFPT2 and at least N additional biomarkers selected from the list of biomarkers in Table 2a, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41. In a further aspect, therapeutic responsiveness is predicted in an individual by conducting an assay on a biological sample from the individual and detecting biomarker values that each correspond to the biomarkers TMEM200A, GJB2, MMP13 and GFPT2 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 41. In a further aspect, therapeutic responsiveness is predicted in an individual by conducting an assay on a biological sample from the individual and detecting biomarker values that each correspond to the biomarker TMEM200A and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44. In a further aspect, therapeutic responsiveness is predicted in an individual by conducting an assay on a biological sample from the individual and detecting biomarker values that each correspond to the biomarker GJB2 and one of at least N additional biomarkers selected from the list of biomarkers in Table 2a, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44. In a further aspect, therapeutic responsiveness is predicted in an individual by conducting an assay on a biological sample from the individual and detecting biomarker values that each correspond to the biomarker MMP13 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44. In a further aspect, therapeutic responsiveness is predicted in an individual by conducting an assay on a biological sample from the individual and detecting biomarker values that each correspond to the biomarker GFPT2 and one of at least N additional biomarkers selected from the list of biomarkers in Table 2B, wherein N equals 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44.

In one exemplary embodiment, the expression signature comprises one or more biomarkers selected from the group consisting of: ALPK2, BGN, COL8A1, FAP, FN1, GJB2, INHBA, ITGA5, LOXL1, LUM, MIR1245, MMP2, NKD2, PLAU, RAB31, SFRP2, THBS2, TIMP3 and VCAN.

In another exemplary embodiment, the expression signature comprises at least ALPK2, BGN, COL8A1, FAP and at least N additional biomarkers selected from the list of biomarkers FN1, GJB2, INHBA, ITGA5, LOXL1, LUM, MIR1245, MMP2, NKD2, PLAU, RAB31, SFRP2, THBS2, TIMP3 and VCAN, wherein N equals 2, 3, 4, 5, 6, 7, 8, 9, 10, 11, 12, 13, 14 or 15. In a further aspect, therapeutic responsiveness is predicted in an individual by conducting an assay on a biological sample from the individual and detecting biomarker values that each correspond to the biomarkers ALPK2, BGN, COL8A and FAP and one of at least N additional biomarkers selected from the list of biomarkers FN1, GJB2, INHBA, ITGA5, LOXL1, LUM, MIR1245, MMP2, NKD2, PLAU, RAB31, SFRP2, THBS2, TIMP3 and VCAN, wherein N equals 2, 3, 4, 5, 6, 7, 8, 9, 10, 11, 12, 13, 14 or 15. In a further aspect, therapeutic responsiveness is predicted in an individual by conducting an assay on a biological sample from the individual and detecting biomarker values that each correspond to the biomarker ALPK2 and one of at least N additional biomarkers selected from the list of biomarkers BGN, COL8A1, FAP, FN1, GJB2, INHBA, ITGA5, LOXL1, LUM, MIR1245, MMP2, NKD2, PLAU, RAB31, SFRP2, THBS2, TIMP3 and VCAN wherein N equals 2, 3, 4, 5, 6, 7, 8, 9, 10, 11, 12, 13, 14 or 15. In a further aspect, therapeutic responsiveness is predicted in an individual by conducting an assay on a biological sample from the individual and detecting biomarker values that each correspond to the biomarker BGN and one of at least N additional biomarkers selected from the list of biomarkers ALPK2, COL8A1, FAP, FN1, GJB2, INHBA, ITGA5, LOXL1, LUM, MIR1245, MMP2, NKD2, PLAU, RAB31, SFRP2, THBS2, TIMP3 and VCAN, wherein N equals 2, 3, 4, 5, 6, 7, 8, 9, 10, 11, 12, 13, 14 or 15. In a further aspect, therapeutic responsiveness is predicted in an individual by conducting an assay on a biological sample from the individual and detecting biomarker values that each correspond to the biomarker COL8A1 and one of at least N additional biomarkers selected from the list of biomarkers ALPK2, BGN, FAP, FN1, GJB2, INHBA, ITGA5, LOXL1, LUM, MIR1245, MMP2, NKD2, PLAU, RAB31, SFRP2, THBS2, TIMP3 and VCAN, wherein N equals 2, 3, 4, 5, 6, 7, 8, 9, 10, 11, 12, 13, 14 or 15. In a further aspect, therapeutic responsiveness is predicted in an individual by conducting an assay on a biological sample from the individual and detecting biomarker values that each correspond to the biomarker FAP and one of at least N additional biomarkers selected from the list of biomarkers ALPK2, BGN, COL8A1, FN1, GJB2, INHBA, ITGA5, LOXL1, LUM, MIR1245, MMP2, NKD2, PLAU, RAB31, SFRP2, THBS2, TIMP3 and VCAN, wherein N equals 2, 3, 4, 5, 6, 7, 8, 9, 10, 11, 12, 13, 14 or 15.

In one exemplary embodiment, the expression signature comprises a set of biomarkers that are down regulated. In one exemplary embodiment the expression signature comprises at least GJB2, INHBA, THBS2, SFRP2, PLAU and at least N additional biomarkers from Table 1A or Table 1B, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, or 70. In another exemplary embodiment, the expression signature comprises at least GJB2 and at least N additional biomarkers from Table 1A or Table 1B, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In another exemplary embodiment, the expression signature comprises INHBA and at least N additional biomarkers from Table 1A or Table 1B, wherein N is. 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In another exemplary embodiment, the expression signature comprises THBS2 and at least N additional biomarkers from Table 1A or Table 1B, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In another exemplary embodiment, the expression signature comprises at least SFRP2 wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, or 74. In another exemplary embodiment, the expression signature comprises PLAU and at least N additional biomarkers from Table 1A or Table 1B, wherein N is 2, 3, 4, 5, 6, 7, 8, 9, 10, 11, 12, 13, 14, 15, 16, 17, 18, 29, 20, 21, 22, 23, 24, 25, 26, 27, 28, 29, 30, 31, 32, 33, 34, 35, 36, 37, 38, 39, 40, 41, 42, 43 or 44, 45, 46, 47, 48, 49, 50, 51, 52, 53, 54, 55, 56, 57, 58, 59, 60, 61, 62, 63, 64, 65, 66, 67, 68, 69, or 70. In another exemplary embodiment the expression signature includes GJB2, INHBA, THBS2, SFRP2, PLAU and at least about 1%, about 5%, about 10%, about 20%, about 30%, about 40%, about 50%, about 60%, about 70%, about 80%, about 90%, about 95%, or about 99% of the biomarkers listed in Table 1A, Table 1B, or a combination thereof.

Classifying New Test Samples Using an Expression Signature

To classify new test samples using an expression signature, such as those described above, the relative expression levels of biomarkers in a cancer tissue are measured to form a test sample expression profile. In certain exemplary embodiments, the test sample expression profile is summarized in the form of a compound decision score ("expression score") and compared to a threshold score that is mathematically derived from a training set of patient data. The score threshold separates a patient group based on different characteristics such as, but not limited to, responsiveness/non-responsiveness to treatment. The patient training set data is preferably derived from cancer tissue samples having been characterized by prognosis, likelihood of recurrence, long term survival, clinical outcome, treatment response, diagnosis, cancer classification, or personalized genomics profile. Expression profiles, and corresponding decision scores from patient samples may be correlated with the characteristics of patient samples in the training set that are on the same side of the mathematically derived score decision threshold. The threshold of the linear classifier scalar output is optimized to maximize the sum of sensitivity and specificity under cross-validation as observed within the training dataset.

The overall expression data for a given sample is normalized using methods known to those skilled in the art in order to correct for differing amounts of starting material, varying efficiencies of the extraction and amplification reactions, etc.

In one embodiment, the biomarker expression profile of a patient tissue sample is evaluated by a linear classifier. As used herein, a linear classifier refers to a weighted sum of the individual biomarker intensities into a compound decision score ("decision function"). The decision score is then compared to a pre-defined cut-off score threshold, corresponding to a certain set-point in terms of sensitivity and specificity which indicates if a sample is above the score threshold (decision function positive) or below (decision function negative).

Using a linear classifier on the normalized data to make a diagnostic or prognostic call (e.g. responsiveness or resistance to therapeutic agent) effectively means to split the data space, i.e. all possible combinations of expression values for all genes in the classifier, into two disjoint halves by means of a separating hyperplane. This split is empirically derived on a large set of training examples, for example from patients showing responsiveness or resistance to a therapeutic agent. Without loss of generality, one can assume a certain fixed set of values for all but one biomarker, which would automatically define a threshold value for this remaining biomarker where the decision would change from, for example, responsiveness or resistance to a therapeutic agent. Expression values above this dynamic threshold would then either indicate resistance (for a biomarker with a negative weight) or responsiveness (for a biomarker with a positive weight) to a therapeutic agent. The precise value of this threshold depends on the actual measured expression profile of all other biomarkers within the classifier, but the general indication of certain biomarkers remains fixed, i.e. high values or "relative over-expression" always contributes to either a responsiveness (genes with a positive weight) or resistance (genes with a negative weights). Therefore, in the context of the overall gene expression classifier, relative expression can indicate if either up- or down-regulation of a certain biomarker is indicative of responsiveness or resistance to a therapeutic agent.

There are a number of suitable methods for measuring expression profiles of test samples depending on the type of biomarker to be assayed. Measuring mRNA in a biological sample may be used as a surrogate for detection of the level of the corresponding protein in the biological sample. Thus, any of the biomarkers or biomarker panels described herein can also be detected by detecting the appropriate RNA. Methods of gene expression profiling include, but are not limited to, microarray, RT-PCT, qPCR, NGS, northern blots, SAGE, mass spectrometry.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample. See Gene Expression Profiling: Methods and Protocols, Richard A. Shimkets, editor, Humana Press, 2004.

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve widespread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Gene expression may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for predicting responsiveness of a cancer therapeutic agent, where the methods comprise detecting, in a biological sample from an individual, at least N biomarker values that each correspond to a biomarker selected from the group consisting of the biomarkers provided in Tables 1A, 1B, 2A, 2B or Groups I and II, wherein a classification, as described in detail below, using the biomarker values indicates whether the individual will be responsive to a therapeutic agent. While certain of the described predictive biomarkers are useful alone for predicting responsiveness to a therapeutic agent, methods are also described herein for the grouping of multiple subsets of the biomarkers that are each useful as a panel of two or more biomarkers. Thus, various embodiments of the instant application provide combinations comprising N biomarkers, wherein N is at least three biomarkers. It will be appreciated that N can be selected to be any number from any of the above-described ranges, as well as similar, but higher order, ranges. In accordance with any of the methods described herein, biomarker values can be detected and classified individually or they can be detected and classified collectively, as for example in a multiplex assay format.

b) Microarray Methods

In one embodiment, the present invention makes use of "oligonucleotide arrays" (also called herein "microarrays"). Microarrays can be employed for analyzing the expression of biomarkers in a cell, and especially for measuring the expression of biomarkers of cancer tissues.

In one embodiment, biomarker arrays are produced by hybridizing detectably labeled polynucleotides representing the mRNA transcripts present in a cell (e.g., fluorescently-labeled cDNA synthesized from total cell mRNA or labeled cRNA) to a microarray. A microarray is a surface with an ordered array of binding (e.g., hybridization) sites for products of many of the genes in the genome of a cell or organism, preferably most or almost all of the genes. Microarrays can be made in a number of ways known in the art. However produced, microarrays share certain characteristics. The arrays are reproducible, allowing multiple copies of a given array to be produced and easily compared with each other. Preferably the microarrays are small, usually smaller than 5 $cm^2$, and they are made from materials that are stable under binding (e.g., nucleic acid hybridization) conditions. A given binding site or unique set of binding sites in the microarray will specifically bind the product of a single gene in the cell. In a specific embodiment, positionally addressable arrays containing affixed nucleic acids of known sequence at each location are used.

It will be appreciated that when cDNA complementary to the RNA of a cell is made and hybridized to a microarray under suitable hybridization conditions, the level of hybridization to the site in the array corresponding to any particular gene will reflect the prevalence in the cell of mRNA transcribed from that gene/biomarker. For example, when detectably labeled (e.g., with a fluorophore) cDNA or cRNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal. Nucleic acid hybridization and wash conditions are chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can be demonstrated that specific hybridization conditions result in specific hybridization by carrying out a hybridization assay including negative controls using routine experimentation.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65 C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B. V. (1993) and Kricka, "Nonisotopic DNA Probe Techniques", Academic Press, San Diego, Calif. (1992).

c) Immunoassay Methods

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Kits

Reagents, tools, and/or instructions for performing the methods described herein can be provided in a kit. For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for performing a gene or gene product expression analysis, such as reagents for performing RT-PCR, qPCR, northern blot, proteomic analysis, or immunohistochemistry to determine expression levels of gene or gene product markers in a sample of a patient. For example, primers for performing RT-PCR, probes for performing northern blot analyses, and/or antibodies for performing proteomic analysis such as Western blot, immunohistochemistry and ELISA analyses can be included in such kits. Appropriate buffers for the assays can also be included. Detection reagents required for any of these assays can also be included. The appropriate reagents and methods are described in further detail below.

The kits featured herein can also include an instruction sheet describing how to perform the assays for measuring gene or gene product expression. The instruction sheet can also include instructions for how to determine a reference cohort, including how to determine expression levels of gene or gene product markers in the reference cohort and how to assemble the expression data to establish a reference for comparison to a test patient. The instruction sheet can also include instructions for assaying gene or gene product expression in a test patient and for comparing the expression level with the expression in the reference cohort to subsequently determine the appropriate chemotherapy for the test patient. Methods for determining the appropriate chemotherapy are described above and can be described in detail in the instruction sheet.

Informational material included in the kits can be descriptive, instructional, marketing or other material that relates to the methods described herein and/or the use of the reagents for the methods described herein. For example, the informational material of the kit can contain contact information, e.g., a physical address, email address, website, or telephone number, where a user of the kit can obtain substantive information about performing a gene expression analysis and interpreting the results, particularly as they apply to a human's likelihood of having a positive response to a specific therapeutic agent.

The kits featured herein can also contain software necessary to infer a patient's likelihood of having a positive response to a specific therapeutic agent from the gene product marker expression.

Therapeutic Agents

As described above, the methods described herein permit the classification of a patient as responsive or non-responsive to a therapeutic agent that targets angiogenic processes and signaling within tumors. Some current such therapeutics used to treat cancer include, but are not limited to, the following agent: VEGF pathway-targeted therapeutic agent, including multi-targeted pathway inhibitors (VEGF/PDGF/FGF/EGFT/FLT-3/c-KIT), Angiopoietin-TIE2 pathway inhibitors, endogenous angiogenic inhibitors, immunomodulatory Agents. VEGF specific inhibitors include, but are not limited to, Bevacizumab (Avastin), Afibercept (VEGF Trap), IMC-1121B (Ramucirumab). Multi-targeted pathway inhibitors include, but are not limited to, Imatinib (Gleevec), Sorafenib (Nexavar), Gefitinib (Iressa), Sunitinib (Sutent), Erlotinib, Tivozinib, Cediranib (Recentin), Pazopanib (Votrient), BIBF 1120 (Vargatef), Dovitinib, Semaxanib (Sugen), Axitinib (AG013736), Vandetanib (Zactima), Nilotinib (Tasigna), Dasatinib (Sprycel), Vatalanib, Motesanib, ABT-869, TKI-258. Angiopoietin-TIE2 pathway inhibitors include, but are not limited to, AMG-386, PF-4856884 CVX-060, CEP-11981, CE-245677, MEDI-3617, CVX-241, Trastuzumab (Herceptin). Endogenous angiogenic inhibitors include, but are not limited to, Thombospondin, Endostatin, Tumstatin, Canstatin, Arrestin, Angiostatin, Vasostatin, Interferon alpha. Immunomodulatory Agents include, but are not limited to, Thalidomide and Lenalidomide.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or scope of the appended claims.

EXAMPLES

Example 1: Tissue Processing, Hierarchical Clustering, Subtype Identification and Classifier Development Tumor Material.

Exemplary expression signatures were identified from gene expression analysis of a cohort of macrodissected epithelial serous ovarian tumor FFPE tissue samples sourced from the NHS Lothian and University of Edinburgh.

The protocol for histological classification of epithelial ovarian cancer to define serous, endometrioid, clear cell and mucinous histologies has recently been updated. One of the consequences of this is that many tumors that would previously been classified as endometrioid are now being classified as serous. (McCluggage, W. G. "Morphological subtypes of ovarian carcinoma: a review with emphasis on new developments and pathogenesis," PATHOLOGY 2011 August; 43(5):420-32). Serous samples that were used in this study were among a larger set of epithelial ovarian cancer samples of all histologies that were harvested between 1984 and 2006. Pathology to assign histology status was performed by the pathologists at each of the centers at the time of harvesting. During March and April 2012, 357 of these epithelial ovarian samples were reviewed for histology classification by two independent consultant ovarian cancer pathologists according to the revised protocol. This resulted in a reclassification of several of these samples as indicated Table 3.

TABLE 3 results of pathology review of 357 epithelial ovarian cancer samples.
(Original histological status is presented in rows, and updated
histological status is presented in columns)

| | Updated | | | | |
|---|---|---|---|---|---|
| Original | CLEAR CELL | ENDO-METRIOID | MUCIN-OUS | SE-ROUS | TO-TAL |
| CLEAR CELL | 19 | 1 | 0 | 5 | 25 |
| ENDOMETRIOID | 2 | 33 | 0 | 38 | 73 |
| MUCINOUS | 0 | 1 | 8 | 1 | 10 |
| OTHER MIXED | 3 | 5 | 0 | 8 | 16 |
| SEROUS | 1 | 3 | 1 | 193 | 198 |
| SEROUS/ENDO | 0 | 2 | 0 | 25 | 27 |
| UNCLASSIFIED | 0 | 0 | 0 | 4 | 4 |
| UNDIFFER-ENTIATED | 1 | 0 | 0 | 3 | 4 |
| TOTAL | 26 | 45 | 9 | 277 | 357 |

The original three serous subtypes identified below, and consequently a 25 gene signature described in the example below (FIG. 1) were identified from 199 samples that were classified as serous according to the original pathologist reports. Bioinformatic analysis was similarly performed on the 277 samples classified as stage III and IV high grade serous ovarian cancer using the updated pathology classification method. This analysis identified the updated serous subgroups detailed in FIG. 2 and consequently used to define a 45 gene signature.

Gene Expression Profiling from FFPE

Total RNA was extracted from macrodissected FFPE tissue using the High Pure RNA Paraffin Kit (Roche Diagnostics GmbH, Mannheim, Germany). RNA was converted into complementary deoxyribonucleic acid (cDNA), which was subsequently amplified and converted into single-stranded form using the SPIA® technology of the WT-Ovation™ FFPE RNA Amplification System V2 (NuGEN Technologies Inc., San Carlos, Calif., USA). The amplified single-stranded cDNA was then fragmented and biotin labeled using the FL-Ovation™ cDNA Biotin Module V2 (NuGEN Technologies Inc.). The fragmented and labeled cDNA was then hybridized to the Almac Ovarian Cancer DSA™. Almac's Ovarian Cancer DSA™ research tool has been optimised for analysis of FFPE tissue samples, enabling the use of valuable archived tissue banks. The Almac Ovarian Cancer DSA™ research tool is an innovative microarray platform that represents the transcriptome in both normal and cancerous ovarian tissues. Consequently, the Ovarian Cancer DSA™ provides a comprehensive representation of the transcriptome within the ovarian disease and tissue setting, not available using generic microarray platforms. Arrays were scanned using the Affymentrix Genechip® Scanner 7G (Affymetrix Inc., Santa Clara, Calif.).

Data Preparation

Quality Control (QC) of profiled samples was carried out using MASS pre-processing algorithm. Different technical aspects were addressed: average noise and background homogeneity, percentage of present call (array quality), signal quality, RNA quality and hybridization quality. Distributions and Median Absolute Deviation of corresponding parameters were analyzed and used to identify possible outliers.

Almac's Ovarian Cancer DSA™ contains probes that primarily target the area within 300 nucleotides from the 3' end. Therefore standard Affymetrix RNA quality measures were adapted—for housekeeping genes intensities of 3' end probesets with ratios of 3' end probeset intensity to the average background intensity were used in addition to usual 3'/5' ratios. Hybridization controls were checked to ensure that their intensities and present calls conform to the requirements specified by Affymetrix.

Pre-processing of the raw data generated from expression profiling of the epithelial serous ovarian cancer training set was performed in Expression Console v1.1 with Robust Multi-array Analysis (RMA).

Hierarchical Clustering and Functional Analysis a. Hierarchical Clustering Analysis Hierarchical clustering techniques were applied to microarray data from the epithelial serous ovarian tumors analysed using the Ovarian Cancer DSA™ (disease specific array) platform. Raw expression data was preprocessed using the standard Robust Multichip Algorithm (RMA) procedure. Non-biological systematic variance in the data set was identified and removed. Those probe sets whose expression levels varied significantly from tumor to tumor were identified. These probe sets formed the intrinsic list.

Two dimensional cluster analysis (tumor, probeset) was performed to establish tumor relationships based on the intrinsic list. Hierarchical agglomerative clustering was applied (Pearson correlation-Original analysis—or Euclidean distance-updated analysis—and Ward's linkage). Optimal partition number was selected using the GAP index (Tibshirani et al., 2002, J. R. Stat. Soc., 63:411-423). All probesets available in the cluster subgroups were mapped to genes names.

b. Functional Analysis of Gene Clusters

To establish the functional significance of the probeset clusters, probesets were mapped to genes (Entrez gene ID) and an enrichment analysis was performed. Enrichment significance was calculated based on the hypergeometric function (False Discovery Rate applied (Benjamini and Hochberg, 1995, J. R. Stat. Soc. 57:289:300)). Over-representation of biological processes and pathways were analysed for each gene group generated by the hierarchical clustering for the epithelial serous ovarian cancer samples using Almac Diagnostics' proprietary Functional Enrichment Tool (FET). Antisense probesets were excluded from the analysis. Hypergeometric p-values were assessed for each enriched functional entity class. Functional entity classes with the highest p-values were selected as representative of the group and a general functional category representing these functional entities was assigned to the gene clusters based on significance of representation (i.e. p-value).

To generate an angiogenesis classifier using the original 199 epithelial serous ovarian tumors, genes in clusters enriched for angiogenesis, vasculature development and immune response general functional terms were grouped into a putative angiogenesis gene group and used for the signature generation. The sample clusters presenting high expression for the genes involved in angiogenesis, vasculature development and immune response general functional terms were selected for classification and labeled as 'angiogenesis'. Those not showing high expression for the genes involved in these functional terms were labeled as 'non-angiogenesis'.

To generate an angiogenesis classifier using the reclassified 265 epithelial serous ovarian tumors, genes in clusters enriched for angiogenesis and vasculature development general functional terms were grouped into a putative angiogenesis gene group and used for the signature generation. The sample clusters presenting high expression for the genes involved in angiogenesis and vasculature development general functional terms were selected for classification and labeled as 'angiogenesis'. Those not showing high expression for the genes involved in these functional terms were labeled as 'non-angiogenesis'.

Classifier Development at a Gene Level

To facilitate validation of the classifier across multiple array platforms, the angiogenesis classifier was generated at the gene level. The following steps outline the procedures that were taken for gene level signature development (each step performed over internal cross validation using 10 repeats of 5-fold cross-validation):

Gene Level Signature Development

Pre-processing:
  RMA background correction.
  Reference set of genes are those genes (sense probesets only) unique to the ovarian DSA platform.
  Gene level summarization was performed in two steps; first probes to probeset summarization was performed by calculating the median expression of the probes in a probeset; secondly, median expression of the (sense only) probesets mapping to each gene in the reference distribution is calculated, yielding a "gene level" expression matrix.
  Quantile normalization was performed on the full gene expression data matrix and a reference quantile derived from the training data was used to normalize the test samples within each round of cross validation.

Feature selection: Filtering 75% of genes by variance, intensity and correlation to cDNA concentration, followed by either recursive feature elimination (RFE) or filter feature selection (FFS) based on CAT scores.

Classification algorithms: Partial Least Squares (PLS), SDA (Shrinkage Discriminate Analysis) and DSDA (Diagonal SDA).

Model Selection

The criteria used for model selection were AUC over internal cross-validation and feature elimination. Functional enrichment of the signatures over cross validation using FET based on the gene ontologies, interim validation sets which included two sets of technical replicates for which standard deviation in signature scores for repeated samples was evaluated over cross-validation and feature elimination and an assessment of the independence to clinical and technical factors over cross validation (factors listed in Table 4).

It should be noted, since the subgroup (i.e. class label) derivation was performed using microarray expression from the same sample cohort that was used for signature development, there was an expected positive bias in any performance estimates based on AUC. This highlights the importance of widening the criteria used for model selection, by including additional metrics such as functional enrichment and assessing the independence to clinical and technical factors.

TABLE 4

List of clinical and technical factors investigated

| Clinical factors: | Technical factors: | Sample processing factors: |
|---|---|---|
| Debulking | Hospital<br>Block age<br>RNA concentration<br>cDNA yield | Post Amp operator |

Calculating Classifier Scores for Validation Data Sets

All datasets were pre-processed using RMA. For each validation set, the probesets that map to the classifier genes were determined, excluding anti-sense probesets (if applicable). Annotation for Affymetrix Plus 2.0 and U133A arrays are available from the Affymetrix website. The median intensity over all probesets mapping to each gene in the classifier was calculated, resulting in a gene intensity matrix. The classifier was then applied to this data matrix to produce a classifier score/prediction for each sample.

Univariate and Multivariate Analysis

Univariate and multivariate analysis may be carried out in relation to the glioblastoma dataset to assess respectively the association between the angiogenesis subtype classifier and survival, and to determine if the association, if any, was independent to known clinical predictors. The p-values for univariate analysis were calculated using logistic regression in MATLAB. For the multivariate analysis we used a likelihood ratio test from logistic regression was used, where the p-values represent the drop in the log-likelihood when comparing the model with the clinical covariates and the predictions to a reduced model with clinical covariates only. The likelihood ratio test measures the importance of the gene predictor in modeling survival, and highlights its independence as a predictor relative to the clinical predictors. In both univariate and multivariate analysis, a p-value<0.05 was used as the criterion for significance. Furthermore, samples with unknown clinical factors were excluded in this assessment.

Results

Identification of Subroups and Generation of Signature from Original and Updated Histology Classification Hierarchical Clustering Analysis Feature selection resulted in the selection of 1200 probesets from the original epithelial serous ovarian cancer data set (199 samples) and 1400 PS from the reclassified epithelial serous ovarian cancer data set (265 samples). The GAP analysis revealed three sample clusters and three probeset cluster groups within both sample sets (FIG. 1, FIG. 6).

Figure 2A:
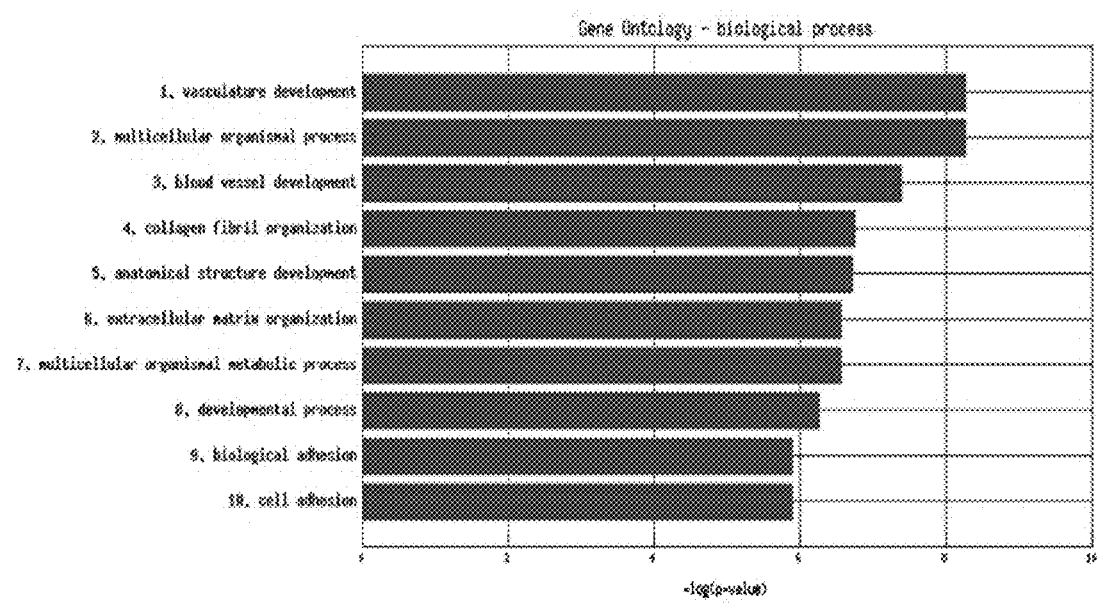
FIG. 2A and FIG. 2B represent the functional analysis results of the angiogenesis probe set cluster in the 199 serous only samples in an epithelial ovarian cancer training set using a functional enrichment analysis.
Figure 2B:
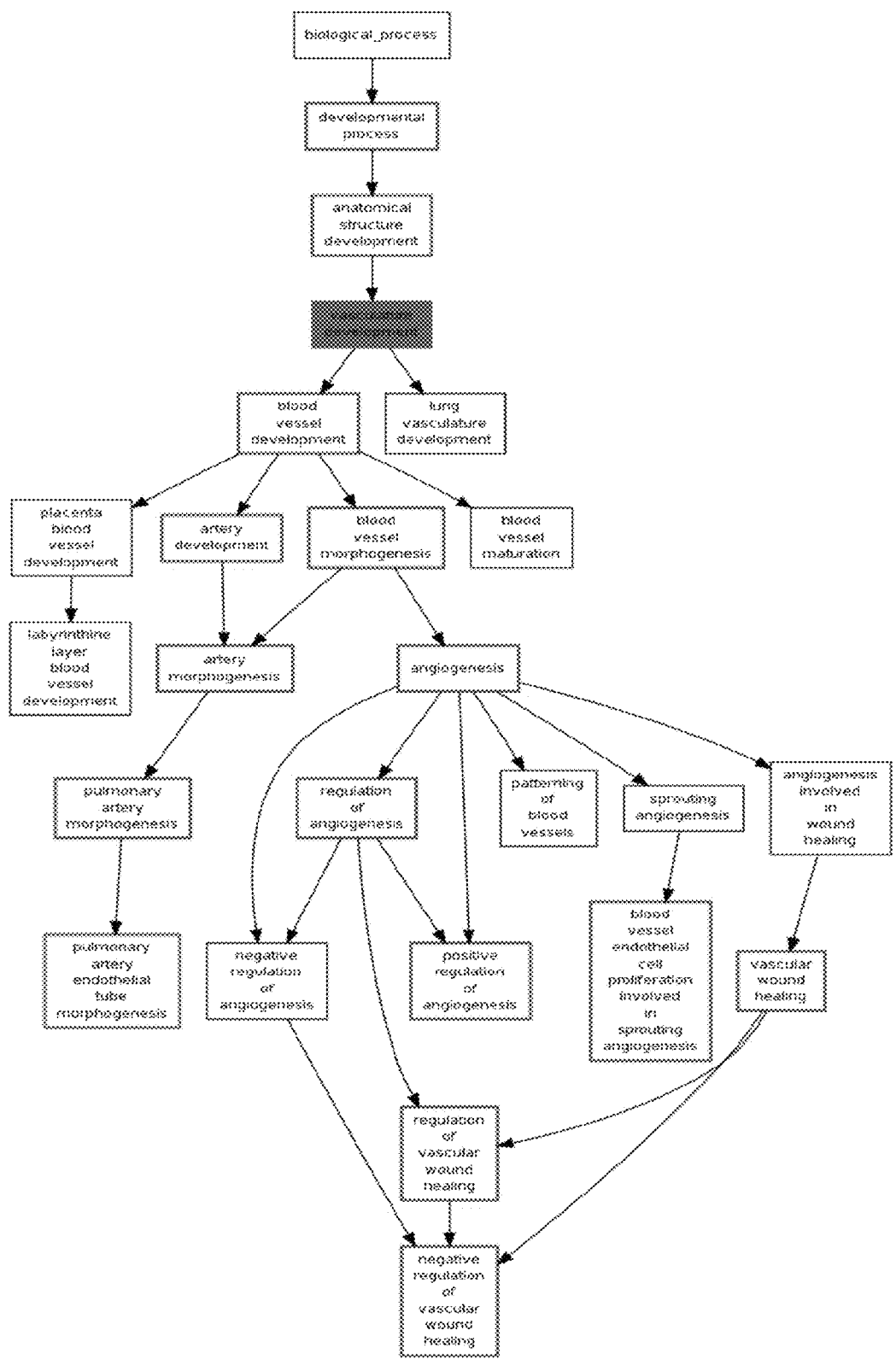

Classification of Tumors into 'Angiogenesis' or 'Non-Angiogenesis' Sample Groups The classification of samples as 'angiogenesis' or 'non-angiogenesis' was based upon the results of the functional analysis of the epithelial serous ovarian cancer dataset (FIG. 1 FIG. 6). The objective of this study was to characterize at a transcriptomic level a set of genes that would be capable of determining responsiveness or resistance of a pathogenic cell to anti-angiogenic agents and potentially identify patients who could benefit from anti-angiogenic therapy. With this in mind, those samples within the epithelial serous ovarian cancer datasets that best represented this biology were to be selected and compared to the remaining samples for classifier generation (see next section). It was decided that the samples from the sample angiogenesis cluster within the original epithelial serous ovarian cancer sample set (199 samples) were the most relevant samples for this selection as these samples demonstrated an up-regulation of genes involved in signaling related to angiogenic and immune response processes and pathways as defined by functional analysis (FIG. 2A and FIG. 2B) It was decided that the samples from sample cluster three within the reclassified epithelial serous ovarian cancer sample set (265 samples) were the most relevant samples for this selection as these samples demonstrated an up-regulation of genes involved in signaling related to angiogenic processes and pathways as defined by functional analysis (FIG. 2A and FIG. 2B)

Figure 12A:
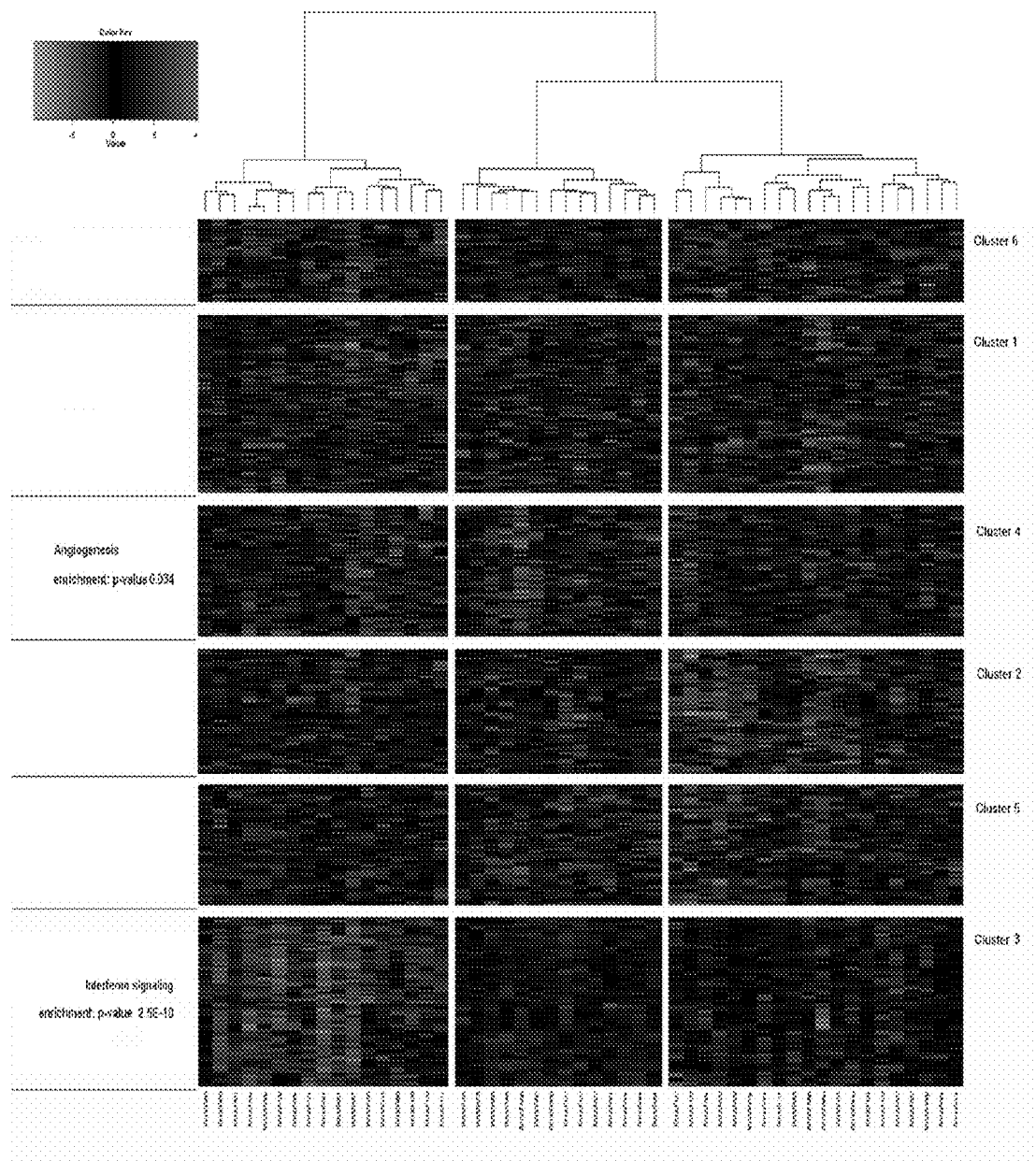
FIG. 12A and FIG. 12B provide heatmaps representing the hierarchical agglomerative clustering analysis of the most variable genes across 51 ER negative samples (FIG. 12A) of a breast cancer sample set and the most variable genes across 56 ER positive samples of a breast cancer sample set (FIG. 12B). The functional analysis of the probe set clusters is summarized on the right hand side of the image for those cluster showing vasculature development/angiogenesis or immune response/IFN signalling.
Figure 12B:
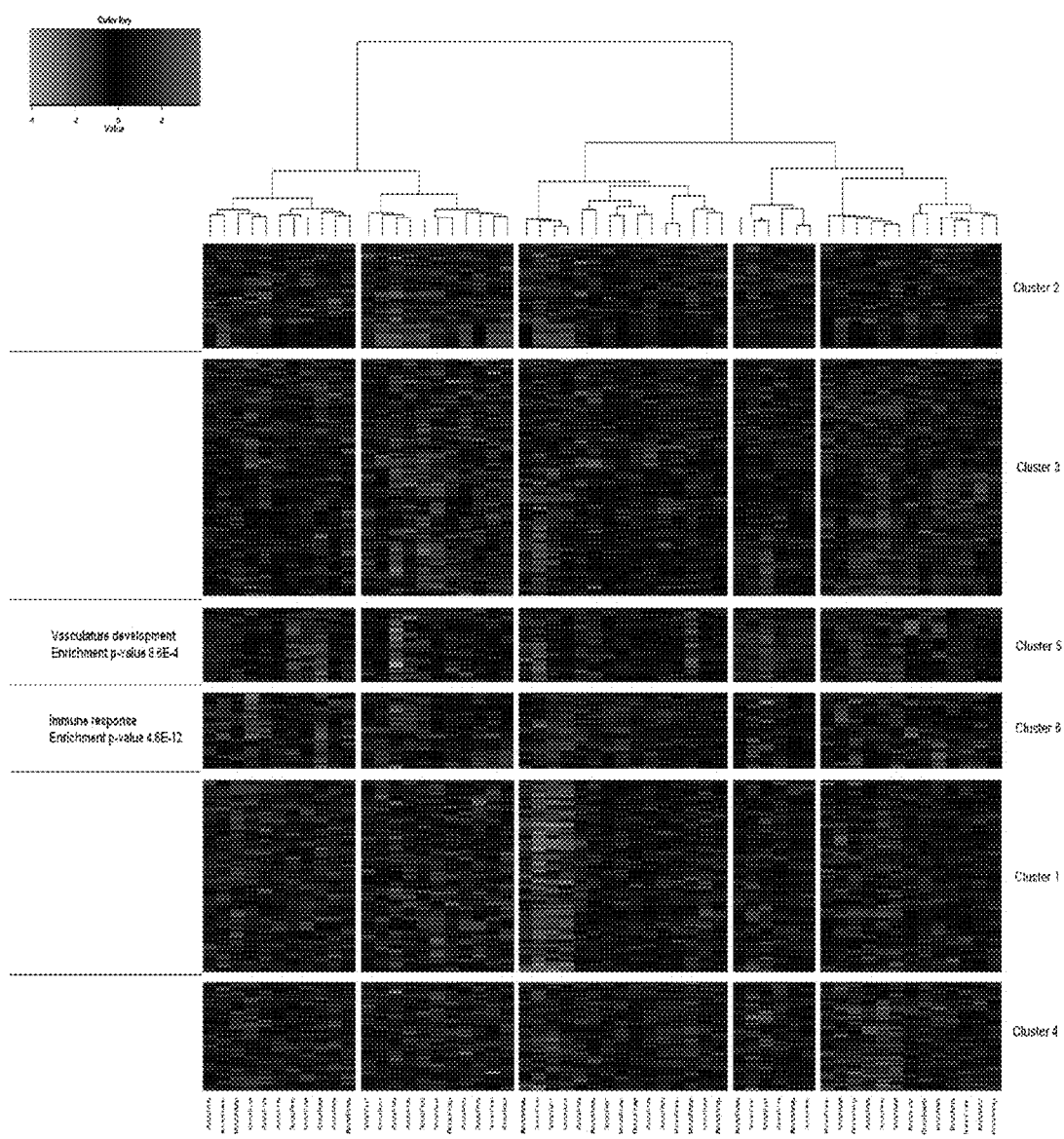

An identical hierarchical clustering approach was applied to 105 breast cancer samples. The dominant biology in Breast cancer is ER status and therefore in order to identify the structure in the biology of the samples this cohort was divided into 2 populations for cluster analysis. We identified angiogenesis and vasculature development subtypes (FIG. 12A and FIG. 12B) demonstrating the expositing of an angiogenesis subtype from breast cancer samples.

Development and Validation of the Angiogenesis Subtype Classifier Models

For ease of reference, the following steps are detailed in reference to expression signatures derived from Table 1A or Table 1B. However, a similar procedure can be applied to other putative clusters of angiogenesis sub-type related biomarkers such as those disclosed in SEQ ID NOs: 632-801 and SEQ ID NOs: 802-974). Following the identification of a class of tumors, that form the putative 'angiogenesis' subgroup, computational classification of these tumors versus all others in the tumor cohort with reference to the functional 'angiogenesis' (angiogenesis, vasculature development, immune response) gene list (Table 1A or Table 1B) was performed to identify a refined gene classification model, which classifies the 'angiogenesis' subtype.

The classification pipeline was used to derive a model using the set of epithelial serous ovarian cancer samples. The classification pipeline has been developed in accordance with commonly accepted good practice (MAQC Consortium, *Nat Biotechnol* 2010). The process will, in parallel: 1) derive gene classification models from empirical data; and 2) assess the classification performance of the models, both under cross-validation. The performance and success of the classifier generation depends on a number of parameters that can be varied, for instance the choice of classification method or probe set filtering. Taking this into account, two feature sets were evaluated (i) the full feature list with 75% variance/intensity filtering (with forced inclusion of the angiogenesis gene list, Table 1A) and (ii) the angiogenesis gene list only; and three classification algorithms were evaluated, namely PLS; SDA and DSDA. RFE was used throughout model development, which is an iterative procedure removing a fraction of the lowest-ranked features at each iteration; stopping when only a minimum number of features remain. The AUC was used to assess the classification performance, as this measure is independent of cut-off between groups and prevalence rates in the data. It is also one of the recognized measurements of choice for classification performance. As such, the best number of features for each model was chosen based on the average AUC under cross-validation.

Figure 3:
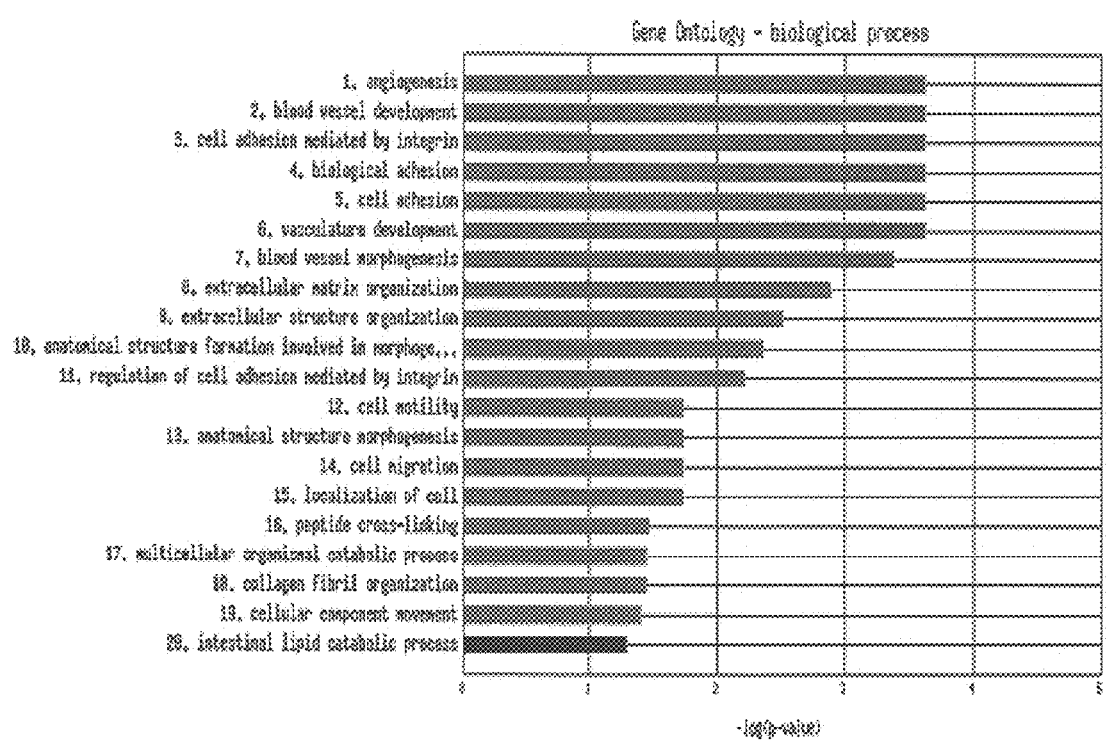
FIG. 3 represents the functional enrichment results of the genes within an exemplary 25-gene expression signature that identifies the molecular subtype related to angiogenesis. Red bars indicate significance of a process at a p-value of 0.05 after False Discovery Rate correction.
Figure 4:
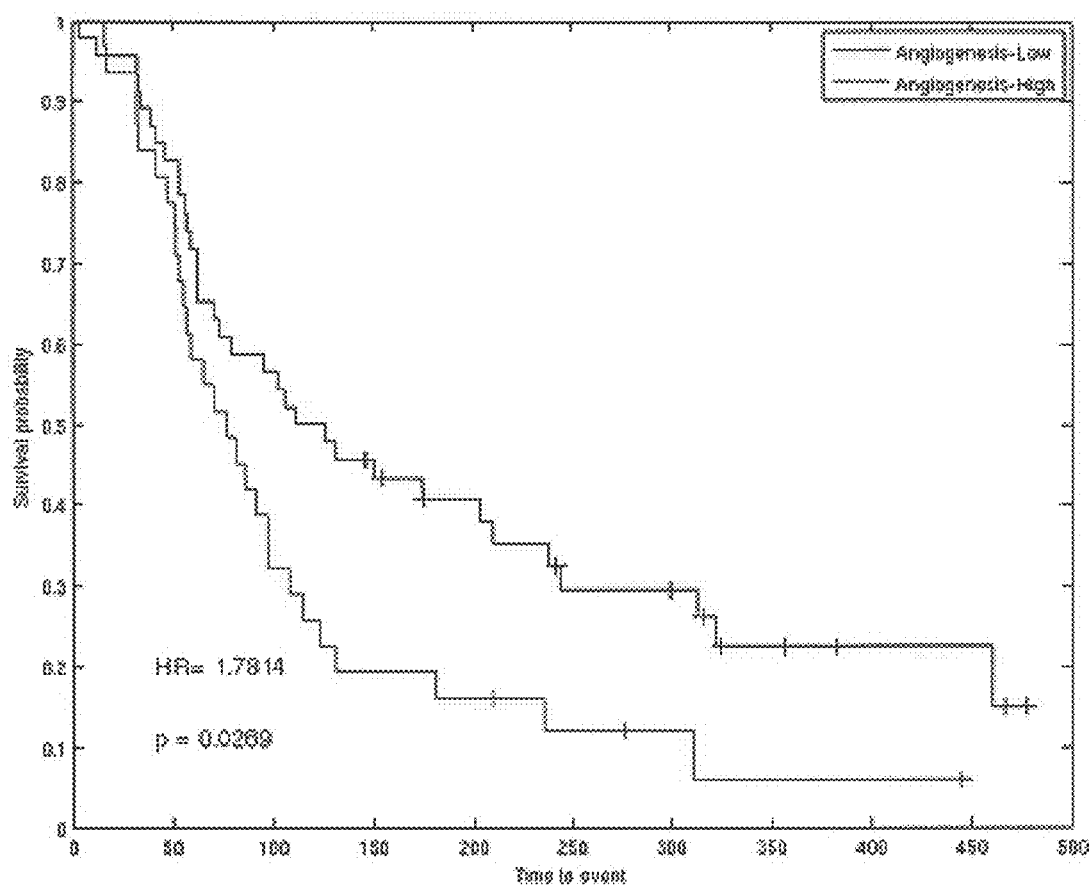
FIG. 4 provides Kaplan-Meier curves for recurrence-free survival (time-to-event in weeks) following initial surgical resection from patients with high-grade glioblastoma without prior treatment (Phillips H S, Kharbanda S, Chen R, Forrest W F et al. "Molecular subclasses of high-grade glioma predict prognosis, delineate a pattern of disease progression, and resemble stages in neurogenesis," CANCER CELL 2006 March; 9(3):157-73. PMID: 16530701; Costa B M, Smith J S, Chen Y, Chen J et al. "Reversing HOXA9 oncogene activation by PI3K inhibition: epigenetic mechanism and prognostic significance in human glioblastoma," CANCER RES 2010 Jan. 15; 70(2):453-62. PMID: 20068170).
Figure 5:
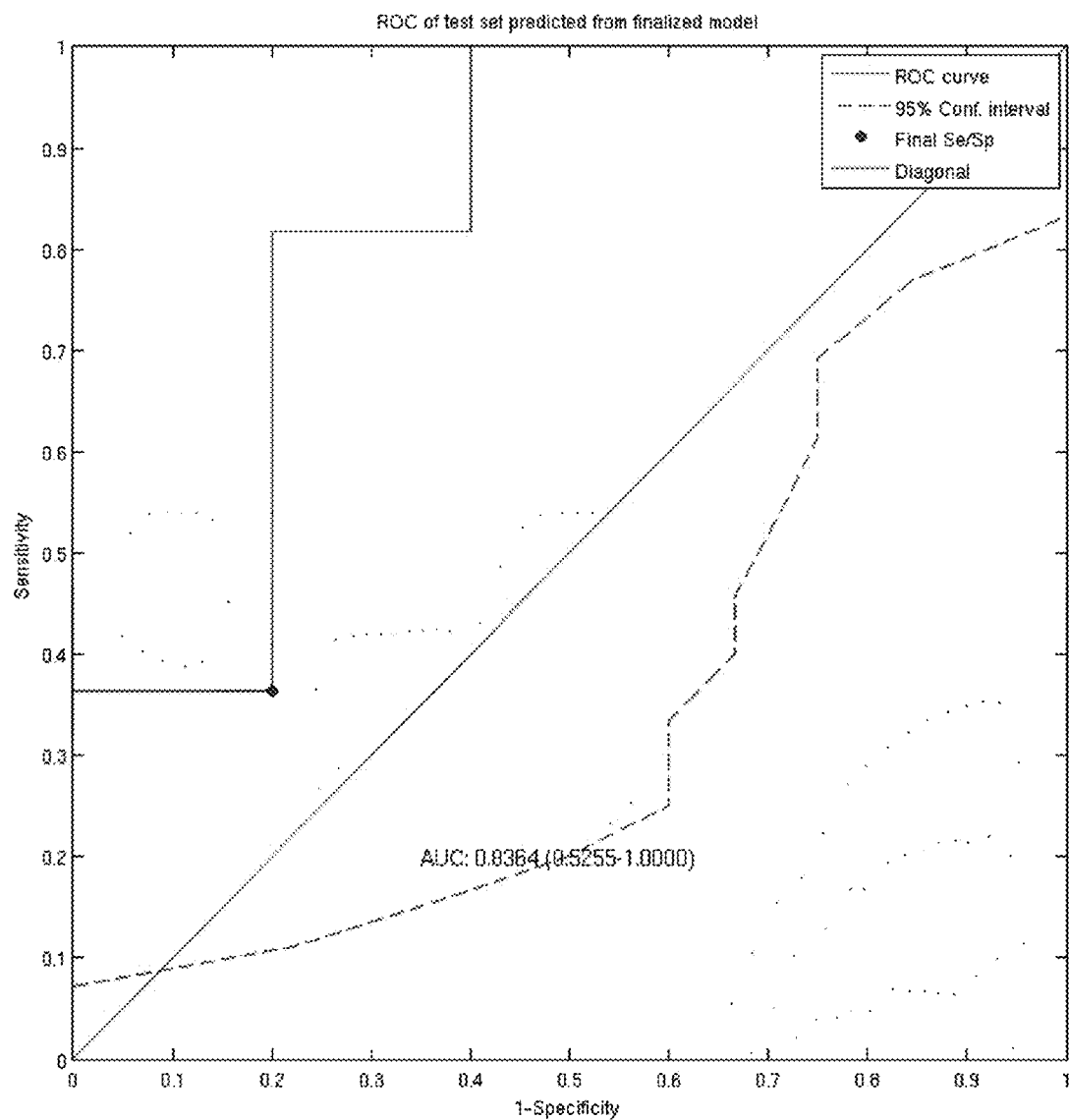
FIG. 5 provides a diagram of a ROC curve of the classification performance of an exemplary 25-gene classifier model within 16 prostate cell-lines following treatment with Dasatanib. The AUC is approximately 0.84 following application of the classifier model. The 95% confidence limits were determined using 1000 bootstrap iterations (Wang X D, Reeves K, Luo F R, Xu L A et al. "Identification of candidate predictive and surrogate molecular markers for dasatinib in prostate cancer: rationale for patient selection and efficacy monitoring," GENOME BIOL 2007; 8(11):R255. PMID: 18047674).
Figure 8:
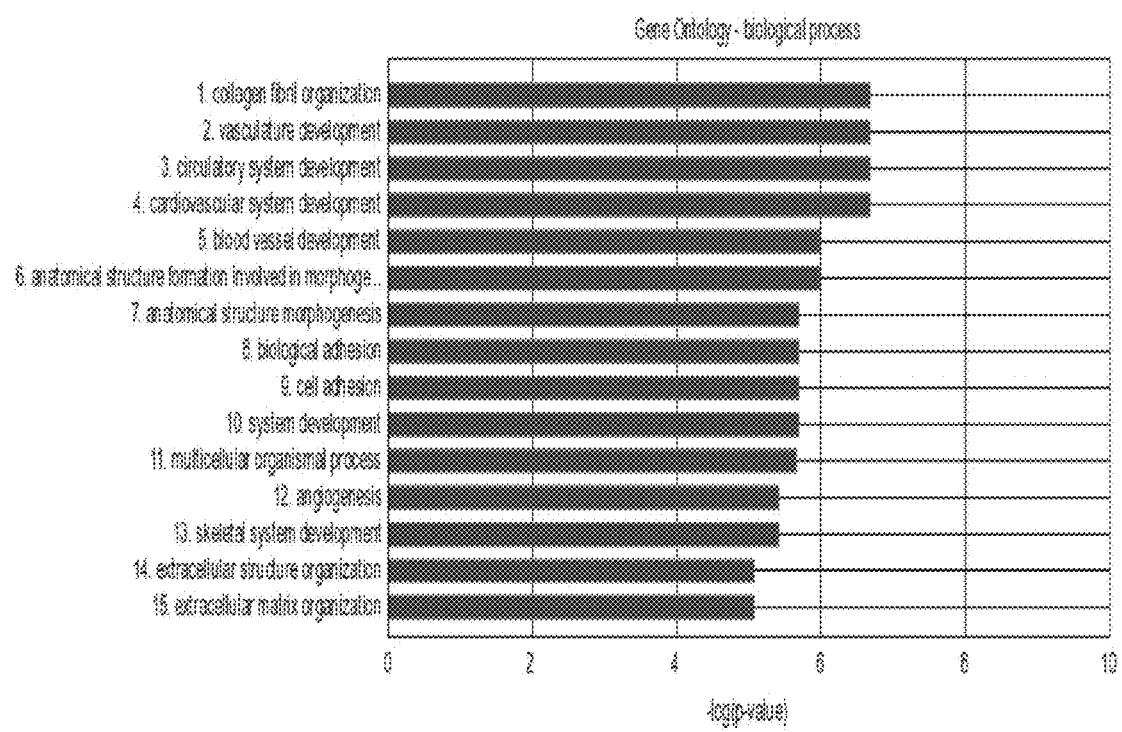
FIG. 8 represents the functional enrichment results of the genes within an exemplary 45-gene classifier model that identifies the molecular sub-type related to angiogenesis. Red bars indicate significance of a process at a p-value of 0.05 after False Discovery Rate correction.
Figure 9:
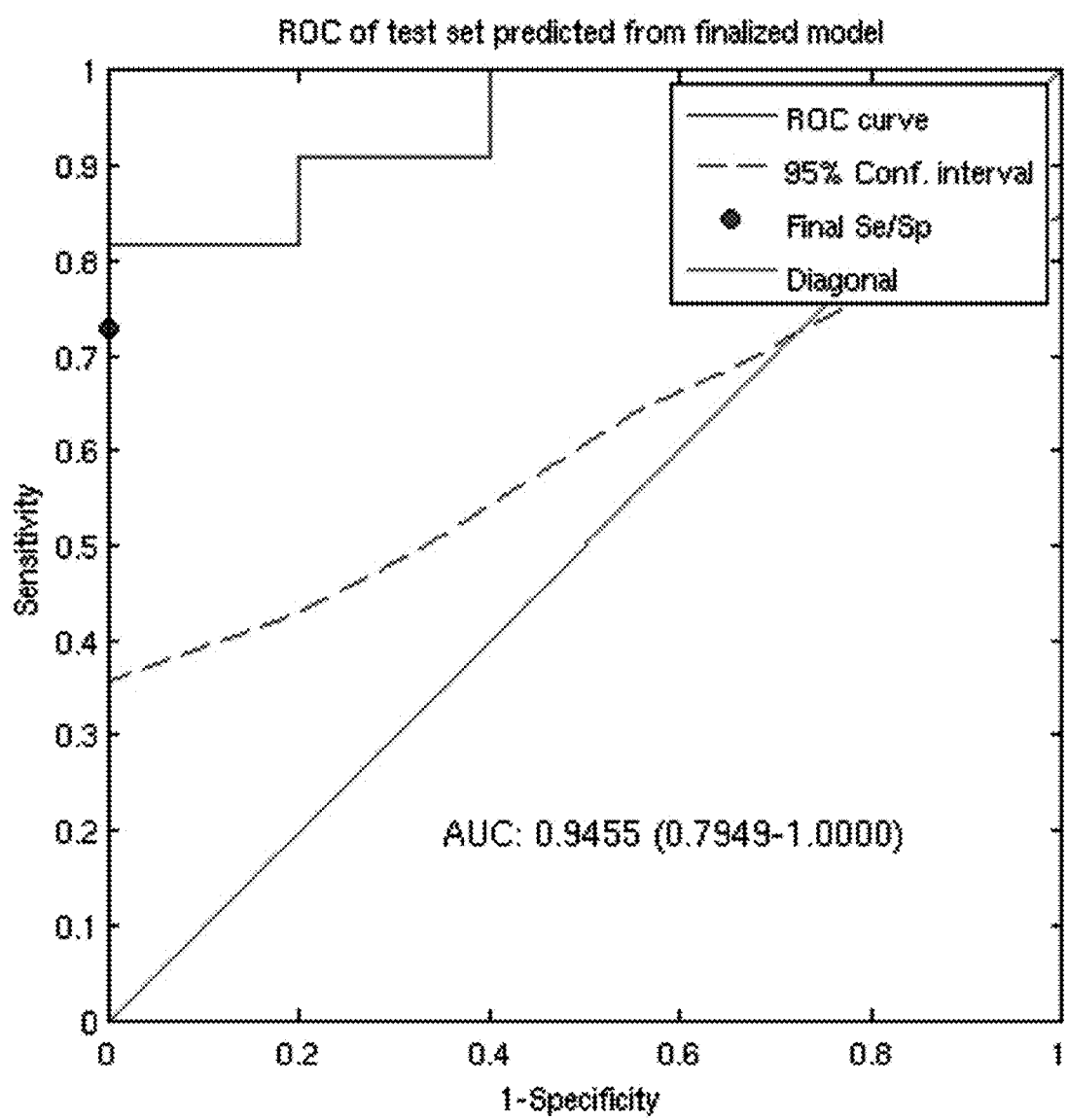
FIG. 9 provides a diagram of a ROC curve of the classification performance of the 45-gene classifier model within 16 prostate cell-lines following treatment with Dasatanib. The AUC is ~0.95 following application of the classifier model. The 95% confidence limits were determined using 1000 bootstrap iterations.

From the analysis described above, the PLS FFS model was deemed to be the most suitable classifier model. Weights were calculated for each gene using PLS regression, resulting in the final gene classifier models (25-gene classifier model for the original approach, and a 45-gene classifier for samples reclassified reflecting recent changes to standard histology protocols) that may be used for validation on external data sets from different array platforms. The gene signature development process was focused upon identification of the ontological processes and pathways relevant to angiogenesis to ensure biological relevance of any signature developed. As such, functional analysis was performed upon both signatures to qualify their relevance to angiogenesis and related processes. The significance processes in FIG. 3 and FIG. 8 are related to angiogenesis and vasculature development.

Example 2: In Silico Validation of the Angiogenesis Subtype and Angiogenesis Classifier Models The performance of both the 25-gene (original approach) and 45-gene (reclassification approach) angiogenesis classifier models were validated by the Area Under the ROC (Receiver Operator Characteristic) Curve (AUC) within the original Almac epithelial serous ovarian cancer dataset and two independent datasets. The AUC is a statistic calculated on the observed disease scale and is a measure of the efficacy of prediction of a phenotype using a classifier model (Wray et. al., PLoS Genetics Vol 6, 1-9). An AUC of 0.5 is typical of a random classifier, and an AUC of 1.0 would represent perfect separation of classes. Therefore, in order to determine if the angiogenesis subtype classifier model is capable of predicting response to, and selecting patients for anti-angiogenic ovarian cancer therapeutic drug classes either as single agent or in combination with standard of care therapies, the hypothesis is that the AUCs following application within these datasets should be above 0.5 with the lowest confidence interval also above 0.5.

Application of Classifier Model to Independent Microarray Clinical Datasets

To assess the prognostic power of the 25-gene and 45-gene classifier models, they were applied to a dataset of 77 glioblastoma samples taken at the time of initial surgical resection from patients (>21 years of age) without prior therapy (Phillips et. al., 2006). This analysis revealed that the 25-gene classifier model was independently associated with prognosis in glioblastoma. Importantly, in a multivariate Cox analysis, the angiogenesis signature was found to be prognostic of survival, independent from World Health Organisation (WHO) tumor grade and/or the presence of necrosis (p=0.37). Both of these clinical factors are correlated with survival in glioblastoma. The angiogenesis-high group was associated with significantly worse survival compared to the angiogenesis-low group (Hazard Ratio=1.7814, p=0.0269). This indicates that the 25-gene classifier is an independent prognostic biomarker of survival in glioblastoma.

Application of the Classifier Models to an Independent Prostate Cancer Cell-Line Dataset To assess the predictive power of the 25-gene and 45-gene classifier models, they were applied to a dataset of 16 prostate cell-lines following treatment with Dasatanib. The cell-lines were defined as being either a 'responder' or 'non-responder' based upon cell-proliferation assays. This analysis revealed that the 25-gene classifier model is associated with response to Dasatanib, with an AUC of 0.8364 (CI=0.5255–1.0000), indicating that the 25-gene classifier is predictive of response to Dasatanib. The analysis revealed that the 45-gene classifier model is associated with response to the same compound, with an AUC of 0.9455 (CI=0.7949–1.0000) indicating that the 45-gene classifier is also predictive of response to Dasatanib.

Figure 10:
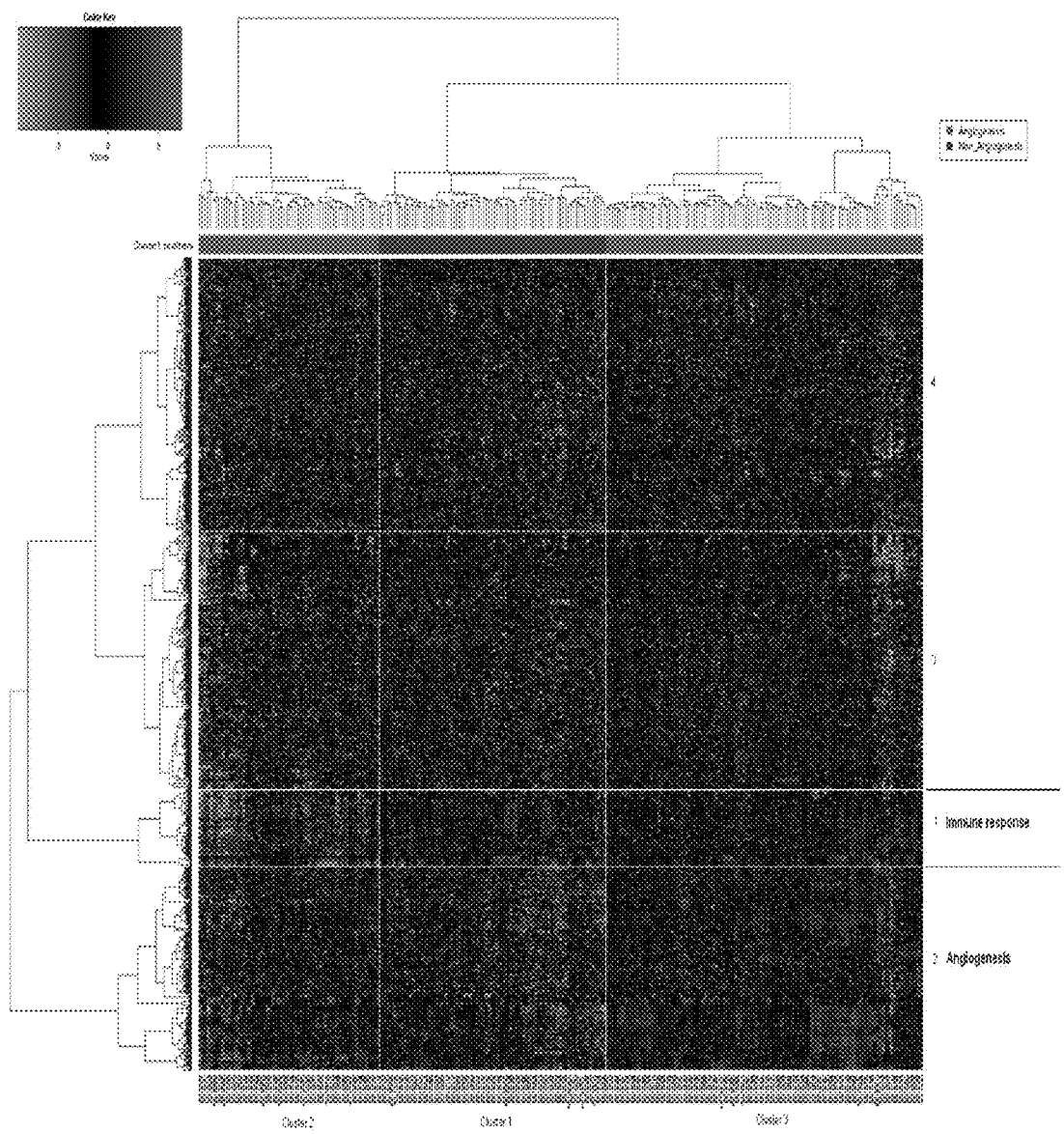
FIG. 10 provides a heatmap representing the hierarchical agglomerative clustering analysis of the most variable genes across 265 serous samples of an epithelial ovarian cancer sample set reclassified according to updated pathological classification criteria. The functional analysis of the probeset clusters is summarized on the right hand side of the image. The legend across the top of the image indicates the classifier group each sample should be assigned to for generation of a non-angiogenesis or non-responsive group classifier.
Figure 11:
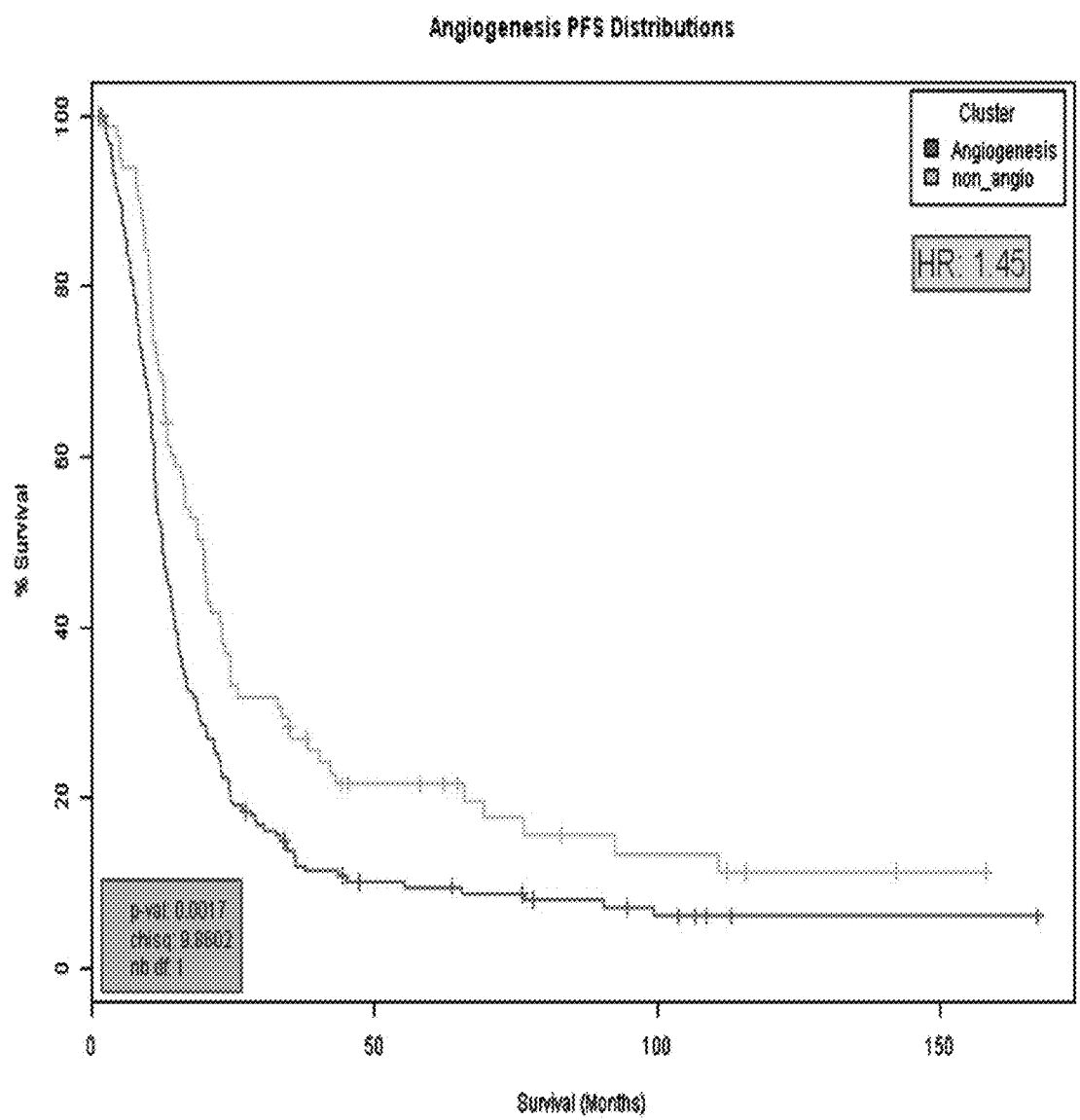
FIG. 11 provides Kaplan-Meier curves for progression-free survival (in weeks) for the non-angiogenesis sample group (FIG. 3, sample cluster 1) versus the angiogenesis sample group (FIG. 10, sample clusters 2 and 3) in the reclassified ovarian sample set.

Example 4: Identification of and in Silico Validation of an Anti-Angiogenic "Non-Responsive" Subgroup of Ovarian Cancer The expression of angiogenesis genes in probeset cluster 2 is down regulated in all samples in Cluster 2 of hierarchical clustering of 265 samples newly classified as serous (FIG. 6 and FIG. 10). These samples in sample cluster 2 have a better prognosis than the rest of the serous samples in samples from cluster 1 and 3 combined together as demonstrated in FIG. 11. This indicated that this group is defined by down regulation of expression of the angiogenesis genes identified in Table 2B. Patients with downregulation of genes involved in angiogeniesis and therefore this subgroup is termed a "non-responsive" group." This phenotype has also been identified in ER+ and ER+ breast cancer as can be see the middle sample group in FIG. 12A and the second sample group in FIG. 12B.

REFERENCES

1. Friedman H S, Prados M D, Wen P Y, et al. Bevacizumab alone and in combination with irinotecan in recurrent glioblastoma. *J Clin Oncol;* 27:4733-40 (2009).
2. Hurwitz H, Fehrenbacher L, Novotny W, et al. Bevacizumab plus irinotecan, fluorouracil, and leucovorin for metastatic colorectal cancer. *N Engl J Med;* 350:2335-42 (2004).
3. Rini B I, Halabi S, Rosenberg J E, et al. Bevacizumab plus interferon alfa compared with interferon alfa monotherapy in patients with metastatic renal cell carcinoma: CALGB 90206. *J Clin Oncol;* 26:5422-8 (2008).
4. Sandler A, Gray R, Perry M C, et al. Paclitaxel-carboplatin alone or with bevacizumab for non-small-cell lung cancer. *N Engl J Med;* 355: 2542-50 (2006).
5. Wolmark N, Yothers G, O'Connell M J, et al. A phase III trial comparing mFOLFOX6 to mFOLFOX6 plus bevacizumab in stage II or III carcinoma of the colon: results of NSABP protocol C-08. *J Clin Oncol;* 27:LBA4 (2009).
6. Yang J C, Haworth L, Sherry R M, et al., A randomized trial of bevacizumab, an anti-vascular endothelial growth factor antibody, for metastatic renal cancer, *N Engl J Med* 349 427-434 (2003).
7. Willett C G, Boucher Y, di Tomaso E, et al., Direct evidence that the VEGF-specific antibody bevacizumab has antivascular effects in human rectal cancer, *Nat. Med.* 10, 145-147 (2004).
8. Miller K, Wang M, Gralow J, et al., Paclitaxel plus bevacizumab versus paclitaxel alone for metastatic breast cancer, *N Engl J Med* 357 2666-2676 (2007).
9. Miller K D, Chap L I, Holmes F A, et al., Randomized phase III trial of capecitabine compared with bevacizumab plus capecitabine in patients with previously treated metastatic breast cancer, *J Clin Oncol* 23 792-799 (2005).
10. O'Shaughnessy J, Miles D, Gray R J, et al., A meta-analysis of overall survival data from three randomized trials of bevacizumab (BV) and first-line chemotherapy as treatment for patients with metastatic breast cancer (MBC), *J Clin Oncol* 28 (suppl) (abstr 1005) (2010).
11. Reck M, von Pawel J, Zatloukal P, et al., Phase III trial of cisplatin plus gemcitabine with either placebo or bevacizumab as first-line therapy for nonsquamous non-small-cell lung cancer: AVAil, *J Clin Oncol* 27, 1227-1234 (2009).
12. Escudier B, Bellmunt J, Negrier S et al., Phase III trial of bevacizumab plus interferon alfa-2a in patients with metastatic renal cell carcinoma (AVOREN): final analysis of overall survival, *J Clin Oncol* 28, 2144-2150 (2010)
13. Burger R A, Sill M W, Monk B J, et. al. Phase II trial of bevacizumab in persistent or recurrent epithelial ovarian cancer or primary peritoneal cancer: a Gynecologic Oncology Group Study. *J Clin Oncol;* 20; 25(33):5165-71 (2007).

We claim:

1. A method of treating a subgroup of subjects from a population of subjects having ovarian cancer, prostate cancer, glioblastoma, or breast cancer comprising: (i) providing a subject from the population of subjects known to overexpress at least one gene relative to a pre-defined cut-off threshold value which separates a particular disease into a first phenotype that indicates responsiveness to an anti-angiogenic agent and a second phenotype that indicates resistance to the anti-angiogenic agent, wherein the at least one gene is selected from the group consisting of GJB2, MMP13, GFPT2, BICC1, CDH11, MRVI1, PMP22, COL11A1, IGFL2, LUM, NTM, BGN, COL3A1, COL10A1, RAB31, ANGPTL2, PLAU, COL8A1, MIR1245, POLD2, NKD2, FZD1, COPZ2, ITGA5, VGLL3, MMP14, VCAN, THBS2, RUNX2, TIMP3, SFRP2, COL1A2, COL5A2, SERPINF1, KIF26B, TNFAIP6, MMP2, FN1, ALPK2, CTSK, LOXL1, and FAP in a tumor sample from the subject; and (ii) administering the anti-angiogenic agent to the subject in an amount sufficient to inhibit angiogenesis in the cancer.

2. The method of claim 1, wherein the method measures the level of mRNA, cRNA, cDNA, or protein of the at least one gene.

3. The method of claim 1, wherein the cancer is ovarian cancer.

4. The method of claim 3, wherein the method measures the level of mRNA, cRNA, cDNA, or protein of the one gene.

5. The method of claim 1, wherein the anti-angiogenic agent is selected from VEGF pathway-targeted therapeutic agents, angiopoietin-TIE2 pathway inhibitors, endogenous angiogenic inhibitors, and immunomodulatory agents.

6. The method of claim 5, wherein the VEGF pathway-targeted therapeutic agent(s) is chosen from bevacizumab (Avastin), aflibercept (VEGF Trap), IMC-1121B (Ramucirumab), imatinib (Gleevec), sorafenib (Nexavar), gefitinib (Iressa), sunitinib (Sutent), erlotinib, tivozinib, cediranib (Recentin), pazopanib (Votrient), BIBF 1120 (Vargatef), dovitinib, semaxanib (Sugen), axitinib (AG013736), vandetanib (Zactima), nilotinib (Tasigna), dasatinib (Sprycel), vatalanib, motesanib, ABT-869, TKI-258, and a combination thereof.

7. The method of claim 6, wherein the VEGF pathway-targeted therapeutic agent is bevacizumab.

8. The method of claim 1, wherein the cancer is prostate cancer.

9. The method of claim 1, wherein the cancer is glioblastoma.

10. The method of claim 1, wherein the cancer is breast cancer.

11. A method of treating ovarian cancer, prostate cancer, glioblastoma, or breast cancer in a patient comprising administering an anti-angiogenic agent to the patient in an amount sufficient to inhibit angiogenesis in the cancer, wherein the patient is known to overexpress at least one gene relative to a pre-defined cut-off threshold value which separates a particular disease into a first phenotype that indicates responsiveness to the anti-angiogenic agent and a second phenotype that indicates resistance to the anti-angiogenic agent, wherein the at least one gene is selected from the group consisting of GJB2, MMP13, GFPT2, BICC1, CDH11, MRVI1, PMP22, COL11A1, IGFL2, LUM, NTM, BGN, COL3A1, COL10A1, RAB31, ANGPTL2, PLAU, COL8A1, MIR1245, POLD2, NKD2, FZD1, COPZ2, ITGA5, VGLL3, MMP14, VCAN, THBS2, RUNX2, TIMP3, SFRP2, COL1A2, COL5A2, SERPINF1, KIF26B, TNFAIP6, MMP2, FN1, ALPK2, CTSK, LOXL1, and FAP in a sample of the cancer.

12. The method of claim 11, wherein the cancer is ovarian cancer.

13. The method of claim 12, wherein the method measures the level of mRNA, cRNA, cDNA, or protein of the one gene.

14. The method of claim 11, wherein the method measures the level of mRNA, cRNA, cDNA, or protein of the at least one gene.

15. The method of claim 11, wherein the anti-angiogenic agent is selected from VEGF pathway-targeted therapeutic agents, angiopoietin-TIE2 pathway inhibitors, endogenous angiogenic inhibitors, and immunomodulatory agents.

16. The method of claim 15, wherein the VEGF pathway-targeted therapeutic agent(s) is chosen from bevacizumab (Avastin), aflibercept (VEGF Trap), IMC-1121B (Ramucirumab), imatinib (Gleevec), sorafenib (Nexavar), gefitinib (Iressa), sunitinib (Sutent), erlotinib, tivozinib, cediranib (Recentin), pazopanib (Votrient), BIBF 1120 (Vargatef), dovitinib, semaxanib (Sugen), axitinib (AG013736), vandetanib (Zactima), nilotinib (Tasigna), dasatinib (Sprycel), vatalanib, motesanib, ABT-869, TKI-258, and a combination thereof.

17. The method of claim 16, wherein the VEGF pathway-targeted therapeutic agent is bevacizumab.

18. The method of claim 11, wherein the patient is a human.

19. The method of claim 11, wherein the cancer is prostate cancer.

20. The method of claim 11, wherein the cancer is glioblastoma.

21. The method of claim 11, wherein the cancer is breast cancer.

* * * * *

SEQUENCE LISTING

<160> NUMBER OF SEQ ID NOS: 974

<210> SEQ ID NO 1
<211> LENGTH: 589
<212> TYPE: DNA
<213> ORGANISM: Homo sapiens

<400> SEQUENCE: 1

```
ctggatatat caagactgag ttgatttctg tgtctgaagt tcaccttct agacttcaga      60 ccacagacaa cctgctcccc atgtctcctg aggagtttga cgaggtgtct cggatagtgg    120
gctctgtaga attcgacagt atgatgaaca cagtatagag catgaatttt tttcatcttc    180
tctggcgaca gttttccttc tcatctgtga ttccctcctg ctactctgtt ccttcacatc    240
ctgtgtttct agggaaatga agaaaggcc agcaaattcg ctgcaacctg ttgatagcaa    300
gtgaattttt ctctaactca gaaacatcag ttactctgaa gggcatcatg catcttactg    360
aaggtaaaat tgaaaggcat tctctgaaga gtgggtttca caagtgaaaa acatccagat    420
acacccaaag tatcaggacg agaatgaggg tcctttggga aaggagaagt taagcaacat    480
ctagcaaatg ttatgcataa agtcagtgcc caactgttat aggttgttgg ataaatcagt    540
ggttatttag ggaactgctt gacgtaggaa cggtaaattt ctgtgggag                 589
```

<210> SEQ ID NO 2
<211> LENGTH: 235
<212> TYPE: DNA
<213> ORGANISM: Homo sapiens

<400> SEQUENCE: 2

```
gcagcttcct gataaagcgt gctgtgctgt gcagtaggaa cacatcctat ttattgtgat      60
gttgtggttt tattatttta aactttgttc catacacttg tataaataca tggatatttt    120
tatgtacaga agtatgtttt ttaaccagtt cacttattgt actttggcaa tttaaaagaa    180
aatcagtaaa atattttgct tgtaaaatgc ttaatatcgt gcctaggtta tgtgg          235
```

<210> SEQ ID NO 3
<211> LENGTH: 139
<212> TYPE: DNA
<213> ORGANISM: Homo sapiens

<400> SEQUENCE: 3

```
cccctccaag accctgtgtt catttggtgt tcctggaagc aggtgctaca acatgtgagg      60
cattcgggga agctgcacat gtgccacaca gtgacttggc cccagacgca tagactgagg    120
tataaagaca agtatgaat                                                   139
```

<210> SEQ ID NO 4
<211> LENGTH: 172
<212> TYPE: DNA
<213> ORGANISM: Homo sapiens

<400> SEQUENCE: 4

```
agccaatgga aaatctgggt tcaaccagcc cctgccattt cttaagactt tttgctgcac      60
tcacaggatc ctgagctgca cttacctgtg agagtcttca aactttttaaa ccttgccagt    120 caggactttt gctattgcaa atagaaaacc caactcaacc tgcttaagca ga             172
```

<210> SEQ ID NO 5
<211> LENGTH: 217
<212> TYPE: DNA
<213> ORGANISM: Homo sapiens

<400> SEQUENCE: 5

```
ttctttgtca atctatggac atgcccatat atgaaggaga tgggtgggtc aaaaagggat      60
atcaaatgaa gtgatagggg tcacaatggg gaaattgaag tggtgcataa cattgccaaa     120
atagtgtgcc actagaaatg gtgtaaaggc tgtttttttt ttttttttta agaaaagtt      180
attaccatgt attttgtgag gcaggtttac aacacta                              217
```

<210> SEQ ID NO 6
<211> LENGTH: 156
<212> TYPE: DNA
<213> ORGANISM: Homo sapiens

<400> SEQUENCE: 6

```
gcagcaacag caaatcacga ccactgatag atgtttattt ttgttggaga catgggatga      60
ttattttctg ttctatttgt gcttagtcca attccttgca catagtaggt acccaattca     120
attactattg aatgaattaa gaattggttg ccataa                               156
```

<210> SEQ ID NO 7
<211> LENGTH: 221
<212> TYPE: DNA
<213> ORGANISM: Homo sapiens

<400> SEQUENCE: 7

```
taatgtcatc ctgtactcgg cacaaatcaa aggccaatac aagtctgaaa agcagaaata      60
aatattttc caggttttg ctcgggcaca tactaactgc tttgggcatt ttaatctggt       120
ctccaaacac caaagaccca tttcgagcct gctattagcc tgctgctgac tctatcactt     180
ggagcaataa tgtggggtta tggtggtgga atcttgtata t                         221
```

<210> SEQ ID NO 8
<211> LENGTH: 145
<212> TYPE: DNA
<213> ORGANISM: Homo sapiens

<400> SEQUENCE: 8

```
tttagcttgt tcacactttg ccctatgaca tttctacatc actggctgct cttcatcaaa      60
cctactataa aaaacattca agttcaactg tttctttggg cctttatttc cttatggagg    120
ccctcgtgtc gtgtaaaact tatat                                           145
```

<210> SEQ ID NO 9
<211> LENGTH: 213
<212> TYPE: DNA
<213> ORGANISM: Homo sapiens

<400> SEQUENCE: 9

```
gaccaacttc tgtattcgtg gaccaaactg aagctatatt tttcacagaa gaagaagcag      60
tgacggggac acaaattctg ttgcctggtg gaaagaaggc aaaggccttc agcaatctat    120
attaccagcg ctggatcctt tgacagagag tggtccctaa acttaaattt caagacggta    180
taggcttgat ctgtcttgct tattgttgcc ccc                                  213
```

<210> SEQ ID NO 10
<211> LENGTH: 287
<212> TYPE: DNA
<213> ORGANISM: Homo sapiens

<400> SEQUENCE: 10

```
gattggatta aagacctggc acttcagtaa ctcagcacgc ttccacttca ctcaacttaa    60
gagagttcat tgacagtgtt aggatgtgaa ggctgggaaa cacttatttt gcttcaagag   120
ttccacttgg ctctcccaaa taggtacctc aaaaactgtt agcaagcggc atttggatgt   180
cttgacaggg gctttgcagg gattttttagg gttttttcca cattgtccac attaatggtt   240
ggcatgattg tgcttgcagg ccaagaaatg atcatacccc ttgccaa                 287

<210> SEQ ID NO 11
<211> LENGTH: 231
<212> TYPE: DNA
<213> ORGANISM: Homo sapiens

<400> SEQUENCE: 11
agctttgtgc tcagatccca ggtcccaagg agtgacaggg gcttcctccc accttctgtc    60
cttgtccagt catgtaaata atgtgctttt tctctccccg agtctttttt ttttaaacct   120
accgtggttc ctcagctaac tgcattccct acccaggcag agactgtcct atgcctcgag   180
cttccaaacg agactcagac cgcgacacag ccaccgtatt tatggaatga c            231

<210> SEQ ID NO 12
<211> LENGTH: 245
<212> TYPE: DNA
<213> ORGANISM: Homo sapiens

<400> SEQUENCE: 12
gaaatacgaa tgtagagatc cctaatcatc aaattgttga ttgaaagact gatcataaac    60
caatgctggt attgcacctt ctggaactat gggcttgaga aaaccccag gatcacttct    120 ccttggcttc cttcttttct gtgcttgcat cagtgtggac tcctagaacg tgcgacctgc   180
ctcaagaaaa tgcagttttc aaaaacagac tcagcattca gcctccaatg aataagacat   240
cttcc                                                               245

<210> SEQ ID NO 13
<211> LENGTH: 190
<212> TYPE: DNA
<213> ORGANISM: Homo sapiens

<400> SEQUENCE: 13
aattcgccaa tcatcccacc atataacctt cgattgtgct tctcaactcc accccataat    60
ttctcccaga gaccatctat caccttttcc ccaaagaaga aacaaaacca gttgcacctt   120
aaaccatgga tatttttcc tcaggggctt taaatagttt cctatgcaac gtgtcttgta   180
gcacaaataa                                                          190

<210> SEQ ID NO 14
<211> LENGTH: 115
<212> TYPE: DNA
<213> ORGANISM: Homo sapiens

<400> SEQUENCE: 14
tgaacaaatg gcctttatta aaaactgagt gactctatat agctgatcag tttttttcacc   60 tggaagcatt tgttttttact ttgatatgac tgtttttcgg acagtttatt tgttg       115

<210> SEQ ID NO 15
<211> LENGTH: 179
<212> TYPE: DNA
<213> ORGANISM: Homo sapiens

<400> SEQUENCE: 15
```

```
tgtggtagcc tcacttttaa tgaacaaatg gcctttatta aaaactgagt gactctatat    60
agctgatcag ttttttcacc tggaagcatt tgtttttact ttgatatgac tgtttttcgg   120
acagtttatt tgttgagagt gtgaccaaaa gttacatgtt tgcaccttttt tagttgaaa    179
```

<210> SEQ ID NO 16
<211> LENGTH: 113
<212> TYPE: DNA
<213> ORGANISM: Homo sapiens

<400> SEQUENCE: 16

```
caaagtgcta ataattaact caaccaggtc tacttttaa tggctttcat aacactaact    60
cataaggtta ccgatcaatg catttcatac ggatatagac ctagggctct gga           113
```

<210> SEQ ID NO 17
<211> LENGTH: 59
<212> TYPE: DNA
<213> ORGANISM: Homo sapiens

<400> SEQUENCE: 17

```
aaagcagact acgagaaaca caaactctac gcctgcgaag tcacccatca gggcctgag     59
```

<210> SEQ ID NO 18
<211> LENGTH: 92
<212> TYPE: DNA
<213> ORGANISM: Homo sapiens

<400> SEQUENCE: 18

```
gctgagcaaa gcagactacg agaaacacaa agtttacgcc tgcgaagtca cccatcaggg    60
cctgagctcg cccgtcacaa agagcttcaa ca                                  92
```

<210> SEQ ID NO 19
<211> LENGTH: 298
<212> TYPE: DNA
<213> ORGANISM: Homo sapiens

<400> SEQUENCE: 19

```
agcagactac gagaaacaca agtttacgc ctgcgaagtc acccatcagg gcctgagctc     60
gcccgtcaca aagagcttca caggggaga gtgttagagg gagaagtgcc cccacctgct    120
cctcagttcc agcctgaccc cctcccatcc tttggcctct gacccttttt ccacagggga   180 cctacccta ttgcggtcct ccagctcatc tttcacctca cccccctcct cctccttggc   240
tttaattatg ctaatgttgg aggagaatga ataaataaag tgaatctttg cacctgtg    298
```

<210> SEQ ID NO 20
<211> LENGTH: 228
<212> TYPE: DNA
<213> ORGANISM: Homo sapiens

<400> SEQUENCE: 20

```
gtcagagccg ttggtgtttt tcattgttta aaatgtcacc tgtaaaatgg gcattattta    60 tgttttttttt tttgcattcc tgataattgt atgtattgta taaagaacgt ctgtacattg   120
ggttataaca ctagtatatt taaacttaca ggcttatttg taatgtaaac caccatttta   180
atgtactgta attaacatgg ttataatacg tacaatcctt ccctcatc                228
```

<210> SEQ ID NO 21
<211> LENGTH: 86
<212> TYPE: DNA

<213> ORGANISM: Homo sapiens

<400> SEQUENCE: 21 actgagggg tcctggtgtg catttgcacc ctaaagctgc ttacggtgaa aaggcaaata    60
ggtatagcta ttttgcaggc accttt    86

<210> SEQ ID NO 22
<211> LENGTH: 158
<212> TYPE: DNA
<213> ORGANISM: Homo sapiens

<400> SEQUENCE: 22
tttggtgcag tttccagggt gcagtacagc agggcctgaa tactggccct ggactccctt    60
ttccagaaca ccaggtgtgg ccacctgggg ctcaggtaca cagtggggtc tctcggaagc   120
caccgtgtgg ttctttcaca ggcacgttta ttttgctg    158

<210> SEQ ID NO 23
<211> LENGTH: 223
<212> TYPE: DNA
<213> ORGANISM: Homo sapiens

<400> SEQUENCE: 23
tggtcatgag aagaaggtaa tttccagcct tcaagaagac agacatttag aagaagagct    60
gaaatgtcag gaacaaaaag aagaacagct gcaggaaggg gtgcaccgga aggagccca   120 gggggccacg tagcagcggc tcagtgggtg gccatcgatt tggaccgtcc cctgcccact   180
tgctccccgt gagcactgcg tacaaacatc caaaagttca aca    223

<210> SEQ ID NO 24
<211> LENGTH: 262
<212> TYPE: DNA
<213> ORGANISM: Homo sapiens

<400> SEQUENCE: 24
ccaggttagg aaaggattca gcactacagc atacccctct acaacataca gccctgtcac    60
attgagatca taatccctcc tgtcccactc ctctctacca accccaccct actagctagg   120
tcttcagtgt tttacattga atattggtac atttttaatta ttttttctca taaatgggtt   180
atttatagaa attttgttaa ctcttgagcc atatgcatgt gtagatactg gcagggctat   240
gtttgtttat gatgctctgc aa    262

<210> SEQ ID NO 25
<211> LENGTH: 245
<212> TYPE: DNA
<213> ORGANISM: Homo sapiens

<400> SEQUENCE: 25
attgtgctat aatccctatt tagttcaaaa ttaaccagaa ttttccatg tgaaatggac    60 caaactcata ttattgttat gtaaatacag agttttaatg cagtatgaca tcccacaggg   120
gaaaagaatg tctgtagtgg gtgactgtta tcaaatattt tatagaatac aatgaacggt   180
gaacagactg gtaacttgtt tgagttccca tgacagattt gagacttgtc aatagcaaat   240
cattt    245

<210> SEQ ID NO 26
<211> LENGTH: 202
<212> TYPE: DNA
<213> ORGANISM: Homo sapiens

<400> SEQUENCE: 26
taatggttaa cgaaccgggt cgacatcaca aaggagggtg gagactcttt ttactaactt        60
gaatgagaca aaagcagtgg tgtcagttta taatcctgat gcatttcagt aataatgtag       120
aaaaacatta ttttaaaaaa gttccaacac acagccatga ggagcctcag ttttgaaaga       180
ggtgcataat aaaactacta ac                                                202

<210> SEQ ID NO 27
<211> LENGTH: 132
<212> TYPE: DNA
<213> ORGANISM: Homo sapiens

<400> SEQUENCE: 27
acagcccacc cttgtgtcca ctgtgacccc tgttcccatg ctgacctgtg tttcctcccc        60
agtcatcttt cttgttccag agaggtgggg ctggatgtct ccatctctgt ctcaacttta       120
tgtgcactga gc                                                           132

<210> SEQ ID NO 28
<211> LENGTH: 53
<212> TYPE: DNA
<213> ORGANISM: Homo sapiens

<400> SEQUENCE: 28
aagcaagata tcaatgtagc agaattgcac ttgtgcctca cgaacataca taa               53

<210> SEQ ID NO 29
<211> LENGTH: 102
<212> TYPE: DNA
<213> ORGANISM: Homo sapiens

<400> SEQUENCE: 29
ttcctgttcc agagaagtgg gctggatgtc tccatctctg tttcaacttc atggtgcgct        60
gagctgcaac ttcttacttc cctaatgaag ttaagaacct ga                          102

<210> SEQ ID NO 30
<211> LENGTH: 162
<212> TYPE: DNA
<213> ORGANISM: Homo sapiens

<400> SEQUENCE: 30
tttcctacca cttaactgca ctgtggctga gttttctgat ctgtaaggtg ggaataataa        60
tgatacctat ctcatagggg aatgaaagga tcaaatgagt tcatatttgt aaagcaattt       120
gaaagagtgc ctagcccaca gtaagtgcta cataagagtt tg                          162

<210> SEQ ID NO 31
<211> LENGTH: 159
<212> TYPE: DNA
<213> ORGANISM: Homo sapiens

<400> SEQUENCE: 31
taacagcaga atctacctcc caactgccat gtgattaaga aatgggtctt gagtcctgtg        60
ctgttggcaa agttccaggc acagttgggg aggggggggt ccttaacaag cgtgactttg       120
ctcattctgt catcactaag gcaataaacc tttgccagg                              159

<210> SEQ ID NO 32
<211> LENGTH: 153
<212> TYPE: DNA

<213> ORGANISM: Homo sapiens

<400> SEQUENCE: 32

| | | |
|---|---|---|
| atgggatggt cggatctcac aggctgagaa ctcgttcacc tccaagcatt tcatgaaaaa | 60 |
| gctgcttctt attaatcata caaactctca ccatgatgtg aagagtttca caaatctttc | 120 |
| aaaataaaaa gtaatgactt agaaactgcc caa | 153 |

<210> SEQ ID NO 33
<211> LENGTH: 114
<212> TYPE: DNA
<213> ORGANISM: Homo sapiens

<400> SEQUENCE: 33

| | |
|---|---|
| tcatccccat ggagcattgc accacccgct ttttcgagac ctgtgacctg gacaatgaca | 60 |
| agtacatcgc cctggatgag tgggccggct gcttcggcat caagcagaag gata | 114 |

<210> SEQ ID NO 34
<211> LENGTH: 112
<212> TYPE: DNA
<213> ORGANISM: Homo sapiens

<400> SEQUENCE: 34

| | |
|---|---|
| atttgggtgg gatgggtagg atgaagtata ttgcccaact ctatgtttct ttgattttaa | 60 |
| cacaattaat taagtgacat gatttttact aatgtattac tgagactagt aa | 112 |

<210> SEQ ID NO 35
<211> LENGTH: 274
<212> TYPE: DNA
<213> ORGANISM: Homo sapiens

<400> SEQUENCE: 35

| | |
|---|---|
| tgtttcacaa tacctcatgc ttcacttagc catggtggac ccagcgggca ggttctgcct | 60 |
| gctttggcgg gcagacacgc gggcgcgatc ccacacaggc tggcggggc cggccccgag | 120 |
| gccgcgtgcg tgagaaccgc gccggtgtcc ccagagacca ggctgtgtcc ctcttctctt | 180 |
| ccctgcgcct gtgatgctgg gcacttcatc tgatcggggg cgtagcatca tagtagtttt | 240 |
| tacagctgtg ttattctttg cgtgtagcta tgga | 274 |

<210> SEQ ID NO 36
<211> LENGTH: 189
<212> TYPE: DNA
<213> ORGANISM: Homo sapiens

<400> SEQUENCE: 36

| | |
|---|---|
| cctctggctt ctcaggcctc tgctctccga cctctctcct ctgaaaccct cctccacagc | 60 |
| tgcagcccat cctcccggct ccctcctagt ctgtcctgcg tcctctgtcc ccgggtttca | 120 |
| gagacaactt cccaaagcac aaagcagttt ttccccctag gggtgggagg aagcaaaaga | 180 |
| ctctgtacc | 189 |

<210> SEQ ID NO 37
<211> LENGTH: 151
<212> TYPE: DNA
<213> ORGANISM: Homo sapiens

<400> SEQUENCE: 37

| | |
|---|---|
| ttggaatgtt gtagttacct actgagtagg cggcgatttt tgtatgttat gaacatgcag | 60 |
| ttcattattt tgtggttcta ttttactttg tacttgtgtt tgcttaaaca aagtgactgt | 120 | ttggcttata aacacattga atgcgcttta t         151

<210> SEQ ID NO 38
<211> LENGTH: 201
<212> TYPE: DNA
<213> ORGANISM: Homo sapiens

<400> SEQUENCE: 38
atctccatca tatgcctgac cccttgctcc cttcaatgct agaaaatcga gttggcaaaa    60
tggggtttgg gccccctcaga gccctgccct gcacccttgt acagtgtctg tgccatggat   120
ttcgttttc ttggggtact cttgatgtga agataatttg catattctat tgtattattt    180
ggagttaggt cctcacttgg g                                              201

<210> SEQ ID NO 39
<211> LENGTH: 138
<212> TYPE: DNA
<213> ORGANISM: Homo sapiens

<400> SEQUENCE: 39
tcatgtttgc tgtagtgctc atatttattg ttgttttgt tttagtactc acttgtttca     60
taatatcaag attactaaaa atgggggaaa ggacttttaa tctttttttc ataatatctt   120
tgacacatat tacagaag                                                 138

<210> SEQ ID NO 40
<211> LENGTH: 205
<212> TYPE: DNA
<213> ORGANISM: Homo sapiens

<400> SEQUENCE: 40
aatcccaatt ttcaggagtg gtggtgtcaa taaacgctct gtggccagtg taaagaaaa     60
tccctcgcag ttgtggacat ttctgttcct gtccagatac cattttttcct agtatttctt   120
tgttatgtcc cagaactgat gttttttttt taaggtactg aaaagaaatg aagttgatgt   180
atgtcccaag ttttgatgaa actgt                                         205

<210> SEQ ID NO 41
<211> LENGTH: 269
<212> TYPE: DNA
<213> ORGANISM: Homo sapiens

<400> SEQUENCE: 41
gcctggcctg attcagggcc ttgtggcccc cagcttctgt ttcaagctgg gcagacccca     60
ggatcccttc cctccctaag gactcagctg aggggcccct ctgccccctt ctacctccac   120
ctcagcaccc tccccagct tgatgtttgg gtctccccag caccctcctc cctggccggt    180
gcaaagtaca gggaggtaaa gcaggaccct tgcagacatg ttgcccagca cacagtaggc   240
cctcaataaa agccatttgc actttaaat                                     269

<210> SEQ ID NO 42
<211> LENGTH: 169
<212> TYPE: DNA
<213> ORGANISM: Homo sapiens

<400> SEQUENCE: 42
gagaagtcac tcacactggc cacaaggacg ctggctactg tctattaaaa ttttgatgtt     60
tctgtgaaat tctcagagtg tttaattgta ctcaatggta tcattacaat tttctgtaag   120
agaaaatatt acttatttat cctagtattc taacctgtc agaataata 169

<210> SEQ ID NO 43
<211> LENGTH: 234
<212> TYPE: DNA
<213> ORGANISM: Homo sapiens

<400> SEQUENCE: 43
ctgtggcatg ctcagaggtt cctgctggat tccagctgga gcggtgtgat acccttcttt    60
ttcagctgtt cgtgccttcc tttcttgtat ccaccaaagt ggagacaaat acatgatttc   120
aaagatacac agtacctact taattccagc tgatgggaga ccaagaatt tgcaagtgga   180 tggtttggta tcactgtaaa taaaagagg gcctgggaat tcttgcgatt ccat          234

<210> SEQ ID NO 44
<211> LENGTH: 168
<212> TYPE: DNA
<213> ORGANISM: Homo sapiens

<400> SEQUENCE: 44
cagctttcag acagagccca cttagcttgt ccacatggat ttcaatgcca atcctccatt    60
tttcctctcc agatattttt gggagtgaca acattctttt catcctactt agcctaccta   120 gattttcat gacgagttaa tgcatgtccg tggttgggtg cacctgta                 168

<210> SEQ ID NO 45
<211> LENGTH: 232
<212> TYPE: DNA
<213> ORGANISM: Homo sapiens

<400> SEQUENCE: 45
tgaaccaaaa tagagtcagc tgacccagca tcagccacac tttgggttgg aaaatgtttg    60
cctgttggaa ttaatttaag cttaagtata tatcaacatt attttattgt gcaattaaaa   120
caatacaaat tcatggtttt ttaaagttaa aaattttaac cactgtaaca acagttttttg   180 tgttattttc tgtattaaac atcttgttgc acgcatttga ggtcatcagg gt            232

<210> SEQ ID NO 46
<211> LENGTH: 234
<212> TYPE: DNA
<213> ORGANISM: Homo sapiens

<400> SEQUENCE: 46
caatgccgtc attttcagtt agatgatttt gcactttgag attaaaatgc catgtttatt    60
tgattagttt tatttttta ttttacagg cttatcagtc tcactgttgg ctgtcattgt     120
gacaaagtca aataaacccc caaggacgac acacagtatg gatcacatat tgtttgacat   180
taagcttttg ccagaaaatg ttgcatgtgt tttacctcga cttgctaaaa tcga           234

<210> SEQ ID NO 47
<211> LENGTH: 147
<212> TYPE: DNA
<213> ORGANISM: Homo sapiens

<400> SEQUENCE: 47
atgttcatag gttctcaacc ctcaccccc accacgggag actagagctg caggatccca    60
ggggaggggt ctctcctccc accccaaggc atcaagccct tctccctgca ctcaataaac   120
cctcaatata tattctcatt gtcaatc                                       147

<210> SEQ ID NO 48
<211> LENGTH: 149
<212> TYPE: DNA
<213> ORGANISM: Homo sapiens

<400> SEQUENCE: 48
aatgttcata ggttctaaac cctcaccccc cccacgggag actagagctg caggatccca    60
ggggaggggt ctctcctccc accccaaggc atcaagccct tctccctgca ctcaataaac   120
cctcaataaa tattctcatt gtcaatcag                                     149

<210> SEQ ID NO 49
<211> LENGTH: 152
<212> TYPE: DNA
<213> ORGANISM: Homo sapiens

<400> SEQUENCE: 49
aatgttcata ggttctaaac cctcaccccc cccacgggag actagagctg caggatccca    60
ggggaggggt ctctcctccc accccaaggc atcaagccct tctccctgca ctcaataaac   120
cctcaataaa tattctcatt gtcaatcagc aa                                 152

<210> SEQ ID NO 50
<211> LENGTH: 150
<212> TYPE: DNA
<213> ORGANISM: Homo sapiens

<400> SEQUENCE: 50
aatgttcata ggttctcaac cctcaccccc caccacggga gactagagct gcaggatccc    60
aggggagggg tctctcctcc caccccaagg catcaagccc ttctccctgc actcaataaa   120
ccctcaataa atattctcat tgtcaatcag                                    150

<210> SEQ ID NO 51
<211> LENGTH: 151
<212> TYPE: DNA
<213> ORGANISM: Homo sapiens

<400> SEQUENCE: 51
atgttcatag gttctcaacc ctcaccccc ccacgggaga ctagagctgc aggatcccag     60
ggagggggtc tctcctccca ccccaaggca tcaagccctt ctccctgcac tcaataaacc   120
ctcaataaat attctcattg tcaatcagca a                                  151

<210> SEQ ID NO 52
<211> LENGTH: 147
<212> TYPE: DNA
<213> ORGANISM: Homo sapiens

<400> SEQUENCE: 52
atgttcatag gttcccaact ctaaccccac ccacgggagc ctggagctgc aggatcccag     60
gggaggggtc tctctcccca tcccaagtca tccagccctt ctccctgcac tcatgaaacc   120
ccaataaata tcctcattga caaccag                                       147

<210> SEQ ID NO 53
<211> LENGTH: 150
<212> TYPE: DNA
<213> ORGANISM: Homo sapiens

<400> SEQUENCE: 53
atgttcatag gttcccaact ctaaccccac ccacgggagc ctggagctgc aggatcccag     60

```
gggaggggtc tctctcccca tcccaagtca tccagcccct ctccctgcac tcatgaaacc    120
ccaataaata tcctcattga caaccagcaa                                    150
```

<210> SEQ ID NO 54
<211> LENGTH: 254
<212> TYPE: DNA
<213> ORGANISM: Homo sapiens

<400> SEQUENCE: 54

```
gcagctattt gagcctgacg cctgagcagt ggaagtccca cagaagctac agctgccagg    60
tcacgcatga agggagcacc gtggagaaga cagtggcccc tacagaatgt tcataggttc   120
taaaccctca ccccccccac gggagactag agctgcagga tcccagggga ggggtctctc   180
ctcccacccc aaggcatcaa gcccttctcc ctgcactcaa taaaccctca ataatattc    240 tcattgtcaa tcag                                                     254
```

<210> SEQ ID NO 55
<211> LENGTH: 239
<212> TYPE: DNA
<213> ORGANISM: Homo sapiens

<400> SEQUENCE: 55

```
aagaacaact cctcaccagt tcatcctgag gctgggagga ccgggatgct ggattctgtt    60
ttccgaagtc actgcagcgg atgatggaac tgaatcgata cggtgttttc tgtccctcct   120
actttccttc acaccagaca gcccctcatg tctccaggac aggacaggac tacagacaac   180
tctttcttta ataaattaa gtctttacaa taaaaacaca actgcaaagt accttcata    239
```

<210> SEQ ID NO 56
<211> LENGTH: 270
<212> TYPE: DNA
<213> ORGANISM: Homo sapiens

<400> SEQUENCE: 56

```
gaaagagcat cgttccaatg cttgttcact gttcctctgt catactgtat ctggaatgct    60
ttgtaatact tgcatgcttc ttagaccaga acatgtaggt cccctgtgt ctcaatactt    120 ttttttcctt aattgcattt gttggctcta ttttaatttt ttctttaa aataaacagc    180 tgggaccatc ccaaaagaca agccatgcat acaactttgg tcatgtatct ctgcaaagca   240
tcaaattaaa tgcacgcttt tgtcatgtca                                    270
```

<210> SEQ ID NO 57
<211> LENGTH: 147
<212> TYPE: DNA
<213> ORGANISM: Homo sapiens

<400> SEQUENCE: 57

```
acttggaagc agatgataca gacttctttt tttcataatc aggttagtgt aagaaattgc    60
catttgaaac aatccatttt gtaactgaac cttatgaaat atatgtattt catggtacgt   120
attctctagc acagtctgag caattaa                                       147
```

<210> SEQ ID NO 58
<211> LENGTH: 97
<212> TYPE: DNA
<213> ORGANISM: Homo sapiens

<400> SEQUENCE: 58

```
ttctccccaa ccacttagta gcaacgctac cccagggggt aatgactgca cactgggctt    60
```

```
cttttcagaa tgaccctaac gagacacatt tgcccaa                                97
```

<210> SEQ ID NO 59
<211> LENGTH: 213
<212> TYPE: DNA
<213> ORGANISM: Homo sapiens

<400> SEQUENCE: 59

```
tgtgttgggg tagactgctc ctgcagagtt tggaagaagt caccagcaaa gccggcctaa       60
ccaagaaaag tcaaggccct tcatgacctt gctgggcaca gaaaacaccc tcgtggagta      120
cactaatttg aactggactg gtctcagtgt gagcacttgg cacactttac taaacacata     180
tacaacccca ccgtgagtca actttaaagt aaa                                  213
```

<210> SEQ ID NO 60
<211> LENGTH: 151
<212> TYPE: DNA
<213> ORGANISM: Homo sapiens

<400> SEQUENCE: 60

```
tgtaatgcta aaactgaaat ggtccgtgtt tgcattgtta aaaatgatgt gtgaaataga      60
atgagtgcta tggtgttgaa aactgcagtg tccgttatga gtgccaaaaa tttgtcttga     120
aggcagctac actttgaagt ggtctttgaa t                                    151
```

<210> SEQ ID NO 61
<211> LENGTH: 116
<212> TYPE: DNA
<213> ORGANISM: Homo sapiens

<400> SEQUENCE: 61

```
ctgggccttg gtccccagaa gatggcggct agggcctcgc cgccaggaca gagaagggac      60
ggggtggctg ggcagtcagg gaaggagggt cgcccggatc cgacattttg gagaga         116
```

<210> SEQ ID NO 62
<211> LENGTH: 220
<212> TYPE: DNA
<213> ORGANISM: Homo sapiens

<400> SEQUENCE: 62

```
gaacaggaac gccttctcaa ggagggattc gagaatgaga gcaagagact tcaaaaagac      60
atatgggata tccagatgag aagcaaatca ttggagccaa tatgtaacat acttttaaaag    120 tccaaggagc aaaatttgcc tgtccagctc cctctcccca agaaacaaca tgaatgagca     180
acttcagagt gtcaaacaac tgccattaaa cttaactcaa                           220
```

<210> SEQ ID NO 63
<211> LENGTH: 262
<212> TYPE: DNA
<213> ORGANISM: Homo sapiens

<400> SEQUENCE: 63

```
taagaatctc acaggacctc ttagtttttg ccctatacgc cgccttcact ccacagcctc      60
acccctccca cccccatact ggtactgctg taatgagcca agtggcagct aaaagttggg     120
ggtgttctgc ccagtcccgt cattctgggc tagaaggcag gggaccttgg catgtggctg     180
gccacaccaa gcaggaagca caaactcccc caagctgact catcctaact aacagtcacg    240
ccgtgggatg tctctgtcca ca                                              262
```

<210> SEQ ID NO 64
<211> LENGTH: 72
<212> TYPE: DNA
<213> ORGANISM: Homo sapiens

<400> SEQUENCE: 64
gttatcaatc tctagttgtc actttcctct tccactttga taccattggg tcattgaata    60 taacttttc ca    72

<210> SEQ ID NO 65
<211> LENGTH: 232
<212> TYPE: DNA
<213> ORGANISM: Homo sapiens

<400> SEQUENCE: 65
tttgttagta catttcagtg tagtcattca tttctagctg tacataggat gaaggagaga    60
tcagatacat gaacatgttt tacatgggtt gctgtattta gaattataaa cattttcat    120 tattggaaag tgtaacgggg accttttgca tacctgttta gaaccaaaac caccatgaca    180 cagttttat agtgtctgta tatttgtgat gcaatggtct tgtaaaggtt tt    232

<210> SEQ ID NO 66
<211> LENGTH: 53
<212> TYPE: DNA
<213> ORGANISM: Homo sapiens

<400> SEQUENCE: 66
gaccaggaat tcggcttcga cgttggccct gtctgcttcc tgtaaactcc ctc    53

<210> SEQ ID NO 67
<211> LENGTH: 76
<212> TYPE: DNA
<213> ORGANISM: Homo sapiens

<400> SEQUENCE: 67
ggaggatgcg ctgtgggggtt gttttgcca taagcgaact tgtgcctgt cctagaagtg    60 aaaattgttc agtcca    76

<210> SEQ ID NO 68
<211> LENGTH: 132
<212> TYPE: DNA
<213> ORGANISM: Homo sapiens

<400> SEQUENCE: 68
aaaagttcac agtcaaatgg ggaggggtat ttttcatgca ggagacccca ggccctggag    60
gctgcaacat acctcaatcc tgtcccaggc cggatcctcc tgaagccctt ttcgcagcac    120
tgctatcctc ca    132

<210> SEQ ID NO 69
<211> LENGTH: 287
<212> TYPE: DNA
<213> ORGANISM: Homo sapiens

<400> SEQUENCE: 69
agtgagactg actgcaagcc ccaccctcct tgagactgga gctggcgtct gcatacgaga    60
gacttggttg aacttggttg gtccttgtct gcaccctcga caagaccaca ctttgggact    120
tgggagctgg ggctgaagtt gctctgtacc catgaactcc cagtttgcga attatagaga    180 caatctatt tgttacttgc acttgttatt cgaaccactg agagcgagat gggaagcata    240
gatatctata tttttatttt tactatgagg gccttgtaat aaatttc              287

<210> SEQ ID NO 70
<211> LENGTH: 36
<212> TYPE: DNA
<213> ORGANISM: Homo sapiens

<400> SEQUENCE: 70
tgggggggca gaggcgtctg accccaggaa cctgca                          36

<210> SEQ ID NO 71
<211> LENGTH: 157
<212> TYPE: DNA
<213> ORGANISM: Homo sapiens

<400> SEQUENCE: 71
tatgaattcc attcaaatcg ttccttttg ttaacagggg gcatggggag gggtggggt   60 gggggggcag aggcgtctga ccccaggaac ctgcagggcg gggctgggtc ggtgcccttt 120
aaggacaatt ttgaccttgt tcaacctttc cacaaag                         157

<210> SEQ ID NO 72
<211> LENGTH: 212
<212> TYPE: DNA
<213> ORGANISM: Homo sapiens

<400> SEQUENCE: 72
gatgcatgag gctctgcaca accactacac gcagaagagc ctctccctgt ctccgggtaa 60
atgagtgcga cggccggcaa gccccgctc cccaggctct cggggtcgcg cgaggatgct  120
tggcacgtac cccgtgtaca tacttcccgg gcgcccagca tggaaataaa gcacccagcg 180
ctgccctggg cccctgcgca actttcttgt ac                              212

<210> SEQ ID NO 73
<211> LENGTH: 225
<212> TYPE: DNA
<213> ORGANISM: Homo sapiens

<400> SEQUENCE: 73
tttgctgtga taaatgaata cggtactttg aaggagaaaa aagttttca atgagctta   60 aactgcaagt gatttaaaaa ttagagaata taattttaa agctattgaa agtttcaacc 120
agaaaacctc aagtgaattt tgtatgtaaa tgaaattttg aatgtaagtt ctgtgattct 180
ttaagcaaac aattagctga aaacttggta ttgttgtagt ttatg                225

<210> SEQ ID NO 74
<211> LENGTH: 287
<212> TYPE: DNA
<213> ORGANISM: Homo sapiens

<400> SEQUENCE: 74
gaaatgcaaa ctatccctgt attttaatat ttgttattct ttcatgaata gaaatttatg 60
tagaagcaaa caaatactt ttacccactt aaaagagaa tataacattt tatgtcacta   120
taatcttttg tttttaagt tagtgtatat tttgttgtga ttatcttttt gtggtgtgaa  180
taaatctttt atcttgaatg taataagaat ttggtggtgt caattgctta tttgttttcc 240
cacggttgtc cagcaattaa taaaacataa ccttttttac tgcctat              287

<210> SEQ ID NO 75

```
<211> LENGTH: 276
<212> TYPE: DNA
<213> ORGANISM: Homo sapiens

<400> SEQUENCE: 75
agaatcatgt acagagctta aatgtaattt atatgttttt aatatgccat tttcattgaa      60
gtattttggt cttaagatga ctttagtaat ttaactgttt atgttaccca cgttgggatc     120
cagttggtct tggtttgctt ctctctgtac cacgtgcaca tgaggtccat tcattttaca     180
gcccctgtta cacacagacc cacaggcagc cgtctgtgcc ccgcacacat tgttggtcct     240
atttgtaaat cccacacccg gtgtatccaa taaagt                               276

<210> SEQ ID NO 76
<211> LENGTH: 222
<212> TYPE: DNA
<213> ORGANISM: Homo sapiens

<400> SEQUENCE: 76
tttcacatag gttagattct cattcacggg actagttagc tttaagcacc ctagaggact      60
agggtaatct gacttctcac ttcctaagtt cccttctata tcctcaaggt agaaatgtct     120
atgtttttta ctccaattca taatctatt cataagtctt tggtacaagt ttacatgata     180
aaaagaaatg tgatttgtct tcccttcttt gcacttttga aa                        222

<210> SEQ ID NO 77
<211> LENGTH: 182
<212> TYPE: DNA
<213> ORGANISM: Homo sapiens

<400> SEQUENCE: 77
atcaaggctc ttccgttcca catccacaca gccaatccaa ttaatcaaac cactgttatt      60
aacagataat agcaacttgg gaaatgctta tgttacaggt tacgtgagaa caatcatgta     120
aatctatatg atttcagaaa tgttaaaata gactaacctc taccagcaca ttaaaagtga     180
tt                                                                    182

<210> SEQ ID NO 78
<211> LENGTH: 212
<212> TYPE: DNA
<213> ORGANISM: Homo sapiens

<400> SEQUENCE: 78
ttcctttagg ccctgtgagc gtcccttgtc aggatacatt ctctcatttt gctgaagctg      60
atttgattgg gtgtctgttt ctcgcagcca aaagagcttt gaatgaggaa agtgcttctg     120
tgctaactcc ccgcgtctcc tgaatttcag tcattcatgt acccgcctcg aaattttgc      180 aatatctgtg taccaactgt ccatttactt aa                                   212

<210> SEQ ID NO 79
<211> LENGTH: 238
<212> TYPE: DNA
<213> ORGANISM: Homo sapiens

<400> SEQUENCE: 79
gtgtgtatgt gtagacaagc tctcgttctg tcacccaggc tggagtgcag tggtgcaatc      60
atggttcact gcagtcttga cctttttgggc tcaagtgatc ctcccacctc agcctcctga    120
gtagctggga ccataggctc acaacaccac acctggcaaa tttgattttt ttttttttc      180 cagagacggg gtctcgcaac attgcccaga cttcctttgt gttagttaat aaagcttt      238
```

<210> SEQ ID NO 80
<211> LENGTH: 262
<212> TYPE: DNA
<213> ORGANISM: Homo sapiens

<400> SEQUENCE: 80

```
gtcctctcta tcctggatga gctcatgaac atttctcttg tgttcctgac tccttcccaa    60
tgaacacctt tctgccaccc caagctttgc tctcctcctc tgtgagctct gggcttccca   120
gtttgtttac ccgggaaagt acgtctagat tgtgtggttt gcctcattgt gctatttgcc   180
cactttcctt ccctgaagaa atatctgtga accttctttc tgttcagtcc taaaattcga   240
aataaagtga gactatggtt ca                                            262
```

<210> SEQ ID NO 81
<211> LENGTH: 129
<212> TYPE: DNA
<213> ORGANISM: Homo sapiens

<400> SEQUENCE: 81

```
agtgggggg cattataaat ctataaaatg tacttctatt ggcatgccta atacgtcttt    60
atatgtatgt atgtgttgtg tacacgatgt tttagtgcta aaaatatgta aaagagctct   120
acttggctt                                                          129
```

<210> SEQ ID NO 82
<211> LENGTH: 178
<212> TYPE: DNA
<213> ORGANISM: Homo sapiens

<400> SEQUENCE: 82

```
aagtctaatt tcgactggtt gtatctcttt atgatttatt gccccctaa caacatttga    60
aacaatataa tattttaaaa tgtataaata attatgaatt tttgtttaga acaaagagga   120
ttactgatat ttgtttccct atgaatggca aaggtttag cttactactg catttctg     178
```

<210> SEQ ID NO 83
<211> LENGTH: 135
<212> TYPE: DNA
<213> ORGANISM: Homo sapiens

<400> SEQUENCE: 83

```
gggcccagct cagaaccggg cagacacccc cttcaaatgt cttcgcacgt aggttttgca    60
cagtgtttat ttgctggtgt ctcagggatt tgacagtttc cttaatattc ccacacatgg   120
ccgagaaaaa taaat                                                   135
```

<210> SEQ ID NO 84
<211> LENGTH: 235
<212> TYPE: DNA
<213> ORGANISM: Homo sapiens

<400> SEQUENCE: 84

```
ttctacacta gtgccatggg aaccaggtct gaaaaagtag agagaagtga aagtagagtc    60
tgggaagtag ctgcctataa ctgagactag acggaaaagg aatactcgtg tattttaaga   120
tatgaatgtg actcaagact cgaggccgat acgaggctgt gattctgcct ttggatggat   180
gttgctgtac acagatgcta cagacttgta ctaacacacc gtaatttggc atttg        235
```

<210> SEQ ID NO 85

<211> LENGTH: 177
<212> TYPE: DNA
<213> ORGANISM: Homo sapiens

<400> SEQUENCE: 85

```
gataacagtc ttgcatgttt atcatgttac aatttaatat tccatcctgc ccaacccttc      60
ctttcccatc ctcaaaaaag ggccatttta tgatgcattg cacaccctct ggggaaattg     120
atctttaaat tttgagacag tataaggaaa atctggttgg tgtcttacaa gtgagct       177
```

<210> SEQ ID NO 86
<211> LENGTH: 236
<212> TYPE: DNA
<213> ORGANISM: Homo sapiens

<400> SEQUENCE: 86

```
attggagtgg atgggttctg ccttaaattg ggaggactcc aagccgggaa ggaaaattcc      60
cttttccaac ctgtatcaat ttttacaact tttttcctga agcagttta gtccatactt     120
tgcactgaca tacttttttcc ttctgtgcta aggtaaggta tccaccctcg atgcaatcca    180
ccttgtgttt tcttagggtg gaatgtgatg ttcagcagca aacttgcaac agactg         236
```

<210> SEQ ID NO 87
<211> LENGTH: 243
<212> TYPE: DNA
<213> ORGANISM: Homo sapiens

<400> SEQUENCE: 87

```
gggatctcct tttgtgaaaa ccagtttgat gtgctaaaag taaaaagtct attttccagt      60
gtggtcttgt tcagaagcag ccagatttcc aatgttgttt ttccctcca ctcagaaacc    120
cctgcccttt cccttcagaa aacgatggca ggcattcctt tgagtttaca agcagagact    180
cactccaacc caaactagct gggagttcag aaccatggtg aataaagaa atgtgcatct     240
ggt                                                                  243
```

<210> SEQ ID NO 88
<211> LENGTH: 221
<212> TYPE: DNA
<213> ORGANISM: Homo sapiens

<400> SEQUENCE: 88

```
cctgtaagac aataggccat gttaattaaa ctgaagaagg atatatttgg ctgggtgttt      60
tcaaatgtca gcttaaaatt ggtaattgaa tggaagcaaa attataagaa gaggaaatta    120
aagtcttcca ttgcatgtat tgtaaacaga aggagatggg tgattccttc aattcaaaag    180
ctctctttgg aatgaacaat gtgggcgttt gtaaattctg g                         221
```

<210> SEQ ID NO 89
<211> LENGTH: 273
<212> TYPE: DNA
<213> ORGANISM: Homo sapiens

<400> SEQUENCE: 89

```
aatgaccacc gccattcaca agaactttga ctgtttgaag ttgatcctga gactcttgaa      60
gtaatggctg atcctgcatc agcattgtat atatggtctt aagtgcctgg cctccttatc    120
cttcagaata tttatttac ttacaatcct caagttttaa ttgattttaa atattttca      180
atacaacagt ttaggtttaa gatgaccaat gacaatgacc acctttgcag aaagtaaact    240
gattgaataa ataaatctcc gttttcttca att                                  273
```

<210> SEQ ID NO 90
<211> LENGTH: 225
<212> TYPE: DNA
<213> ORGANISM: Homo sapiens

<400> SEQUENCE: 90
gagtaccgcg cagacattaa aagtcatgta aagaacatt tgactgaaag aaaaatgctc      60
cttgaatatt aaaaggttgt aaaaatagtg catgttatgt gatttcaatt ttgttttta     120 aaatatgggt gtatgcttgt atacgtagag cagataaaaa agacggaagg catactaaaa    180
aatgttgagt ggttatcttt gtatggtgga acaaagtcac tgtaa                    225

<210> SEQ ID NO 91
<211> LENGTH: 182
<212> TYPE: DNA
<213> ORGANISM: Homo sapiens

<400> SEQUENCE: 91
atgctgagtg acactcttgt gtatatttcc aaattttgt acagtcgctg cacatatttg      60
aaatcatata ttaagacttt ccaaagatga ggtccctggt ttttcatggc aacttgatca    120
gtaaggattt caccctctgtt tgtaactaaa accatttact atatgttaga catgacattc    180
tt                                                                    182

<210> SEQ ID NO 92
<211> LENGTH: 157
<212> TYPE: DNA
<213> ORGANISM: Homo sapiens

<400> SEQUENCE: 92
tgtgttttca gagctaggta cagaggaatg tttgctacct ttagcggtga aaaagaaag      60 agagtcaaga attttgttgg attgtgtttg tgtgtgcata tatttgatat catcattata    120
tttgtaatct ttggacttgt aatcatagcc tgtttat                              157

<210> SEQ ID NO 93
<211> LENGTH: 201
<212> TYPE: DNA
<213> ORGANISM: Homo sapiens

<400> SEQUENCE: 93
ctccctccct ttatagaatg tcaaccaaag agtgccctcc tccctctca gcctcctctt      60 tagctagcct ccccatctca tcacaacgca tgtctgtgac ctttggtaat catttacagt    120
gccacacgga accctgtatt ttgcacacag caaaacaaac aatgtttagc tttatttatg    180
gtatttgatg ctgtaaatgg a                                               201

<210> SEQ ID NO 94
<211> LENGTH: 35
<212> TYPE: DNA
<213> ORGANISM: Homo sapiens

<400> SEQUENCE: 94
atattattgg attatggttc ctgaaggtca ttaaa                                35

<210> SEQ ID NO 95
<211> LENGTH: 249
<212> TYPE: DNA
<213> ORGANISM: Homo sapiens

<400> SEQUENCE: 95

```
tctccagagg gcacttcggc tgcctttgct tcctttcatt cgaggcccgg ctcttgctga      60
cagaataggt tccgttttgg gcggtggttc tcgagcctgc cattcaaaac caaagcaaat     120
tggagcattt ctcacaacat ggtattgaag ttcctttttg ttctcaaaag ttgtgaccgt     180
gttaaattgt actcccttag tcctgtaagg tatgttaagt gaatcgcagt tacgctgtac     240
ttttattaa                                                             249
```

<210> SEQ ID NO 96
<211> LENGTH: 203
<212> TYPE: DNA
<213> ORGANISM: Homosapiens

<400> SEQUENCE: 96

```
ctgccgagcc tctttggacc cagatctgtt catgcttttg tcttcgtcac tgcggcgggg      60
ccctttgatg tcttcatctg tatggggtgg aaaaatcacc gggaatcccc cttcagttct     120
ttgaaaaagt tccatgactc gaatatctga atgaagaaa acaaaccgac tcacaaacct     180
ccaagtagct ccaaatgcaa ttt                                             203
```

<210> SEQ ID NO 97
<211> LENGTH: 73
<212> TYPE: DNA
<213> ORGANISM: Homo sapiens

<400> SEQUENCE: 97

```
tctgtaattc attgagcagt tagctcattt gagataaagt caaatgccaa acactagctc      60
tgtattaatc ccc                                                         73
```

<210> SEQ ID NO 98
<211> LENGTH: 123
<212> TYPE: DNA
<213> ORGANISM: Homo sapiens

<400> SEQUENCE: 98

```
atggtataat ggttgactgg gtttctctgt atagtactgg catggtacgg agatgtttca      60
cgaagtttgt tcatcagact cctgtgcaac tttcccaatg tggcctaaaa atgcaacttc     120
ttt                                                                   123
```

<210> SEQ ID NO 99
<211> LENGTH: 132
<212> TYPE: DNA
<213> ORGANISM: Homo sapiens

<400> SEQUENCE: 99

```
atattttgtg ttgatcatta tttccattct taatgtgaaa aaagtaatt atttatactt      60
attataaaaa gtatttgaaa tttgcacatt taattgtccc taatagaaag ccacctattc    120
tttgttggat tt                                                         132
```

<210> SEQ ID NO 100
<211> LENGTH: 189
<212> TYPE: DNA
<213> ORGANISM: Homo sapiens

<400> SEQUENCE: 100

```
tgaggccgac agcgtcttca gcggcttcct catcttccca tctgcctgag ccagggaagg      60
accccctccc ccacccacct ctctggcttc catgctccgc ctgtaaaatg ggggcgctat     120
```

```
tgcttcagct gctgaaggga gggggctggc tttgagagcc ccaggactgg ctgccccgtg     180
acacatgct                                                             189

<210> SEQ ID NO 101
<211> LENGTH: 265
<212> TYPE: DNA
<213> ORGANISM: Homo sapiens

<400> SEQUENCE: 101
aaaagggtca catttaccag ggctttgagg ccgacagcgt cttcagcggc ttcctcatct      60
tcccatctgc ctgagccagg gaaggacccc ctcccccacc cacctctctg gcttccatgc     120
tccgcctgta aaatggggggc gctattgctt cagctgctga agggaggggg ctggctttga    180 gagcccagg actggctgcc ccgtgacaca tgctttaaga gctcgttttt ttagacctct      240
tcctggaata aacatctgtg tctgt                                           265

<210> SEQ ID NO 102
<211> LENGTH: 174
<212> TYPE: DNA
<213> ORGANISM: Homo sapiens

<400> SEQUENCE: 102 cacccccagga ctttatcaac ttgttcaagt tctgaatccc agcacatgac aacacttcag     60
aagggtcccc ctgctgactg gagagctggg aatatggcat ttggacactt catttgtaaa    120
tagtgtacat tttaaacatt ggctcgaaac ttcagagata agtcatggag agga          174

<210> SEQ ID NO 103
<211> LENGTH: 239
<212> TYPE: DNA
<213> ORGANISM: Homo sapiens

<400> SEQUENCE: 103
gggatacagt tccatattgc cttaaacctc cttgttttag acacactaac atttatacca     60
aattgcagat tattttgcag agagggaatt gcatgtttgt gttgtatatt tagtatgaac    120 tttttttcaga atataatatt ttttagttat caaaagtagt tggaaaacat ttgcaagact   180
atgaacatag aattgctgct tttatatttt aactgcagat tgtgaatttc actgcctta    239

<210> SEQ ID NO 104
<211> LENGTH: 110
<212> TYPE: DNA
<213> ORGANISM: Homo sapiens

<400> SEQUENCE: 104
gacttcttgc ttgtacatat aggagcaata ctattatatt atgtagtccg ttaacactac     60
ttaaaagttt agggttttct cttggttgta gagtggccca gaattgcatt               110

<210> SEQ ID NO 105
<211> LENGTH: 292
<212> TYPE: DNA
<213> ORGANISM: Homo sapiens

<400> SEQUENCE: 105
acagtgttgt atgaggtttg aggattttga tccaagctgg tcccactcag tccatagcag     60
agaatgaaag ggcccagaga gggtggtgac ctctgcctga agtcacacag tgagtcgagg    120
acagggaggt gaccccaggt ttctatgtgt agggcgggag gatgttttgg gacacagttc    180
```

```
aattctcatt tgtcacacac tttggctatt agagatcaac cccttcgctc ctgtgtcttg    240
caatggcagc cttggcaaac gctaaatgaa atcgtgaca acacttgtgt ta            292

<210> SEQ ID NO 106
<211> LENGTH: 223
<212> TYPE: DNA
<213> ORGANISM: Homo sapiens

<400> SEQUENCE: 106
tcatgttaaa gagccgtgtc tcccgccagc actcctcacc ccggtatgaa tgtgtttcct    60
ccacattgta tatccttcca ccctctggct gcctagatca gtaaataaaa ttgatgtaat    120
ataatttata agtaacactg ttgaaaccct gatcccagtg gaggctgtaa cccacctgcc    180
cccgcaccac cccctgacc cctgttaccg catttgtgtg tat                      223

<210> SEQ ID NO 107
<211> LENGTH: 275
<212> TYPE: DNA
<213> ORGANISM: Homo sapiens

<400> SEQUENCE: 107
gttatggtgc taatgtactt tcacttttaa actctagatc agaattgttg acttgcattc    60
agaacataaa tgcacaaaat ctgtacatgt ctcccatcag aaagattcat tggcatgcca    120
caggggattt tcctccttca tcctgtaaag gtcaacaata aaaaccaaat tatggggctg    180
cttttgtcac actagcatag agaatgtgtt gaaatttaac tttgtaagct tgtatgtggt    240
tgttgatctt ttttttcctt acagacaccc ataat                              275

<210> SEQ ID NO 108
<211> LENGTH: 196
<212> TYPE: DNA
<213> ORGANISM: Homo sapiens

<400> SEQUENCE: 108
tctggcccgc aatactgtag gaacaagcat gatcttgtta ctgtgatatt taaatatcc     60 acagtactca cttttccaa atgatcctag taattgccta gaaatatctt tttcttacct     120
gttatttatc aatttttccc agtattttta tacggaaaaa attgtattga aaacacttag    180
tatgcagttg ataaga                                                   196

<210> SEQ ID NO 109
<211> LENGTH: 129
<212> TYPE: DNA
<213> ORGANISM: Homo sapiens

<400> SEQUENCE: 109
gctgcggaga gctcatggaa ggcgagtggg aacccggctg cctgcctttt ttttgatcc    60 agaccctcgg cacctgctac ttaccaactg gaaaatttta tgcatcccat gaagcccaga   120
tacacaaaa                                                          129

<210> SEQ ID NO 110
<211> LENGTH: 296
<212> TYPE: DNA
<213> ORGANISM: Homo sapiens

<400> SEQUENCE: 110
tgaggatgtc accaattaac cagaaatcca gttatttcc gccctcaaaa tgacagccat    60
ggccggccgg gtgcttttgg gggctcgtcg gggggacagc tccactttga ctggcacagt    120
```

```
ctttgcatgg agacttgagg agggagggct tgaggttggt gaggttaggt gcgtgtttcc    180
tgtgcaagtc aggacatcag tttgattaaa ggtggtgcca atttatttac atttaaactt    240
gtcagggtat aaaatgacat cccattaatt atattgttaa tcaatcacgt gtatag        296

<210> SEQ ID NO 111
<211> LENGTH: 108
<212> TYPE: DNA
<213> ORGANISM: Homo sapiens

<400> SEQUENCE: 111
acatgcagta ctgtataccc cccatccctc cctcggtcca ctgaacttca gagcagttcc    60
cattcctgcc ccgcccatct ttttgtgtct cgctgtgata gatcaata                 108

<210> SEQ ID NO 112
<211> LENGTH: 243
<212> TYPE: DNA
<213> ORGANISM: Homo sapiens

<400> SEQUENCE: 112
acaaaagagc cagagttctg gacccatgtt tggagcattt gtagccttat ttttttgcgt    60
gtgaatcttt taccctgaaa aaaagccata atgaattaag ccagactgac cacttgcttg    120
gagtgtgtgc ttgaaaaaac cagagcaata ctgttgggta ttgtatcagg cttcagtaca    180
aactggtaac accaatgtgg atcctgacag ctttcagttt tagcaaaaat acacgtgaaa    240
tct                                                                   243

<210> SEQ ID NO 113
<211> LENGTH: 52
<212> TYPE: DNA
<213> ORGANISM: Homo sapiens

<400> SEQUENCE: 113
agtgcaacgt attcaagtcc tcaatatcct gatcataata ccatgctata gg             52

<210> SEQ ID NO 114
<211> LENGTH: 294
<212> TYPE: DNA
<213> ORGANISM: Homo sapiens

<400> SEQUENCE: 114
tccatcaggg ccagattttc cacgtctcca tctcagtaca caatcattta atatttccct    60
gttttacccc tattcaagca actagaggcc agaaaatggg caaattatca ctaacaggtc    120
tttgactcag gttccagtag ttcattttaa tgcctagatt cttttgtggt tgttgctggc    180
ccaatgagtc cctagtcaca tcccctgcca gagggagttt ttttttgtg agagacactg     240 taaacgacac aagagaacaa gaataaaaca ataactgtgt gtgttttggc tgag           294

<210> SEQ ID NO 115
<211> LENGTH: 277
<212> TYPE: DNA
<213> ORGANISM: Homo sapiens

<400> SEQUENCE: 115
acaggttagt tcagtcaaag caggcaaccc ccttgtgggc actgaccctg ccactggggt    60
catggcggtt gtggcagctg ggaggtttg gccccaacag ccctcctgtg cctgcttccc     120
tgtgtgtcgg ggtcctccag ggagctgacc cagaggtgga ggccacggag gcagggtctc    180
```

```
tggggactgt cgggggggtac agagggagaa ggctctgcaa gagctccctg gcaataccccc    240 cttgtgtaat tgctttgtgt gcgacaggga ggaagtt                               277

<210> SEQ ID NO 116
<211> LENGTH: 173
<212> TYPE: DNA
<213> ORGANISM: Homo sapiens

<400> SEQUENCE: 116
ggcttcctac cttgcaacaa ataattgca ccaactcctt agtgccgatt ccgcccccag        60
agagtcctgg agccacagtt ttttttgctt tgcattgtag gagagggaat aagtgctaga      120
gactatgtcg ctttcctgag ctaccgagag cgctcgtgaa ctggaatcaa ctg            173

<210> SEQ ID NO 117
<211> LENGTH: 217
<212> TYPE: DNA
<213> ORGANISM: Homo sapiens

<400> SEQUENCE: 117
agaagtggta aaagtggata atcttgtctt gtactttatt ttagaggaaa agctgtcagt       60
ttttcactgc tgaatatgat gttaactatg aactttttat acatgtattt actatgttga     120
ggtaatttcc ttttactcct ggtttaagtg tttttgttt tttttgttt ttttttttt         180 ttaaatcatg gaaggacttg ggttttatca aatgtct                              217

<210> SEQ ID NO 118
<211> LENGTH: 286
<212> TYPE: DNA
<213> ORGANISM: Homo sapiens

<400> SEQUENCE: 118
actttgccgg cgagcacacc gcctacccgc acggctgggt ggagacggcg gtcaagttgg       60
cgctgcgcgc cgccatcaag atcaacagcc ggaaggggcc tgcatcggac acggccagcc     120
ccgaggggca cgcatttgac atggaggggc aggggcatgt gcatggggtg ccagcagcc      180 cctcgcatga cctggcaaag gaagaaggca gccaccctcc agtccaaggc cagttatctt     240
tccaaaacac gacccacacg aggacctcgc attaaagtat tttcgg                    286

<210> SEQ ID NO 119
<211> LENGTH: 168
<212> TYPE: DNA
<213> ORGANISM: Homo sapiens

<400> SEQUENCE: 119
catttcatgt ttggcgggca tgtgagtgca caagatggaa agagcgattg gagcatcctg       60
gtataattac ccccattgtg cttttaatgg aaatttcaaa ggacgggagt attttgttgg     120
ttggtgtcca ggtttgtggc actgttccaa gaggccttac acacacac                  168

<210> SEQ ID NO 120
<211> LENGTH: 150
<212> TYPE: DNA
<213> ORGANISM: Homo sapiens

<400> SEQUENCE: 120
aatgttcata ggttctcaac cctcaccccc caccacggga gactagagct gcaggatccc       60
aggggagggg tctctcctcc caccccaagg catcaagccc ttctccctgc actcaataaa     120
ccctcaataa atattctcat tgtcaatcaa                                      150
```

<210> SEQ ID NO 121
<211> LENGTH: 177
<212> TYPE: DNA
<213> ORGANISM: Homo sapiens

<400> SEQUENCE: 121
ctactgccag ggaaatgcta cattattttt ctaattggaa gtataattag agtgatgttg    60
gtagggtaga aaagaggga gtcacttgat gctttcaggt taatcagagc tatgggtgct    120
acaggcttgt ctttctaagt gacatattct tatctaattc tcagatcagg ttttgaa     177

<210> SEQ ID NO 122
<211> LENGTH: 124
<212> TYPE: DNA
<213> ORGANISM: Homo sapiens

<400> SEQUENCE: 122
ggcagcatac tgagaccctg cctttaaaaa caaacagaac aaaaacaaaa caccagggac    60
acatttctct gtcttttttg atcagtgtcc tatacatcga aggtgtgcat atatgttgaa   120
tgac                                                                124

<210> SEQ ID NO 123
<211> LENGTH: 64
<212> TYPE: DNA
<213> ORGANISM: Homo sapiens

<400> SEQUENCE: 123
atgttcatag gttctcaacc ctcaccccccc accacgggag actagagctc aggatcccag    60
ggga                                                                 64

<210> SEQ ID NO 124
<211> LENGTH: 167
<212> TYPE: DNA
<213> ORGANISM: Homo sapiens

<400> SEQUENCE: 124
tctgagcggg tcatggggca acacggttag cggggagagc acggggtagc cggagaaggg    60
cctctggagc aggtctggag gggccatggg gcagtcctgg gtgtggggac acagtcgggt   120
tgacccaggg ctgtctccct ccagagcctc cctccggaca atgagtc                 167

<210> SEQ ID NO 125
<211> LENGTH: 36
<212> TYPE: DNA
<213> ORGANISM: Homo sapiens

<400> SEQUENCE: 125
caccactaaa agatcgcagt ttgcctggtg cagtgg                              36

<210> SEQ ID NO 126
<211> LENGTH: 129
<212> TYPE: DNA
<213> ORGANISM: Homo sapiens

<400> SEQUENCE: 126
aatgcatatg gaggtaggct gaaaagaatg taattttttat tttctgaaat acagatttga    60
gctatcagac caacaaacct tccccctgaa aagtgagcag caacgtaaaa acgtatgtga   120
agcctctct                                                            129

<210> SEQ ID NO 127
<211> LENGTH: 150
<212> TYPE: DNA
<213> ORGANISM: Homo sapiens

<400> SEQUENCE: 127
aatgttcata ggttctcatc cctcaccccc caccacggga gactagagct gcaggatccc    60
aggggagggg tctctcctcc caccccaagg catcaagccc ttctccctgc actcaataaa   120
ccctcaataa atattctcat tgtcaatcaa                                    150

<210> SEQ ID NO 128
<211> LENGTH: 83
<212> TYPE: DNA
<213> ORGANISM: Homo sapiens

<400> SEQUENCE: 128
ttccaccatc aaatgctgta gaatgcttgg cactccctaa ccaaatgctg tctccataat    60
gccactggtg ttaagatata ttt                                            83

<210> SEQ ID NO 129
<211> LENGTH: 121
<212> TYPE: DNA
<213> ORGANISM: Homo sapiens

<400> SEQUENCE: 129
atataccata ggctaaaact aaggctttca ctctagaatg caaagctgtt ttgcagctgt    60
tttcccttaa agatgtcctg ttgctttagt gatatttaga cccctctcag ttaagaaatg   120
c                                                                   121

<210> SEQ ID NO 130
<211> LENGTH: 257
<212> TYPE: DNA
<213> ORGANISM: Homo sapiens

<400> SEQUENCE: 130
ttatctgaag gttaaagggc aagtgtttgg tatagaagag cagtatgtgt taagaaaaga    60
aaaatattgg ttcacgtaga gtgcaaatta gaactagaaa gttttatacg attatcattt   120
tgagatgtgt taaagtaggt tttcactgta aaatgtatta gtgttctgc attgccatag   180 ggcctggtta aaactttctc ttaggtttca ggaagactgt cacatacagt aagcttttt   240 ccttctgact tataata                                                  257

<210> SEQ ID NO 131
<211> LENGTH: 285
<212> TYPE: DNA
<213> ORGANISM: Homo sapiens

<400> SEQUENCE: 131
caagacctag gctcatggac gagatgggaa ggcacaggga gaagggataa ccctacaccc    60 agacccagg ctggacatgc tgactgtcct ctcccctcca gcctttggcc ttggcttttc   120
tagcctattt acctgcaggc tgagccactc tcttcccttt cccagcatc actccccaag   180 gaagagccaa tgttttccac ccataatcct ttctgccgac ccctagttcc ctctgctcag   240
ccaagcttgt tatcagcttt cagggccatg gttcacatta gaata                   285

<210> SEQ ID NO 132
<211> LENGTH: 105

```
<212> TYPE: DNA
<213> ORGANISM: Homo sapiens

<400> SEQUENCE: 132
gtatttattg agtcacggat tattgtgcat caagcaattg ttaatatgac ctggtcctat    60
ggggtagaac ttaggaaaaa taaagttggt tcttattcaa tattt                  105

<210> SEQ ID NO 133
<211> LENGTH: 205
<212> TYPE: DNA
<213> ORGANISM: Homo sapiens

<400> SEQUENCE: 133
atggacccac cttactggcc agtctgcatc cttgcctaga ccattctccc caccagatgg    60
acttctcctc cagggagccc accctgaccc accccactg cacccctcc ccatgggttc    120 tctccttcct ctgaacttct ttaggagtca ctgcttgtgt ggttcctggg acacttaacc   180
aatgccttct ggtactgcca ttctt                                         205

<210> SEQ ID NO 134
<211> LENGTH: 189
<212> TYPE: DNA
<213> ORGANISM: Homo sapiens

<400> SEQUENCE: 134
ctggttttag cattattaga ataagacttt atacattaac taaagtggag ctttaatcac    60 tataaaagc aaaagtatct atagacacag acacttgcct atacagagac ataaccacac   120
acactcagag gatagtgaac aaatctgtct ttgacttacg acccattttg caagacttaa   180
agccggaag                                                           189

<210> SEQ ID NO 135
<211> LENGTH: 248
<212> TYPE: DNA
<213> ORGANISM: Homo sapiens

<400> SEQUENCE: 135
atgccctgag gccagttggc gagggtggc tcctgagggt ttttataccc tttgtttgct    60
aatgtttaat tttgcatcat aatttctaca ttgtccctga gtgtcagaac tataatttat   120
tccatttctc tctgtgtctg tgccaagaaa cgcaggctct gggcctgccc cttgcccagg   180
aggccttgcc agcctgtgtg cttgtgggaa caccttgtac ctgagcttac aggtaccaat   240
aaagaggc                                                            248

<210> SEQ ID NO 136
<211> LENGTH: 99
<212> TYPE: DNA
<213> ORGANISM: Homo sapiens

<400> SEQUENCE: 136
gcccgaatca tgacagtcag caacatgata cctggatcca gccattcctg aagcccaccc    60
tgcacctcat tccaactcct accgcgatac agacccaca                          99

<210> SEQ ID NO 137
<211> LENGTH: 250
<212> TYPE: DNA
<213> ORGANISM: Homo sapiens

<400> SEQUENCE: 137
```

```
gctataaagt gcttgaccag taatgtggtt gtaattttgt gtatgttccc ccacatcgcc      60
cccaacttcg gatgtgdggt caggaggttg aggttcacta ttaacaaatg tcataaatat     120
ctcatagagg tacagtgcca atagatattc aaatgttgca tgttgaccag agggatttta     180
tatctgaaga acatacacta ttaataaata ccttagagaa agattttgac ctggctttag     240
ataaaactgt                                                            250
```

<210> SEQ ID NO 138
<211> LENGTH: 55
<212> TYPE: DNA
<213> ORGANISM: Homo sapiens

<400> SEQUENCE: 138

```
atactggaaa cctaactgca atgtggatgt tttacccaca tgacttatta tgcat           55
```

<210> SEQ ID NO 139
<211> LENGTH: 237
<212> TYPE: DNA
<213> ORGANISM: Homo sapiens

<400> SEQUENCE: 139

```
agaagaccca cgtgctaggg gatgaggggc ttcctgggtc ctgttcccta ccccatttgt      60
ggtcacagcc atgaagtcac cgggatgaac ctatccttcc agtggctcgc tccctgtagc     120
tctgcctccc tctccatatc tccttcccct acacctccct ccccacacct ccctactccc     180
ctgggcatct tctggcttga ctggatggaa ggagacttag gaacctacca gttggcc        237
```

<210> SEQ ID NO 140
<211> LENGTH: 216
<212> TYPE: DNA
<213> ORGANISM: Homo sapiens

<400> SEQUENCE: 140

```
gaggcagagg cttgggtaaa ctcattccac aaaccctatg ggggctgcca cgtcacaggc      60
ccaaaggact cttcttcagc agcatctttg caaaatgtct ttctctcaat gaagagcata     120
tctggacgac tgtgcaatgc tgtgtgctcc cgggatcagt aacccttccg ctgttcctga     180
aataaccttt cataaagtgc tttgggtgcc attcca                               216
```

<210> SEQ ID NO 141
<211> LENGTH: 156
<212> TYPE: DNA
<213> ORGANISM: Homo sapiens

<400> SEQUENCE: 141

```
gatgtatagc tttagcttta gcctggcaac ctggagaatc cacatacctt gtgtattgaa      60
ccccaggaaa aggaagaggt cgaaccaacc ctgcggaagg agcatggttt caggagttta     120
ttttaagact gctgggaagg aaacaggccc cattttt                              156
```

<210> SEQ ID NO 142
<211> LENGTH: 151
<212> TYPE: DNA
<213> ORGANISM: Homo sapiens

<400> SEQUENCE: 142

```
ctgactctgg gttcgttggg gacatgagat tttattttttt gtgagtgaga ctgagggatc     60
gtagattttt acaatctgta tctttgacaa ttctgggtgc gagtgtgaga gtgtgagcag     120
ggcttgctcc tgccaaccac aattcaatga a                                    151
```

<210> SEQ ID NO 143
<211> LENGTH: 151
<212> TYPE: DNA
<213> ORGANISM: Homo sapiens

<400> SEQUENCE: 143
gcagaaatat gtaaccttag actcagccag tttcctctgc agctgctaaa actacatgtg    60
gccagctcca ttcttccaca ctgcgtacta catttcctgc cttttctttt cagtgttttt   120
ctaagactaa ataaatagca aactttcacc t                                  151

<210> SEQ ID NO 144
<211> LENGTH: 132
<212> TYPE: DNA
<213> ORGANISM: Homo sapiens

<400> SEQUENCE: 144
caactctaac cccacccacg ggagcctgga gctgcaggat cccaggggag gggtctctct    60
ccccatccca agtcatccag cccttctccc tgcactcatg aaaccccaat aaatatcctc   120
attgacaacc aa                                                       132

<210> SEQ ID NO 145
<211> LENGTH: 80
<212> TYPE: DNA
<213> ORGANISM: Homo sapiens

<400> SEQUENCE: 145
cctttgactt ctgaccctct catcctggat ggtgtgtggt ggcacaggaa ccccgcccc    60 aacttttgga ttgtaataaa                                               80

<210> SEQ ID NO 146
<211> LENGTH: 94
<212> TYPE: DNA
<213> ORGANISM: Homo sapiens

<400> SEQUENCE: 146
ctgggcttgg gtgcccatat aggaggtctg tatgttcacc aacagtgcgg aggggtcaca    60
cattgcaaaa cactgcccag aacagtaaaa agag                               94

<210> SEQ ID NO 147
<211> LENGTH: 264
<212> TYPE: DNA
<213> ORGANISM: Homo sapiens

<400> SEQUENCE: 147
atgagaatga tggttgaagg ttacatttta ggaaatgaag aaacttagaa aattaatata    60
aagacagtga tgaatacaaa gaagattttt ataacaatgt gtaaaatttt tggccaggga   120
aaggaatatt gaagttagat acaattactt acctttgagg gaataattg ttggtaatga   180 gatgtgatgt ttctcctgcc acctggaaac aaagcattga agtctgcagt tgaaaagccc   240
aacgtctgtg agatccagga aacc                                          264

<210> SEQ ID NO 148
<211> LENGTH: 286
<212> TYPE: DNA
<213> ORGANISM: Homo sapiens

<400> SEQUENCE: 148

```
taaagacgca tgttatggtg ctaatgtact ttcacttta aactctagat cagaattgtt      60
gacttgcatt cagaacataa atgcacaaaa tctgtacatg tctcccatca gaaagattca    120
ttggcatgcc acaggggatt ctcctccttc atcctgtaaa ggtcaacaat aaaaaccaaa    180 ttatgggggct gcttttgtca cactagcata gagaatgtgt tgaaatttaa ctttgtaagc   240
ttgtatgtgg ttgttgatct ttttttttcct tacagacacc cataat                  286
```

<210> SEQ ID NO 149
<211> LENGTH: 42
<212> TYPE: DNA
<213> ORGANISM: Homo sapiens

<400> SEQUENCE: 149

```
ccattcctcg ccctgtcccc acagccgagt cctgcatcag cc                        42
```

<210> SEQ ID NO 150
<211> LENGTH: 189
<212> TYPE: DNA
<213> ORGANISM: Homo sapiens

<400> SEQUENCE: 150

```
ttaccctcca aaagcaagta gccaaagccg ttgccaaacc ccacccataa atcaatgggc     60
cctttattta tgacgacttt atttattcta atatgatttt atagtattta tatatattgg   120
gtcgtctgct tcccttgtat ttttcttcct tttttgtaa tattgaaaac gacgatataa    180
ttattataa                                                            189
```

<210> SEQ ID NO 151
<211> LENGTH: 211
<212> TYPE: DNA
<213> ORGANISM: Homo sapiens

<400> SEQUENCE: 151

```
gtcaggtctt ggtaggtgcc tgcatctgtc tgccttctgg ctgacaatcc tggaaatctg     60
ttctccagaa tccaggccaa aaagttcaca gtcaaatggg gaggggtatt cttcatgcag   120
gagaccccag gccctggagg ctgcaacata cctcaatcct gtcccaggcc ggatcctcct   180
gaagcccttt tcgcagcact gctatcctcc a                                   211
```

<210> SEQ ID NO 152
<211> LENGTH: 211
<212> TYPE: DNA
<213> ORGANISM: Homo sapiens

<400> SEQUENCE: 152

```
gaaaaaactt tctctttgcc atttcttctt cttcttttt aactgaaagc tgaatccttc     60
catttcttct gcacatctac ttgcttaaat tgtgggcaaa agagaaaaag aaggattgat   120
cagagcattg tgcaatacag tttcattaac tccttccccc gctcccccaa aaatttgaat   180
ttttttttca acactcttac acctgttatg g                                   211
```

<210> SEQ ID NO 153
<211> LENGTH: 89
<212> TYPE: DNA
<213> ORGANISM: Homo sapiens

<400> SEQUENCE: 153

```
tgactgaatt gctgacccctt caagctctgt cctatccat tacctcaaag cagtcattcc      60
ttagtaaagt ttccaacaaa tagaaatta                                        89
```

<210> SEQ ID NO 154
<211> LENGTH: 162
<212> TYPE: DNA
<213> ORGANISM: Homo sapiens

<400> SEQUENCE: 154

```
gcattctcaa gaggtcgtgc caatcagcca ctgaaaggaa aggcatcact atggactttc      60
tctattttaa aatggtaaca atcagaggaa ctataagaac acctttagaa ataaaaatac     120
tgggatcaaa ctggcctgca aaaccatagt cagttaattc tt                        162
```

<210> SEQ ID NO 155
<211> LENGTH: 86
<212> TYPE: DNA
<213> ORGANISM: Homo sapiens

<400> SEQUENCE: 155

```
atcatttcat agtcatttat gtttcatcgg tcctcatgtg tactagtgcg ttattttact      60
tatactcccg gatatcatat tattta                                           86
```

<210> SEQ ID NO 156
<211> LENGTH: 233
<212> TYPE: DNA
<213> ORGANISM: Homo sapiens

<400> SEQUENCE: 156

```
gaaacacaag agacttaaag gacaggagga ggagatggcc ataggagagg agggttcctc      60
ttaggtcaga tggaggttct cagagccaag tcctccctct ctactggagt ggaaggtcta    120
ttggccaaca atcctttctg cccacttccc cttccccaat tactattccc tttgacttca    180
gctgcctgaa acagccatgt ccaagttctt cacctctatc caaagaactt gat           233
```

<210> SEQ ID NO 157
<211> LENGTH: 146
<212> TYPE: DNA
<213> ORGANISM: Homo sapiens

<400> SEQUENCE: 157

```
atgttcatag gttctcaacc ctcaccccca ccacgggaga ctagagctgc aggatcccag      60
gggaggggtc tctcctccca ccccaaggca tcaagcccctt ctccctgcac tcaataaacc    120
ctcaataaat attctcattg tcaagg                                          146
```

<210> SEQ ID NO 158
<211> LENGTH: 265
<212> TYPE: DNA
<213> ORGANISM: Homo sapiens

<400> SEQUENCE: 158

```
aacaaaatat ttctcccta gtgagagaaa gaggtcctca gagagtagca gctcacataa      60
ctgggaccag aggaagaagc aacacattgt cttctccaaa ctccaagaat gaaaaggctc    120
tgggccgcaa aataaactcc tgggaatcat caaggagtgg gcattcattc ctgagcaact    180
tgcacttgag gaatggtgaa ctggtcatcc atgaaaaagg gttttactac atctattccc    240
aaacatactt tcgatttcag gagga                                          265
```

<210> SEQ ID NO 159
<211> LENGTH: 186
<212> TYPE: DNA

<213> ORGANISM: Homo sapiens

<400> SEQUENCE: 159

```
gctgagcaaa gcagactacg agaaacacaa agtctacgcc tgcgaagtca cccatcaggg      60
cctgagctcg cccgtcacaa agagcttcaa caggggagag tgttagaggg agaagtgccc     120
ccacctgctc ctcagttcca gcctgacccc ctcccatcct ttggcctctg acccttttc      180
cacagg                                                                186
```

<210> SEQ ID NO 160
<211> LENGTH: 41
<212> TYPE: DNA
<213> ORGANISM: Homo sapiens

<400> SEQUENCE: 160

```
tacaagacca cgcctcccgt gctggactcc gacggctcct t                          41
```

<210> SEQ ID NO 161
<211> LENGTH: 45
<212> TYPE: DNA
<213> ORGANISM: Homo sapiens

<400> SEQUENCE: 161

```
aacagaaaag aaactgtaga ccttgggaca atcaacattt aaata                      45
```

<210> SEQ ID NO 162
<211> LENGTH: 211
<212> TYPE: DNA
<213> ORGANISM: Homo sapiens

<400> SEQUENCE: 162

```
gaaaaaactt tctctttgcc atttcttctt cttcttttt aactgaaagc tgaatccttc       60
catttcttct gcacatctac ttgcttaaat tgtgggcaaa agagaaaaag aaggattgat     120
cagagcattg tgcaatacag tttcattaac tccttccctc gctcccccaa aaatttgaat     180
tttttttca acactcttac acctgttatg g                                     211
```

<210> SEQ ID NO 163
<211> LENGTH: 105
<212> TYPE: DNA
<213> ORGANISM: Homo sapiens

<400> SEQUENCE: 163

```
ggacctgaag ggtgacatcc caggaggggc ctctgaaatt tcccacaccc cagcgcctgt      60
gctgaggact ccctccatgt ggccccaggt gccaccaata aaaat                     105
```

<210> SEQ ID NO 164
<211> LENGTH: 175
<212> TYPE: DNA
<213> ORGANISM: Homo sapiens

<400> SEQUENCE: 164

```
tcatgatttg tgtagcgtgg aatgtgtttg ctcaatgtga agggttttca ttgctcaatt      60
tctctgtgta agtcttttcc ttaaggtaat aaaccatcag caaagtcaca tactggagtt     120
ggtggcttttt tttgtacagg cagttgttat gagacaatga tggagcattg agcat         175
```

<210> SEQ ID NO 165
<211> LENGTH: 65
<212> TYPE: DNA
<213> ORGANISM: Homo sapiens

<400> SEQUENCE: 165
ttaactccat atgtgttcct cttgttttaa ttttgtcaac cagtgcaagt gaccgacaaa    60
attcc                                                                65

<210> SEQ ID NO 166
<211> LENGTH: 114
<212> TYPE: DNA
<213> ORGANISM: Homo sapiens

<400> SEQUENCE: 166
aaggagctga cacacggaga gtcacaggct atacagctgc ttcgagcagc gggaatgttt    60
gtcttgggat tagatgctga cgtgtggtga aatgttacag agagcccaga ggaa         114

<210> SEQ ID NO 167
<211> LENGTH: 100
<212> TYPE: DNA
<213> ORGANISM: Homo sapiens

<400> SEQUENCE: 167 tgccccctt aaggctagag gtgagcatgt ccctcacaat tgcacatgtc aagccatcag    60
caaggcgcat cacacaaaag gcaccaagac gtgaaacttt                          100

<210> SEQ ID NO 168
<211> LENGTH: 273
<212> TYPE: DNA
<213> ORGANISM: Homo sapiens

<400> SEQUENCE: 168
gagtctgtga ccgatgcaat tctacagaca gaccagattt tcacagaaaa ggaaaaggag    60
attgaagtgg aatgtgtaaa agctgaatct gcacaggctt cagcaaaaat ggtggaggaa   120
atgcaaataa agtatcagca gatgatggaa gagaaagaga agagttatca agaacatgtg   180
aaacaattga ctgagaagat ggagagggag agggcccagt tgctggaaga gcaagagaag   240
accctcacta gtaaacttca ggtatccaaa tgc                                273

<210> SEQ ID NO 169
<211> LENGTH: 36
<212> TYPE: DNA
<213> ORGANISM: Homo sapiens

<400> SEQUENCE: 169
agcaggatca agggccggaa ataaaggctg ttgtaa                              36

<210> SEQ ID NO 170
<211> LENGTH: 109
<212> TYPE: DNA
<213> ORGANISM: Homo sapiens

<400> SEQUENCE: 170
agaattattg catttgagct ccgctcccct tccgaaccaa ggtataaaag taaatcaagc    60
cccttcctcg gggccgagag aattttggaa agtcaagcct tctcttggc              109

<210> SEQ ID NO 171
<211> LENGTH: 115
<212> TYPE: DNA
<213> ORGANISM: Homo sapiens

<400> SEQUENCE: 171

```
gcatgctcag tctttcctc ttatctacaa tacaaagggt ttgtctgaaa agtctggttt    60
tttttctttt tacaaatgta ccttagctgc atcaacagga gtaagatgta gaaaa        115
```

<210> SEQ ID NO 172
<211> LENGTH: 175
<212> TYPE: DNA
<213> ORGANISM: Homo sapiens

<400> SEQUENCE: 172

```
atagagagta gatcagcgat tgtgaggagg taggggttaa agaaggattt tactacaaag    60
gtgcaatgca aggaagtttt gggggtgatg aactgtcctg tatcccgatt gtggtggcag   120
ttacatgaat ctatatttgt gttaagatct atagatctgt actccctcaa aaagt        175
```

<210> SEQ ID NO 173
<211> LENGTH: 279
<212> TYPE: DNA
<213> ORGANISM: Homo sapiens

<400> SEQUENCE: 173

```
gtaggtttgg gagtataacg gtcacccagg gaggggtga agacggagaa gacttacata    60
gcacggtcag gttagggctg gacagatgag gaagagctag caaaggggc ttgaggagca   120 gtggccacta agacaggagt gtgacatttt agaagccaaa agaagaccat gtaattcaag   180
ggagaggtat gatttgctgg gtcagatcta aaaataaatc acacgttttt ttaaactgta   240
gtaattaacc actgaaaact tatgagtgat ccaatatta                          279
```

<210> SEQ ID NO 174
<211> LENGTH: 74
<212> TYPE: DNA
<213> ORGANISM: Homo sapiens

<400> SEQUENCE: 174

```
cgatatgact tccatgtaaa cgttcatcca ctctgcctgc ttacaccctg ccctcatgct    60
aatgtaataa actc                                                     74
```

<210> SEQ ID NO 175
<211> LENGTH: 48
<212> TYPE: DNA
<213> ORGANISM: Homo sapiens

<400> SEQUENCE: 175

```
gccgagatcg tgctagggtg actggagcaa aacccttca agaaaaga                 48
```

<210> SEQ ID NO 176
<211> LENGTH: 164
<212> TYPE: DNA
<213> ORGANISM: Homo sapiens

<400> SEQUENCE: 176

```
gtgtggatgc taaggtgttt gttttgtttt gtatttttat gtagcgcgtg ggtattgtgc    60
ctagaaatga agtcattatt agggatttaa atatgcaact catggagtgg atgagaccag   120
ctagaaagat aatagagtgt gaagaggaga tcggaaattc aata                    164
```

<210> SEQ ID NO 177
<211> LENGTH: 34
<212> TYPE: DNA
<213> ORGANISM: Homo sapiens

<400> SEQUENCE: 177

```
attccaggac tttggcgcct tcaccgggag catg                                    34
```

<210> SEQ ID NO 178
<211> LENGTH: 32
<212> TYPE: DNA
<213> ORGANISM: Homo sapiens

<400> SEQUENCE: 178

```
cacaaagctc tgtcaataag tgatacatgt tt                                      32
```

<210> SEQ ID NO 179
<211> LENGTH: 141
<212> TYPE: DNA
<213> ORGANISM: Homo sapiens

<400> SEQUENCE: 179

```
atttttgcct ttccgtttct gtctatgatg taggcttctg aggagaacca agaagcttgg        60
ctttagtggt agaatgacag aacttaggga tcccttgcag gctagaacaa agttctgacc       120
cttagaccaa atctttatgt t                                                 141
```

<210> SEQ ID NO 180
<211> LENGTH: 211
<212> TYPE: DNA
<213> ORGANISM: Homo sapiens

<400> SEQUENCE: 180

```
gtttgtgtgg gaactttgca agtcagtttc cctgtatgaa gtgatggaga gagtgattaa        60
gatactgagc tttctctgtg ttcttgccgt taaccattgc cggtttgtgg gagattaaga       120
agtcgatgcg ttttatggag aattaattta ttttgatata gacagatgga cgggtcatga       180
aaatttgttg acatacttta ctaaactgct a                                      211
```

<210> SEQ ID NO 181
<211> LENGTH: 127
<212> TYPE: DNA
<213> ORGANISM: Homo sapiens

<400> SEQUENCE: 181

```
tttttttagtt gccaacagtt gtattttttgc tgattattta tgaccttaaa taatatattt      60
ttttttttaa gaagacattt tgttacataa ggaaaacttt tttattcaat ggaataaatt       120
atggcat                                                                 127
```

<210> SEQ ID NO 182
<211> LENGTH: 251
<212> TYPE: DNA
<213> ORGANISM: Homo sapiens

<400> SEQUENCE: 182

```
gaacaggagc aactactaaa agagggattt caaaagaaa gcagaataat gaaaaatgag         60
atacaggatc tccagacgaa aatgagacga cgaaaggcat gtaccataag ctaaagacca       120
gagccttcct gtcacccta accaaggcat aattgaaaca attttagaat ttggaacaag        180
cgtcactaca tttgataata attagatctt gcatcataac accaaaagtt tataaaggca      240
tgtggtacaa t                                                            251
```

<210> SEQ ID NO 183
<211> LENGTH: 248
<212> TYPE: DNA

<213> ORGANISM: Homo sapiens

<400> SEQUENCE: 183

| gcaagcacac gcagaaggca cacagggaca ggacgcccca tggagccccg aattgaccct | 60 |
| cactgcctcc aaagcccaga gcctgcctgt cagcccagct ggagggcccg aggctgcagg | 120 |
| gtgtcctccc acagtcccgc tgtttcctgt gcattcgtga cccgcttccc tcccaccctg | 180 |
| tctcctgtct ccatcgttgg attatctttg aaccccttg tgtggatcat tttgagccgc | 240 |
| ctggcctt | 248 |

<210> SEQ ID NO 184
<211> LENGTH: 71
<212> TYPE: DNA
<213> ORGANISM: Homo sapiens

<400> SEQUENCE: 184

| tattgcccgg ctcctagaat ttatttattt cctgacttac agcaagcgag ttatcgtctt | 60 |
| ctgtattttg t | 71 |

<210> SEQ ID NO 185
<211> LENGTH: 163
<212> TYPE: DNA
<213> ORGANISM: Homo sapiens

<400> SEQUENCE: 185

| ctttcattgg aagttcatca ctgttaggcg ttatcttgag tattataaca aagcaaatcc | 60 |
| acaagtattc aatataagat taggaaaaaa attcctgcga tactttgttg tcaaacactt | 120 |
| gccactgata gacgttattt tagcttttaa ggcctgtcac att | 163 |

<210> SEQ ID NO 186
<211> LENGTH: 258
<212> TYPE: DNA
<213> ORGANISM: Homo sapiens
<220> FEATURE:
<221> NAME/KEY: misc_feature
<222> LOCATION: (61)..(61)
<223> OTHER INFORMATION: n is a, c, g, or t

<400> SEQUENCE: 186

| atggagtata agctgtttgt agtcaggcct ggagtaatga gggtacctaa atactgaagg | 60 |
| nattttatg cagattgact gaaacctgaa tcaaattgga aggagagggc tgaattttga | 120 |
| tagactggaa gtattagaga attttctata ctttgactca aggaatggtc aacttttagg | 180 |
| aaaagcaact atattatgtc tgttaagatc atagaatctt aacctgaaag ggaccttgga | 240 |
| gactatttag tacaactc | 258 |

<210> SEQ ID NO 187
<211> LENGTH: 89
<212> TYPE: DNA
<213> ORGANISM: Homo sapiens

<400> SEQUENCE: 187

| ttttgaatga actctgagtc agttgaaata gggtaccatc taggtcagtt taagaagagt | 60 |
| cagctcagag aaagcaagca taagggaaa | 89 |

<210> SEQ ID NO 188
<211> LENGTH: 193
<212> TYPE: DNA
<213> ORGANISM: Homo sapiens

```
<220> FEATURE:
<221> NAME/KEY: misc_feature
<222> LOCATION: (120)..(125)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t

<400> SEQUENCE: 188
gaagaaagct aactcagtac actaagagtg atttacatgc ctgcaaataa tttgtgtctg    60
gggtcttgac cctccccaaa tgccttgtta tttatatctc tgcttttaga taacagatgn   120
nnnnntntct atgggcttgt accggcagag gcaacagcag gtccttaaga ctccccaggt   180
gccatgatga aaa                                                      193

<210> SEQ ID NO 189
<211> LENGTH: 173
<212> TYPE: DNA
<213> ORGANISM: Homo sapiens

<400> SEQUENCE: 189
gtaccatctt acatgcttaa ataactccac atttatttgt gtttattact ctgtgttata    60
aatatacatt tgttggtctc tctcttggat tattttgttt ctttgtcctg taactaccac   120
tgaaagggtg caatacagct ttcttgaaat gtgtattgaa cggatgaatg tat          173

<210> SEQ ID NO 190
<211> LENGTH: 265
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, or t

<400> SEQUENCE: 190
gattcggagt cttgattttg caaaggtaac aaaagacatg nttttttata agacttttca    60
tcataagttt attttattca acagaagcaa aatctaatat aatggaaaaa ataaagatct   120
gtgataaatc tgatctgtgt ggataaacac aattagaaag atttaaagat taagtattga   180
aacaaactac caaatatttt taatactgat ttgtaaaaat ttcagtacat ttttcttctt   240
tgcttaattc tactgggtcc tgttt                                         265

<210> SEQ ID NO 191
<211> LENGTH: 217
<212> TYPE: DNA
<213> ORGANISM: Homo sapiens

<400> SEQUENCE: 191
gttcccagtg acacttcaga gagctggtag ttagtagcat gttgagccag gcctgggtct    60
gtgtctcttt tctctttctc cttagtcttc tcatagcatt aactaatcta ttgggttcat   120
tattggaatt aacctggtgc tggatatttt caaattgtat ctagtgcagc tgattttaac   180
aataactact gtgttcctgg caatagtgtg ttctgat                            217

<210> SEQ ID NO 192
<211> LENGTH: 168
<212> TYPE: DNA
<213> ORGANISM: Homo sapiens

<400> SEQUENCE: 192
```

```
gatacactat acaatcctat gaccaatctc atctacaact ttattcaaat tttatagagg    60
ctgaggtgga aggatcactt gagtttgaaa ccagcctggg caacatagtg agacccgtc    120 tctacaaaaa gtaggaaaaa aaaaatagcg aggtgttgtg gtacacgc                168

<210> SEQ ID NO 193
<211> LENGTH: 115
<212> TYPE: DNA
<213> ORGANISM: Homo sapiens

<400> SEQUENCE: 193
ttctagtaat tatcaattgt cctggtctgg ctgcttagag tatcagtttg ctcaaaattg    60
cttgaatcat taaagcaaat actaattgtg agcattgacc agatcttaag ttaaa        115

<210> SEQ ID NO 194
<211> LENGTH: 193
<212> TYPE: DNA
<213> ORGANISM: Homo sapiens
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t

<400> SEQUENCE: 194
tgtctatggc tgtttttgtg caaaatggca gagttgggtt cagagttagc aacagagagc    60
ttgtagcctg caagcctaga gtatttacta tctggatttc tacaaaaaaa aaaaaaaaaa   120
aatttggggg gggcccgtaa cccaatncgc ccctatagtg agtngtatta caatccacct   180
ggccgcgttt tac                                                     193

<210> SEQ ID NO 195
<211> LENGTH: 233
<212> TYPE: DNA
<213> ORGANISM: Homo sapiens
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 195
tggagtaaca cccagatctc tgcagcagtt aagcntgggg gcctagaact agnctagagn    60
tagaagaagg gacaaatgca atccgacctt tggatctaca cattcctctt gcttcaatgg   120
gtgtcattta agaattagag gaaaatatta ggagatggag aactagagtt gaggaaacca   180
aaagaagagg agtcacagaa aaccagctct ctctgtgcaa ggcatcttga aag          233

<210> SEQ ID NO 196
<211> LENGTH: 139
<212> TYPE: DNA
<213> ORGANISM: Homo sapiens

<400> SEQUENCE: 196
caatattaaa aaaggctctg tatgcatggt ggggctatgt aagtactctt taaaactatg    60
```

```
gccctattaa tcttacaagt gttacttatg ggtcaagcaa tgtaaactgt ataaatgtaa      120
aaacaacccc tccacacac                                                   139

<210> SEQ ID NO 197
<211> LENGTH: 178
<212> TYPE: DNA
<213> ORGANISM: Homo sapiens

<400> SEQUENCE: 197
ctttggatag aggtgaagaa cttggacatg gctgtttcag gcagctgaag tcaaagggaa       60
tagtaattgg ggaaggggaa gtgggcagaa aggattgttg gccaatatac cttccactcc      120
agtagagagg gaggacttgg ctctgagaac ctccatctga cctaagagga accctcct        178

<210> SEQ ID NO 198
<211> LENGTH: 163
<212> TYPE: DNA
<213> ORGANISM: Homo sapiens

<400> SEQUENCE: 198
ctgcaaaagc cgagatgggt tccatgcagt tctccagtgg gacatcagtg cttatccgaa       60
tgtcatcaat ggcaatctct ccggaacgtc ctttccctat cactccctcg aacacaatct      120
ggtactccat gtcgtagctg ggcaggatga tccgcccgtg ctt                        163

<210> SEQ ID NO 199
<211> LENGTH: 104
<212> TYPE: DNA
<213> ORGANISM: Homo sapiens

<400> SEQUENCE: 199
ttcagcaagg actggtcttt ctatctcttg tactacactg aattcacccc cactgaaaaa       60
gatgagtatg cctgccgtgt gaaccatgtg actttgtcac agcc                       104

<210> SEQ ID NO 200
<211> LENGTH: 222
<212> TYPE: DNA
<213> ORGANISM: Homo sapiens
<220> FEATURE:
<221> NAME/KEY: misc_feature
<222> LOCATION: (93)..(93)
<223> OTHER INFORMATION: n is a, c, g, or t

<400> SEQUENCE: 200
tttcaaagaa ggtcaagtaa cagtcataca gctagaaaag tccctgaaaa aaagaattgt       60
taagaagtat aataacctttt tcaaaaccca cantgcagct tagttttcct ttatttattt    120
gtggtcatga agactatccc catttctcca taaaatcctc cctccatact gctgcattat     180
ggcacaaaag actctaagtg ccaccagaca gaaggaccag ag                         222

<210> SEQ ID NO 201
<211> LENGTH: 267
<212> TYPE: DNA
<213> ORGANISM: Homo sapiens

<400> SEQUENCE: 201
ttgctttgta tgcactttgt ttttttcttt gggtcttgtt ttttttttcc acttagaaat       60
tgcatttcct gacagaagga ctcaggttgt ctgaagtcac tgcacagtgc atctcagccc      120
acatagtgat ggttcccctg ttcactctac ttagcatgtc cctaccgagt ctcttctcca     180
```

```
ctggatggag gaaaaccaag ccgtggcttc ccgctcagcc ctccctgccc ctcccttcaa    240
ccattcccca tgggaaatgt caacaag                                        267
```

<210> SEQ ID NO 202
<211> LENGTH: 108
<212> TYPE: DNA
<213> ORGANISM: Homo sapiens

<400> SEQUENCE: 202

```
ggtggaagac cagtaattgc tggaagactg gatttgctgg aagacttgat ttactggaag    60
acttggagct tcttggaaga catggattgt ccggaagaca tggattgt              108
```

<210> SEQ ID NO 203
<211> LENGTH: 209
<212> TYPE: DNA
<213> ORGANISM: Homo sapiens

<400> SEQUENCE: 203

```
tgggagccgt cttcccagtc caccgtcccc atcgtgggca ttgttgctgg cctggctgtc    60
ctagcagttg tggtcatcgg agctgtggtc gctgctgtga tgtgtaggag aagagctca    120 ggtggaaaag gagggagcta ctctcaggct gcgtgcagcg acagtgccca gggctctgat    180
gtgtctctca cagcttgaaa agcctgaga                                      209
```

<210> SEQ ID NO 204
<211> LENGTH: 146
<212> TYPE: DNA
<213> ORGANISM: Homo sapiens

<400> SEQUENCE: 204

```
gctttgatat ttcaatgtta gcctcaattt ctgaacacca taggtagaat gtaaagcttg    60
tctgatcgtt caaagcatga atggatact tatatggaaa ttctgctcag atagaatgac   120
agtccgtcaa aacagattgt ttgcaa                                         146
```

<210> SEQ ID NO 205
<211> LENGTH: 48
<212> TYPE: DNA
<213> ORGANISM: Homo sapiens

<400> SEQUENCE: 205

```
agtgccaaag gatcttcccc ctgacacaac tctgctagac ctgcaaaa                 48
```

<210> SEQ ID NO 206
<211> LENGTH: 150
<212> TYPE: DNA
<213> ORGANISM: Homo sapiens

<400> SEQUENCE: 206

```
gtgtcatgta agattactgc ttgcctctct aaggaaggtc gtgactgttt aaatagacgg    60
gcaaggtgga acctttgaa agatgagctt ttgaatataa gttgtctgct agatcatggt   120
ttgtattgaa ctaacaaggt ttgcagatct                                     150
```

<210> SEQ ID NO 207
<211> LENGTH: 186
<212> TYPE: DNA
<213> ORGANISM: Homo sapiens

<400> SEQUENCE: 207

```
tattcctgca ccaactgacc tgaagttcac tcaggtcaca cccacaagcc tgagcgccca    60
```

```
gtggacacca cccaatgttc agctcactgg atatcgagtg cgggtgaccc ccaaggagaa      120
gaccggacca atgaaagaag tcaaccttgc tcctgacagc tcatccgtgg ttgtatcagg      180
acttat                                                                186
```

<210> SEQ ID NO 208
<211> LENGTH: 276
<212> TYPE: DNA
<213> ORGANISM: Homo sapiens

<400> SEQUENCE: 208

```
aacaatgtca gattttaact atgaaaacga cattaccttg tgcattttta tattgattcc      60 tattttttt ttaagattaa agtttaaatg ttttccacta gtcatttcac ttctaacttg      120
gtataggaag cttagctctc tacataccta tcatgtgccc tgtatcacag aagattcagg      180
aaaaatgcac ttgggaatca agaaaatgg aacttctttt tgaaaagaca agcaaccatg      240
ttaactgtat tgacacatcc tcaataaaac ctgttg                               276
```

<210> SEQ ID NO 209
<211> LENGTH: 158
<212> TYPE: DNA
<213> ORGANISM: Homo sapiens

<400> SEQUENCE: 209

```
tttgcattcc tgataattgt atgtattgta taaagaacgt ctgtacattg ggttataaca      60
ctagtatatt taaacttaca ggcttatttg taatgtaaac caccatttta atgtactgta      120
attaacatgg ttataatacg tacaatcctt ccctcatc                             158
```

<210> SEQ ID NO 210
<211> LENGTH: 225
<212> TYPE: DNA
<213> ORGANISM: Homo sapiens

<400> SEQUENCE: 210

```
tagaggcttc ttagattctc ccagcatccg cctttccctt tagccagtct gctgtcctga      60
aacccagaag tgatggagag aaaccaacaa gagatctcga accctgtcta gaaggaatgt      120
atttgttgct aaatttcgta gcactgttta cagttttcct ccatgttatt tatgaatttt      180
atattccgtg aatgtatatt gtcttgtaat gttgcataat gttca                     225
```

<210> SEQ ID NO 211
<211> LENGTH: 174
<212> TYPE: DNA
<213> ORGANISM: Homo sapiens

<400> SEQUENCE: 211

```
gatcagcaaa caggaatacg atgaagccgg gccttccatt gtccaccgca aatgcttcta      60
aaacactttc ctgctcctct ctgtctctag cacacaactg tgaatgtcct gtggaattat      120
gccttcagtt cttttccaaa tcattcctag ccaaagctct gactcgttac ctat           174
```

<210> SEQ ID NO 212
<211> LENGTH: 168
<212> TYPE: DNA
<213> ORGANISM: Homo sapiens

<400> SEQUENCE: 212

```
atattttaca gggtggagtg tactatatac tattaccttt gaatgtgttt gcagagctag      60
```
tggatgtgtt tgtctacaag tatgattgct gttacataac accccaaatt aactcccaaa    120
ttaaaacaca gttgtgctgt caatacctca tactgcttta cctttttt                 168

<210> SEQ ID NO 213
<211> LENGTH: 165
<212> TYPE: DNA
<213> ORGANISM: Homo sapiens

<400> SEQUENCE: 213
ctcagggagc gaacgtggat gaaaaccaca gggattccgg acgccagacc ccattttata    60
cttcactttt ctctacagtg ttgttttgtt gttgttggtt tttattttt atactttggc     120 cataccacag agctagattg cccaggtctg ggctgaataa aacaa                    165

<210> SEQ ID NO 214
<211> LENGTH: 208
<212> TYPE: DNA
<213> ORGANISM: Homo sapiens

<400> SEQUENCE: 214
ccaaacactg acattaccta cacttccact acccaaagac aaaatgtgcc cactgtgtgc    60
ttttgagtgt attttctttt agtttgtttt ttgttgggtg catatttatg ataataacaa    120
tgatggactt caattgtact cactgttcta ttgttggttt taattagcag caagttgtga    180
tcactttccc aggtgaataa atcatttc                                       208

<210> SEQ ID NO 215
<211> LENGTH: 245
<212> TYPE: DNA
<213> ORGANISM: Homo sapiens

<400> SEQUENCE: 215
agatgctgtg taactaaact gaaataattc aattacttat tatttagaat gttaaagctt    60
atgatagtct tttctaattc ttaacactca tacttgaaat ctttccgagt ttccccagaa    120
gagaatatgg gattttttt gacattttg acccatttaa taatgctctt gtgtttacct      180
agtatatgta gactttgtct tatgtgtcaa aagtcctagg aaagtggttg atgttctta     240 tagca                                                                245

<210> SEQ ID NO 216
<211> LENGTH: 257
<212> TYPE: DNA
<213> ORGANISM: Homo sapiens

<400> SEQUENCE: 216
ttgttactgc tgattcttgt aaatcttttt gcttctactt tcatcttaaa ctaatacgtg    60
ccagatataa ctgtcttgtt tcagtgagag acgccctatt tctatgtcat ttttaatgta    120
tctatttgta caattttaaa gttcttattt tagtatacgt ataaatatca gtattctgac    180
atgtaagaaa atgttacggc atcacactta tattttatga acattgtact gttgctttaa    240
tatgagcttc aatataa                                                   257

<210> SEQ ID NO 217
<211> LENGTH: 174
<212> TYPE: DNA
<213> ORGANISM: Homo sapiens

<400> SEQUENCE: 217
tttcaaatcc ttcatcatgt cagttccaat gaggtgggga tggagaagac aattgttgct    60
tatgaaagaa agctttagct gtctctgttt tgtaagcttt aagcgcaaca tttcttggtt    120
ccaataaagc attttacaag atcttgcatg ctactcttag atagaagatg ggaa          174

<210> SEQ ID NO 218
<211> LENGTH: 191
<212> TYPE: DNA
<213> ORGANISM: Homo sapiens

<400> SEQUENCE: 218
taggtggtag atattgaggc caagaatatt gcaaaataca tgaagcttca tgcacttaaa    60
gaagtatttt tagaataaga atttgcatac ttacctagtg aaacttttct agaattattt    120
ttcactctaa gtcatgtatg tttctctttg attatttgca tgttatgttt aataagctac    180
tagcaaaata a                                                          191

<210> SEQ ID NO 219
<211> LENGTH: 116
<212> TYPE: DNA
<213> ORGANISM: Homo sapiens

<400> SEQUENCE: 219
tgctgtgaaa gaggctggct acacaatcga atggtttgag gtgatctcgc aaagttattc    60
ttccaccatg gccaacaacg aaggactttt ctccctggtg gcgaggaagc tgagca         116

<210> SEQ ID NO 220
<211> LENGTH: 181
<212> TYPE: DNA
<213> ORGANISM: Homo sapiens

<400> SEQUENCE: 220
gagttgtatc gtgtggtgta ttttttaaaa aatttgattt agcattcata ttttccatct    60
tattcccaat taaaagtatg cagattattt gcccaaatct tcttcagatt cagcatttgt    120
tctttgccag tctcattttc atcttcttcc atggttccac agaagctttg tttcttgggc    180
a                                                                     181

<210> SEQ ID NO 221
<211> LENGTH: 248
<212> TYPE: DNA
<213> ORGANISM: Homo sapiens

<400> SEQUENCE: 221
tgttttcaaa ttgccattgc tactattgct tgtcggtgtt attttatttt attgttttttg    60 actttggaag agatgaactg tgtatttaac ttaagctatt gctcttaaaa ccagggagtc    120
agaatatatt tgtaagttaa atcattggtg ctaataataa atgtggattt tgtattaaaa    180
tatatagaag caatttctgt ttacatgtcc ttgctacttt taaaaacttg catttattcc    240
tcagattt                                                              248

<210> SEQ ID NO 222
<211> LENGTH: 227
<212> TYPE: DNA
<213> ORGANISM: Homo sapiens

<400> SEQUENCE: 222
tatttgaact atatgttgaa gacatctacc agtttctcca aatgcctttt ttaaaactca    60
tcacagaaga ttggtgaaaa tgctgagtat gacactttc ttcttgcatg catgtcagct    120
acataaacag ttttgtacaa tgaaaattac taatttgttt gacattccat gttaaactac    180
ggtcatgttc agcttcattg catgtaatgt agacctagtc catcaga    227

<210> SEQ ID NO 223
<211> LENGTH: 194
<212> TYPE: DNA
<213> ORGANISM: Homo sapiens

<400> SEQUENCE: 223
gaagtttaat tcatagtaat ttcactctct gcattgactt atgagataat taatgattaa    60
actattaatg ataaaaataa tgcatttgta ttgttcataa tatcatgtgc acttcaagaa    120
aatggaatgc tactcttttg tggtttacgt gtattatttt caatatctta atacccctaat    180 aaagagtcca taaa    194

<210> SEQ ID NO 224
<211> LENGTH: 217
<212> TYPE: DNA
<213> ORGANISM: Homo sapiens

<400> SEQUENCE: 224
tgattagccc caagtagaaa gtcctgtggt tttatgttta atggtaatag ttgatcatat    60
atggcataat tttctatcag cttcctactc agtcactata aacacagact tgaaatagta    120
ctttaaatgt ccaaatacct aaatgtgcta aactggaggt aactatttct aggtagttga    180 attttgaaa gtcatgatca gccacacaac tgttttg    217

<210> SEQ ID NO 225
<211> LENGTH: 293
<212> TYPE: DNA
<213> ORGANISM: Homo sapiens

<400> SEQUENCE: 225
ttgcttttca ttcagatgta tacataaact tatttaaaat gtcatttaag tgaaccattc    60
caaggcataa taaaacccga ggtagcaaat gaaaattaaa gcatttattt tggtagttct    120
tcaataatga tgcgagaaac tgaattccat ccagtagaag catctccttt tgggtaatct    180
gaacaagtgc caacccagat agcaacatcc actaatccag caccaattcc ttcacaaagt    240
ccttccacag aagaagtgcg atgaatatta attgttgaat tcatttcagg gct    293

<210> SEQ ID NO 226
<211> LENGTH: 95
<212> TYPE: DNA
<213> ORGANISM: Homo sapiens

<400> SEQUENCE: 226
ctgtcaggaa ctcctcactg tttaaatatt tatttattgt gacaaatgga gctggtttcc    60
tagatatgaa tgatgtttgc aatccccatt ttcct    95

<210> SEQ ID NO 227
<211> LENGTH: 210
<212> TYPE: DNA
<213> ORGANISM: Homo sapiens

<400> SEQUENCE: 227
gctgctgtag aatagcacag acgtggatga taaattatcc ccagaagcag catgacagaa    60
tgcctcgggg agcacttgga agggaaattg cagttctgtt gaaatagagg aaaatccctt    120
ggtaaagaca cagcctgtta ggctcgtgtg ggcctccagt atgttcacca ggggaatggc    180

```
tgggatttct cggcactctg catcatccat                                      210
```

<210> SEQ ID NO 228
<211> LENGTH: 243
<212> TYPE: DNA
<213> ORGANISM: Homo sapiens

<400> SEQUENCE: 228

```
ttaatatttg ttattctctc atgaatagaa atttatgtag aagcaaacaa aatactttta     60
cccacttaaa aagagaatat aacattttat gtcactataa tcttttgttt tttaagttag    120
tgtatatttt gttgtgatta tcttttgtg gtgtgaataa atcttttatc ttgaatgtaa     180
taagaatttg gtggtgtcaa ttgcttattt gttttcccac ggttgtccag caattaataa    240
aac                                                                  243
```

<210> SEQ ID NO 229
<211> LENGTH: 37
<212> TYPE: DNA
<213> ORGANISM: Homo sapiens

<400> SEQUENCE: 229

```
gatgcttaac aaaggttacc ataagccaca aattcat                              37
```

<210> SEQ ID NO 230
<211> LENGTH: 264
<212> TYPE: DNA
<213> ORGANISM: Homo sapiens

<400> SEQUENCE: 230

```
aatgcaaact atcactgtat tttaatattt gttattctct catgaataga aatttatgta     60
gaagcaaaca aatactttt acccacttaa aaagagaata taacatttta tgtcactata    120
atcttttgtt ttttaagtta gtgtatattt tgttgtgatt atcttttgt ggtgtgaata    180
aatctttat cttgaatgta ataagaattt ggtggtgtca attgcttatt tgttttccca    240
cggttgtcca gcaattaata aaac                                           264
```

<210> SEQ ID NO 231
<211> LENGTH: 269
<212> TYPE: DNA
<213> ORGANISM: Homo sapiens

<400> SEQUENCE: 231

```
gcttatttga caacgtttca gcgactccgt tggccactcc gagaggtggg ccagtctgtg     60
gatcagagat gcaccaccaa gccaagggaa cctgtgtccg gtattcgata ctgcgacttt    120
ctgcctggag tgtatgactg cacatgactc ggggggtggg aaaggggtcg gctgaccatg    180
ctcatctgct ggtccgtggg acggtgccca agccagaggc tgggttcatt tgtgtaacga    240
caataaacgg tacttgtcat ttcgggcaa                                      269
```

<210> SEQ ID NO 232
<211> LENGTH: 179
<212> TYPE: DNA
<213> ORGANISM: Homo sapiens

<400> SEQUENCE: 232

```
agaggttata ggtcactcct ggggcctctt ggtccccca cgtgacagtg cctgggaatg      60
tattattctg cagcatgacc tgtgaccagc actgtctcag tttcactttc acatagatgt    120
``` cccttcttg gccagttatc ccttccttt agcctagttc atccaatcct cactgggtg    179

<210> SEQ ID NO 233
<211> LENGTH: 220
<212> TYPE: DNA
<213> ORGANISM: Homo sapiens

<400> SEQUENCE: 233
ctgtatcact gccttcgttt atatttttt aactgtgata atccccacag gcacattaac    60
tgttgcactt ttgaatgtcc aaaatttata ttttagaaat aataaaaga aagatactta   120 catgttccca aaacaatggt gtggtgaatg tgtgagaaaa actaacttga tagggtctac   180
caatacaaaa tgtattacga atgccctgt tcatgttttt                         220

<210> SEQ ID NO 234
<211> LENGTH: 127
<212> TYPE: DNA
<213> ORGANISM: Homo sapiens

<400> SEQUENCE: 234
gggcccctaa tatcccagtt taatattcca atacctaga agaaaacccg agggacagca    60
gattccacag gacacgaagg ctgccctgt aaggtttcaa tgcatacaat aaagagctt    120 tatccct                                                           127

<210> SEQ ID NO 235
<211> LENGTH: 225
<212> TYPE: DNA
<213> ORGANISM: Homo sapiens

<400> SEQUENCE: 235
cccaaacctg tactgtcccg gaggaggttg ggaggtggag gcccagcatc ccgcgcagat    60
gacaccatca accgccagag tcccagacac cggttttcct agaagcccct cacccccact   120
ggcccactgg tggctaggtc tccccttatc cttctggtcc agcgcaagga ggggctgctt   180
ctgaggtcgg tggctgtctt tccattaaag aaacaccgtg caacg                  225

<210> SEQ ID NO 236
<211> LENGTH: 41
<212> TYPE: DNA
<213> ORGANISM: Homo sapiens

<400> SEQUENCE: 236
ttaatctatg tgcaccgttg ggaccaatgc cttaattaaa g                       41

<210> SEQ ID NO 237
<211> LENGTH: 160
<212> TYPE: DNA
<213> ORGANISM: Homo sapiens

<400> SEQUENCE: 237
cttctcactg gacagcacta gtttttgcc tgggaagtcg tggacagtaa cagtgactgg    60
aacatcccct tgcgcgtcgt gggcctccag caccatggtc tcctcgctct ccagccgcaa   120
gatgttgggg gtgatgatag agtacatggg actccccaga                        160

<210> SEQ ID NO 238
<211> LENGTH: 179
<212> TYPE: DNA
<213> ORGANISM: Homo sapiens

<400> SEQUENCE: 238

```
gggtcagcac agtcttctca ctggacagca ctagttttt gcctgggaag tcgtggacag    60
taacagtgac tggaacatcc ccttgcgcgt cgtgggcctc cagcaccatg gtctcctcgc   120
tctccagccg caagatgttg ggggtgatga tagagtacat gggactcccc agagccagg    179

<210> SEQ ID NO 239
<211> LENGTH: 164
<212> TYPE: DNA
<213> ORGANISM: Homo sapiens

<400> SEQUENCE: 239
gtagtgagtt ttccttggtc ggcgtttggc tgagaaggct gcaactggcc tgagacgagt    60
ctggtcccga cgatgctgtg ctctgcctcc tcctgctgct gctgacaacc aagccctccc   120
agaatttaaa tgctgctgca gacatcctcc accaacacag ggag                    164

<210> SEQ ID NO 240
<211> LENGTH: 167
<212> TYPE: DNA
<213> ORGANISM: Homo sapiens

<400> SEQUENCE: 240
aagaaggaat gatcactctt ggagaggaag ctggtctcag aaacaccttc tgtgactgag    60
tgcccattgc tcagccatgt gatgttgacc acaggaggaa agatgttgtc cacaagacag   120
atgaggatgt tgggctgacc cagtgtcacg ggagacttgg aaaacac                 167

<210> SEQ ID NO 241
<211> LENGTH: 183
<212> TYPE: DNA
<213> ORGANISM: Homo sapiens

<400> SEQUENCE: 241
ggattataat atcctcactg gccacaatct gtaaaagtcg atactggcac ttttttttgcc   60 ccctcaaagg aaatatgcta atagacagcc cctttgcaaa tataattcct ccttcccaac   120
ccttcaaatt gctaaggccc cactggtcag caccttccct ttcgagtcca ggactactgt   180
tct                                                                 183

<210> SEQ ID NO 242
<211> LENGTH: 237
<212> TYPE: DNA
<213> ORGANISM: Homo sapiens

<400> SEQUENCE: 242
acaaaagctc ccctgatcca actagcacac tgtcaaatac agtgtcatat gagaggtcca    60
cagacggtag tttccaagac cgtttcaggg aattcgagga ttccaccta aaacctaaca   120 gaaaaaaacc cactgaaaat attatcatag acctggacaa agaggacaag gatttaatat   180
tgacaattac agagagtacc atccttgaaa ttctacctga gctgacatcg gataaaa      237

<210> SEQ ID NO 243
<211> LENGTH: 197
<212> TYPE: DNA
<213> ORGANISM: Homo sapiens

<400> SEQUENCE: 243
agtgctaagg agtatagcag atgacttata tgtgtgttgg ctgggagaat atcatcttaa    60
agtgagagtg atgttgtgga gacagttgaa atgtcagtgc tagagcctct gtggtgtgaa   120
```

```
tgggcacgtt aggttgttgc attagaaagt gactgtttct gacagaaatt tgtagctttg    180
tgcaaactca cccacca                                                  197

<210> SEQ ID NO 244
<211> LENGTH: 131
<212> TYPE: DNA
<213> ORGANISM: Homo sapiens

<400> SEQUENCE: 244
ctacttcccc gaaccggtga cggtgtcgtg gaactcaggc gccctgacca gcggcgtgca    60
caccttcccg gctgtcctac agtcctcagg actctactcc ctcagcagcg tggtgaccgt   120
gccctccagc a                                                       131

<210> SEQ ID NO 245
<211> LENGTH: 95
<212> TYPE: DNA
<213> ORGANISM: Homo sapiens

<400> SEQUENCE: 245
ccagacctac acctgcaacg tagatcacaa gcccagcaac accaaagtgg acaagacagt    60
tgagcgcaaa tgttgtgtcg agtgcccacc gtgcc                              95

<210> SEQ ID NO 246
<211> LENGTH: 131
<212> TYPE: DNA
<213> ORGANISM: Homo sapiens

<400> SEQUENCE: 246
gtaatttgtg attgtcgagg aagaggtgtg gctgttggtg tgatagtaat actgctggtg    60
actttattgg ttgttttgtt tagtgccccg ttaattaagc cttgagttcg gttatcctgc   120
agtggtgctg a                                                       131

<210> SEQ ID NO 247
<211> LENGTH: 38
<212> TYPE: DNA
<213> ORGANISM: Homo sapiens

<400> SEQUENCE: 247
tttcccccac tgtctggaca ctggtgaatg acattaga                           38

<210> SEQ ID NO 248
<211> LENGTH: 173
<212> TYPE: DNA
<213> ORGANISM: Homo sapiens

<400> SEQUENCE: 248
gaaggagaac gaatccagtg gaaagaaagc tggtgaggga aaagatgccc tgcagaaaag    60 tccccttttcc cccactgtct ggacactggt gaatgacatt agaagagacc caccccattc   120
aagtcccctc actggctcct tttctcccca ctacaccact tccaaaatct gaa          173

<210> SEQ ID NO 249
<211> LENGTH: 298
<212> TYPE: DNA
<213> ORGANISM: Homo sapiens

<400> SEQUENCE: 249
tgactttgtc acaatgacag ccaacagtga gactgataag cctgtaaaaa taaaaaaata    60
agactaatca aatagacatg gcattttaat ctcaaagtgc aaaatcatct aactgaaaat   120
```

```
gacggcattg aaaaattcca gtggttaaaa atgaatcaaa acttcattac gcaggcagtg      180
gaagtgtgtt gaaagattta ccaggggtgt caagttttag acactcagaa aggcaccatt      240
ctagccatct tgattggata acatgtatat acttatgtcc ctacgatatt caaaagat        298
```

<210> SEQ ID NO 250
<211> LENGTH: 145
<212> TYPE: DNA
<213> ORGANISM: Homo sapiens

<400> SEQUENCE: 250

```
gataccgact gaccgtgggc cttacccgaa gaggacagcc catgcagtac aatgtgggtc       60
cctctgtctt caagtaccca ctgaggaatc tgcagcctgc atctgagtac accgtattcc      120
tcgtggccat aaagggcaac caaga                                            145
```

<210> SEQ ID NO 251
<211> LENGTH: 111
<212> TYPE: DNA
<213> ORGANISM: Homo sapiens

<400> SEQUENCE: 251

```
ttaagacatt ggagtgattt ctggaaatgt tttctttaag aaggctcacg tgatgtttgt       60
gtttacttgt ggttgcccta cctatgctg cataaatcct tgaaaggaaa g                111
```

<210> SEQ ID NO 252
<211> LENGTH: 137
<212> TYPE: DNA
<213> ORGANISM: Homo sapiens

<400> SEQUENCE: 252

```
ttaagacatt ggagtgattt ctggaaatgt tttctttaag aaggctcacg tgatgtttgt       60
gtttacttgt ggttgcccta cctatgctg cataaatcct tgaaaggaaa ggttttagtt      120
agttgctttc tttcttc                                                     137
```

<210> SEQ ID NO 253
<211> LENGTH: 203
<212> TYPE: DNA
<213> ORGANISM: Homo sapiens

<400> SEQUENCE: 253

```
tttttctttg ggctactgta ccctgcttcc agtgctgacc ccggcataag tccatctctg       60
cagaagccat ttcaggagta cctggaggct aacggcaca agcttcacca caaaagcgaa      120
atggacacac cacaggtaag actttaatcc ggtttcttct cccctctggg aagtttcggg     180
ctgaaattac attcacagct ctc                                              203
```

<210> SEQ ID NO 254
<211> LENGTH: 243
<212> TYPE: DNA
<213> ORGANISM: Homo sapiens

<400> SEQUENCE: 254

```
ttcctgcttt tcttcccaaa tgtgtctttt tctttgggct actgtaccct gcttccagtg       60
ctgaccccgg cataagtcca tctctgcaga agccatttca ggagtacctg gaggctcaac      120
ggcacaagct tcaccacaaa agcgaaatgg acacaccaca ggtaagactt taatccggtt      180
tcttctcccc tctgggaagt ttcgggctga aattacattc acagctctca ctcacatttt      240
```

```
tag                                                                    243

<210> SEQ ID NO 255
<211> LENGTH: 292
<212> TYPE: DNA
<213> ORGANISM: Homo sapiens

<400> SEQUENCE: 255
cgcggtctga gtctcgtttg gaagctcgag gcataggaca gtctctgcct gggtagggaa      60
tgcagttagc tgaggaacca cggtaggttt taaaaaaaaa gactcgggga gagaaatagc     120
acattattta catgactgga caaggacaga aggtgggagg aagcccctgt cactccttgg     180
gacctgggat ctgagcacaa agctgagtgg gaaacagtgg gggctccgaa gcgcccagca     240
gggccagcgc cctcctttct agaccccgac tgcccttggt cttctgccct tt             292

<210> SEQ ID NO 256
<211> LENGTH: 156
<212> TYPE: DNA
<213> ORGANISM: Homo sapiens

<400> SEQUENCE: 256
ctgagtaaat gggactgctg tcgttggatg gcactgcgca gctcaggggt gggctctggg      60
aggcggaggc ggaggaggcc gctggagatg gtgctgagga cgaggaggcc ggtgggttgg     120
tcatgctcac taggccactg accaagctga agaggg                               156

<210> SEQ ID NO 257
<211> LENGTH: 249
<212> TYPE: DNA
<213> ORGANISM: Homo sapiens
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t

<400> SEQUENCE: 257
attgatttca caagtcttca ggttgtttat agacatagct atagacaaca tctcagtttc      60
atacagaact cattcaatca tataaaaata aacacaaatt tacattgact catcaactat     120
acaatttaaa aaggcacttg anaggggtat tgtattattg catttgtggt atgcatttga     180
aatagttnta agtacattaa tgaaatttgt aagaattcct cttttgcact tattcccatc     240
tttaattaa                                                             249

<210> SEQ ID NO 258
<211> LENGTH: 62
<212> TYPE: DNA
<213> ORGANISM: Homo sapiens

<400> SEQUENCE: 258
gtccccaaat gacccacatg attcaaagtg caaatttact ccaacctgca agagaaaacg      60
aa                                                                     62

<210> SEQ ID NO 259
<211> LENGTH: 126
<212> TYPE: DNA
<213> ORGANISM: Homo sapiens

<400> SEQUENCE: 259
```

```
actagtctca gtaatacatt agtaaaaatc atgtcactta attaattgtg ttagaatcaa    60
agaaacatag agttgggcaa tatacttcat cctacccatc ccacccaaat cttactctac   120
tcatct                                                              126
```

<210> SEQ ID NO 260
<211> LENGTH: 149
<212> TYPE: DNA
<213> ORGANISM: Homo sapiens

<400> SEQUENCE: 260

```
aaaaatttat ttactagtct cagtaataca ttagtaaaaa tcatgtcact taattaattg    60
tgttagaatc aaagaaacat agagttgggc aatatacttc atcctaccca tcccacccaa   120
atcttactct actcatctca ttctcatta                                     149
```

<210> SEQ ID NO 261
<211> LENGTH: 163
<212> TYPE: DNA
<213> ORGANISM: Homo sapiens

<400> SEQUENCE: 261

```
agaattaact gactatggtt ttgcaggcca gtttgatccc agtattttta tttctaaagg    60
ggttcttata gttcctctga ttgttaccat tttaaaatag agaaagtcca tagtgatgcc   120
tttcctttca gtggctgatt ggcacgacct cttgagaatg cat                     163
```

<210> SEQ ID NO 262
<211> LENGTH: 269
<212> TYPE: DNA
<213> ORGANISM: Homo sapiens

<400> SEQUENCE: 262

```
atttgcattt taccatgggt cctcaataaa taaatagaat gttgtttttt gtattttaag    60 ttttttttttg tttttcccct cagaggaagg atgaaaaaaa gaattaactg actatggttt   120
tgcaggccag tttgatccca gtattttttat ttctaaaggg gttcttatag ttcctctgat  180
tgttaccatt ttaaaataga gaaagtccat agtgatgcct ttcctttcag tggctgattg   240
gcacgacctc ttgagaatgc atgcatgaa                                     269
```

<210> SEQ ID NO 263
<211> LENGTH: 105
<212> TYPE: DNA
<213> ORGANISM: Homo sapiens

<400> SEQUENCE: 263

```
atttccatca catatgtgcc aagacttgtg ttctgtatcc aggagtgtgt tagatactaa    60
catagtgttt catttacatg tgtgtgaaac ctgggtgaag agcca                   105
```

<210> SEQ ID NO 264
<211> LENGTH: 174
<212> TYPE: DNA
<213> ORGANISM: Homo sapiens

<400> SEQUENCE: 264

```
ccatcagttt ttccaatgtg aatggactgg ttcatatcac accatattta gagatacaag    60
gtgattataa ctaacgtgtc tacaagacat actgggtcaa acaatgtgat caatccaaag   120
ggtatctttt taaaaagaat ttaagtactc agctgcaaag ataagttcac taat         174
```

<210> SEQ ID NO 265
<211> LENGTH: 218
<212> TYPE: DNA
<213> ORGANISM: Homo sapiens

<400> SEQUENCE: 265
gtacatggtc tggagtaacc tttatatgaa gtggctgccc aggtgtgtgg cttaggacta    60
gatctccagg ttgcacaaag ttggcattgg gtttagtttg cattttttcca ttctgaagat   120 ggccctcctt ggatttcatc caggaaatcc atagctttct gttaacagga catggagtag   180
actggctgca tttgaaggac agcacagatc cctcatca                            218

<210> SEQ ID NO 266
<211> LENGTH: 103
<212> TYPE: DNA
<213> ORGANISM: Homo sapiens

<400> SEQUENCE: 266
aaaccttgtt ttattcagcc cagacctggg agatctagct ctgtggtatg gccaaagtat    60
aaaaaataaa aaccaacaac aacaaaacaa cactgtagag aaa                      103

<210> SEQ ID NO 267
<211> LENGTH: 194
<212> TYPE: DNA
<213> ORGANISM: Homo sapiens

<400> SEQUENCE: 267
tcaaactcag gtatgtgaca ctctacagtt caatgctagc acacctgtgt gaggcttaac    60
aacatgagga actgatagcc agtgatacac aaatccagca cttcctctcc atttactctg   120
tcaggctgta tatggggagc aacacatatg gctttgtggc agccagaaag tgaaggtctt   180
tttaggaggt gaca                                                      194

<210> SEQ ID NO 268
<211> LENGTH: 61
<212> TYPE: DNA
<213> ORGANISM: Homo sapiens

<400> SEQUENCE: 268
ttcccagcac cggaaggtct cagacttcat attccagcat aaacacagtg ctcccctccc    60
c                                                                    61

<210> SEQ ID NO 269
<211> LENGTH: 268
<212> TYPE: DNA
<213> ORGANISM: Homo sapiens

<400> SEQUENCE: 269
gtaaagcttt ggcacataca gtataaaaaa taatcaccca ccataattat accaaattcc    60
tcttatcaac tgcatactaa gtgttttcaa tacaattttt tccgtataaa aatactggga   120
aaaattgata aataacaggt aagagaaaga tatttctagg caattactag gatcatttgg   180
aaaaagtgag tactgtggat atttaaaata tcacagtaac aagatcatgc ttgttcctac   240
agtattgcgg gccagacact taagtgaa                                       268

<210> SEQ ID NO 270
<211> LENGTH: 37
<212> TYPE: DNA
<213> ORGANISM: Homo sapiens

<400> SEQUENCE: 270
tgggctggag ccgcacacgc tctcctccca tgttaaa                                    37

<210> SEQ ID NO 271
<211> LENGTH: 112
<212> TYPE: DNA
<213> ORGANISM: Homo sapiens

<400> SEQUENCE: 271
atagatgaca taagttacca tactcaaatg taagatagdg agaggtagaa gaaatagctg           60
agaacttgaa aagatgtact gttattgtca acaaaccaat gtcttctccc tt                 112

<210> SEQ ID NO 272
<211> LENGTH: 158
<212> TYPE: DNA
<213> ORGANISM: Homo sapiens

<400> SEQUENCE: 272
ttttcgtagt ccaaaggctt tattgttctg ctgaaatgct tacaaatact gaaaaccccc          60
agcctgggcc caggcaacca agggctcaat gctgggaagg agagcagggg aggtgggctt         120
agtgttaagg cgtgaagggc gaggccagac agctggag                                 158

<210> SEQ ID NO 273
<211> LENGTH: 75
<212> TYPE: DNA
<213> ORGANISM: Homo sapiens

<400> SEQUENCE: 273
catctctgac tttaatggct taagcaagaa catggtttcc gtggctcccc ctggactgaa          60
tgctggagga tatat                                                           75

<210> SEQ ID NO 274
<211> LENGTH: 182
<212> TYPE: DNA
<213> ORGANISM: Homo sapiens

<400> SEQUENCE: 274
tgagtaggtg agtttattgg gacttacaca caggtcaatc ctgggcggcg acaagacagc          60
tctagagatc tgagcttcct cccaatgcta aactgctttc atgctaattt tctgactgtt        120
tacttaccgg gtaagagcga tgggactgtt ttcattggtt ggttctcaca tactctctgg        180
ga                                                                       182

<210> SEQ ID NO 275
<211> LENGTH: 121
<212> TYPE: DNA
<213> ORGANISM: Homo sapiens

<400> SEQUENCE: 275
cctggatctc acagacgttg ggcttttcaa ctgcagactt caatgctttg tttccaggtg          60
gcaggagaaa catcacatct cattaccaac aattatttcc ctcaaaggta agtaattgta        120
t                                                                        121

<210> SEQ ID NO 276
<211> LENGTH: 177
<212> TYPE: DNA
<213> ORGANISM: Homo sapiens

<400> SEQUENCE: 276
cagtggtttg caagcatggt ttcctggatc tcacagacgt tgggcttttc aactgcagac    60
ttcaatgctt tgtttccagg tggcaggaga acatcacat ctcattacca acaattattt   120
ccctcaaagg taagtaattg tatctaactt caatattcct ttccctggcc aaaaatt     177

<210> SEQ ID NO 277
<211> LENGTH: 237
<212> TYPE: DNA
<213> ORGANISM: Homo sapiens

<400> SEQUENCE: 277
agacccctga cacagaccac tagaagattc cgggaacgtt gggagtcacc tgattctgca    60
aagataaata atatccctgc attatcaaaa taaagtagca gacctctcaa ttcacaatga   120
gttaactgat aaacaaaac agaagtcaga caatgtttta aattgaatga tcatgtaaat   180
attacacatc aaaccaatga catgggaaaa tgggagcttc taatgaggac aaacaaa    237

<210> SEQ ID NO 278
<211> LENGTH: 43
<212> TYPE: DNA
<213> ORGANISM: Homo sapiens

<400> SEQUENCE: 278
caatggttga gccctgtca agtgccagtc atgatagtag taa                      43

<210> SEQ ID NO 279
<211> LENGTH: 198
<212> TYPE: DNA
<213> ORGANISM: Homo sapiens

<400> SEQUENCE: 279
gggatttctt ggtttgtgaa acaggagag gagaaatatc tcatacaagt gaaaggatac    60
tggagagaga aattacccat ttctaaaaaa aaaccacact ctgtcgtatc tgtgttaatg   120
ttttctagca tgtactctgg tttcaacaga cacaaattta tatgttaacc cagttttctt   180
gccgttctgt aagtgttt                                                 198

<210> SEQ ID NO 280
<211> LENGTH: 70
<212> TYPE: DNA
<213> ORGANISM: Homo sapiens

<400> SEQUENCE: 280
tgtctttgag gctaatggac ccgtggggct tgtaatctgt ctctttctac tatttacatc    60
tgatttaaat                                                          70

<210> SEQ ID NO 281
<211> LENGTH: 94
<212> TYPE: DNA
<213> ORGANISM: Homo sapiens

<400> SEQUENCE: 281
gcctcccatt caagtgaagt tataatttac actgagggtt tcaaaattcg actagaagtg    60
gagatatatt atttatttat gcactgtact gtat                               94

<210> SEQ ID NO 282
<211> LENGTH: 165
<212> TYPE: DNA
<213> ORGANISM: Homo sapiens

<400> SEQUENCE: 282
tttcctgccc caaggcagat ccacatcacc gaagctccct agaggggcaa aagatggagt    60
gagccacagg aagtttgggg cgtggtgagt tggaatgata cgtccatttc tctatgaaat   120
atttgctact agactgttca tttctctctg acatgtttgt tgaat                   165

<210> SEQ ID NO 283
<211> LENGTH: 208
<212> TYPE: DNA
<213> ORGANISM: Homo sapiens

<400> SEQUENCE: 283
catccgccag ggcccacacc cccttcctac tcccagacac ccaccctcgc ttcagccaca    60
gtttcctcat ctgtccagtg ggtaggttgg actggaaaat ctcttttga ctcttgcaat   120 ccacaatctg acattctcag gaagccccca agttgatatt tctatttcct ggaatggttg   180
gattttagtt acagctgtga tttggaag                                      208

<210> SEQ ID NO 284
<211> LENGTH: 227
<212> TYPE: DNA
<213> ORGANISM: Homo sapiens

<400> SEQUENCE: 284
agcccaactt cttacccgaa agcatcactg ccttggcccc tccctcccgg ctgcccccat    60
cacctctact gtctcctccc tgggctaagc aggggagaag cgggctgggg gtagcctgga   120
tgtgggccaa gtccactgtc ctccttggcg gcaaaagccc attgaagaag aaccagccca   180
gcctgccccc tatcttgtcc tggaatattt ttggggttgg aactcaa                 227

<210> SEQ ID NO 285
<211> LENGTH: 57
<212> TYPE: DNA
<213> ORGANISM: Homo sapiens

<400> SEQUENCE: 285
tattgaggac ccatggtaaa atgcaaatag atccggtgtc taaatgcatt catattt       57

<210> SEQ ID NO 286
<211> LENGTH: 135
<212> TYPE: DNA
<213> ORGANISM: Homo sapiens

<400> SEQUENCE: 286
tacccgggaa agtacgtcta gattgtgtgg tttgcctcat tgtgctattt gcccactttc    60
cttccctgaa gaaatatctg tgaaccttct ttctgttcag tcctaaaatt cgaaataaag   120
tgagactatg gttca                                                    135

<210> SEQ ID NO 287
<211> LENGTH: 247
<212> TYPE: DNA
<213> ORGANISM: Homo sapiens

<400> SEQUENCE: 287
caaactattt ttccacctcc aaaagaaatt aacacatgga catttttaaag tctttagtat   60 aaagaaaatt tgtattcaat gtgttaagca ttaacatgta tttatttgt gtatccactc   120 catctgattt ttctgagcca ttttgatttg ttccttcatt aaaaaaaatc tcttaaagtt   180

```
atttagtgtc taaaagtgac tgacttaaat tatgtggtgc caatctgtaa tgtctttgaa    240 ttcettt                                                              247

<210> SEQ ID NO 288
<211> LENGTH: 174
<212> TYPE: DNA
<213> ORGANISM: Homo sapiens

<400> SEQUENCE: 288
ttgcatggag acttgaggag ggagggcttg aggttggtga ggttaggtgc gtgtttcctg    60
tgcaagtcag gacatcagtc tgattaaagg tggtgccaat ttatttacat ttaaacttgt   120
cagggtataa aatgacatcc cattaattat attgttaatc aatcacgtgt atag         174

<210> SEQ ID NO 289
<211> LENGTH: 126
<212> TYPE: DNA
<213> ORGANISM: Homo sapiens

<400> SEQUENCE: 289
ggatccaaga gctgactatg cctgcattgc tgagaacaaa cccacctgag caccccagac   60
accttcctca acccaggcgg gtggacaggg tcccctgtg gtccagccag taaaaaccat    120
ggtccc                                                              126

<210> SEQ ID NO 290
<211> LENGTH: 132
<212> TYPE: DNA
<213> ORGANISM: Homo sapiens

<400> SEQUENCE: 290
acagcccacc cttgtgtcca ctgtgacccc tgttcccatg ctgacctgtg tttcctcccc   60
agtcatcttt cttgttccag agaggtgggg ctggatgtct ccatctctgt ctcaacttta  120
cgtgcactga gc                                                       132

<210> SEQ ID NO 291
<211> LENGTH: 173
<212> TYPE: DNA
<213> ORGANISM: Homo sapiens

<400> SEQUENCE: 291
aaatgctcct tgaatattaa aaggttgtaa aaatagtgca tgttatgtga tttcaatttt   60
gttttttaaa atatgggtgt atgcttgtat acgtagagca gataaaaaag acggaaggca  120
tactaaaaaa tgttgagtgg ttatctttgt atggtggaac aaagtcactg taa          173

<210> SEQ ID NO 292
<211> LENGTH: 274
<212> TYPE: DNA
<213> ORGANISM: Homo sapiens

<400> SEQUENCE: 292
ggcacgtggc ttcatgtcag taagcaagat gcttcttaat aacccacctt ctgccccact   60
ctattcctta tcctgctgcc cctgtagggg tcaagggccc tccgtctaca ccctcttctt  120
ctcctccatc ctttattcag agtcatctcg cccttcccca tgggtggggg aacctgtgtt  180
tgtttgtgtg cacatgtaaa ttttaaatat tttaagcaga aagtccttac ctcctgtaac  240
acatcaataa agtacaatca ttgtgagccc tttc                               274
```

```
<210> SEQ ID NO 293
<211> LENGTH: 185
<212> TYPE: DNA
<213> ORGANISM: Homo sapiens

<400> SEQUENCE: 293
attcactttt gttaacagta tttctctttt attctgttat atagtggatg atatacacag    60
tggcaaaaca aaagtacatt gcttaaaata tatagtgaaa aatgtcacta tatcttccca   120
tttaacattg tttttgtata ttgggtgtag atttctgaca tcaaaacttg gacccttgga   180
aaaca                                                               185

<210> SEQ ID NO 294
<211> LENGTH: 42
<212> TYPE: DNA
<213> ORGANISM: Homo sapiens

<400> SEQUENCE: 294
tcatgacgag ttaatgcatg tccgtggttg ggtgcacctg ta                       42

<210> SEQ ID NO 295
<211> LENGTH: 250
<212> TYPE: DNA
<213> ORGANISM: Homo sapiens

<400> SEQUENCE: 295
gatttctcat gacgagttaa tgcatgtccg tggttgggtg cacctgtagt tctgtttatt    60
ggtcagtgga aatgaaaaaa aaaaaaaaaa aaagtctgcg ttcattgcag ttccagtttc   120
tcttccattc tgtgtcacag acaccaacac accactcatt ggaaaatgga aaaaaaaaac   180
aaaaaaaaaa caaaaaaatg tacaatggat gcattgaaat tatatgtaat tgtataaatg   240
gtgcaacagt                                                          250

<210> SEQ ID NO 296
<211> LENGTH: 247
<212> TYPE: DNA
<213> ORGANISM: Homo sapiens

<400> SEQUENCE: 296
ggcaggcttc tctgtagaac cccaggggct tcggcccaga ccacagcgtc ttgccctgag    60
cctagagcag ggagtcccga acttctgcat tcacagacca cctccacaat tgttataacc   120
aaaggcctcc tgttctgtta tttcacttaa atcaacatgc tattttgttt tcactcactt   180
ctgactttag cctcgtgctg agccgtgtat ccatgcagtc atgttcacgt gctagttacg   240
tttttct                                                             247

<210> SEQ ID NO 297
<211> LENGTH: 112
<212> TYPE: DNA
<213> ORGANISM: Homo sapiens

<400> SEQUENCE: 297
attttagtat ggtgtctgtt tatgtaactc tgacttgctg gaaagttga aactccaaat     60 aatctgaaac tagaaaagaa atagcacata attactacct tccccttggc gg           112

<210> SEQ ID NO 298
<211> LENGTH: 278
<212> TYPE: DNA
<213> ORGANISM: Homo sapiens
```

<400> SEQUENCE: 298

```
aaatggcttc cgatttccag cttgggcctg gggattggag atgtccccac tgagagtagg    60
gcacaagtga ggaaatggtt tggagaggaa gatgataagt tacatcatgg atgtgctgag   120
tctgagttgc ctatgggact tggaatgggg ggtggcaaaa ggtgtgtgat cttgagcaag   180
atattcaact cttctgggcc ttggtcttct catttgtaaa acggtgataa gaatattact   240
tcccatttgt gttgctgtga atattaaatg cgctacca                           278
```

<210> SEQ ID NO 299
<211> LENGTH: 137
<212> TYPE: DNA
<213> ORGANISM: Homo sapiens

<400> SEQUENCE: 299

```
gtgggcagca cttagattcg gagccatgga tagtccggag tccaaggtct ctgggtgagc    60
agacagtcgg ccaaaggcca gcctggagtc aaagagacca gaccctgct tagattgcca   120
tactcgcacc attccaa                                                  137
```

<210> SEQ ID NO 300
<211> LENGTH: 252
<212> TYPE: DNA
<213> ORGANISM: Homo sapiens

<400> SEQUENCE: 300

```
agttcggcaa aggtgtccta gaaatggcca gagtttttga cagacagagt gtagtctcct    60
tattagaaga aaggaaaaaa aagcagaggc caaagaagtt ttgtgtttgc tgatgagagc   120
cccactcatt tgcgaaacgc acgtaaaaca aagtgaaccg tgactgttaa actagggatg   180
ggaaattttg catcttgggg ggctgtacat ttatttattt agttgaagat tcactgatcc   240
cactttgaaa ta                                                       252
```

<210> SEQ ID NO 301
<211> LENGTH: 106
<212> TYPE: DNA
<213> ORGANISM: Homo sapiens

<400> SEQUENCE: 301

```
gtgcatgtgt gtgctgtgtc tttgtgtgtg tgctgtgtgc tagtgtgtgt gctgtgtgtg    60
catgtgtgtg cgtgtgctgt gcgtttgtgt gctgtgtgct cgtgtg                 106
```

<210> SEQ ID NO 302
<211> LENGTH: 294
<212> TYPE: DNA
<213> ORGANISM: Homo sapiens

<400> SEQUENCE: 302

```
tgggaagcgg cgagatcctc gggctggggg tgcccacgtt tgctacctcc ccctgtgaaa    60
tcgctggtgc tcacaattgt cttttcacagt gtatgtgatt ttttttaagga aaaaaaaaa   120
atccctattt aagatttga aggtgctacc attattttgc cacagacttt gaagaaactt   180
ttggatgtgg ggcatcatcc gcatctttct ctctcctcca aatgacaaag tttggggaat   240
ttttgaattt tcctagcatc gcccttgtgc tcatcaggta atctgctaag gagg          294
```

<210> SEQ ID NO 303
<211> LENGTH: 238
<212> TYPE: DNA
<213> ORGANISM: Homo sapiens

<400> SEQUENCE: 303

```
acccatcctg ttcgtgaata ggtctcaggg gttggggag ggactgccag atttggacac      60
tatattttt tttaaattca acttgaagat gtgtatttcc cctgaccttc aaaaaatgtt     120
ccaaggtaag cctcgtaaag gtcatcccac catcaccaaa gcctccgttt ttaacaacct    180
ccaacacgat ccatttagag gccaaatgtc attctgcagg tgccttcccg atggatta     238
```

<210> SEQ ID NO 304
<211> LENGTH: 258
<212> TYPE: DNA
<213> ORGANISM: Homo sapiens

<400> SEQUENCE: 304

```
cattctttcc tccacaggat tgctttgtcc atctcctgct ttcatttcaa gtgcataaac      60
aaaacctcaa agggcctggg aaggtgaggc aggccagagt ctgtgttctg tgttgagtgt    120
caagctattt gttaagaagg tttgcaacag gcctttggtg tgggctttgc cagagactgt    180
tttgaacact ttgcttgaga tccgtgccct gtaaaatgga tatgatgttt tactgatgtc    240
tgtaatacat ttgtaaac                                                  258
```

<210> SEQ ID NO 305
<211> LENGTH: 85
<212> TYPE: DNA
<213> ORGANISM: Homo sapiens

<400> SEQUENCE: 305

```
ttaagcgcat tagaaaacaa ttgtttgtaa tggaatcaaa gtgtttccct ggacagtttg      60
atgtgcttat ggttgagatt tataa                                           85
```

<210> SEQ ID NO 306
<211> LENGTH: 299
<212> TYPE: DNA
<213> ORGANISM: Homo sapiens
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 306

```
atttgcaaca gcctagtgga tttggtaggg tcctgaatca tctctataag gcaaacaagg      60
aaattgtaac acaaagaaat aaacatattg aatataattg ctattctgta agacatacag    120
tctgtgnaag atgtatctta tttacagaga cattttgaa aattaaaata ttaaatactt    180
tttgttatat aganacaatg atctggaagt ataaaagaa aatattatc ttgttgatgt     240
aaatatgata tccttatata tattagaatc caataagata tcatgggcgc aatattagc    299
```

<210> SEQ ID NO 307
<211> LENGTH: 229
<212> TYPE: DNA
<213> ORGANISM: Homo sapiens

<400> SEQUENCE: 307

```
gatggctggg agataagtcc ttgaatggag gaaccaagag gtgagttaga ggcataaact      60
aaggaatttc agttagtagg gtttaggagt gacagtctag aatgagtgga gactaggaga    120
```

```
ttcatcttga tgcaagcata cttagatcca tgttactcag gatagcatag gtgagagagg      180
agctggtaga attttaatgt catacctggg tagtacaact ggttattat                  229

<210> SEQ ID NO 308
<211> LENGTH: 213
<212> TYPE: DNA
<213> ORGANISM: Homo sapiens

<400> SEQUENCE: 308 tatttttccgg ttgacccccag aattcattag attttttttaa aaaacaattt caaaatagtt   60
gctgttttaa attagttgca tccagttcat atcaatgttt gcatgctttt tagtctttgt     120
tatttattga aaacctttgg tacctaaact taagtttgat tgtttcagtg tgtacttggt     180
aaatatgtca gtggcctttt aactaaacat caa                                  213

<210> SEQ ID NO 309
<211> LENGTH: 174
<212> TYPE: DNA
<213> ORGANISM: Homo sapiens

<400> SEQUENCE: 309
caccccagga ctttatcaac ttgttcaagt tctgaatccc agcacatgac aacacttcag      60
aagggtcccc ctgctgactg gagagctggg aatatggcat ttggacactt catttgtaaa    120
tagtgtacat tttaaacatt ggctcgaaac ttcagagata agtcatggag agga           174

<210> SEQ ID NO 310
<211> LENGTH: 32
<212> TYPE: DNA
<213> ORGANISM: Homo sapiens

<400> SEQUENCE: 310
atggacaatt ctgtaccccca ataatcagaa ca                                  32

<210> SEQ ID NO 311
<211> LENGTH: 166
<212> TYPE: DNA
<213> ORGANISM: Homo sapiens
<220> FEATURE:
<221> NAME/KEY: misc_feature
<222> LOCATION: (101)..(101)
<223> OTHER INFORMATION: n is a, c, g, or t

<400> SEQUENCE: 311
agagaggttt gtcccatata tcttgttcca gcagccatat atcttgtggt ctacagcctg      60
aagcatgatt tcccttgaag tcttggggtt gtttaaagga nagtcccttc aatataaaac    120
ctctgaaata ttagtgagaa tggctcacta atgtgaacaa tgttta                   166

<210> SEQ ID NO 312
<211> LENGTH: 213
<212> TYPE: DNA
<213> ORGANISM: Homo sapiens

<400> SEQUENCE: 312
tacaaagaat atttgggccc agtgctacag aaaaacatga actacatctt atcgtcacaa      60
aatagccatt ataaaatgaa ttttgcagcc tctgtttttt tgaactttga aataaaatgt    120
tcagacaaat attcaacttt ttaaaaacct ccattcattg atagcctgag aaatgtacaa    180
tgaacatgtt taggcagact gctagtattt tgc                                 213
```

```
<210> SEQ ID NO 313
<211> LENGTH: 225
<212> TYPE: DNA
<213> ORGANISM: Homo sapiens

<400> SEQUENCE: 313
cctccaccaa tcatactttg acatttatct atttccttct ccacttatgg atgtaattgg      60
cttgctatag aaactacagt tcagatgctt tgaatgtatg aactacaatg aacaataaag     120
tcctcttctt ttgaagcata ttttggcttc agctttaaga taatcttatg acaagaaggg     180
tcacactgat tcacttaata aattccattc ttacctaaca caagg                     225

<210> SEQ ID NO 314
<211> LENGTH: 259
<212> TYPE: DNA
<213> ORGANISM: Homo sapiens

<400> SEQUENCE: 314
gctggtgtgt ggatcggatg ggcaagtccc tgccagggtc tccagatggc aatggaagct      60
cctcctgccc cactgggagt agcggctaaa gctgggggat agaggggctg cagggccact     120
ggaaggaaca tggagctgtc atcactcaac aaaaaaccga ggccctcaat ccaccttcag     180
gccccgcccc atgggcccct caccgctggt tggaaagagt gttggtgttg gctggggtgt     240
caataaagct gtgcttggg                                                  259

<210> SEQ ID NO 315
<211> LENGTH: 217
<212> TYPE: DNA
<213> ORGANISM: Homo sapiens

<400> SEQUENCE: 315
gaccccagtg gaaaacaaag ccaaacaaaa ctgaaccaca aaaaaaggc tggtgttcac       60 caaaaccaaa cttgttcatt tagataattt gaaaaagttc catagaaaag gcgtgcagta     120
ctaagggaac aatccatgtg attaatgttt tcattatgtt catgtaagaa gccccttatt     180
tttagccata attttgcata ctgaaaatcc aataatc                              217

<210> SEQ ID NO 316
<211> LENGTH: 243
<212> TYPE: DNA
<213> ORGANISM: Homo sapiens

<400> SEQUENCE: 316
gagtaaaaag aacccttgc tgagtaacca agcctttaat tttgtgtttt tatgaaagga       60
attaaaatac ccacgataaa tatttaccac aacctgtgtc agataaatgg gaaattaaac     120
acagattgta caatgtgagc ttgggagtta atggcccaga ttttactgtt aggcagtaag     180
agttggagta ggtagtcttg ttatcatgag aagaaccttg aacagataca actaatttac     240
ata                                                                   243

<210> SEQ ID NO 317
<211> LENGTH: 172
<212> TYPE: DNA
<213> ORGANISM: Homo sapiens

<400> SEQUENCE: 317
aacacccata atcaatcaca gagataacca ctgttcataa ttccttccag tcttcttact      60
tggcacatat acatttgtct ttctttatat atgacatatg gatattttac aaagttagga    120
```
tcctactcta tgcactgctt ggtgatcgga tctattcaat gtacaaaata tt    172

<210> SEQ ID NO 318
<211> LENGTH: 100
<212> TYPE: DNA
<213> ORGANISM: Homo sapiens

<400> SEQUENCE: 318
ttttctaacc ttgattgacc atgggcaaat gaaactgcag aaagtgaaac tgcggatagg    60
ggggatgact gtattcaata gattccgaca ttatgtctgc    100

<210> SEQ ID NO 319
<211> LENGTH: 32
<212> TYPE: DNA
<213> ORGANISM: Homo sapiens

<400> SEQUENCE: 319
ttataatgag tgcgatatat gttgtcgagg ct    32

<210> SEQ ID NO 320
<211> LENGTH: 210
<212> TYPE: DNA
<213> ORGANISM: Homo sapiens

<400> SEQUENCE: 320
gttttgatgc tgtgtgctttt tggctgggcc tcgggctcca ggccctggga ccccttgcca    60
gggagacccc cgaacctttg tgccaggaca cctcctggtc ccctgcacct ttcctgttcg    120
gtttagaccc ccaaactgga gggggcatgg agaaccgtag agcgcaggaa cgggtgggta    180
attttagaga caaaagccaa ttaaagtcca    210

<210> SEQ ID NO 321
<211> LENGTH: 115
<212> TYPE: DNA
<213> ORGANISM: Homo sapiens

<400> SEQUENCE: 321
ttcattgagg ttcgtgtgtg ctgtgttcgc gtgtgtgtgc tgtgtgtgca tgtgtgtgct    60
gtgtcttagt gtgtgtgctg tgtgctagtg tgtgtgctgt ggggtaccga gctcg    115

<210> SEQ ID NO 322
<211> LENGTH: 241
<212> TYPE: DNA
<213> ORGANISM: Homo sapiens

<400> SEQUENCE: 322
ttcatcatat ccaagttcac tctgtcttcc tgagcagtgg aagatcatat tgctgtaact    60
tcttttaagt agttgatgtg gaaaacattt taaagtgaat ttgtcaaaat gctggttttg    120
tgttttatcc aacttttgtg catatatata agtatgtca tggcatggtt tgcttaggag    180
ttcagagttc cttcatcatc gaaatagtga ttaagtgatc ccagaacaag gaatactaga    240
g    241

<210> SEQ ID NO 323
<211> LENGTH: 148
<212> TYPE: DNA
<213> ORGANISM: Homo sapiens
<220> FEATURE:
<221> NAME/KEY: misc_feature
<222> LOCATION: (89)..(89)
<223> OTHER INFORMATION: n is a, c, g, or t -continued

```
<220> FEATURE:
<221> NAME/KEY: misc_feature
<222> LOCATION: (91)..(93)
<223> OTHER INFORMATION: n is a, c, g, or t

<400> SEQUENCE: 323
gtcattgata cctgtagtaa gttgacaatg tggtgaaatt tcaaaattat atgtaacttc    60
tactagtttt actttctccc ccaagtctnt nnnaactcat gattttaca cacacaatcc   120 agaacttatt atatagcctc taagtctt                                     148

<210> SEQ ID NO 324
<211> LENGTH: 198
<212> TYPE: DNA
<213> ORGANISM: Homo sapiens

<400> SEQUENCE: 324
gattttcttt tgacacagct ccaaggccac cagctatgca aggccacaag ttatgcacta    60
tatgattaac tgcttttgtt ttactttgt aagtccactt ataaaaaccc tgctctgtct   120
ttgtttaatg ctcagctttt tggatttgaa tccactcagc cggtgcacac cttaaaataa  180
acatcctcct gtactctc                                                198

<210> SEQ ID NO 325
<211> LENGTH: 269
<212> TYPE: DNA
<213> ORGANISM: Homo sapiens

<400> SEQUENCE: 325
agacctagaa ggttgtagat gggaaatcag gaatgatttg aactgataaa gatttcagac    60
tcataagaac acattttata aatgttaaac acaaaaacta catgactgaa gatagaagag   120
aatgcgatgg attttattac acatggtgga agagagaaga ggcgtgtagg tttgcaaaca   180
aagttaagaa ataggaaact gaattttca ttgtacagaa aatgtatctc ttggggaggg   240
cctgtgtacc cccattctct gattataaa                                    269

<210> SEQ ID NO 326
<211> LENGTH: 243
<212> TYPE: DNA
<213> ORGANISM: Homo sapiens

<400> SEQUENCE: 326 ggatttttc ccctgtagta gtgaggtaac atgcttgaat gtcactgtga tatttatttc    60
ctctttgttc agttgttttt gaattcctgt taagtacatg ttttaatact ttgagcgatt   120
taagatactt ttcttttttgc ccatcatttt ccccaaggaa tgtaattcac ataaatccaa  180
agctcatttt ttttttttatt gtacacaagt agtataatgt ttgcttttcc caataaacct  240
caa                                                                243

<210> SEQ ID NO 327
<211> LENGTH: 178
<212> TYPE: DNA
<213> ORGANISM: Homo sapiens
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
```

<221> NAME/KEY: misc_feature
<222> LOCATION: (123)..(123)
<223> OTHER INFORMATION: n is a, c, g, or t

<400> SEQUENCE: 327

```
gagacaagga cagacaaatt ttctggctgt ccccatttct cctggggag gggtttgggg    60
ctggtttgac tttaattggt gggngggtng tttctgccgc tctgtttgct gcagtccccg   120
tgncctgctt ggggactgag aaatttgagc caggtatcca gagccacagc ccatcttg    178
```

<210> SEQ ID NO 328
<211> LENGTH: 238
<212> TYPE: DNA
<213> ORGANISM: Homo sapiens

<400> SEQUENCE: 328

```
agttggtgcc ctgattccat ttttctcaag ttgtagaaga aacaaactaa tttacggtag    60
gagaaattca aattcagatt ctccccatcc ccaccagtta cctttggttg gtggagaggg   120
ggagaattgg caggaaaggg gcacaaagaa acttttgggg gtgatggaaa tattttgtac   180
cttgctttag atgttggtca gatggaatat acgtttgtgg aaacctgcca aactgtac    238
```

<210> SEQ ID NO 329
<211> LENGTH: 155
<212> TYPE: DNA
<213> ORGANISM: Homo sapiens

<400> SEQUENCE: 329

```
aaacattacc gggcatggta gcttgcacct gcagtcccag ctacttggga gactgaggtg    60
agaggatcac ctgagtgtag gaggtgaaag cctcaccgaa ctatgactga accactgcac   120
tccagcgtgg gcacttggca ccagagcaag attct                              155
```

<210> SEQ ID NO 330
<211> LENGTH: 47
<212> TYPE: DNA
<213> ORGANISM: Homo sapiens

<400> SEQUENCE: 330

```
gggatgcata aagtatgagt gccttttagg atgggaattg agatgta                 47
```

<210> SEQ ID NO 331
<211> LENGTH: 235
<212> TYPE: DNA
<213> ORGANISM: Homo sapiens
<220> FEATURE:
<221> NAME/KEY: misc_feature
<222> LOCATION: (157)..(157)
<223> OTHER INFORMATION: n is a, c, g, or t

<400> SEQUENCE: 331

```
aggatttccc aaaccagccg aggcccagc accgccgtc tccccagaag ccccctcctc    60
cttcccccat gggtcatatg ttgaaagtct attttaaaaa ctatgttcct tgccgtagat   120
tgcagagcta atttatcacg tttctctcct gtgagancc cccttttata tgatatatcc   180
agaggaagtt ttgtaatata aaacaggacg cccacactga tggttttgca ctggt        235
```

<210> SEQ ID NO 332
<211> LENGTH: 38
<212> TYPE: DNA
<213> ORGANISM: Homo sapiens

<400> SEQUENCE: 332

```
tttggatttg aatccactca gccggtgcac accttaaa                               38
```

<210> SEQ ID NO 333
<211> LENGTH: 265
<212> TYPE: DNA
<213> ORGANISM: Homo sapiens

<400> SEQUENCE: 333

```
tgttttagaa ccagccgtat tttacatgaa gctgtataat taattgtcat tattttttgtt      60 agcaaagatt aaatgtgtca ttggaagcca tcccttttt tacatttcat acaacagaaa       120
ccagaaaagc aatactgttt ccattttaag gatatgatta atattattaa tataataatg      180
atgatgatga tgatgaaaac taaggatttt tcaagagatc tttctttcca aaacattttt     240
ggacagtacc tgattgtatt ttttt                                            265
```

<210> SEQ ID NO 334
<211> LENGTH: 56
<212> TYPE: DNA
<213> ORGANISM: Homo sapiens

<400> SEQUENCE: 334

```
cacaatctga gcacgctacc aaatctcaaa atatcctaag actaacaaag gcagct           56
```

<210> SEQ ID NO 335
<211> LENGTH: 289
<212> TYPE: DNA
<213> ORGANISM: Homo sapiens

<400> SEQUENCE: 335

```
tcccaagtag tgctgactga ctctcctggt gacaggggtt tgtgtccgag ccctgcggt        60 caaggagtgt ggagcaaaac gtgggtacta gggtgggagg cggggaaagg ccacagcaca      120
ctggcgctcc agcaaagcca aatcatgtct cctctggcca ctgcggtcct ctccttggta      180
catgtcatcc cccagaggag tatccaaagc tattccacta tgcactcatc aaccctggct     240
tgtcagcctt ggggaaggtc actttattca taaaaatgcc tctttgagt                  289
```

<210> SEQ ID NO 336
<211> LENGTH: 212
<212> TYPE: DNA
<213> ORGANISM: Homo sapiens

<400> SEQUENCE: 336

```
cctgagtcct gggatcagac accccttcac gtgtatcccc acacaaatgc aagctcacca      60
aggtcccctt tcagtcccct tccctacacc ctgaccggcc actgccgcac acccacccag     120
agcacgccac ccgccatggg agtgtgctca ggagtcgcgg gcagcgtgga catctgtccc     180 agaggggca gaatctccaa tagaggactg ag                                     212
```

<210> SEQ ID NO 337
<211> LENGTH: 294
<212> TYPE: DNA
<213> ORGANISM: Homo sapiens

<400> SEQUENCE: 337

```
cagggttcct ttgcctgcta acaagcccac gtggaccagt ttgaatgtct ttcctttaca       60
cctatgtttt taagtagtca aacttcaaga aacaatttaa acaagttttt gttgcatatg     120
tgtttgtgaa cttgtatttg tatttagtag gcttctatat tgcatttaac ttgttttttgt    180
```

| | |
|---|---|
| aactcctgat ttttccttttt cggatactat tgatgaataa agaaattaaa gtgatagttt | 240 |
| tattggtttc ctttccccca attaaggcca aataaagtcg tgagaacatt accc | 294 |

<210> SEQ ID NO 338
<211> LENGTH: 52
<212> TYPE: DNA
<213> ORGANISM: Homo sapiens

<400> SEQUENCE: 338

| | |
|---|---|
| gaggccggtg ccagtgcagg tccttggtgt gctgtgtgcc ggtcccctgg gc | 52 |

<210> SEQ ID NO 339
<211> LENGTH: 297
<212> TYPE: DNA
<213> ORGANISM: Homo sapiens

<400> SEQUENCE: 339

| | |
|---|---|
| atggtaatgt aggatccttt cacagagtgc caggctaaag agctgaactt tgtggtggaa | 60 |
| gagacagacc ccctatgtgc tctgtagaca cctgtgatga agtagaactc atgaggtat | 120 |
| gaagagaaac atttgtaatt tgagtgatta aactaggaac gaaagaggag gggagaaata | 180 |
| ggaagagaga atcaccggcc ctgttgactg atttgagctg ggaatgaaga agaaaaccct | 240 |
| gcaggtgtgg gcaccaatgt ttgaaacccc cacagtgtga gtctcaactc tgtgtga | 297 |

<210> SEQ ID NO 340
<211> LENGTH: 223
<212> TYPE: DNA
<213> ORGANISM: Homo sapiens

<400> SEQUENCE: 340

| | |
|---|---|
| ccatgtcagc ctggatagag gtatatgacg tgtgccaaga atttatccca gactcccctg | 60 |
| tgtgacagct tcataataaa gttacttaac tgtgcctctt cctccttcct ctccccacac | 120 |
| aggatggatg ggcatctttc tccttgacca ccctactctc ccttcctccc ctgatcacct | 180 |
| cccctccctg ctctcccctg gtgatggact tctaacatga gat | 223 |

<210> SEQ ID NO 341
<211> LENGTH: 238
<212> TYPE: DNA
<213> ORGANISM: Homo sapiens

<400> SEQUENCE: 341

| | |
|---|---|
| actggtatat tattgcttca tgttttgtac catcataaga ttttgtgcag atttttttta | 60 |
| cagaaattat tatttttat gacaatatga cacttgtaaa ttgttgtttc aaaatgaaca | 120 |
| gcgaagcctt aactttaaat gacatttgta ttttcagaca ctgagtagca taaaaaccac | 180 |
| atagaactga actgtaactt aaattccaaa ctatgactac tacattccaa agaaacag | 238 |

<210> SEQ ID NO 342
<211> LENGTH: 129
<212> TYPE: DNA
<213> ORGANISM: Homo sapiens

<400> SEQUENCE: 342

| | |
|---|---|
| cgtccccaac atgcatctca ctctgggtgt cttggtcttt tatttttgt aagtgtcatt | 60 |
| tgtataactc taaacgccca tgatagtagc ttcaaactgg aaatagcgaa ataaaataac | 120 |
| tcagtctgc | 129 |

<210> SEQ ID NO 343
<211> LENGTH: 277
<212> TYPE: DNA
<213> ORGANISM: Homo sapiens

<400> SEQUENCE: 343

| | | | | | |
|---|---|---|---|---|---|
| tggaggattc | aagatgagca | ggtatgtttt | ctgctttcaa | taactcattt | tctgctgcag | 60 |
| agatagcctt | gtaagcaagc | aaaggaaaac | tttgacattt | ctctgcaaag | ataatgcatt | 120 |
| acatataagg | gtgtgtctgg | gagggtacca | ggtgcctgtc | agcaaaagtt | gcaaaaacag | 180 |
| cttgataagg | gtattaagtg | ggcctgttgg | gaaaggcagg | agtgtcaaat | gtcggacaga | 240 |
| actccagaca | gagaaatcca | gatatccagt | aggttag | | | 277 |

<210> SEQ ID NO 344
<211> LENGTH: 231
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (169)..(170)
<223> OTHER INFORMATION: n is a, c, g, or t
<220> FEATURE:
<221> NAME/KEY: misc_feature
<222> LOCATION: (172)..(176)
<223> OTHER INFORMATION: n is a, c, g, or t
<220> FEATURE:
<221> NAME/KEY: misc_feature
<222> LOCATION: (178)..(180)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (186)..(187)
<223> OTHER INFORMATION: n is a, c, g, or t

<400> SEQUENCE: 344

| | | | | | |
|---|---|---|---|---|---|
| gaatggcaaa | acacaaatgg | caacataaat | gtccatttga | cttacctaac | ttcacaactt | 60 |
| tcaagttgag | gatgtcattt | attcttgaat | tntgtttttt | tactnagatg | ctttcaatta | 120 |
| atagccctat | atttttgtgc | aggcgaactg | tataacaggn | ataaaaaann | annnnnannn | 180 |
| antgannagg | aggagaaatt | ctcacagaac | accatatgag | ctttagacca | a | 231 |

<210> SEQ ID NO 345
<211> LENGTH: 262
<212> TYPE: DNA
<213> ORGANISM: Homo sapiens

<400> SEQUENCE: 345

| | | | | | |
|---|---|---|---|---|---|
| gaggtgtgat | tttaaggcat | tgttatattt | ttttttattt | gtgagtgttt | taaaattttg | 60 |
| tatttctttt | aaactttta | ttttagaaaa | atttccaaca | tatatagaag | tagactattg | 120 |
| taaggaaccc | ttatgtaccc | tccaccagct | tcaacaacta | tcaacaaaag | tttgatcttg | 180 |

```
ttttaaccac attcctttcc aattttttgtg tttaccccca gattattttg aagcaaattc      240
ctgacctcat aacattttca aa                                                262

<210> SEQ ID NO 346
<211> LENGTH: 187
<212> TYPE: DNA
<213> ORGANISM: Homo sapiens

<400> SEQUENCE: 346
ttcagtttgt cctcataggg aatcaagtat tttagctagg tgatgtcttg caagtacgtt      60
ccactttgtt acaatctact atctgtatat actatttgta tcttaattct tttatgagat     120
gttctgtaac attttctca ctttgacaaa tgtttttaga ctgtacagtc aagatctggc     180
gcttggg                                                               187

<210> SEQ ID NO 347
<211> LENGTH: 180
<212> TYPE: DNA
<213> ORGANISM: Homo sapiens

<400> SEQUENCE: 347
acagtgattc cccacgtgtg ttcatctgca cccaccgagc caggcagagg ccagccctcc     60
gtggtgcaca cagcacgcgc ctcagtccat cccattttag tctttaaacc ctcaggaagt    120
cacagtctcc ggacaccaca ccacatgagc ccaacaggtc cacgatggat ccaccagtcc    180

<210> SEQ ID NO 348
<211> LENGTH: 55
<212> TYPE: DNA
<213> ORGANISM: Homo sapiens

<400> SEQUENCE: 348
cagatcgaca cgcagctagc ctcctgcatt gtatggttat aaatagcacc ctagt          55

<210> SEQ ID NO 349
<211> LENGTH: 207
<212> TYPE: DNA
<213> ORGANISM: Homo sapiens

<400> SEQUENCE: 349
aagtgttcta caaagaatc cctgtggtta gcttactctt aggttagatc ttctaataag      60
gctgaaattc aaaatcaaaa ccttagtgtg tccgagtcca gcctgggttc cagcattctg    120
ttcaggccac ttctgaacgg ccgaaggtgc cccattccag acctgcccat tgatggaca     180 gagcagacag cccggaacag attcaag                                         207

<210> SEQ ID NO 350
<211> LENGTH: 241
<212> TYPE: DNA
<213> ORGANISM: Homo sapiens
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (97)..(97)
<223> OTHER INFORMATION: n is a, c, g, or t

<400> SEQUENCE: 350
taagaattta tgaaactggg caagttattt cctgggactc aatggtaaag acacagcagt      60
aatccaaatt ttccatcttt gaatttttcc atncttncag tcaatattag taatacctgg    120
```
gtcaaagggg agagttaggc ataccaatta atgatcatca gaaatgacat agtcctacaa    180
aagcaaagaa aatttagaga cactttctta aaaatacgac tcttggtact gttgaagaaa    240
a                                                                    241

<210> SEQ ID NO 351
<211> LENGTH: 261
<212> TYPE: DNA
<213> ORGANISM: Homo sapiens

<400> SEQUENCE: 351
agccgctgcc aagtctgtat gagaagaaca taatgaagcc tgactcagct aatgtcacaa     60
catggtgcta cttcttcttc tttttgttaa cagcaacgaa ccctagaaat atatcctgtg    120
tacctcactg tccaatatga aaaccgtaaa gtgcccttata ggaatttgcg taactaacac    180
accctgcttc attgacctct acttgctgaa ggagaaaaag acagcgataa gctttcaata    240
gtggcatacc aaatggcact t                                              261

<210> SEQ ID NO 352
<211> LENGTH: 274
<212> TYPE: DNA
<213> ORGANISM: Homo sapiens

<400> SEQUENCE: 352
ggttgagttt gtccattgct agggagagac ttccagtaat aaaatttact attctagatg     60
cttctactgt tatgttttat ctgcccattt atctttctta gttaccagga gaaatgtgtg    120
acacctatat tataatgaaa acaatcttat tacttatagt ttatctatat taaacaaatt    180
taattgcatt ttaaagcatt ctttgatatt gttgcttttg caataaatat ggataatctt    240
ggttataagg gagttaaaac aatgctgtaa taaa                                274

<210> SEQ ID NO 353
<211> LENGTH: 179
<212> TYPE: DNA
<213> ORGANISM: Homo sapiens

<400> SEQUENCE: 353
tcatggaatg ctacatgctt tctgtttttt tcattttgga tttctccaaa actaactgaa     60
tttaagcttc aggtccctt gtatgcagta gaaaggaatt attaaaaaca ccaccaaaga    120
aaataaatat atcctacttg aaatttactt tatggactta cccactgcta gaataaatg    179

<210> SEQ ID NO 354
<211> LENGTH: 249
<212> TYPE: DNA
<213> ORGANISM: Homo sapiens

<400> SEQUENCE: 354
cggttgttaa aactggttta gcacaattta tattttccct ctcttgcctt ttttatttgc     60
aataaaaggt attgagccat tttttaaatg acattttga taaattatgt ttgtactagt    120
tgatgaagga gttttttta acctgtttat ataattttgc agcagaagcc aaatttttg    180 tatattaaag caccaaattc atgtacagca tgcatcacgg atcaatagac tgtacttatt    240
ttccaataa                                                            249

<210> SEQ ID NO 355
<211> LENGTH: 64
<212> TYPE: DNA

<213> ORGANISM: Homo sapiens

<400> SEQUENCE: 355

```
ccatgaagga gcaagttttg tatttgtgac ctcagctttg ggaataaagg atcttttgaa    60
ggcc                                                                64
```

<210> SEQ ID NO 356
<211> LENGTH: 57
<212> TYPE: DNA
<213> ORGANISM: Homo sapiens

<400> SEQUENCE: 356

```
atgaggcaga atctggttgg gtatgtttct tatatatgtt tgaagcagat ggctgac      57
```

<210> SEQ ID NO 357
<211> LENGTH: 141
<212> TYPE: DNA
<213> ORGANISM: Homo sapiens

<400> SEQUENCE: 357

```
attttttgcct ttccgtttct gtctatgatg taggcttctg aggagaacca agaagcttgg   60
ctttagtggt agaatgacag aacttaggga tcccttgcag gctagaacaa agttctgacc  120
cttagaccaa atctttatgt t                                            141
```

<210> SEQ ID NO 358
<211> LENGTH: 108
<212> TYPE: DNA
<213> ORGANISM: Homo sapiens

<400> SEQUENCE: 358

```
gaggaggtgg gcctcgttag actgctcaga ttactggaac ctcgttatca catcccattc    60
tacaagtttt tcactgaatg tttcctgaca tctataaatg agggtgcc               108
```

<210> SEQ ID NO 359
<211> LENGTH: 158
<212> TYPE: DNA
<213> ORGANISM: Homo sapiens

<400> SEQUENCE: 359

```
gttcaaatga tctacactta catttttgcaa atctttttttt ttaaattttt taaatttat   60
atttttttc cagccaactc aaggccaaaa aaaatttctt aatatagtta ttatgcgagg   120
ggaggggaag caaaggagca caggtagtcc acagaata                          158
```

<210> SEQ ID NO 360
<211> LENGTH: 157
<212> TYPE: DNA
<213> ORGANISM: Homo sapiens

<400> SEQUENCE: 360

```
aggtggtttt gataacacac ttataaggct ttctgtaaaa ggtactatag aagggcgaag    60
aatcgttcaa ctgtcaatca gcctcttgat tctttgtaaa ttgccagggt gggtgggtac  120
atatctcttc ttgattctgc atttcatact taactat                           157
```

<210> SEQ ID NO 361
<211> LENGTH: 273
<212> TYPE: DNA
<213> ORGANISM: Homo sapiens

<400> SEQUENCE: 361

```
gactgagtga gtaactgcaa gctacagggg gcagcttacg tatggcacac agggtggggc      60
tagcttggtt tcataggctc tctgtggatt ggatgattta ataatttttg gtgggccctg     120
gggtttaggg actgtcccta gttgtttggt gctaggtccc agggcagatt agggcagatg     180
tgagtgtgag agcatgataa ggaaagtctt caaggtgtgg aattactcaa ctgctggaga     240
aagggaattt atcagccttt agccagggcc tca                                  273
```

<210> SEQ ID NO 362
<211> LENGTH: 257
<212> TYPE: DNA
<213> ORGANISM: Homo sapiens

<400> SEQUENCE: 362

```
gaaagcctga gtttgcaacc agttgtaggg ttttttgttgt gtttttttttt ttttttttgaa      60 ataaaactat aatataaatt ctcctattaa ataaaattat tttaagtttt agtgtcaaaa     120
gtgagatgct gagagtaggt gataatgtat attttacaga gtgggggttg gcaggatggt     180
gacattgaac atgattgctc tctgtctctt tttttcagctt atgggtattt atcttctatt     240
agtatttgta tcttcag                                                    257
```

<210> SEQ ID NO 363
<211> LENGTH: 268
<212> TYPE: DNA
<213> ORGANISM: Homo sapiens

<400> SEQUENCE: 363

```
atgagtcaaa atccgctctc catgcttact cttgacaccc cattgaagcc actcattgtg      60
tgtgcgtctg ggtgtgaagt ccagctccgt gtggtcctgt gcttgtactg ccctgctttg     120
cagttccttt gcacttactc atcgagtgct gttttgaaat gctgacatta tataaacgta     180
aaagaaaatg taaaaaaaaa aaacccacac acaaacaaac ccatacgatc tgtatttgta     240
tatacacgtg tccgtacaag tataacta                                       268
```

<210> SEQ ID NO 364
<211> LENGTH: 290
<212> TYPE: DNA
<213> ORGANISM: Homo sapiens

<400> SEQUENCE: 364

```
gaccaaatgg attagactgt aaactgcaaa gtgctgtccg cacatgaggt catctgatta      60
ctgtcctcag atctcttttg tagaggattt caatgtattt ctttatcatt tgagtgtgtg     120
tgtgatggac gaatatgtgt gtgagtttga gaagcatatc gttcgtgtcc agttactttg     180
caaatttgtg gacatttgtg attggacaga ggggtttgtg ctgtggccta acacttgcca     240
agtgaggtgt aggttatgcc tatatgcaaa ttaaacttca cctttcttga                290
```

<210> SEQ ID NO 365
<211> LENGTH: 205
<212> TYPE: DNA
<213> ORGANISM: Homo sapiens

<400> SEQUENCE: 365

```
cctttctaag gatgagggaa tccacaacag acttctctcta gaaaacacta atgatggaca      60 acttttggt gtcatcaatg agttggctac taccttgatg taaaaatttg taaggaaaat     120
tttcaccatt tcgagtgtca agtgtatttt taactgtctg gtttgtactt ttatgacttt     180
```
tgtactacca aagcggagtt aaaaa                                                   205

<210> SEQ ID NO 366
<211> LENGTH: 278
<212> TYPE: DNA
<213> ORGANISM: Homo sapiens

<400> SEQUENCE: 366
ctatcaggta ctgtgctcat ctgaacaaca aacctcaaca acacgcaatt tatccatgta    60
attaacctgc acatgtaccc ccgaaaccta aaataaaagt tcaaaaaaaa cctgtggtat   120
ttaaataggt attgtgtcta aaaatgcatg ctatctaaaa atgtagtttt attgcactgt   180
ataagaatac gagaggttta aaatagacac tctaaaagtt ataagcccta atttacatat   240
attctctagc ctttctccac cttctatcta ccaaaaaa                           278

<210> SEQ ID NO 367
<211> LENGTH: 41
<212> TYPE: DNA
<213> ORGANISM: Homo sapiens

<400> SEQUENCE: 367
tcctcatggt ggcagcgctc atagcgaaag cctactgtaa t                        41

<210> SEQ ID NO 368
<211> LENGTH: 133
<212> TYPE: DNA
<213> ORGANISM: Homo sapiens

<400> SEQUENCE: 368
aatgcagaat attcctctga acacttccct catacatcat tcaatattat aaattaaaca    60
caaagagcct ctccacttag atttttatca tgcatcctac attgtaatgt ctttactctt   120
ccatagaaaa ggt                                                     133

<210> SEQ ID NO 369
<211> LENGTH: 74
<212> TYPE: DNA
<213> ORGANISM: Homo sapiens

<400> SEQUENCE: 369
ggtgcaatta ttatactgcg aaaatgaaaa tattgcatac taaacagtac ctagggtatg    60
atctcaatgt aaaa                                                     74

<210> SEQ ID NO 370
<211> LENGTH: 172
<212> TYPE: DNA
<213> ORGANISM: Homo sapiens

<400> SEQUENCE: 370
aactgtgacc gtttctgtgt gaagattttt agctgtattt gtggtctctg tatttatatt    60
tatgtttagc accgtcagtg ttcctatcca atttcaaaaa aggaaaaaaa agagggaaaa   120
ttacaaaaag agagaaaaaa agtgaatgac gtttgtttag ccagtaggag aa           172

<210> SEQ ID NO 371
<211> LENGTH: 258
<212> TYPE: DNA
<213> ORGANISM: Homo sapiens

<400> SEQUENCE: 371
actcaaggct gtgaacaaac atacgctgct ttattctttc caattttttct cttgttttct    60

-continued

| | |
|---|---|
| agaactctta tccatatgtt tttaaaataa gtacctaaaa gtggtttgat agtgtcctaa | 120 |
| acgactttt taacttccta aatggaaaga gcataacaat gtagttgatt ggtaagattt | 180 |
| acagggattt ggtttctgag tttgaggcac attcccagtg aataagctga gtcccatacc | 240 |
| acactcaaaa ggttttaa | 258 |

<210> SEQ ID NO 372
<211> LENGTH: 103
<212> TYPE: DNA
<213> ORGANISM: Homo sapiens

<400> SEQUENCE: 372

| | |
|---|---|
| attaaagtac tcaagttagt tgttttgcag agatgttgcc ttcagatgtt aatcaggtct | 60 |
| ctcaagtttc atggagtcta tgctgatcct ttaattgaca aat | 103 |

<210> SEQ ID NO 373
<211> LENGTH: 258
<212> TYPE: DNA
<213> ORGANISM: Homo sapiens

<400> SEQUENCE: 373

| | |
|---|---|
| ggatgaagtg gcacacactc taactgaaag cagagtatta agaacacta gacatccctt | 60 |
| tttaacatcc ttgaaatatt ccttccagac aaaagaccgt ttgtgttttg tgatggaata | 120 |
| tgttaatggg ggcgagctgt ttttccattt gtcgagagag cgggtgttct ctgaggaccg | 180 |
| cacacgtttc tatggtgcag aaattgtctc tgccttggac tatctacatt ccggaaagat | 240 |
| tgtgtaccgt gatctcaa | 258 |

<210> SEQ ID NO 374
<211> LENGTH: 252
<212> TYPE: DNA
<213> ORGANISM: Homo sapiens

<400> SEQUENCE: 374

| | |
|---|---|
| ggttctgtaa ggtctttatt tcccataagt aaatattgcc atgggagggg ggtggaggtg | 60 |
| gcaaggaagg ggtgaagtgc tagtatgcaa gtgggcagca attattttg tgttaatcag | 120 |
| cagtacaatt tgatcgttgg catggttaaa aaatggaata taagattagc tgttttgtat | 180 |
| tttgatgacc aattacgctg tattttaaca cgatgtatgt ctgttttgt ggtgctctag | 240 |
| tggtaaataa at | 252 |

<210> SEQ ID NO 375
<211> LENGTH: 210
<212> TYPE: DNA
<213> ORGANISM: Homo sapiens

<400> SEQUENCE: 375

| | |
|---|---|
| tttcaagatc ttttgctcac aattcactgc aactgagggg atgtgaatat cattatgcaa | 60 |
| taaattaaga gccacagttg gctgaggtga tatgaaagcc aacctgccta aggggggtat | 120 |
| gaaagatgtg tatctttcca aacttttaaa acaacgtaag tctgagataa gaacatattt | 180 |
| gatggcactg tttggaaaga ggtgtcctta | 210 |

<210> SEQ ID NO 376
<211> LENGTH: 258
<212> TYPE: DNA
<213> ORGANISM: Homo sapiens

<400> SEQUENCE: 376

```
ctcaccagga ctcgtctctc cattcccgtc agagtttgct tgatttccc tttcctttcc      60
ttctcgggga ccagttctta cttcctttta tttttagctt tgcactccat gtggtttcag    120
ggttcagttt gatccatcaa aaggttcttt ttttataatc cctttgaaa atgataatca     180
aaggaagaga tgtggtgttt ggtcatgtgg aaaactcaat gtataattta gacgtctgtc    240
aaaaatccga caaataaa                                                   258
```

<210> SEQ ID NO 377
<211> LENGTH: 218
<212> TYPE: DNA
<213> ORGANISM: Homo sapiens

<400> SEQUENCE: 377

```
gtttcaattg attcacaact ttaaaaaata tccacagagg cgtaagagga gatattgtat     60
tgcacccacg aaccagtttt atgctgttta agaaagggac attcaagaaa caaaaggga    120
gctttgggaa atttgaacaa taataatag tagaataaaa aattcagaga aagtttggat    180
gataaatttg agccaatctc ccagtaagca gagcaaaa                             218
```

<210> SEQ ID NO 378
<211> LENGTH: 267
<212> TYPE: DNA
<213> ORGANISM: Homo sapiens

<400> SEQUENCE: 378

```
atgactgtgc tagagccacc ctctcacttt agcctcctga gtagctggga ctacaggtgc     60
ttcccactgt gcctggccaa ttaacaattt cattttatt tttagtagag atgagatctc    120
actatgttgc ccaggctggt cctgaactcc tgagctcaag agatcctccc accttggcct   180
cccaaagtac tgggattaca aacaagagcc actgtgcctg accaggctct aagattgcta    240
atctggctat agaaggacta atgttag                                         267
```

<210> SEQ ID NO 379
<211> LENGTH: 230
<212> TYPE: DNA
<213> ORGANISM: Homo sapiens

<400> SEQUENCE: 379

```
aagccgaggg gcccgagact ctgcagcggg gccagaaaga gaagagtggg ggaggaggcc     60
gggagtggtg catggaccag ggggtagagg gaggtgggtg tggacctggg gtcggcgcc    120
agtcagcttg cagcctatga aggacggaag ggagggctac agagataggg gaagagtggg   180
gctgaggata gccagagcgg cttggcacac agttttaggg taaaagcatc                230
```

<210> SEQ ID NO 380
<211> LENGTH: 196
<212> TYPE: DNA
<213> ORGANISM: Homo sapiens

<400> SEQUENCE: 380

```
tttatttata ccaagcctcc tcctgaaatt tctcttcctt tctttctacc tacccaagac     60
ataccacgtg cttcaataac cagtcccttc ctcctacaaa cactacaacc tggaaagcac    120
tcttgctttt ctgaagtcct ctatacttag tgtaactctt ctgtgatgaa gattaaagtg    180
tattatggca actctc                                                     196
```

<210> SEQ ID NO 381
<211> LENGTH: 267
<212> TYPE: DNA
<213> ORGANISM: Homo sapiens

<400> SEQUENCE: 381
aggcattata tatactacac agagtacaat taaaccataa ttgggaatta tattttgttt    60
ttttcttccc aggcaataca cctctgaaca tgtgtgtgat aaatgggttt gctaatgtgc   120
tgttttaaag tataaagcat aatatgtttt ggttaacaca atgtactttt tgaactataa   180
atctttattt taatatggaa atgtttggaa caggagatgc aagccactaa cagagaactt   240
taataattct accctgtatt ttataaa                                      267

<210> SEQ ID NO 382
<211> LENGTH: 280
<212> TYPE: DNA
<213> ORGANISM: Homo sapiens

<400> SEQUENCE: 382
acccacactt aaactaaagg ctaagaatat aggcttgatg ggaaattgaa ggtaggctga    60
gtattgggaa tccaaattga attttgattc tccttggcag tgaactactt tgaagaagtg   120
gtcaatgggt tgttgctgcc atgagcatgt acaacctttg gagctagaag ctcctcagga   180
aagccagttc tccaagtttt taacctgtgg cactgaaagg aatgttgagt tacctcttca   240
tgttttagac agcaaaccct atccattaaa gtacttgtta                         280

<210> SEQ ID NO 383
<211> LENGTH: 72
<212> TYPE: DNA
<213> ORGANISM: Homo sapiens

<400> SEQUENCE: 383
acatgagtat ggaatggtgt tttattatga ctttagtttg cattttcctc aattctcgtt    60
aaatccttca tt                                                       72

<210> SEQ ID NO 384
<211> LENGTH: 260
<212> TYPE: DNA
<213> ORGANISM: Homo sapiens

<400> SEQUENCE: 384
gagtaggttc ggtctgaaag gtgtggcctt tatatttgat ccacacacgt tggtctttta    60
accgtgctga gcagaaaaca aaacaggtta agaagagccg ggtggcagct gacagaggaa   120
gccgctcaaa taccttcaca ataaatagtg gcaatatata tatagtttaa gaaggctctc   180
catttggcat cgtttaattt atatgttatg ttctaagcac agctctcttc tcctattttc   240
atcctgcaag caactcaaaa                                              260

<210> SEQ ID NO 385
<211> LENGTH: 222
<212> TYPE: DNA
<213> ORGANISM: Homo sapiens

<400> SEQUENCE: 385
atgattatag aaggctgtct tagtgcaaaa acatactta catttcagac atatccaaag    60
ggaatactca catttgtta agaagttgaa ctatgactgg agtaaaccat gtattccctt   120
atcttttact ttttttctgt gacatttatg tctcatgtaa tttgcattac tctggtggat   180

```
tgttctagta ctgtattggg cttcttcgtt aatagattat tt                         222
```

```
<210> SEQ ID NO 386
<211> LENGTH: 216
<212> TYPE: DNA
<213> ORGANISM: Homo sapiens

<400> SEQUENCE: 386
gcaatatatt tgtgattccc catgtaattc ttcaatgtta aacagtgcag tcctctttcg       60
aaagctaaga tgaccatgcg ccctttcctc tgtacatata cccttaagaa cgcccctcc      120 acacactgcc cccagtata tgccgcattg tactgctgtg ttatatgcta tgtacatgtc      180
agaaaccatt agcattgcat gcaggtttca tattct                                216
```

```
<210> SEQ ID NO 387
<211> LENGTH: 35
<212> TYPE: DNA
<213> ORGANISM: Homo sapiens

<400> SEQUENCE: 387
ttggatagca gctatcttgt tggatgtgag gtgga                                 35
```

```
<210> SEQ ID NO 388
<211> LENGTH: 258
<212> TYPE: DNA
<213> ORGANISM: Homo sapiens

<400> SEQUENCE: 388
atgaaaggtg gaagttctac ctagatttga atgagtgttt ttttaaggga atgagaatgt      60
catggtgcta aacctgacaa ataagagatc attgaaatgc tgaaaatttt aacagttttt     120
ttaaaagtat tgagggggca aaaattacca attatggtat acaaaaataa gcctataaat     180
gtgtttcaca ttgctaactt gagtttcagt tgattcagtt tgtaataact agtaatgagc     240
ttctgtttac aataaaaa                                                    258
```

```
<210> SEQ ID NO 389
<211> LENGTH: 275
<212> TYPE: DNA
<213> ORGANISM: Homo sapiens
<220> FEATURE:
<221> NAME/KEY: misc_feature
<222> LOCATION: (195)..(195)
<223> OTHER INFORMATION: n is a, c, g, or t

<400> SEQUENCE: 389
ccacagtgtt cccactaatg ctatttttta attttttaat ttagtttgtc ataatttggt      60
ttcatcaact cctttgtttt ttccttcttt tttttttttt gagatgaggt ctcactatct     120
tgcccagact ggtttcgaat tgccctccag caattctccc acctcagcct tcagagtagc     180
tggcattgtg ggtangcacc actgtgccca gctcctgttt tataataaat aagccagagc     240
tctatctcca aatggtgcaa atcatcaatg ctatt                                275
```

```
<210> SEQ ID NO 390
<211> LENGTH: 281
<212> TYPE: DNA
<213> ORGANISM: Homo sapiens

<400> SEQUENCE: 390
gggcccctgg tatttatagg gtccaagagg aggcacctgc ttttcaactg caccctcagt      60
gctgcctctt cacggcccct aaacgtttcc ctttgaggtt gtgatgctgg gaatcacaga     120
```

```
cttcactctc tgcctgcacc cttccccgag gtctcatctt ttctgggtcc cacatctttg    180
taataatgtg aaaaagcaca atttgtctga tcaccccca ggtggttccc caccttatta    240
tcactacctg atccgagtta ctgcaataag tacggtgtcg c                       281
```

<210> SEQ ID NO 391
<211> LENGTH: 274
<212> TYPE: DNA
<213> ORGANISM: Homo sapiens

<400> SEQUENCE: 391

```
tgctcagtgt catgctgtgt gtgcatgtgt gtgctgtgtg ttttgtgtgt gtgctgtgtt    60
catgtgtgct gtgcatgcgt gtgtgctgtg tgtgcctgtg tgtgcggtgt gctgtgtcct    120
tgtgtgtgct gtgtgtgcgt gtgctgtgtg catgtgtgtg ctgtgttatg tcgtgtgtgc    180
agtgtgtgct gtgtccgatg tgtgctgtgt acacatgaga gagcagagtg tacatgtgtg    240
tgctgagtct atcagaagat gtgtgtagct gcgg                               274
```

<210> SEQ ID NO 392
<211> LENGTH: 89
<212> TYPE: DNA
<213> ORGANISM: Homo sapiens

<400> SEQUENCE: 392

```
tgtgcccagc ctaagccatt tcttaaaata aaaatgctaa aggactagta agtaaaaata    60
aaacttccta tgggatttcc cagtggaaa                                     89
```

<210> SEQ ID NO 393
<211> LENGTH: 72
<212> TYPE: DNA
<213> ORGANISM: Homo sapiens

<400> SEQUENCE: 393

```
gggagattgg tggcccttgc caggaagtgt cttaacactt tgtggatact gctgcctgtt    60
gtctttaaaa gc                                                        72
```

<210> SEQ ID NO 394
<211> LENGTH: 177
<212> TYPE: DNA
<213> ORGANISM: Homo sapiens

<400> SEQUENCE: 394

```
gataacagtc ttgcatgttt atcatgttac aatttaatat tccatcctgc ccaacccttc    60
ctttcccatc ctcaaaaaag ggccatttta tgatgcattg cacaccctct ggggaaattg    120
atctttaaat tttgagacag tataaggaaa atctggttgg tgtcttacaa gtgagct      177
```

<210> SEQ ID NO 395
<211> LENGTH: 117
<212> TYPE: DNA
<213> ORGANISM: Homo sapiens

<400> SEQUENCE: 395

```
ttaaacagtc tagagtgaag ggaatgtttt aaaatccaga ggcgatcaag tgaagccaac    60
ctttggaggc ccgtagaagt catttggagg aatttggact tcgtgcagta ggaaaga      117
```

<210> SEQ ID NO 396
<211> LENGTH: 164
<212> TYPE: DNA

<213> ORGANISM: Homo sapiens

<400> SEQUENCE: 396

| cagggggggcc tgagagtaac agtgaggatt atccaggtgc cctgagtgta acagtgagga | 60 |
| ttatccaggg gggccctgag tgtaacagcg aggattatcc aggggggccct gagtgcaaca | 120 |
| gtgaggatta tccaggggggg cctgagtgta acagtgagga ttat | 164 |

<210> SEQ ID NO 397
<211> LENGTH: 259
<212> TYPE: DNA
<213> ORGANISM: Homo sapiens
<220> FEATURE:
<221> NAME/KEY: misc_feature
<222> LOCATION: (139)..(139)
<223> OTHER INFORMATION: n is a, c, g, or t

<400> SEQUENCE: 397

| caaaaatgag tcacaactct tgattccatc cacctccaaa atccaggtat tttccttaat | 60 |
| tctcattctt tcacaactcc acatatatcc atatcctcat tatctcagga caacgtgacc | 120 |
| atttcttgcc acttcccanc acttccatgc ctaccaaaga agcctatctt ctctcaccag | 180 |
| gaccactgaa aaagtcttgc aactgatttc ccttgtcctc ttcttgcctc tctacagtca | 240 |
| attctctata caacagtca | 259 |

<210> SEQ ID NO 398
<211> LENGTH: 104
<212> TYPE: DNA
<213> ORGANISM: Homo sapiens

<400> SEQUENCE: 398

| tgctgcggtc gcctctctca ggctcccccg ctccccgggg cctccgcttc tcagccgggt | 60 |
| gctgtgcgtt tgagtgtgtg ctgctgctcg ctgtgtgtgc tgtg | 104 |

<210> SEQ ID NO 399
<211> LENGTH: 147
<212> TYPE: DNA
<213> ORGANISM: Homo sapiens

<400> SEQUENCE: 399

| tatatacatg gtgctcaata gcaacatctt agcagatgaa gcagtttatg attccactcc | 60 |
| ctcctgtatg acaggtagcc actatactga atcaaggtgc tgaactcaaa tcacaaaatt | 120 |
| ctggcttacc gatacaacaa ccaatac | 147 |

<210> SEQ ID NO 400
<211> LENGTH: 208
<212> TYPE: DNA
<213> ORGANISM: Homo sapiens

<400> SEQUENCE: 400

| ctctgagttt tatatgctgg aatccaatgc agagttggtt tgggactgtg atcaagacac | 60 |
| cttttattaa taaagaagag acacaggtgt agatatgtat atacaaaaag atgtacggtc | 120 |
| tggccaaacc accttcccag cctttatgca aaaaagggg agaatcaaag ctttcatttc | 180 |
| agaaatgttg cgtggaaaag tatctgta | 208 |

<210> SEQ ID NO 401
<211> LENGTH: 139
<212> TYPE: DNA
<213> ORGANISM: Homo sapiens

<400> SEQUENCE: 401

```
aaaaagagag aatatgtcct gtgttagctt gcttaggaaa taagagaga gagagagagg    60
gagggaggga aagagagaaa gagagagaga gaaagagagt gagagaaaga gagagcaaga  120
gagcaagagt aagaaagaa                                                139
```

<210> SEQ ID NO 402
<211> LENGTH: 243
<212> TYPE: DNA
<213> ORGANISM: Homo sapiens

<400> SEQUENCE: 402

```
ggcagtagat agtcaaagtc aaatcatttc taatgtttta aaaatgtgct ggtcattttc    60
tttgaaattg acttaactat tttcctttga agagtctgta gcacagaaac agtaaaaaat  120
ttaacttcat gacctaatgt aaaaaagagt gtttgaaggt ttacacaggt ccaggccttg  180
ctttgttacc attctgatgt tggactaatt gactaatcac ctacttatca gacaggaaac  240
ttg                                                                 243
```

<210> SEQ ID NO 403
<211> LENGTH: 298
<212> TYPE: DNA
<213> ORGANISM: Homo sapiens

<400> SEQUENCE: 403

```
agaggcccat gccaacagtc taatctaaga gattagtctt tcaaactcac catccagttg    60
cctgttacag aataactctt cttaactaaa aacctagtca acaaggaag ctgtaggtga   120
ggagatctgt ataatattct aatttaagta agtttgagtt tagtcactgc aaatttgact  180
gtgactttaa tctaaattac tatgtaaaca aaaagtagat agtttcactt tttaaaaaat  240
ccattactgt tttgcatttc aaaagttgga ttaaagggtt gtaactgact acagcatg    298
```

<210> SEQ ID NO 404
<211> LENGTH: 193
<212> TYPE: DNA
<213> ORGANISM: Homo sapiens

<400> SEQUENCE: 404

```
agagggaact gtgcagtccc caggccgccc cggctccggg ctagaggcaa taaataaacc    60
cgatcctgcc gggcacagcc gcgcccgcgc ctccggcgcc gtccccgggc tgacggggga  120
gggagcggag aagcgagcgc agattctgcg tataaatcag ctctggagca gacacagccc  180
ggctgtgaaa agc                                                      193
```

<210> SEQ ID NO 405
<211> LENGTH: 275
<212> TYPE: DNA
<213> ORGANISM: Homo sapiens

<400> SEQUENCE: 405

```
gtaggtttgg gagtataacg gtcacccagg gaggggtga agacggagaa gacttacata    60
gcacggtcag gttagggctg gacagatgag gaagagctag caaggggggc ttgaggagca  120
gtggccacta agacaggagt gtgacatttt agaagccaaa agaagaccat gtaattcaag  180
ggagaggtat gatttgctgg gtcagatcta aaaataaatc acacgttttt ttaaaactgta 240
gtaattaacc actgaaaact tatgagtgat ccaat                             275
```

<210> SEQ ID NO 406
<211> LENGTH: 143
<212> TYPE: DNA
<213> ORGANISM: Homo sapiens

<400> SEQUENCE: 406
gtgtgagcca ctgctggcta attttttgtat tttcagtaga acgggggctt caccatattg    60
gccaggctgg tcttgaactc cttccctcgc tcccccaaaa atttgaattt ttttttcaac    120
acttttacac ctgttatgga aaa    143

<210> SEQ ID NO 407
<211> LENGTH: 263
<212> TYPE: DNA
<213> ORGANISM: Homo sapiens

<400> SEQUENCE: 407
gagatcactt ggtaactggt ttcatgtgta tccaaaaatc agcatttgga tttaagcttt    60
ctgaatttgg tagtttaaga aacagattta gttttcagt ggttttaact catgtgaaat    120
aatgattttc caccagcttt gatgcaaaga gatataattt taatgaacga tttatccagc    180
agtttgttcc aggggttgcc tctccttatt tacggggatt actttgtaca tgcagataag    240
ttttcgcaaa cctatttcca ttt    263

<210> SEQ ID NO 408
<211> LENGTH: 300
<212> TYPE: DNA
<213> ORGANISM: Homo sapiens

<400> SEQUENCE: 408
gatgataatc tttactggtg aaaaggatgg aaaaataaat caacaaatgc aaccagtttg    60
tgagaaaaaa aaaaaaaagc cgaaaaaaaa aaaaaaaaca cctgaatgcg aagagctcg    120 gctcccgttt agcattttgt acttaaggaa ataaaaaacc aacaaggat ctcacatttt    180 cttaaaaagt gaagattgct gtatactatt tattcaactt ataatttatg ttactccttg    240
atctttgtct tttgtcatga caaagcattt atttaataaa gttatgcatt cagttcccaa    300

<210> SEQ ID NO 409
<211> LENGTH: 238
<212> TYPE: DNA
<213> ORGANISM: Homo sapiens

<400> SEQUENCE: 409
agaattccag ataaacacac agcctttccc ataccttttt ttttcttact ataaaatatt    60
ataagatcca ttgatgtcca aataatacca ccgagcatct cttcacctct cctcctcttg    120
gtccacttgc taatgcccag ttttcttctc catttccact ttttcttagg ctccctattt    180
actattcatt ttgacttcct tctgttttat ttttttccct ttagcattgc atgtgaat    238

<210> SEQ ID NO 410
<211> LENGTH: 101
<212> TYPE: DNA
<213> ORGANISM: Homo sapiens

<400> SEQUENCE: 410
tgagtgtgct gtgctcgcgt gtgtgctgtg ttcatgcgtg tgctgtgtgt tgtgtgtgtg    60
tagctgcggg gatgcataaa gtatgagtgc ttttttaggat g    101

```
<210> SEQ ID NO 411
<211> LENGTH: 34
<212> TYPE: DNA
<213> ORGANISM: Homo sapiens

<400> SEQUENCE: 411
tttatgaaca gcagactcta tgtaaaggca tttt                              34

<210> SEQ ID NO 412
<211> LENGTH: 168
<212> TYPE: DNA
<213> ORGANISM: Homo sapiens

<400> SEQUENCE: 412
aggagggaaa ataatagccc agtgagagct gaatgaaaag ggactgaatt taaatatttg   60
taagaacttt gtgatgatga gtaattgtca gacgtgggat agataactga gaggctcaga  120
atctttacca aggatatttt ttaggataag gtagctgcct gttcatga              168

<210> SEQ ID NO 413
<211> LENGTH: 150
<212> TYPE: DNA
<213> ORGANISM: Homo sapiens

<400> SEQUENCE: 413
agggacccag taagaccaaa ggaggggagg acagagcatg aaaaccaaaa tccatgcaaa   60
tgaaatgtaa ttggcacgac cctcaccccc aaatcttaca tctcaattcc catcctaaaa  120
agcactcata ctttatgcat ccccgcagct                                  150

<210> SEQ ID NO 414
<211> LENGTH: 124
<212> TYPE: DNA
<213> ORGANISM: Homo sapiens

<400> SEQUENCE: 414
ggctcaggtc ctccctacaa gacctaccac tcacccatgc ctatgccact ccatctggac   60
atttaatgaa actgagagac agaggcttgt ttgctttgcc ctcttttcct ggtcaccccc  120
actc                                                              124

<210> SEQ ID NO 415
<211> LENGTH: 93
<212> TYPE: DNA
<213> ORGANISM: Homo sapiens

<400> SEQUENCE: 415
tggagaagca ctggtgtctg cagcacccct cagttcctgt gcctcagccc acaggccact   60
gtgataatgg tctgtttagc acttctgtat tta                               93

<210> SEQ ID NO 416
<211> LENGTH: 76
<212> TYPE: DNA
<213> ORGANISM: Homo sapiens

<400> SEQUENCE: 416
ggaggatgcg ctgtggggtt gttttttgcca taagcgaact ttgtgcctgt cctagaagtg   60
aaaattgttc agtcca                                                  76

<210> SEQ ID NO 417
<211> LENGTH: 220
<212> TYPE: DNA
```

<213> ORGANISM: Homo sapiens

<400> SEQUENCE: 417

| tctggtagat aaagccctag accttgtcca cactctcacc cccatcccca actttccctg | 60 |
| gaccggtgcc gcccccactt gatgcttgct caaggccggg gactggagcg ggctacttgt | 120 |
| atatttcgtt gtcagtctgc agaatgtgtt tgattttttat ttttccctcc ttctctgaca | 180 |
| tgtgtcaagg aataaagact ggatacaggt ccattacgtc | 220 |

<210> SEQ ID NO 418
<211> LENGTH: 98
<212> TYPE: DNA
<213> ORGANISM: Homo sapiens

<400> SEQUENCE: 418

| tggatcgatg atgagtcccc ccaaaaaaac attccttgga aaagctgaac aaaatgagtg | 60 |
| aaaactcata ccgtcgttct cagcggaact gaggtcca | 98 |

<210> SEQ ID NO 419
<211> LENGTH: 97
<212> TYPE: DNA
<213> ORGANISM: Homo sapiens

<400> SEQUENCE: 419

| ggccaaaaag tctacattgc gtgtgtggat ggatgaatga gcagtgggag tgcagcgcca | 60 |
| ggtgacaaga tgttgtgagg ggttttgagt catccag | 97 |

<210> SEQ ID NO 420
<211> LENGTH: 87
<212> TYPE: DNA
<213> ORGANISM: Homo sapiens

<400> SEQUENCE: 420

| gccctgcgcc ggcaaccacc tagtggccca gggaaggccg ataatttaaa cagtctccca | 60 |
| ccacctaccc caagagatac tggttgt | 87 |

<210> SEQ ID NO 421
<211> LENGTH: 36
<212> TYPE: DNA
<213> ORGANISM: Homo sapiens

<400> SEQUENCE: 421

| aaaaaagttc aactagtatg aaagggttat aaagta | 36 |

<210> SEQ ID NO 422
<211> LENGTH: 116
<212> TYPE: DNA
<213> ORGANISM: Homo sapiens

<400> SEQUENCE: 422

| gtgagtaaat aatgttctag tgcaacagga caaactactc tctccacagg aaacccaacc | 60 |
| acaacaggat caatagaaag aaaagagaaa acgttagccc ccaactacaa ataaat | 116 |

<210> SEQ ID NO 423
<211> LENGTH: 264
<212> TYPE: DNA
<213> ORGANISM: Homo sapiens

<400> SEQUENCE: 423

| tttcttcttt atgtccaatt ttgtgggtgg gaggaggatt tagtctcttc ctgatttcga | 60 |

```
agagctcatt tactatttcg ggaaataaga tttggattgt caaccattat agctattttt      120
tacacacttt tcaactttgt ttttgttata agaatgtgta tgattgttac atgtccaagt      180
ataaccatgt tcgcttttat ggcttttgag tttcatgtca ttttttggaaa gatatatata     240 ttgagtccat aaaacccttc acct                                             264
```

<210> SEQ ID NO 424
<211> LENGTH: 119
<212> TYPE: DNA
<213> ORGANISM: Homo sapiens

<400> SEQUENCE: 424

```
actttaataa aggttatcca taccaataaa aagtgtacaa cacagcattt tctgttaaat      60
tattattggt tttcagttgt aatttggtat tttttctggc atgcgtttat taatttatt      119
```

<210> SEQ ID NO 425
<211> LENGTH: 279
<212> TYPE: DNA
<213> ORGANISM: Homo sapiens

<400> SEQUENCE: 425

```
gtaggtttgg gagtataacg gtcacccagg gaggggtga agacggagaa gacttacata      60
gcacggtcag gttagggctg gacagatgag gaagagctag caaagggggc ttgaggagca     120
gtggccacta agacaggagt gtgacatttt agaagccaaa agaagaccat gtaattcaag     180
ggagaggtat gatttgctgg gtcagatcta aaaataaatc acacgttttt ttaaactgta     240
gtaattaacc actgaaaact tatgagtgat ccaatatta                             279
```

<210> SEQ ID NO 426
<211> LENGTH: 130
<212> TYPE: DNA
<213> ORGANISM: Homo sapiens

<400> SEQUENCE: 426

```
gggacaaggt cccttggtgc tgatggcctg aaggggcctg agctgtgggc agatgcagtt      60
ttctgtgggc ttggggaacc tctcacgttg ctgtgtcctg gtgagcagcc cgaccaataa     120
acctgctttt                                                             130
```

<210> SEQ ID NO 427
<211> LENGTH: 262
<212> TYPE: DNA
<213> ORGANISM: Homo sapiens

<400> SEQUENCE: 427

```
tttcactctt gctgtctgct cctctcacat catccttgcc tctgtctgtt taatcctcct      60
gtccttcatt ttcctttttt gcctctgcat tcagcatttc tacttccaat ctccctcctc     120
tgctctttct tatttcctct gatctgcaga cttgcttctg tccctccctt ctgttcccct     180
cctggatgtg tctttggcca acctttcctt ctctgagact tcgtgttctt gttggtagat     240
gggggctgat acttctgggt ct                                               262
```

<210> SEQ ID NO 428
<211> LENGTH: 140
<212> TYPE: DNA
<213> ORGANISM: Homo sapiens

<400> SEQUENCE: 428

```
ttattattat gaaccttcag cctactttct tgagtgccgt aaaagtgctt gtaaattttt      60 tttttttta agaagaaaga aaaaaatggt gtttgacgtt gatggaaatt caaaatata       120 tatggaactg aaacattaac                                                 140

<210> SEQ ID NO 429
<211> LENGTH: 143
<212> TYPE: DNA
<213> ORGANISM: Homo sapiens

<400> SEQUENCE: 429 cttgttctt tgaagcttgt gctgaggttt tagcttttct atgttttata tgccgctgct      60
ttgaaagaga acctagattc tatagttgta ttattgttgt ttcatacttt aaatttatat    120
ggctgtggaa aaacgaatta aaa                                             143

<210> SEQ ID NO 430
<211> LENGTH: 151
<212> TYPE: DNA
<213> ORGANISM: Homo sapiens

<400> SEQUENCE: 430
gtgtgtcaag gatttgacaa actgccattt ttctccagaa gtcaagcccc taagtgattg     60
tctagaggca agaattttt gatatgttgt ctcaacaatg cttctcactt cgtcttcagg    120
tgccccaacc cgcaagtaca catactatgt a                                    151

<210> SEQ ID NO 431
<211> LENGTH: 150
<212> TYPE: DNA
<213> ORGANISM: Homo sapiens

<400> SEQUENCE: 431
aatgttcata ggttctcaac cctcaccccc caccacggga gactagagct gcaggatccc     60
aggggagggg tctctcctcc caccccaagg catcaagccc ttctccctgc actcaataaa    120
ccctcaataa atattctcat tgtcaatcaa                                      150

<210> SEQ ID NO 432
<211> LENGTH: 115
<212> TYPE: DNA
<213> ORGANISM: Homo sapiens

<400> SEQUENCE: 432
gatgggaatt gagatgtaag atttggggt gagggtcgtg ccaattacat ttcatttgca     60
tggattttgg ttttcatgct ctgtcctccc ctcctttggt cttactgggt ccctc          115

<210> SEQ ID NO 433
<211> LENGTH: 223
<212> TYPE: DNA
<213> ORGANISM: Homo sapiens

<400> SEQUENCE: 433
tacattgtaa gagcaacatc ctacgttaat aaatgttcta gcccggtgct tcgcgaacat    60
ttatgtgcat acaaatcacc tgggatcttg ttagaaggca gtaggtctgg ggtgggcct    120 gagattctgc atttctaacc aggtcctggg agatgctgat gctatcgagc cacaaccaca   180
ctttgagtag caagcctctg gcctatcctt attgtttgtt ata                      223

<210> SEQ ID NO 434
<211> LENGTH: 272
```

<212> TYPE: DNA
<213> ORGANISM: Homo sapiens

<400> SEQUENCE: 434

```
tttcactctt gctgtctgct cctctcacat catccttgcc tctgtctgtt taatcctcct      60
gtccttcatt ttccttttt gcctctgcat tcagcatttc tacttccaat ctccctcctc     120
tgctctttct tatttcctct gatctgcaga cttgcttctg tccctcctt ctgttcccct     180
cctggatgtg tctttggcca accttttcctt ctctgagact tcgtgttctt gttggtagat    240
gggggctgat acttctgggt cttgggcatg tc                                   272
```

<210> SEQ ID NO 435
<211> LENGTH: 221
<212> TYPE: DNA
<213> ORGANISM: Homo sapiens

<400> SEQUENCE: 435

```
ttgctggggc ttgtcctaga ggctccagct ttggcacagt ggttcctggc tgctgccatg      60
tttcagatga ggagggagag aaggaggccg ccagactcga gaggtgggag gaactccttg    120
cacacaccct gagcttttgc cactttatc atttttgagc aactcccttt cagctaaaag     180
gccacccctt tatcgcattg ctgtccttgg gtagaatata a                        221
```

<210> SEQ ID NO 436
<211> LENGTH: 183
<212> TYPE: DNA
<213> ORGANISM: Homo sapiens

<400> SEQUENCE: 436

```
acaaaactct ccaataatga ctctgctcag ctcaggggca gcaggagtgg agtgtcgggg      60
gcccttggtg ctgagtgaag ataaattaaa aatcccaaca agccagtgac attatgtaca    120
ggaggaaagg ggtggggctt ccaggacaga ggccgagggt ggcagggcag gacttggagt    180
ggc                                                                  183
```

<210> SEQ ID NO 437
<211> LENGTH: 237
<212> TYPE: DNA
<213> ORGANISM: Homo sapiens

<400> SEQUENCE: 437

```
cagacacatg agcaggactt tggggagtgt gttttatatc tgtcagatgc ctagaacagc      60
acctgaaata tgggactcaa tcattttagt cccctcttt ctataagtgt gtgtgtgcgg    120
atatgtgtgc tagatgttct tgctgtgtta ggaggtgata aacatttgtc catgttatat    180
aggtggaaag ggtcagacta ctaaattgtg aagacatcat ctgtctgcat ttattga      237
```

<210> SEQ ID NO 438
<211> LENGTH: 189
<212> TYPE: DNA
<213> ORGANISM: Homo sapiens

<400> SEQUENCE: 438

```
tcaagttaat ggcagctaaa acgctcccag tccatttatt ggccacatga ggtggtcgtc      60
aagaaacaag ttagaaggtt atgacaggaa gtagtataat aaatgcccgg cagtacgagg    120
ggttcaacag aagtgaacaa ggcacaagaa agaggtctgt gttcaggaaa caggccagtc    180
cccacatgg                                                            189
```

<210> SEQ ID NO 439
<211> LENGTH: 246
<212> TYPE: DNA
<213> ORGANISM: Homo sapiens

<400> SEQUENCE: 439

```
tgaactaaaa ctatgagcct tattcaatat ctataattct atgattttt taaattatgg      60
gaaattaatg aaagatgttt acatgaataa tgtttgccct tactgtgtta tgaatgagtt     120
ttttgtagtg tgtctgggtg catgatgcaa gagagtagga aaaatgtttt tgaaacaaaa     180
cttgacaaat atttgtaatg aaagtaaatt taaagattgc tataattgcg ctatagaaac     240
aatgca                                                                246
```

<210> SEQ ID NO 440
<211> LENGTH: 65
<212> TYPE: DNA
<213> ORGANISM: Homo sapiens

<400> SEQUENCE: 440

```
ttaacagtac atttgtgtgg ctctcaaaca tccctttgga agggattgtg tgtactatgt      60
aatat                                                                  65
```

<210> SEQ ID NO 441
<211> LENGTH: 120
<212> TYPE: DNA
<213> ORGANISM: Homo sapiens

<400> SEQUENCE: 441

```
tacaatgatg gttgagtgaa aatacagaag gggggtttga gtattcagat ttcataaaac      60
acttccttgg aatatagctg cattaacttg gaaagaagcc tgttgggcca gaagacagaa     120
```

<210> SEQ ID NO 442
<211> LENGTH: 156
<212> TYPE: DNA
<213> ORGANISM: Homo sapiens

<400> SEQUENCE: 442

```
aactgatggg aaaggaccaa ttatttatag tttcccaaca aaagttttaa gattttttac      60
ctttgcatca gtgcattttt atttatatca aaaggtgcta aaatgattca atttgcattt     120
tttgatcctg tagtgcctct atagaagtac ccacag                               156
```

<210> SEQ ID NO 443
<211> LENGTH: 169
<212> TYPE: DNA
<213> ORGANISM: Homo sapiens

<400> SEQUENCE: 443

```
tgttaaactt tggaacacct accaaaaaat aagtttgata acatttaaaa gatgggcgtt      60
tcccccaatg aaatacacaa gtaaacattc caacattgtc tttaggagtg atttgcacct     120
tgcaaaaatg gtcctggagt tggtagattg ctgttgatct tttatcaat                 169
```

<210> SEQ ID NO 444
<211> LENGTH: 87
<212> TYPE: DNA
<213> ORGANISM: Homo sapiens

<400> SEQUENCE: 444

```
aaatgacttt caactaacct tgtgaatctt ttgcagtgta ctgtgtgcaa taccaagggc      60
```

```
atagctccct gtaatttggg aaataca                                      87

<210> SEQ ID NO 445
<211> LENGTH: 96
<212> TYPE: DNA
<213> ORGANISM: Homo sapiens

<400> SEQUENCE: 445
catatatttt ttgctacttt tgctgtttta ttttttaaa ttatgttcta aacctatttt  60
cagtttaggt ccctcaataa aaattgctgc tgcttc                           96

<210> SEQ ID NO 446
<211> LENGTH: 269
<212> TYPE: DNA
<213> ORGANISM: Homo sapiens

<400> SEQUENCE: 446
tgctggcact gatattatcc atcatctctt tttggacact tctgtaaatg tgattggatt  60
gtttgaaaga agatttaaag tttcaaagtt ttttgttctg tttttgcttt gcatttggag 120
aaaatattga agcagggta tgttgtttca ttcaccttga aaaaaccatg agtaaatggg  180
gatatagaat ctctgaatag ctcgctaaaa gattcaagca agggacatga attttgttcc 240
atctatcaat aatatccaga agaacaact                                   269

<210> SEQ ID NO 447
<211> LENGTH: 188
<212> TYPE: DNA
<213> ORGANISM: Homo sapiens

<400> SEQUENCE: 447
tctgtgtgtg tcctagcatg gagagttcct tccttttccc ttcagttagg ttgacccttt  60
ccatttgttt agtatccgtg cacatgtcgt actagacccc aatcaagttg cttatttaaa 120
attctttcag ctgtttccct attatttcct tactttgctg aacatgtccg ctgttttacc 180
tcactgct                                                          188

<210> SEQ ID NO 448
<211> LENGTH: 246
<212> TYPE: DNA
<213> ORGANISM: Homo sapiens

<400> SEQUENCE: 448
ggagccaaca attcgagtgc aaacatgatg gctcagaccc ttctctgccc tttactagcc  60
ttcatgatct gtcgggtctc agcagctcag gccacaggag gaggtgggtc tcctgactgg 120
cctgtgcatt ctcccaaaca agatgtttaa gactcttctt tatctcgtca caaacgcaca 180
ggacacacac gcacacacat gcacacacag tttacaaacg cacggtacac acacgcatga 240
cacatg                                                            246

<210> SEQ ID NO 449
<211> LENGTH: 217
<212> TYPE: DNA
<213> ORGANISM: Homo sapiens

<400> SEQUENCE: 449
agcgaaggga aggttgcggg agaaagagcg ggggccgggg ccagacgcca agaggggcgc  60
ggggagcaca gagaagcgga gggaagggcg ccacgtcgag gggccggggg aggcggtgac 120
```

```
tgggggcgg agtggaggct gcacccggac cgcgggcgcc cagctcggtt tgggccgacg        180
gagccctctg ccgtcgcgag cccgggcctc gggaggg                                217

<210> SEQ ID NO 450
<211> LENGTH: 172
<212> TYPE: DNA
<213> ORGANISM: Homo sapiens

<400> SEQUENCE: 450
tgcagtgcta gtcccggcat cctgatggct ccgacaggcc tgctccagag cacggctgac        60
catttttgct ccgggatctc agctcccgtt ccccaagcac actcctagct gctccagtct       120
cagcctgggc agcttccccc tgccttttgc acgtttgcat ccccagcatt tc               172

<210> SEQ ID NO 451
<211> LENGTH: 188
<212> TYPE: DNA
<213> ORGANISM: Homo sapiens

<400> SEQUENCE: 451
tattcctggt agaggaattt ctgtatttga aaattctcca gaaggaataa tataaactgt        60
ggactttggg tgataatgat atgtaggttc gtcagttgtt aacaaatgta tccctctgtt       120
gggggctatt gataatgggg aaggctgtgc atgtgtggga gtaggaggtg tatgggacat       180
ctctgtac                                                               188

<210> SEQ ID NO 452
<211> LENGTH: 242
<212> TYPE: DNA
<213> ORGANISM: Homo sapiens

<400> SEQUENCE: 452
aaagagtcaa ctttccggcg gcgggggaga aatgataaaa gagagagagg agggcagatc        60
accacctaga agcacatcct tgttcgcag aggggggaga aaaagtcgga gagaaagaat       120
gaaagagggg aaaaaaggca gttcggcacc cggagaaagg aggcaattcg gggagaggag       180
gaggagaaga agaaaacaca cacgcgcgca cgcacacaca caccgcggag agaaaagaac       240
ag                                                                     242

<210> SEQ ID NO 453
<211> LENGTH: 33
<212> TYPE: DNA
<213> ORGANISM: Homo sapiens

<400> SEQUENCE: 453
gtgagcccat atcgtactgc tgcagtccag cct                                    33

<210> SEQ ID NO 454
<211> LENGTH: 83
<212> TYPE: DNA
<213> ORGANISM: Homo sapiens

<400> SEQUENCE: 454
taaccttagg aaaccagaat agcgtttggc agacacgacg ttttcagttt accttgaca         60 cctgccccac tccatttgc ttt                                                83

<210> SEQ ID NO 455
<211> LENGTH: 232
<212> TYPE: DNA
<213> ORGANISM: Homo sapiens
```

<400> SEQUENCE: 455

```
tgaaccaaaa tagagtcagc tgacccagca tcagccacac tttgggttgg aaaatgtttg    60
cctgttggaa ttaatttaag cttaagtata tatcaacatt attttattgt gcaattaaaa   120
caatacaaat tcatggtttt ttaaagttaa aaattttaac cactgtaaca acagtttttg   180
tgttattttc tgtattaaac atcttgttgc acgcatttga ggtcatcagg gt           232
```

<210> SEQ ID NO 456
<211> LENGTH: 275
<212> TYPE: DNA
<213> ORGANISM: Homo sapiens

<400> SEQUENCE: 456

```
acacaataca atcaggagtt ttcaaatttt tgattcagta tttgaatttc ttcttcataa    60
atgtagttgg aatttatcct agtattttc tttacctgaa ggagggccat ttattttta    120
tttcactaca tttttctttg catgattatt aaaataaaaa ctgcctctgt tgtgtttctc   180
actggaggct ggaatgaatg atcactagaa cacaaagag tgaatgatga cacttgaagt   240
caaagcagtt gtactgatca ccagaaccaa taaag                              275
```

<210> SEQ ID NO 457
<211> LENGTH: 220
<212> TYPE: DNA
<213> ORGANISM: Homo sapiens

<400> SEQUENCE: 457

```
ctaattgatt agaactgagt cttttatatc aagctaatat ctagctttta tatcaagcta    60
atatcttgac ttctcagcat catagaaggg ggtactgatt tcctaaagtc tttcttgaat   120
ttctattatg caaaattgcc ctgaggccgg gtgtggtggc tcacacctgt aatcccagca   180
ctttgggagg ctgaggtggg aagatcccctt actgccagga                        220
```

<210> SEQ ID NO 458
<211> LENGTH: 187
<212> TYPE: DNA
<213> ORGANISM: Homo sapiens

<400> SEQUENCE: 458

```
ttctttatag tgttatgctt attttcaatt ttttttttcc tgattctgtc tggtacttag    60
aattgtagtg tcttcatcat caattaaaga aaactgtcta atgaattca tggatgtaaa   120
tattagtggt ccttaatgtc tttgattgct ggacatgaaa caaactgcca attaaatttt   180
gcggaga                                                             187
```

<210> SEQ ID NO 459
<211> LENGTH: 176
<212> TYPE: DNA
<213> ORGANISM: Homo sapiens

<400> SEQUENCE: 459

```
tcctgcaggc atccgtgggg gaaaaaaaat ctctcagaac cctcaactat tctgttccac    60
acccaatgct gctccaccct cccccagaca cagcccaagt ccctccgcgg ctggagcgaa   120
gccttctgca gcaggaactc tggaccctg ggcctcatca cagcaatatt taacaa       176
```

<210> SEQ ID NO 460
<211> LENGTH: 266
<212> TYPE: DNA

<213> ORGANISM: Homo sapiens

<400> SEQUENCE: 460

| | | | | | |
|---|---|---|---|---|---|
| aaatgtttga | cattcattat | cagaatgagg | gaaaatttaa | acaattccgt | tttttctttt | 60 |
| gctagtaggc | atattatgct | aataaaatta | ctaaattaaa | agtgtgtcaa | ggatttgaca | 120 |
| aactgccatt | tttctccaga | agtcaagccc | ctaagtgatt | gtctagaggc | aagaattttt | 180 |
| tgatatgttg | tctcaacaat | gcttctcact | tcgtcttcag | gtgccccaac | ccgcaagtac | 240 |
| acatactatg | tactcacttg | aaaatg | | | | 266 |

<210> SEQ ID NO 461
<211> LENGTH: 286
<212> TYPE: DNA
<213> ORGANISM: Homo sapiens

<400> SEQUENCE: 461

| | | | | | |
|---|---|---|---|---|---|
| aactggggc | tctgtggggg | ctctgtatat | agctatgaag | aaaacacaaa | gtgtataaat | 60 |
| ctgagtatat | atttacatgt | cttttaaaa | gggtcgttac | cagagattta | cccatcgggt | 120 |
| aagatgctcc | tggtggctgg | gaggcatcag | ttgctatata | ttaaaaacaa | aaaagaaaaa | 180 |
| aaaggaaaat | gttttaaaa | aggtcatata | ttttttgcta | cttttgctgt | tttatttttt | 240 |
| taaattatgt | tctaaaccta | ttttcagttt | aggtccctca | ataaaa | | 286 |

<210> SEQ ID NO 462
<211> LENGTH: 278
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n is a, c, g, or t

<400> SEQUENCE: 462

| | | | | | |
|---|---|---|---|---|---|
| gctggtctcg | ggcaacaagc | agcctcctag | gagcagaagg | tgatggaggg | ccacgggggc | 60 |
| agggaggagc | agatggccat | gtggctcagc | ccctgcctgg | gaaagcgagt | ccacagttca | 120 |
| ctaacaaaca | caataccatc | cacaaacaag | tagcccacaaa | gaccacagtt | agcaaacaca | 180 |
| cacagtcaca | cacacacaca | cacacacaca | catnacggga | ggtgggcagg | accgcagtct | 240 |
| gcagtgggga | ggcaagtgtt | agttgcatca | tcaggtgg | | | 278 |

<210> SEQ ID NO 463
<211> LENGTH: 122
<212> TYPE: DNA
<213> ORGANISM: Homo sapiens

<400> SEQUENCE: 463

| | | | | | |
|---|---|---|---|---|---|
| aggtggtgtt | ggcagaggct | atcgggctgg | acaaggacaa | acccaaccgt | gtgaccaaag | 60 |
| tggctgtgaa | gatgttgaag | tcggacgcaa | cagagaaaga | cttgtcagac | ctgatctcag | 120 |
| aa | | | | | | 122 |

<210> SEQ ID NO 464
<211> LENGTH: 161
<212> TYPE: DNA
<213> ORGANISM: Homo sapiens

<400> SEQUENCE: 464

| | | | | | |
|---|---|---|---|---|---|
| aatgaaattg | ttaattggcc | aggcacagtg | ggaagcacct | gtagtcccag | ctactcagga | 60 |
| ggctaaagtg | agagggtggc | tctagcacag | tcatcaaggc | tgcaggaggc | tatgatggag | 120 |

```
ccactgcact ccagcctaga tgacaaggtg agacgctgtc t                    161
```

<210> SEQ ID NO 465
<211> LENGTH: 162
<212> TYPE: DNA
<213> ORGANISM: Homo sapiens

<400> SEQUENCE: 465

```
tgttttgac atcagctgta atcattcctg tgctgtgttt tttattaccc ttggtaggta    60
ttagacttgc cctttttaa aaaaaggttt ttgcatcgtg gaagcatttg acccagagtg   120
gaacgcgtgg cctatgcagg tggattcctt caggtctttc ct                    162
```

<210> SEQ ID NO 466
<211> LENGTH: 114
<212> TYPE: DNA
<213> ORGANISM: Homo sapiens

<400> SEQUENCE: 466

```
tttttagtt gccaacagtt tatgtttgct gattatttat gacctgaaat tatatatttt    60 ttttttaag aagacatttt gttacataag gatgactttt ttatacaaag gaaa         114
```

<210> SEQ ID NO 467
<211> LENGTH: 223
<212> TYPE: DNA
<213> ORGANISM: Homo sapiens

<400> SEQUENCE: 467

```
gcatttgaat tgactaggct tttcctatat aaaaaactca aaacttgtta actctgtact    60
ttaataaaat ttaaaattaa aactgtgttg ttttttttctc ttctgctaga tacatatata   120
attaaagtac tcaagttagt tgttttgcag agatgttgcc ttcagatgtt aatcaggtct   180
ctcaagtttc atggagtcta tgctgatcct ttaattgaca aat                    223
```

<210> SEQ ID NO 468
<211> LENGTH: 289
<212> TYPE: DNA
<213> ORGANISM: Homo sapiens

<400> SEQUENCE: 468

```
tatacagaat agtcactggt cttgggctaa atggtgactt caagtgtagt ggctgcatag    60
tcaaaaatga attagatgag tacaaaagtg acgaaatgaa agaatgtcaa gaatggacca   120
caaagacagt gttttatgac ctaaagatta agatttatcc atttgtgtac aattgtggac   180
tatataaaat aaaacaagac tttgacctca gtggataaga agtatttgga tgtactaatc   240 aatattttg gtctgggtca gtggtgggtt catctgtgtt tgttgtatt               289
```

<210> SEQ ID NO 469
<211> LENGTH: 36
<212> TYPE: DNA
<213> ORGANISM: Homo sapiens

<400> SEQUENCE: 469

```
agcaggatca agggccggaa ataaaggctg ttgtaa                             36
```

<210> SEQ ID NO 470
<211> LENGTH: 156
<212> TYPE: DNA
<213> ORGANISM: Homo sapiens

```
<400> SEQUENCE: 470
aatatacctg atgcgctgta gaatgaaaat gtaaaagata acctgtatgt gttccgagct      60 ttaattttt gtttacaaat tgaacagtgt tacatgggct gtccagtcct gattatagag       120
aggaagaaat ggtaacagta tggcagataa gaatta                                156

<210> SEQ ID NO 471
<211> LENGTH: 298
<212> TYPE: DNA
<213> ORGANISM: Homo sapiens

<400> SEQUENCE: 471
agcaggagta agtttctcat cccatgggcg accagggcca tctcctccca ccagtggccc      60
ccactcacag ggagctggca atgccctacc tgcctgttct ccagatggag aaacaggctc      120
tgagatttca caggtcttgc ccaaagtcat tgatttttgat gattaaaaag aataaacaca    180
gtgtttcctg agtagcagtg attgttatgc cttgctattt taataaagat tctatttttcg    240 tataacattg tcaagtggaa acatgctgaa atctattaaa ccatctttgt ttgtggaa       298

<210> SEQ ID NO 472
<211> LENGTH: 98
<212> TYPE: DNA
<213> ORGANISM: Homo sapiens

<400> SEQUENCE: 472
aaagagtcaa ctttccggcg gcgggggaga atgataaaaa gagagagagg agggcagatc      60
accacctaga agcacatcct ttgttcgcag aggggga                              98

<210> SEQ ID NO 473
<211> LENGTH: 103
<212> TYPE: DNA
<213> ORGANISM: Homo sapiens

<400> SEQUENCE: 473
gtttgtcttg cgcagtgctt actccagctg tggcatgcag gtgtcagcaa gtatgatcag      60
caatgaggcg gtggtcaata tcctgtcgag ctcatcacca cag                        103

<210> SEQ ID NO 474
<211> LENGTH: 191
<212> TYPE: DNA
<213> ORGANISM: Homo sapiens

<400> SEQUENCE: 474
aatctctttt tttctggagg ctggcacctg attttgtatc ccctgtagc agcattactg       60 aaatacatag gcttatatac aatgcttctt tcctgtatat tctcttgtct ggctgcaccc    120
ctttttcccg cccccagatt gataagtaat gaaagtgcac tgcagtgagg gtcaaaggag    180
agtcaacata t                                                          191

<210> SEQ ID NO 475
<211> LENGTH: 220
<212> TYPE: DNA
<213> ORGANISM: Homo sapiens

<400> SEQUENCE: 475
tgcccccagt atgtttagga cgcgagcccc agaaggattt gggagtaaac ttaacattca      60
ctgtgttttt gctttgcatc cgccatttgt gtgtgttttt ggactgtggg ctgtgtgtac    120
cttggttggt gactcagtga gaagaagcag gaatgccaaa gatactatga atgttttgag    180
```

```
ttttgttgct gttgttgttg agaggttgtt tcactggtat               220
```

<210> SEQ ID NO 476
<211> LENGTH: 258
<212> TYPE: DNA
<213> ORGANISM: Homo sapiens

<400> SEQUENCE: 476

```
gatcgtctgg taactttcta actttaaata atatgtttga gcaataattt cttgacttac    60
tgactttaca acatctttaa taattcccca ttacaaaaga taaggattta acttacacta   120
tcgccacttt cctttgtcca tctctctcca aatgtctgat agttacatca cttttttaata 180
catctattgg tttgatttta tagctttgaa caatacacta atcctctagt tcttgttcca  240
ttaactgaag atcttttc                                                 258
```

<210> SEQ ID NO 477
<211> LENGTH: 233
<212> TYPE: DNA
<213> ORGANISM: Homo sapiens

<400> SEQUENCE: 477

```
gaaacacaag agacttaaag gacaggagga ggagatggcc ataggagagg agggttcctc    60
ttaggtcaga tggaggttct cagagccaag tcctccctct ctactggagt ggaaggtcta  120
ttggccaaca atcctttctg cccacttccc cttccccaat tactattccc tttgacttca  180
gctgcctgaa acagccatgt ccaagttctt cacctctatc caaagaactt gat         233
```

<210> SEQ ID NO 478
<211> LENGTH: 96
<212> TYPE: DNA
<213> ORGANISM: Homo sapiens

<400> SEQUENCE: 478

```
ggatcgatga tgagtccccc ataaaaacat tccttggaaa agctgaacaa aatgagtgag    60
aactcatacc gtcgttctca tcggaactga ggtcca                             96
```

<210> SEQ ID NO 479
<211> LENGTH: 181
<212> TYPE: DNA
<213> ORGANISM: Homo sapiens

<400> SEQUENCE: 479

```
tggtgacaga gtttgggacc gaggtggagc ccgagtttgg gaccaaggtg gagcccgagt    60
ttgagaccca gttggagcct gagtttgaga cccagctgga acccgagttt gaggaagagg  120
aggaggagga gaaagaggag gagatagcca ctggccaggc attcccttc acaacagtag   180
a                                                                   181
```

<210> SEQ ID NO 480
<211> LENGTH: 135
<212> TYPE: DNA
<213> ORGANISM: Homo sapiens

<400> SEQUENCE: 480

```
gatatcagat cagttgagac taacagttga aagcagtaaa catattacgg acatattatt    60
gataaaagac atttatgaag aggataaaact gtgaaggtgt acagacacta aaccatagtt 120
gctaaacaca tacaa                                                    135
```

<210> SEQ ID NO 481
<211> LENGTH: 80
<212> TYPE: DNA
<213> ORGANISM: Homo sapiens

<400> SEQUENCE: 481
agagccagga cagtgaggtc aactttgaca attccatcca cccagaagtc ttggagctgc     60
tgcttgacta tgcgtactcc                                                 80

<210> SEQ ID NO 482
<211> LENGTH: 96
<212> TYPE: DNA
<213> ORGANISM: Homo sapiens

<400> SEQUENCE: 482
ggatcgatga tgagtccccc ataaaaacat tccttggaaa agctgaacaa aatgagtgag     60
aactcatacc gtcgttctca tcagaactga ggtcca                               96

<210> SEQ ID NO 483
<211> LENGTH: 290
<212> TYPE: DNA
<213> ORGANISM: Homo sapiens

<400> SEQUENCE: 483
ttgacagtct gccttactat gaaattctag gtacaaaaat tttccttaag ctctgaagat     60
gttgatccat tgacttctgg cattcagtgt tgctgatgac aaatctgtta gcagtctatt    120
tctcatccat ttttgtgttg agctaatcgt gatgacctca tttgtttttct ccctggccac    180 tttaatatct tccttctatc cttaatattc caaaatttta caatattgtg tctagatgta    240
gattgtattg ggccctctca atctggagac ttagcttgct ctgttcttca                290

<210> SEQ ID NO 484
<211> LENGTH: 197
<212> TYPE: DNA
<213> ORGANISM: Homo sapiens

<400> SEQUENCE: 484
atgtcaagaa aatgacggtc acagaccagg tgaactgccc caagctctcg taaccaggtt     60
ctacagggag gctgcaccca ctccatgtta cttctgcttc gctttcccct accccacccc    120 cccccataa agacaaacca atcaaccacg acaaggaag ttgacctgaa catgtaacca     180
tgccctaccc tgttacc                                                   197

<210> SEQ ID NO 485
<211> LENGTH: 113
<212> TYPE: DNA
<213> ORGANISM: Homo sapiens

<400> SEQUENCE: 485
tgtcactggt gaaagacgac ttggtgccca attttttaata aacacaatgc tattagcgtc     60
actccaattt agtgtctgat tgttaaatgt taatgtactg cactctacag ttt           113

<210> SEQ ID NO 486
<211> LENGTH: 183
<212> TYPE: DNA
<213> ORGANISM: Homo sapiens

<400> SEQUENCE: 486
ggattataat atcctcactg gccacaatct gtaaaagtcg atactggcac ttttttttgcc     60

```
ccctcaaagg aaatatgcta atagacagcc cctttgcaaa tataattcct ccttcccaac    120
ccttcaaatt gctaaggccc cactggtcag caccttccct ttcgagtcca ggactactgt    180
tct                                                                  183

<210> SEQ ID NO 487
<211> LENGTH: 275
<212> TYPE: DNA
<213> ORGANISM: Homo sapiens

<400> SEQUENCE: 487
agcattaata atttccatgc atgtgtcttt ttccagtagg tatggttgaa tttatgtaaa     60
tttattgcta atcccatccc ttacgattta gagtataagc tgcgcaaggg cagaagtttt    120
tatttggttt gttcatggat gtattttaag agctgagaac agggcctgga cacaataagc    180
attcaataaa tatttactga atgaatgaac tcctacctat attcctattt ataatttggc    240
tccactttat cctactttag ctcccattca attca                               275

<210> SEQ ID NO 488
<211> LENGTH: 123
<212> TYPE: DNA
<213> ORGANISM: Homo sapiens

<400> SEQUENCE: 488
catttaaata agaggagatc cacaaagagc aacagagata agagaagaaa ggaaataatc     60
aataaaataa ttcaagaaaa tccaaggaca tgagttttca gattgtaaga gactacttga    120
gtg                                                                  123

<210> SEQ ID NO 489
<211> LENGTH: 99
<212> TYPE: DNA
<213> ORGANISM: Homo sapiens

<400> SEQUENCE: 489
aattcatatc ccctgttcgt ctcatgcgcg tcctccgtcc ccaatctaaa aagcaattga     60
aaaggtctat gcaataaagg cagtcgcttc attcctctc                            99

<210> SEQ ID NO 490
<211> LENGTH: 97
<212> TYPE: DNA
<213> ORGANISM: Homo sapiens

<400> SEQUENCE: 490
tggatcgatg atgagtcctc caaaaaaaca ttccttggaa aagctgaaca aaatgagtga     60
gaactcatac cgtcgttctc atcggaactg aggtcca                              97

<210> SEQ ID NO 491
<211> LENGTH: 119
<212> TYPE: DNA
<213> ORGANISM: Homo sapiens

<400> SEQUENCE: 491
attttctatc tgtggttgga ttcagaccac atgaacactg agggctgact gtagttttga     60
atgtctgtta ctgaggaggc accagcataa agtatttat cacttcagac gctgacaat     119

<210> SEQ ID NO 492
<211> LENGTH: 121
<212> TYPE: DNA
```

<213> ORGANISM: Homo sapiens

<400> SEQUENCE: 492

```
ttatatttat gtttagcacc gtcagtgttc ctatccaatt tcaaaaaagg aaaaaaaga      60
gggaaaatta caaaagaga gaaaaaaagt gaatgacgtt tgtttagcca gtaggagaaa    120
a                                                                   121
```

<210> SEQ ID NO 493
<211> LENGTH: 168
<212> TYPE: DNA
<213> ORGANISM: Homo sapiens

<400> SEQUENCE: 493

```
gtttgagcta tcgaagagta agtaaccaga aatttgagaa cagcctgggc agcatagtga     60
gaccccatct ttacaaaaac ttcacagatt agccaggtat ggtggcattt tcctgtagtc   120
ccagctactc agaatgctga ggcaggagag tggcttgtga ccaagagt                168
```

<210> SEQ ID NO 494
<211> LENGTH: 47
<212> TYPE: DNA
<213> ORGANISM: Homo sapiens

<400> SEQUENCE: 494

```
aggataaact tgtgtggtgt agagaagtta aaatcctcac gttgtac                   47
```

<210> SEQ ID NO 495
<211> LENGTH: 286
<212> TYPE: DNA
<213> ORGANISM: Homo sapiens

<400> SEQUENCE: 495

```
acttcaggga agtttcataa aaggaagaat tttaactcag cgtagaaaga tgggtaaatt     60
ttcctcatgt gaaggtgtac tgcctggggt gctgcaggct ggagatgagt attaaaatag   120
gaggagagtg agtgaaagca caggaggagg aagggtcagg caagtttggt gaacacagca   180
actggctata gaacaggagc agtgggagaa agtccagaaa ggtctgctga gcttcagttg   240
tacaaagctg tggagtttgg cctttggtca tggctagatt aggtct                  286
```

<210> SEQ ID NO 496
<211> LENGTH: 94
<212> TYPE: DNA
<213> ORGANISM: Homo sapiens

<400> SEQUENCE: 496

```
tggatcgatg atgacctcaa tacatgcatt ccttggaaag ctgaacaaaa tgagtgaaaa     60
ctctataccg tcgtcctcgt caaactgagg tcca                                94
```

<210> SEQ ID NO 497
<211> LENGTH: 174
<212> TYPE: DNA
<213> ORGANISM: Homo sapiens

<400> SEQUENCE: 497

```
gtttgaggta tttaactgac acctaagtgg atctgttgag gaaacagttg gatatacaaa     60
tttagtgttt aaggcagact tccaggcttg aaggaaaaat tggaagtca tcacgacata   120
tatgtggtat ttaaaattgt gaggttcaag gaccaagccc cataccattt agag          174
```

<210> SEQ ID NO 498
<211> LENGTH: 255
<212> TYPE: DNA
<213> ORGANISM: Homo sapiens

<400> SEQUENCE: 498

```
tggagatagc tcttaaagat ataaatgttt atggctgaaa tgttatggca tcttggattt      60
gctttaaaat aacccagctt gctgcaggag gtgggtattg tgtgtgtggg aaggtgggga     120
ggctgcggga ggaagagatg acccaagatt aggcagatgt tgttaactgt ggaagcaggg     180
tggtgagtgg gggctcatga cattatgctc tctactttgt gtacgtgtga acatttccgt     240
aataaaagat gcctt                                                      255
```

<210> SEQ ID NO 499
<211> LENGTH: 137
<212> TYPE: DNA
<213> ORGANISM: Homo sapiens

<400> SEQUENCE: 499

```
ggattttttc ccctgtagta gtgaggtaac atgcttgaat gtcactgtga tatttatttc      60
ctctttgttc agttgttttt gaattcctgt taagtacatg ttttaatact ttgagcgatt     120
taagatactt ttctttt                                                    137
```

<210> SEQ ID NO 500
<211> LENGTH: 33
<212> TYPE: DNA
<213> ORGANISM: Homo sapiens

<400> SEQUENCE: 500

```
aaacgatgat aatctttact ggtgaaaagg atg                                   33
```

<210> SEQ ID NO 501
<211> LENGTH: 195
<212> TYPE: DNA
<213> ORGANISM: Homo sapiens

<400> SEQUENCE: 501

```
tatgagttat tcaaggagga gacttttttaa agacagcaac gcaattcttg taacttgtgt      60
aaatagcccc atctttcaga gtgataccat ttctacattt gataatgcct gtattcctgt     120
aggatgtata tagtttaggg gattttttttt tgtttggtt ttgttttttta gaagtcaata     180 tgtctggttt tattt                                                      195
```

<210> SEQ ID NO 502
<211> LENGTH: 255
<212> TYPE: DNA
<213> ORGANISM: Homo sapiens

<400> SEQUENCE: 502

```
attattttga tagcagatgt gctatttatt tatttaatat gtataaggag cctaaacaat      60
agaaagctgt agagattggg tttcattgtt aattggtttg ggagcctcct atgtgtgact     120
tatgacttct ctgtgttctg tgtatttgtt tgaattaatg acctgggata taaagctatg     180
ctagctttca aacaggagat gcctttcaga aatttgtata ttttgcagtt gccagaccaa     240
taaaatacct ggttg                                                      255
```

<210> SEQ ID NO 503
<211> LENGTH: 217
<212> TYPE: DNA

<213> ORGANISM: Homo sapiens

<400> SEQUENCE: 503

```
gtgtgttaaa atgagggtct cactgcttta ggattgaagt ggctggaaag agtgatgcct    60
ggggaaggag atggagttat gagggtactg tggctggtac tttctgtact aaacatttcc   120
tttttctatt ttaccactaa ttttgtttta aactgtgagc cgtccaagtc agaagaagac   180
agcaaaaaaa gcaactttc caacatacaa tttactt                             217
```

<210> SEQ ID NO 504
<211> LENGTH: 92
<212> TYPE: DNA
<213> ORGANISM: Homo sapiens

<400> SEQUENCE: 504

```
cctgcctggg aaagcgagtc cacagttcac taacaaacac aataccatcc acaaacaagt    60
agccacaaag accacagtta gcaaacacac ac                                  92
```

<210> SEQ ID NO 505
<211> LENGTH: 251
<212> TYPE: DNA
<213> ORGANISM: Homo sapiens

<400> SEQUENCE: 505

```
atataattgg acaaacgctg gcaaaaagaa aaaatggta agcaaaaaac ccaagataaa    60
gtttcgagga catcaggcct tttgaaatac aatgtcaaat gacacattgt acggtttcaa   120
aaaatccgct agacatgtca taagttttaa ctgtaatgcc caggaaagga tatcttaaaa   180
tattctaaac ttgtgtaaca aaggaataat taactgtaat agttttttcaa taaatcgagt   240
tgggtgtttc c                                                         251
```

<210> SEQ ID NO 506
<211> LENGTH: 261
<212> TYPE: DNA
<213> ORGANISM: Homo sapiens

<400> SEQUENCE: 506

```
gaatggttac tgtttatact gtggtatgtt tttgattaca gcagataatg ctttcttttc    60
cagtcgtctt tgagaataaa ggaaaaaaaa tcttcagatg caatggtttt gtgtagcatc   120
ttgtctatca tgttttgtaa atactggaga agctttgacc aatttgactt agagatggaa   180
tgtaactttg cttacaaaaa ttgctattaa actcctgctt aaggtgttct aattttctgt   240
gagcacacta aaagcgaaaa a                                              261
```

<210> SEQ ID NO 507
<211> LENGTH: 175
<212> TYPE: DNA
<213> ORGANISM: Homo sapiens

<400> SEQUENCE: 507

```
tatttcttgc tattgtgata tgacaagaga cttaacttat cttgctctgt tttcccctgt    60
acacgctgta tagggggtc aatgtgatgc tgctggagac gagaataaac tggactagaa   120
tagtgcattg tatttagtct gtattgatca tggatgccct ccttaatagc catat        175
```

<210> SEQ ID NO 508
<211> LENGTH: 251
<212> TYPE: DNA
<213> ORGANISM: Homo sapiens

```
<400> SEQUENCE: 508
gaaccgcaga ttatggttaa tccaattctg tgcacctgag gtccataaat aaaagaataa      60
gtattgaaat gaaagaatga cagaaagaat gaatggacac atgaacgact gaattagaaa     120
tggaaatgcc tggcacagcc aggaaggagc tgcccatggg attgtcattc atttcactct     180
gggcacctga ggtccataag cgtgaaaaga ggcaggaaga gaagtgtcag ggagtcaaag     240
atagagctaa g                                                          251

<210> SEQ ID NO 509
<211> LENGTH: 237
<212> TYPE: DNA
<213> ORGANISM: Homo sapiens

<400> SEQUENCE: 509
ttattttatt tcgctatttc cagtttgaag ctactatcat gggcgtttag agttatacaa      60
atgacactta caaaaaataa aagaccaaga cacccagagt gagatgcatg ttggggacgg     120
gggaggctgg cagcaggggg gccccggcgg ctcacccccag ggctcccgga gggggctgtt    180
tccatccacc acccaaaaaa acaccacaag ggtcagtcct agcccacccg acagctt        237

<210> SEQ ID NO 510
<211> LENGTH: 133
<212> TYPE: DNA
<213> ORGANISM: Homo sapiens

<400> SEQUENCE: 510
gtatggatgg gtatgttgag actcaattac tttttttatta gcttcccgt ttggaagatc     60 ccaaacacca agatggaag gtgaaaataa agactgcgtg accgggaaga agtttgaat      120 tactaatagt ggg                                                        133

<210> SEQ ID NO 511
<211> LENGTH: 263
<212> TYPE: DNA
<213> ORGANISM: Homo sapiens

<400> SEQUENCE: 511
aatcaaccaa tgcaaccagt ttgtgagaaa aaaaaaaaaa agccgaaaaa aaaaaaaaaa      60
aacacctgaa tgcggaagag ctcggctccc gtttagcatt ttgtacttaa ggaaataaaa     120
aaccaacaaa ggatttcaca ttttttttaaa aagtgaagat tgctgtatac tatttattca   180
acttataatt tatgttactc cttgatcttt gtcttttgtc atgacaaagc atttatttaa    240
taaagttatg cattcagcaa ctt                                             263

<210> SEQ ID NO 512
<211> LENGTH: 48
<212> TYPE: DNA
<213> ORGANISM: Homo sapiens

<400> SEQUENCE: 512
taggttgtca acaggtacta tttgtcacat aactaacttt cgaggcac                   48

<210> SEQ ID NO 513
<211> LENGTH: 161
<212> TYPE: DNA
<213> ORGANISM: Homo sapiens

<400> SEQUENCE: 513
```

```
attagtgaac ttatctttgc agctgagtac ttaaattctt tttaaaaaga tacccttggg      60
attgatcaca ttgtttgacc cagtatgttt tgtagacacg ttagttataa tcaccttgta     120
tctctaaata tggtgtgata tgaaccagtc cattcacatt g                         161
```

<210> SEQ ID NO 514
<211> LENGTH: 286
<212> TYPE: DNA
<213> ORGANISM: Homo sapiens

<400> SEQUENCE: 514

```
gtcttcacca actaagaaag ctctgttatt ctggcctggg tgcttgctcc agactcagga      60
acatctggtc aacacaagca tcactgggct ggggaattgt gtgtgtgctg catcatctcc    120
gactctcttg tagttccttc cttccctccc tcactcttac atgcagacac agacagacac    180
agtctggttg ggacatgcag tggcagctcc tggtgtataa catctttcac acaccttgag    240
tctatctgct tgctgccttt gactgatcct gaaatggttg gccttt                   286
```

<210> SEQ ID NO 515
<211> LENGTH: 208
<212> TYPE: DNA
<213> ORGANISM: Homo sapiens

<400> SEQUENCE: 515

```
gaggccccag aggacttatc tcagctgtac atgctctgcc tgtggagaca tggcttttct      60
ttgtgctgtg gcagactggg gctttggaag tggtgtatgt ttaacttacc tgagagtgag    120
agatgtgtag gaagaatagc tggaagaaag tgaaagatga gtgccagtac ttttggcctg    180
ttatccagta gagagaaagt gacagtga                                       208
```

<210> SEQ ID NO 516
<211> LENGTH: 201
<212> TYPE: DNA
<213> ORGANISM: Homo sapiens

<400> SEQUENCE: 516

```
aactctgtaa ggaggaccat gtcagactat tgtaagctaa gcattaggac tgatacaaat      60
aatatatgct cctggcatag aaaaataaac cacagagaac gagttcaaag aatagcaaag    120
aaagaaagag gacccagtgg gcgaaagatg agagtgtact tttaccaaaa gttatctaag    180
cctgagcact tgaagtctgc a                                              201
```

<210> SEQ ID NO 517
<211> LENGTH: 119
<212> TYPE: DNA
<213> ORGANISM: Homo sapiens
<220> FEATURE:
<221> NAME/KEY: misc_feature
<222> LOCATION: (91)..(91)
<223> OTHER INFORMATION: n is a, c, g, or t

<400> SEQUENCE: 517

```
aaaatagaga gacatacctg gctccaaaac aaggctgtat cttctgccac tgtaataaaa      60
tagatgcaat tgaggttcat aaataaaaga ntaaatactt aaacgtgaaa ggtgactaa     119
```

<210> SEQ ID NO 518
<211> LENGTH: 36
<212> TYPE: DNA
<213> ORGANISM: Homo sapiens

<400> SEQUENCE: 518
ataatgaaag ttagtaacgt ccattattta ataaag 36

<210> SEQ ID NO 519
<211> LENGTH: 91
<212> TYPE: DNA
<213> ORGANISM: Homo sapiens

<400> SEQUENCE: 519
tgtacagggt cattttgaca gtaactggta tattcctttg cattttatgt tgcattgcca 60 attttagtg tatccagttt gaaagtataa t 91

<210> SEQ ID NO 520
<211> LENGTH: 178
<212> TYPE: DNA
<213> ORGANISM: Homo sapiens

<400> SEQUENCE: 520
tactgatctt tatattacag atttttttt cttttaggat tagttcagct tgccccccct 60
ttccatttcc accatttata gtgagcctct ccataattag tgccaaccat tagtttcgtt 120 catatttta caccaggagt caacaaactg tggccattgg ccaaatatgg cctcccaa 178

<210> SEQ ID NO 521
<211> LENGTH: 242
<212> TYPE: DNA
<213> ORGANISM: Homo sapiens

<400> SEQUENCE: 521
aggaagtacc cgctccataa gacccttaca tttggacagt caaggtgcac aattgtatgt 60
gaccacaacc atgcaccttg gacataaatg tgtgtaactg cacatggccc atcccatctg 120
aataaggtcc tactctcaga ccccttttgc agtacagtag gtgtgctgat aaccaaggcc 180
cctcttcctg gcctgttaac gtatgtgatt atatttgtct gggttccagt gtataagaca 240
tg 242

<210> SEQ ID NO 522
<211> LENGTH: 199
<212> TYPE: DNA
<213> ORGANISM: Homo sapiens

<400> SEQUENCE: 522
gggagtcaat gaatagtacc taaaatggaa accaaacaaa acaacttcag gaagtaacaa 60
gggcttgctt agagacatga cggtaaaccc tgaaccatca gctaaagag gtagatagca 120 gtggttgccc ctggggagag gtaaatgtga tggagaggga acaactgtgt acaaacatgt 180
gactttacgt tttgatcaa 199

<210> SEQ ID NO 523
<211> LENGTH: 127
<212> TYPE: DNA
<213> ORGANISM: Homo sapiens

<400> SEQUENCE: 523
aagagttaaa cagtctagag tgaagggaat gttttaaaat ccagaggcga tcaagtgaag 60
ccaacctttg gaggcccgta gaagtcattt ggaggaattt ggacttcgtg cagtaggaaa 120
gagggaa 127

<210> SEQ ID NO 524

```
<211> LENGTH: 46
<212> TYPE: DNA
<213> ORGANISM: Homo sapiens

<400> SEQUENCE: 524 gacagggggtt ctaattactg tctgtgagag ttactactttt gtaact              46

<210> SEQ ID NO 525
<211> LENGTH: 115
<212> TYPE: DNA
<213> ORGANISM: Homo sapiens

<400> SEQUENCE: 525
taatattttt tgctgcctag gcaaatggct tttgtgaaaa cacttgtatg aaaagcaata  60
caccatttgt ttttacttac caatcactat cattaggttt tgatgcaaat gggaa       115

<210> SEQ ID NO 526
<211> LENGTH: 138
<212> TYPE: DNA
<213> ORGANISM: Homo sapiens

<400> SEQUENCE: 526
ttcccaagcc catgagtcct tgaaaatatt ttttatatat acagtaactt tatgtgtaaa  60
tacataagcg gcgtaagttt aaaggatgtt ggtgttccac gtgttttatt cctgtatgtt 120
gtccaattgt tgacagtt                                                138

<210> SEQ ID NO 527
<211> LENGTH: 269
<212> TYPE: DNA
<213> ORGANISM: Homo sapiens

<400> SEQUENCE: 527
cttaggatat gaaatcttca gaggatggta gaagagaaag gtaaatgcca taagaaagta  60
gagtacttgt ggtcattgaa accatggaat ttactcaggg atagtgtata tagtgagaaa 120
tcaggtaact aagatttgag cctaaacgta atctgtaaaa ggggagctca aggaaaagg  180 gaatgggagg accggatttt gtaaggatag tagggcaaat gttaagagag agaatgagag 240
agttgagtat ggcaaagagt gactcaatt                                    269

<210> SEQ ID NO 528
<211> LENGTH: 282
<212> TYPE: DNA
<213> ORGANISM: Homo sapiens

<400> SEQUENCE: 528
tcacctcctg ctggctaccg gggcaggcat gcacccggtg ccagcccgc tctgggcacc   60 acctgccttc cagcccctcc aggacccggt ccccctgctg cccctcactt caggagggggc 120 ctggagcagg gtgaggctgg actttggggg gctgtgaggg aaatatactg gggtccccag 180
attttgcttt aagggggcca gacccttgc caggctggat tgtacgggcc ccaccttcgc  240
tgtgttcttg ctgcaaagtc tggtcaataa atcactgcac tg                    282

<210> SEQ ID NO 529
<211> LENGTH: 131
<212> TYPE: DNA
<213> ORGANISM: Homo sapiens

<400> SEQUENCE: 529
atacctgtta aatagatcaa ttttgattgc ctactatgtg aactcactgt taaaggcact  60
```

```
gaaaatttat catatttcat ttagccacag ccaaaaataa cgcaataacct atgttagcat    120 tttgtgaact c                                                          131
```

<210> SEQ ID NO 530
<211> LENGTH: 183
<212> TYPE: DNA
<213> ORGANISM: Homo sapiens

<400> SEQUENCE: 530

```
tcacctgagg cgttcaaaag atataaccaa ataaacaagt catccacaat caaaatacaa    60
cattcaatac ttccaggtgt gtcagacttg ggatgggacg ctgatataat agggtagaaa   120
gaagtaacac gaagaagtgg tggaaatgta aaatccaagt catatggcag tgatcaatta   180
tta                                                                  183
```

<210> SEQ ID NO 531
<211> LENGTH: 263
<212> TYPE: DNA
<213> ORGANISM: Homo sapiens

<400> SEQUENCE: 531

```
ttgttggtag agacggtgat tcactatgtt ggccaggcta gtcacgaact cctgacctcg    60
tgatccgccc acctcggcct cccaaagtgc tgggattaca ggtgtgagcc accgtgcccg   120
gcctcttttt atttattcct aaaatattac cttgaggcca aattctgcgc ttaaggagaa   180
tgtgcaccaa gtgctggggt gggggctggt tataaacgag gccacaaatc atgcttgtta   240
ataaattgtg tggttcaaat ctg                                            263
```

<210> SEQ ID NO 532
<211> LENGTH: 140
<212> TYPE: DNA
<213> ORGANISM: Homo sapiens
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 532

```
cacagccaaa acctctacat ccctacattc acacacttcc tccacacacc atcctgaagt    60
caccccaact nctaccacca anatcaccac caanccacc agtataggaa gcagcacacc    120
catggcccac actacctcag                                                140
```

<210> SEQ ID NO 533
<211> LENGTH: 134
<212> TYPE: DNA
<213> ORGANISM: Homo sapiens

<400> SEQUENCE: 533

```
cagaggagct ttattagagg gacagggtga acatatttta caccggccga gcagggacct    60
taagaagcag gcgtgggagc agggtcccag ctcagacgag ttccaccttg gcattggggt   120
acaccgccac cacg                                                      134
```

<210> SEQ ID NO 534
<211> LENGTH: 207
<212> TYPE: DNA
<213> ORGANISM: Homo sapiens

<400> SEQUENCE: 534
gagtatgagt atgcctgagt gtgaatgtgt atgagtgtga atgagtgtgt gcacatgagt    60
gcacgggtgt cagcatgtgt atataagtgt gggcatgtgt atgtgattgt gtgagtgtgg    120
gcaggtgagt gtgttgggga tgtgggttag ggtggggagt ggtgctttct ctagtgtgtc    180
ctccggaaca tcttgcctac ctagcaa                                        207

<210> SEQ ID NO 535
<211> LENGTH: 113
<212> TYPE: DNA
<213> ORGANISM: Homo sapiens

<400> SEQUENCE: 535
gaaaactgtt agatgcacac tgttgatttt catggtggat tcaagaactc cctagtgagg    60
agctgaactt gctcaatcta aggctgattg tcgtgttcct cttttaaattg ttt          113

<210> SEQ ID NO 536
<211> LENGTH: 66
<212> TYPE: DNA
<213> ORGANISM: Homo sapiens

<400> SEQUENCE: 536
gtttttatta aaacacaaac gcacacacac acaaaattag ccaggcatgg tggtccatcc    60
ctgtaa                                                               66

<210> SEQ ID NO 537
<211> LENGTH: 66
<212> TYPE: DNA
<213> ORGANISM: Homo sapiens

<400> SEQUENCE: 537 gtcacccag agtcattgtc acctcagagt cattgtcact ccagagtcat tgtcacctca    60
gagtca                                                               66

<210> SEQ ID NO 538
<211> LENGTH: 128
<212> TYPE: DNA
<213> ORGANISM: Homo sapiens

<400> SEQUENCE: 538
caggctgggc cgtgagcagg tgggccgttg agttacctct gtgctggatc ccgtgccccc    60
acttgcctac cctctgtcct gccttgttat tgtaagtgcc ttcaatactt tgcattttgg    120
gataataa                                                             128

<210> SEQ ID NO 539
<211> LENGTH: 49
<212> TYPE: DNA
<213> ORGANISM: Homo sapiens

<400> SEQUENCE: 539
tgattactag tgtaaactgg ttattgagat agattatgac attggtgga                49

<210> SEQ ID NO 540
<211> LENGTH: 209

<212> TYPE: DNA
<213> ORGANISM: Homo sapiens

<400> SEQUENCE: 540
cagagtcatt cattgtcacc ccagagtcat tgtcacccga gtcattgtca gctcagagtc    60
attgtcaccc cagagtcatt gtcacccccag agtcattgtc accccattgt caccccagag   120
tcattgtcac ctcagagtca ttgtcactcc agagtcattg tcacctcaga gtcaatgtca   180
ccccagagtc atcgtcaccc cagagacat                                     209

<210> SEQ ID NO 541
<211> LENGTH: 237
<212> TYPE: DNA
<213> ORGANISM: Homo sapiens

<400> SEQUENCE: 541
aataaatgcc tcaggcgtgc tttttgattc atttgataaa caaagcatct tttatgtgga    60 ataccatt tgggtcctg aggataagag agatgagggc attagatcac tgacagctga     120
agatagaaga acatctttgg tttgattgtt taaataatat ttcaatgcct attctttgca   180
aggtactatg tttcgtaaat taaataggtc tggcccagaa gacccactca attgcct      237

<210> SEQ ID NO 542
<211> LENGTH: 62
<212> TYPE: DNA
<213> ORGANISM: Homo sapiens

<400> SEQUENCE: 542
tatgtaatta aagatgaag cgtagtgaat tgtacagctg ttgtaataat gacctatttc    60
ta                                                                  62

<210> SEQ ID NO 543
<211> LENGTH: 277
<212> TYPE: DNA
<213> ORGANISM: Homo sapiens

<400> SEQUENCE: 543
tacccccttt tatatctaat gtagaaaaag cgaaattgaa tctggaaagc aaactgttgt    60
atatagttgc ggtaacaatc atgaagagag agccgggctg tcccctcagt aattcatttt   120
aaataacaaa ttatttaaaa ataaaattca tgccagagcc agctgaagag gccttccttc   180
atcaccactg aggccacccc caatctgggc cctctgtcca tctggcatgt ctcctcccag   240
caagattcat ctgttcaatg ccatttgcgt ttcaata                            277

<210> SEQ ID NO 544
<211> LENGTH: 203
<212> TYPE: DNA
<213> ORGANISM: Homo sapiens

<400> SEQUENCE: 544
ttttcccaac tctatagcta gatttaaaag tcccagtaaa attttgtaaa caaaatcata    60
taagaaaagg caaggctggc tcttccctat ggtcctttag tggagctata tttgcataga   120
tcctagacaa atgatgcaaa acaaattccc tccaatttcc actagcaatc tccctaattc   180
gctcaaccct tacataagca tca                                           203

<210> SEQ ID NO 545
<211> LENGTH: 75
<212> TYPE: DNA

<213> ORGANISM: Homo sapiens

<400> SEQUENCE: 545
agaacctgag tataaattta ctttctcaaa ttcttgccat gagaggttga tgagttaatt    60
aaaggagaag attcc    75

<210> SEQ ID NO 546
<211> LENGTH: 248
<212> TYPE: DNA
<213> ORGANISM: Homo sapiens

<400> SEQUENCE: 546
aaaaactcaa cctatctggt gttttatttt aatggataaa aatgtaatttt ttttaaggta    60 gcaacttatt tccaaattaa tatagatgaa aaatagatac caattagact aaattgaaag   120 cttttttgttc tatatttgca tagcctttga aatatttctt agtgcctagg aggtctgggg   180
attcctcttt cgtggtggtc actaacctta cttgatgcag ataaaatcac ttgtcaatgc   240
aaaatgtg    248

<210> SEQ ID NO 547
<211> LENGTH: 174
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t

<400> SEQUENCE: 547
acgagccctc tcacagtgga atggagngca cggtctgaat ctgcacagag caagatgctg    60
agtggagtcg ggggcttngt gctgggcctg ctcttncttg gggccgggct gttcatctac   120
ttnaggaatc agaaaggaca ctctggactt cagccaacag gattcctgaa ctga   174

<210> SEQ ID NO 548
<211> LENGTH: 251
<212> TYPE: DNA
<213> ORGANISM: Homo sapiens

<400> SEQUENCE: 548
agagagtgga catttgtcgg gaaactccta acatatgccc ccattctgga gagaacacag    60
agtacgacac aatccctcac actaatagaa caatcctaaa ggaagatcca gcaaatacgg   120
tttactccac tgtggaaata ccgaaaaaga tggaaaatcc ccactcactg ctcacgatgc   180
cagacacacc aaggctattt gcctatgaga atgttatcta gacagcagtg cactgcccct   240
aagtctctgc t    251

<210> SEQ ID NO 549
<211> LENGTH: 88
<212> TYPE: DNA
<213> ORGANISM: Homo sapiens

<400> SEQUENCE: 549

```
gccctcatgg ttggcatcac atatgcctgc atgccattaa caccagctgg ccctacccct    60
ataatgatcc tgtgtcctaa attaatat                                       88
```

<210> SEQ ID NO 550
<211> LENGTH: 284
<212> TYPE: DNA
<213> ORGANISM: Homo sapiens

<400> SEQUENCE: 550

```
aactgaaatg tcaacctgtg gactgtggca ttcctgaatc cattgagaat ggtaaagttg    60
aagacccaga gagcactttg tttggttctg tcatccgcta cacttgtgag gagccatatt   120
actacatgga aaatggagga ggtggggagt atcactgtgc tggtaacggg agctgggtga   180
atgaggtgct gggcccggag ctgccgaaat gtgttccagt ctgtggagtc cccagagaac   240
cctttgaaga aaaacagagg ataattggag gatccgatgc agat                    284
```

<210> SEQ ID NO 551
<211> LENGTH: 214
<212> TYPE: DNA
<213> ORGANISM: Homo sapiens

<400> SEQUENCE: 551

```
gacttattcc cgctgactga gtttttgagg ggctaccagg aaagcgcctc caaccctagc    60
aaaagtgcaa gatggggagt gagaggctgg aatggaggg gcagagccag gaagatcccc   120
cagaaaagaa agctacagaa gaaactgggg ctcctccagg gtggcagcaa caataaatag   180
acacgcacgg cagccacagc ttgggtgtgt gttc                               214
```

<210> SEQ ID NO 552
<211> LENGTH: 72
<212> TYPE: DNA
<213> ORGANISM: Homo sapiens

<400> SEQUENCE: 552

```
gaatggcagt accagaaggc attggttaag tgtcccagga accacacaag cagtgactcc    60
taaagaagtt ca                                                        72
```

<210> SEQ ID NO 553
<211> LENGTH: 180
<212> TYPE: DNA
<213> ORGANISM: Homo sapiens

<400> SEQUENCE: 553

```
gcttccttaa aggtcagaac atcaggccaa agtacaacgt ttaatttcag aacttgcctt    60
ccaatttacg cattttcaat ttgctctccc catttgttga gtcagaagaa gcagcattgc   120
ccagaaacag gtattacgta acatgcacat actttaaaaa gtactcatcc cttgttttct   180
```

<210> SEQ ID NO 554
<211> LENGTH: 173
<212> TYPE: DNA
<213> ORGANISM: Homo sapiens

<400> SEQUENCE: 554

```
gctgagtatg ttaagctctt tatgactgtt tttgtagtgg tatagagtac tgcagaatac    60
agtaagctgc tttattgtag catttcttga tgttgcttag tcacttattt cataaacaac   120
```

```
ttaatgtttt gaataatttc ttactaaaca ttttgttatt gggcaagtga ttg         173
```

<210> SEQ ID NO 555
<211> LENGTH: 243
<212> TYPE: DNA
<213> ORGANISM: Homo sapiens

<400> SEQUENCE: 555

```
aaaacttggc acttttcgt gtggatcttg ccacatttct gatcagaggt gtacactaac    60
atttcccccg agctcttggc ctttgcattt atttatacag tgccttgctc ggcgcccacc  120 acccctcaa gccccagcag ccctcaacag gcccagggag ggaagtgtga gcgccttggt  180
atgacttaaa attggaaatg tcatctaacc attaagtcat gtgtgaacac ataaggacgt  240
gtg                                                                 243
```

<210> SEQ ID NO 556
<211> LENGTH: 201
<212> TYPE: DNA
<213> ORGANISM: Homo sapiens

<400> SEQUENCE: 556

```
ccctgctgcc tctgatcgta ggaattgagg agtgtcccgc cttgtggctg agaactggac    60
agtggcaggg gctggagatg ggtgtgtgtg tgtgtgtgtg tgtgtgtgtg tgtgtgcgcg   120
cgcgccagtg caagaccgag attgagggaa agcatgtctg ctgggtgtga ccatgtttcc   180
tctcaataaa gttcccctgt g                                             201
```

<210> SEQ ID NO 557
<211> LENGTH: 174
<212> TYPE: DNA
<213> ORGANISM: Homo sapiens

<400> SEQUENCE: 557

```
tgggcgtccg ggcccccaat attcacgcac tcgcaccacg cactcatatt ccctcacccc    60
accatcacgg ccccaaagaa ggtcttccct ctcgcgaagt ccaccatatc ggggtgactg   120
atgttggacg tacaccctct cgcccctccg gagctgcacc aggccgccga accc          174
```

<210> SEQ ID NO 558
<211> LENGTH: 259
<212> TYPE: DNA
<213> ORGANISM: Homo sapiens

<400> SEQUENCE: 558

```
ctacaacagg caggtactgc tgccaggggg ctttgaacta gtgcctgcta cccaggacac    60
ccgggccatg cccctggctg ggcagcctgg cacaagtgaa gaagaaggca gtgggaaaac   120
tgggtttatt tcaaggcagc agcctgagcc caggagcaga ggacccagtt gttataaggc   180
gctgggagag gatgggcagc tcccactgcc ccagagcgga gctcgaagca cccaggttgc   240
ccacggaaaa tccaataaa                                                259
```

<210> SEQ ID NO 559
<211> LENGTH: 60
<212> TYPE: DNA
<213> ORGANISM: Homo sapiens

<400> SEQUENCE: 559

```
tttctggggt ctttgagctc caaaaaataa acacttcctt tgagggagag ccccccccca    60
```

<210> SEQ ID NO 560
<211> LENGTH: 159
<212> TYPE: DNA
<213> ORGANISM: Homo sapiens

<400> SEQUENCE: 560
gagcttcctt cttcgttctt ggcaccatct tatgaaaagg gtccagatta agattttga      60 ctgagtcatt ctaaagtaag ttgcaagacc catgatacta gaccactaaa tacttcatca    120
cacacctcct aagaataaga accaacatta tcacaccaa                            159

<210> SEQ ID NO 561
<211> LENGTH: 278
<212> TYPE: DNA
<213> ORGANISM: Homo sapiens

<400> SEQUENCE: 561
ggaagccatt atcctaaatg aactcactca gaaacagaaa accaaatacc acatgttctc     60
acttataagt agaagctaaa cattgagtac acatggatac aaagaaggga accgcagaca    120
ctggggccta cctgaggtcg gagcatggaa ggagggtgag gatcaaaaaa ctacctatct    180
ggtactatgc tttttatctg gatgatgaaa taatctgtac aacaaaccct ggtgacatgc    240
aatttaccta tatagcaagc ctacacatgt gcccctga                            278

<210> SEQ ID NO 562
<211> LENGTH: 241
<212> TYPE: DNA
<213> ORGANISM: Homo sapiens

<400> SEQUENCE: 562
ttcccatctc gtccatgagc ctaggtcttg gagccttgtg ttggaggctg ctgtgatgtc     60
aggaacgggg atctttctag cttttggcca cttcctggga cctcacgccc ctgttgacag    120
atggagattg ggcagcaggg ccttgctgca ttgttatctg ctgttccgac ttggtttgtc    180
ttgtccaagg gtgacgaaag agccaggcac cagggtctca tgggatgagg tccaactttt    240
t                                                                    241

<210> SEQ ID NO 563
<211> LENGTH: 283
<212> TYPE: DNA
<213> ORGANISM: Homo sapiens

<400> SEQUENCE: 563
gtgagaggta acactctaaa tagcccattt catgctcaag acatccaagt caaagaaacc     60
caatagcaca ggtgagtccc ctctgttccc cccaacacc ccactcacat cagggcccct    120
gccctggagt gtcacccttta ttagctgtga gagacacccc agagccctgg gcactgtcag    180 tgattgggggt agaacaaaaa caggacctgg tcagagccca cagatgtggc tagaggaact    240
gtggggtggt gagctccctc ataggctcct gaccacaata tcc                      283

<210> SEQ ID NO 564
<211> LENGTH: 186
<212> TYPE: DNA
<213> ORGANISM: Homo sapiens

<400> SEQUENCE: 564
gagacttgta tgaaagatgg ctgtgcctct gcctgtctcc cccaccgggc tgggagctct     60
gcagagcagg aaacatgact cgtatatgtc tcaggtccct gcagggccaa gcacctagcc    120

```
tcgctcttgg caggtactca gcgaatgaat gctgtatatg ttgggtgcaa agttccctac    180
ttcctg                                                              186

<210> SEQ ID NO 565
<211> LENGTH: 267
<212> TYPE: DNA
<213> ORGANISM: Homo sapiens

<400> SEQUENCE: 565
gcatttcaaa gtgacttcta tgaagctttt tttttaatgt gaaattttca gaatgttgtt    60
tttttcatgt agatactcca ggaagagtta agcactgctt tcagttttaa tatccaccct   120
gaggggtcgc tgcttgaggg ctcttatccc aggggacttt ttaattcgga tgttacttaa   180
tgtggcttct ctaatgtagt ttctttgatt accgactaca caattatgta ccatcacagt   240
attagtggaa aagtaccatg tgattta                                       267

<210> SEQ ID NO 566
<211> LENGTH: 45
<212> TYPE: DNA
<213> ORGANISM: Homo sapiens

<400> SEQUENCE: 566
tgcttataca cttacacttt atgcacaaaa tgtagggtta taata                    45

<210> SEQ ID NO 567
<211> LENGTH: 241
<212> TYPE: DNA
<213> ORGANISM: Homo sapiens

<400> SEQUENCE: 567
aactggaccc tgtcgttctc catcttctca gtcagttgtt tcaagtgttc ctgataactc    60
ctctccttct gttccatcat ctgctcattc tttctttgca tttcctgcaa cattttttgct  120 gaagcctgtg cagactcagc tttcacaagt tccacttcaa tctccttttc tttttctgtg   180
agagtctggt ctgtctggag aattgcatca gtcatagact ccttggattt caagtatgtc   240
t                                                                   241

<210> SEQ ID NO 568
<211> LENGTH: 159
<212> TYPE: DNA
<213> ORGANISM: Homo sapiens

<400> SEQUENCE: 568
gagcttcctt cttcgttctt ggcaccatct tatgaaaagg gtccagatta agattttga     60 ctgagtcatt ctaaagtaag ttgcaagacc catgatacta gaccactaaa tacttcatca   120
cacacctcct aagaataaga accaacatta tcacaccaa                          159

<210> SEQ ID NO 569
<211> LENGTH: 107
<212> TYPE: DNA
<213> ORGANISM: Homo sapiens

<400> SEQUENCE: 569
tactcccgag gctctgtaca ttgctgccac atactcctgc cagcttgggg gagtgttcct    60
tcaccctcac agtatttatt atcctgcacc acctcactgt tccccat                 107

<210> SEQ ID NO 570
<211> LENGTH: 273
```

```
<212> TYPE: DNA
<213> ORGANISM: Homo sapiens

<400> SEQUENCE: 570
tagaagatga cctcgttccg gagctgggta tttcaaattt gctttcatcc agccactgcc    60
caaagccatt ttcctgccta ctggatgctt acagtgactg tggatacggg ggttcccttt   120
ccccattcag tgacatgtcc tctttgcttg gtgtaaacca ttcttgggag gacacttttg   180
ccaatgaact ctttccccag ctgattagtg tctaaggaat gatccaatac tgttgccctt   240
ttccttgact attacactgc ctggaggata gca                                273

<210> SEQ ID NO 571
<211> LENGTH: 228
<212> TYPE: DNA
<213> ORGANISM: Homo sapiens

<400> SEQUENCE: 571
atgtaggaga acgtgccta ttcacacttt gggaagacgc taatttgtga cattttttt     60 tcaagcctgc catcaaggac attttttaag acccaactgg catgagttgg ggtaatttcc  120
tattattttc attttggaca acttttttaa cttatattct ttatagagga ttccccaaaa  180
tgtgctcctc attttggcc tctcatgttc caaacctcat tgaataaa                 228

<210> SEQ ID NO 572
<211> LENGTH: 286
<212> TYPE: DNA
<213> ORGANISM: Homo sapiens

<400> SEQUENCE: 572
gctgtgttgg ccctcacttg ggattctcag cagttacatg aaagttgtgc tgataatctc    60
ttctcttgta ccaattttag tcaggcagaa aatggtaaac atgagggtgc tcttgtgact   120
taatttttgt tcaagggact aaattgctta tgtttattcc ctgtcagcgg agtggagaat   180
gtcattcatc aataaaccaa agccaatagc tggagaattg agatctggtt gaaagtggtt   240
tatggtttac atgctgtact atcctgagga attgcgagat attgct                  286

<210> SEQ ID NO 573
<211> LENGTH: 266
<212> TYPE: DNA
<213> ORGANISM: Homo sapiens
<220> FEATURE:
<221> NAME/KEY: misc_feature
<222> LOCATION: (214)..(214)
<223> OTHER INFORMATION: n is a, c, g, or t

<400> SEQUENCE: 573
ccctgcgcct atcaggtcgt gagtccaggg gtctacaagt cccgggcccc ccagttcacg    60
attctggcgc ggacttcgct cccccaagac aacactcgga agccagggcc cgcggcctac   120
aacgtggatc agcaccggaa gccccgcggc tggagtttcg ggatccggca ctcggactac   180
ctggccccgc tggtgaccga cgcggacaac tgançcgcca ggcgggagcg gccccacacg   240
tgtttgctta aagtctgcga gtccgc                                        266

<210> SEQ ID NO 574
<211> LENGTH: 270
<212> TYPE: DNA
<213> ORGANISM: Homo sapiens

<400> SEQUENCE: 574
```

```
ccagggctga gagacacgtg aaggaagatg atgggaggaa aagcccagga gaagtcccac      60
cagggaccag cccagcctgc atacttgcca cttggccacc aggactcctt gttctgctct     120
ggcaagagac tactctgcct gaacactgct tctcctggac cctggaagca gggactggtt     180
gagggagtgg ggaggtggta agaacacctg acaacttctg aatattggac attttaaaca     240
cttacaaata aatccaagac tgtcatattt                                      270

<210> SEQ ID NO 575
<211> LENGTH: 227
<212> TYPE: DNA
<213> ORGANISM: Homo sapiens

<400> SEQUENCE: 575
gaagatgaag cccatgctc agtcccctcc catccccac gcagctccac cccagtccca       60
agccaccagc tgtttgctcc tggtgggagg tggcctcctc agcccctcct ttctgacctt     120
taacctcact ctcaccttgc accgtgcacc aaccttcac ccctcctgga aagcaggcct      180
gatggcttcc cactggcctc caccacctga ccagagtgtt ctcttca                   227

<210> SEQ ID NO 576
<211> LENGTH: 279
<212> TYPE: DNA
<213> ORGANISM: Homo sapiens

<400> SEQUENCE: 576
gcatttgctg tgtttcgtta gcatctggct ccaggacaga ccttcaactt ccaaattgga     60
tactgctgcc aagaagttgc tctgaagtca gtttctatca ttttgctctt tgattcaaag    120 cactgttttct ctcactgggc ctccaaccat gttcccttt ttttagcacc acaaataatc    180 aaacccaac atgactgttt gttttccttt aaaaatatgc accaaatcat ctctcatcac    240
ttttctttga gggtttagt agacagtagg agttaataa                            279

<210> SEQ ID NO 577
<211> LENGTH: 123
<212> TYPE: DNA
<213> ORGANISM: Homo sapiens
<220> FEATURE:
<221> NAME/KEY: misc_feature
<222> LOCATION: (52)..(52)
<223> OTHER INFORMATION: n is a, c, g, or t

<400> SEQUENCE: 577
gcggactcgc agactttaag caaacacgtg tggggccgct cccgcctggg tngcagttgt     60
ccgcgtcggt caccagcggg gccaggtagt ccgagtgccg gatcccgaaa ctccagccgc    120
ggg                                                                  123

<210> SEQ ID NO 578
<211> LENGTH: 82
<212> TYPE: DNA
<213> ORGANISM: Homo sapiens

<400> SEQUENCE: 578
gtgctcagta gtcagactgg atagtccgtt tttgcttatc cgttagccgt ggggatttag     60
caggaagctg tgagagcagt tt                                              82

<210> SEQ ID NO 579
<211> LENGTH: 151
<212> TYPE: DNA
<213> ORGANISM: Homo sapiens
```

<400> SEQUENCE: 579
acacagaaga gtgacatgtt tacaaacctc aagccagcct tgctcctggc tggggcctgt    60
tgaagatgct tgtattttac ttttccattg taattgctat cgccatcaca gctgaacttg   120
ttgagatccc cgtgttactg cctatcagca t                                  151

<210> SEQ ID NO 580
<211> LENGTH: 82
<212> TYPE: DNA
<213> ORGANISM: Homo sapiens

<400> SEQUENCE: 580
tttaaaatac tcagaggaca ggatcactgt ggaatcgaat cagaagtggt ggctggaatt    60
ccacgcaccg atcagtactg gg                                             82

<210> SEQ ID NO 581
<211> LENGTH: 109
<212> TYPE: DNA
<213> ORGANISM: Homo sapiens

<400> SEQUENCE: 581
aagagaagac tcacagtatc aggtctactg aaggagatac ggtgattcct gttcttggct    60
ttgtagattc atctggtata aacagcactc ctgagttatg accttttga              109

<210> SEQ ID NO 582
<211> LENGTH: 118
<212> TYPE: DNA
<213> ORGANISM: Homo sapiens

<400> SEQUENCE: 582
tttgaagatt agaaatttag ccgtaggtaa agaatacaaa ggaaaaataa ttttaaaatc    60
atcaaccaga tcaacaaaat atatgttaat gccgagactt tgaattagag tgcgaatt    118

<210> SEQ ID NO 583
<211> LENGTH: 242
<212> TYPE: DNA
<213> ORGANISM: Homo sapiens

<400> SEQUENCE: 583
catcttctag cagatctttt tcagttaaga ttacttgttc ttccatgtat tcatatttag    60
ccagctcctt gatcagccgc agtatgtcac tgcagtcggc ggcagtggct gggcggatca   120
cgaatttagc cattttcgtc ttttgctttt cttcccttg cggaccaggc ccctgtactt    180
gaacagtagg aggaggtggt tcctcattcg tctcccggga gcgtcctctt ctcagtcagg   240
ct                                                                  242

<210> SEQ ID NO 584
<211> LENGTH: 34
<212> TYPE: DNA
<213> ORGANISM: Homo sapiens

<400> SEQUENCE: 584
gaaatcattg tgggattgct agctttccct ctta                                34

<210> SEQ ID NO 585
<211> LENGTH: 272
<212> TYPE: DNA
<213> ORGANISM: Homo sapiens

<400> SEQUENCE: 585

```
caacctctta caacccaggc attcctttct atcgataatt actctttcaa ccaattgcca      60
atcagaaaat tgttatatct acctataatc tagaagcccc cacatcaagt tgttttgcct     120
ttctggacag gaccaatgta tatcttaaat gtatttgatt gatctctcat gtctccctaa     180
aatgtataaa accacgctgt tccccgacca cctggagcac atgttctcag ggtctcctga     240
gggctgtgtc acaggccatg ttcacttaca tt                                   272
```

<210> SEQ ID NO 586
<211> LENGTH: 189
<212> TYPE: DNA
<213> ORGANISM: Homo sapiens

<400> SEQUENCE: 586

```
ccctgcagag aatcacgtcc tggaactgca tgttcttgcg actcttggga cttcatttta      60
acttctcgct gccccagcca tgttttcaac catggcatcc ctcccccaat tagttccctg     120
tcatcctcgt caaccttctc tgtaagtgcc tggtaagctt gcccttgctt aagaactcaa     180
aacatagct                                                             189
```

<210> SEQ ID NO 587
<211> LENGTH: 163
<212> TYPE: DNA
<213> ORGANISM: Homo sapiens

<400> SEQUENCE: 587

```
tgagcagact gcaccccaag ctcccgactc caggtcccct gatcttgggg cctgtttccc      60
atgggattca agagggacag ccccagcttt gtgtgtgttt aagcttagga atcgccttta     120
tggaaagggc tatgtgggag agtcagctat cttgtctggt ttt                       163
```

<210> SEQ ID NO 588
<211> LENGTH: 296
<212> TYPE: DNA
<213> ORGANISM: Homo sapiens
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t

<400> SEQUENCE: 588

```
atgggtgtag atcaaggcag gagcaggaac caaaagaaa ggcataaaca taagaaaaaa       60
aatggaaggg gtggnaaaca gagtacaata acatgagtaa tttgatgggg gctattatga     120
actgagaaat gaactttgaa aagtatcttg gggccaaatc atgtagactc ttgagtgatg     180
tgttaaggaa tgctatgagt gctgagaggg catcagaagt ccttgagagc ctccagagaa     240
aggctcttaa aaatgcagcg cnatctccag tgacagaaga tactgctaga aatctg         296
```

<210> SEQ ID NO 589
<211> LENGTH: 246
<212> TYPE: DNA
<213> ORGANISM: Homo sapiens

<400> SEQUENCE: 589

```
tgtacagatt caagcaatgg atgcaaggaa catgctgtat gtaatagaag aaagaagtcc      60
acgttttcgg cagaagtagt gagtcagtgt ggaagagagg tgagggtgtg ctttactttt     120
```

```
tgataaagag aaagatgttt actcataaac ccttcaaaag gtattaacaa atgtttacca      180
aacctattgc tttattttaa aaacataatt tgtgttttct atttgtaaga tctgacattt      240
cgaggc                                                                 246
```

<210> SEQ ID NO 590
<211> LENGTH: 121
<212> TYPE: DNA
<213> ORGANISM: Homo sapiens

<400> SEQUENCE: 590

```
ggcagcgacc cggaaacagc gtatcactga gaccgagtcg ccttatcagg agctccaggg      60
tcagaggtcg gatgtctaca gcgacctcaa cacacagagg ccgtattaca aatgagcccg     120
a                                                                      121
```

<210> SEQ ID NO 591
<211> LENGTH: 262
<212> TYPE: DNA
<213> ORGANISM: Homo sapiens

<400> SEQUENCE: 591

```
tggtgaccag ttctcggttt catagttttt actatcagtt tgcctttggg attctttgaa      60
agctcttgag gcttttttccg cagcttctag gagatgtgtt aggtcattaa cagtaatgct     120
cctacagttt tgttcccat ccaaccacca tttgatttca cttttgtaga cttgacctag      180
tgtatctgaa atataggaat ttttaggtgc tttcattttg gcctgacgtg cccagtccag     240
agctgtgtta aagtccttct ct                                               262
```

<210> SEQ ID NO 592
<211> LENGTH: 226
<212> TYPE: DNA
<213> ORGANISM: Homo sapiens

<400> SEQUENCE: 592

```
gtcattcaca actgatttca agagtcacct tcaccaggaa gtcttccttg accaccatca      60
ttcctgcctg attagagggc ttcctcatgg taatatgtgt tctcaagttt tcagtgtcaa     120
ggaatgccat cccagaagct cattttcaga tgcacaacag ccagaacagt ctcaagcagc     180
attctagagc ttggaattta agaactacgc attgcctata aagtga                    226
```

<210> SEQ ID NO 593
<211> LENGTH: 272
<212> TYPE: DNA
<213> ORGANISM: Homo sapiens

<400> SEQUENCE: 593

```
agagctcttg agtgggctag tgactccccc tgcagcctgg tggagatggt gtgaggagcg      60
aagagccctc tgctctagga tttgggttga aaaacagaga gagaagtggg gagttgccac     120
aggagctaac acgctgggag gcagttgggg gcgggtgaac tttgtgtagc cgaggccgca     180 ccctcccctca ttccaggctc attcattttc atgctccatt gccagactct gctgggagc     240 ccgtccagaa tgtcctccca ataaaactcc at                                    272
```

<210> SEQ ID NO 594
<211> LENGTH: 151
<212> TYPE: DNA
<213> ORGANISM: Homo sapiens

<400> SEQUENCE: 594

```
tagggattaa cttcctgtat gctgcaactc atgaacttgg ccattctttg ggtatgggac      60
attcctctga tcctaatgca gtgatgtatc caacctatgg aaatggagat ccccaaaatt     120
ttaaactttc ccaggatgat attaaaggca t                                    151
```

<210> SEQ ID NO 595
<211> LENGTH: 243
<212> TYPE: DNA
<213> ORGANISM: Homo sapiens

<400> SEQUENCE: 595

```
tccectgctt gaacactgaa gggcaggtgg tgggccatgg ccatggtccc cagctgagga      60
gcaggtgtcc ctgagaaccc aaacttccca gagagtatgt gagaaccaac caatgaaaac     120
agtcccatcg ctcttacccg gtaagtaaac agtcagaaaa ttagcatgaa agcagtttag     180
cattgggagg aagctcagat tctagagct gtcttgtcgc cgcccaggat tgacctgtgt      240
gta                                                                   243
```

<210> SEQ ID NO 596
<211> LENGTH: 82
<212> TYPE: DNA
<213> ORGANISM: Homo sapiens

<400> SEQUENCE: 596

```
cagatgttgg tatctgcagg gatcctggaa ccaaacccct gcagatacta agggctgacg      60
atctaggtaa gactggattt aa                                              82
```

<210> SEQ ID NO 597
<211> LENGTH: 236
<212> TYPE: DNA
<213> ORGANISM: Homo sapiens

<400> SEQUENCE: 597

```
actctcaggc tgcgtccagc gacagtgccc agggctctga tgtgtctctc acagcttgaa      60
aagcctgaga cagctgtctt gtgagggact gagatgcagg atttcttcac gcctcccctt     120
tgtgacttca agagcctctg gcatctcttt ctgcaaaggc acctgaatgt gtctgcgtcc     180
ctgttagcat aatgtgagga ggtggagaga cagcccaccc ttgtgtccac tgtgac         236
```

<210> SEQ ID NO 598
<211> LENGTH: 119
<212> TYPE: DNA
<213> ORGANISM: Homo sapiens

<400> SEQUENCE: 598

```
gccagagaga ccaagtgtta tgtaagaagt agtgtcggct gtgtagaacc actgactaca      60
caggccgaag ttactgagaa cttggacaga aaaatagcc agcaagtgtt caaactact       119
```

<210> SEQ ID NO 599
<211> LENGTH: 264
<212> TYPE: DNA
<213> ORGANISM: Homo sapiens

<400> SEQUENCE: 599

```
gccaacagca tcttttccgg gttcctgctc tttccagata tggaggcctg acctgtgggc      60
tgcttcacat ccaccccggc tcccctgcc agcaacgctc actctacccc caacaccacc     120
ccttgcccag ccaatgcaca cagtagggct tggtgaatgc tgctgagtga atgagtaaat     180
```

```
aaacttttca aggccaaggg acagtggttt aattcaactc tgtgtcccag cacctggcac      240
accagaagtg ccatgctcag aaat                                             264

<210> SEQ ID NO 600
<211> LENGTH: 273
<212> TYPE: DNA
<213> ORGANISM: Homo sapiens

<400> SEQUENCE: 600
ttcaaactca atgatgctac catgcctctc caacattttc aacccctga cattatcttg      60 gatcctatgg tttctccatc caattctttg aatttcccag tctcccctat gtaaaactta     120
gcaacttggg ggacctcatt cctgggacta tgctgtaacc aaattattgt ccaaggctat     180 attttggga tgaatataat ttgaggaagg gagttaaaga ccctcctggg gctctcagtg      240
tgccatagag gacagcaact ggtgattgtt tca                                  273

<210> SEQ ID NO 601
<211> LENGTH: 275
<212> TYPE: DNA
<213> ORGANISM: Homo sapiens

<400> SEQUENCE: 601
acttacatac tagcttccaa ggacaggtgg aggtagggcc agcctggcgg gagtggagaa     60
gcccagtctg tcctatgtaa gggacaaagc caggtttaat ggtactgggt aggggcact    120 gccaagacaa taagctaggc tactgggtcc agctactact ttggtgggat tcaggtgagt    180
ctccatgcac ttcacatgtt acccagtgtt cttgttactt ccaaggagaa ccaagaatgg    240
ctctgtcaca ctcgaagcca ggtttgatca ataaa                               275

<210> SEQ ID NO 602
<211> LENGTH: 261
<212> TYPE: DNA
<213> ORGANISM: Homo sapiens

<400> SEQUENCE: 602
tcactcccac ctgttactgc tgggagtcaa gtcagctagg aaggaagcag gacatttttt     60
caaacagcaa gtggggccca tggaactgaa tctttactcc ttggtgcacc gcttttgtcg    120
tgcgttgcct tgctccgttt ttcccaaaaa gcactggctt catcaaggcc accgacgatt    180
tcctgagtgc actgggaaat ttgggtatag gtcaggcttg gcagccttga tcccaggaga    240
gtactaatgg taacaagtca a                                              261

<210> SEQ ID NO 603
<211> LENGTH: 241
<212> TYPE: DNA
<213> ORGANISM: Homo sapiens

<400> SEQUENCE: 603
ttgttcccga ctagctgcct tgcacattat tttcattttc ctggaatttg atacagagag     60
caatttatag ccaattgata gcttatgctg tttcaatgta aattcgtggt aaataactta    120
ggaactgcct tttctttttc tttgaaaacc tactataac tgttgctaat aagaatgtgt     180
attgttcagg acaacttgtc tccatacagt tgggttgtaa ccctcatgct tggcccaaat    240
a                                                                    241

<210> SEQ ID NO 604
```

```
<211> LENGTH: 107
<212> TYPE: DNA
<213> ORGANISM: Homo sapiens

<400> SEQUENCE: 604
taaatataat atcgacacag tgctttccgt ggcactgcat acaatctgag gcctcctctc      60
tcagttttta tatagatggc gagaacctaa gtttcagttg attttac                   107

<210> SEQ ID NO 605
<211> LENGTH: 252
<212> TYPE: DNA
<213> ORGANISM: Homo sapiens
<220> FEATURE:
<221> NAME/KEY: misc_feature
<222> LOCATION: (180)..(182)
<223> OTHER INFORMATION: n is a, c, g, or t

<400> SEQUENCE: 605
gtggagcagt tggactgctc tctctgctct caggatgata ctgtgagaac aatttaaata     60
tgctaagcac atgtcaggaa acagttttgt ggtctttgga cactcgctgt agccattccg    120
ttccatttca ggtgatttta ttcatttcat ttgtagaata aaataaatcc atttcacacn    180
nncacacaca cacacacaca cacacacaca caccctctat acaccactaa agcctcccat    240
taaacccata ga                                                        252

<210> SEQ ID NO 606
<211> LENGTH: 96
<212> TYPE: DNA
<213> ORGANISM: Homo sapiens

<400> SEQUENCE: 606
tcgacacagt gctttccgtg gcactgcata caatctgagg cctcctctct cagttttat     60 atagatggcg agaacctaag tttcagttga ttttac                              96

<210> SEQ ID NO 607
<211> LENGTH: 181
<212> TYPE: DNA
<213> ORGANISM: Homo sapiens
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t

<400> SEQUENCE: 607
gccagagaag cgattagaaa cccctgaggg ccgattactg acnncataaa tcatgagttt     60
gggggctttg cctgggtnnt gttggtacca ggagacatng ttataaccan caacgtcact   120
gctggttcca gtgcaggaga tggtgatcga ctgtccagga gacccagaca cggaggcagg   180
c                                                                    181

<210> SEQ ID NO 608
<211> LENGTH: 115
```

```
<212> TYPE: DNA
<213> ORGANISM: Homo sapiens

<400> SEQUENCE: 608
aggagctgag gtgctacccg agcccccatt caccccacc tgcccacttg ggaatctgag      60
gcagaggagg gtgaggcctg tgtgccaacc ttgttcacat accaccttcg tcccc         115

<210> SEQ ID NO 609
<211> LENGTH: 53
<212> TYPE: DNA
<213> ORGANISM: Homo sapiens

<400> SEQUENCE: 609
aagcaagata tcaatgtagc agaattgcac ttgtgcctca cgaacataca taa            53

<210> SEQ ID NO 610
<211> LENGTH: 155
<212> TYPE: DNA
<213> ORGANISM: Homo sapiens

<400> SEQUENCE: 610
gttgttgatc atggatcata ctccccttgt ttctttgggt gagaagggat cgcagtttgg     60
aaactccggc ggctgcgtgc ggggtttcag tcccagctgt aggcttgtaa atacccgccc    120
cgccaaaccg catagagaac gtggcagcaa gctga                               155

<210> SEQ ID NO 611
<211> LENGTH: 190
<212> TYPE: DNA
<213> ORGANISM: Homo sapiens

<400> SEQUENCE: 611
cacagggaaa tcagggttac aaatcttctt gatccacttc tctcaggatc ccctctcttc     60
ctacccttcc tcaccacttc cctcagtccc aactcctttt ccctatttcc ttctcctcct   120
gtctttaaag cctgcctctt ccaggaagac cccctattg ctgctgggc tccccatttg     180 cttactttgc                                                          190

<210> SEQ ID NO 612
<211> LENGTH: 63
<212> TYPE: DNA
<213> ORGANISM: Homo sapiens

<400> SEQUENCE: 612
attagaacct tagtataaat ttactttctc aaattcttgc catgagaggt tgatgagtta     60
att                                                                  63

<210> SEQ ID NO 613
<211> LENGTH: 281
<212> TYPE: DNA
<213> ORGANISM: Homo sapiens

<400> SEQUENCE: 613
ggagacagat ggagggtacc ctatttacaa ctgagtcagc caagccactg atgggaatat     60
acagatttag gtgctaaacc atttattttc cacggatgag tcacaatttg aagaatcaaa   120
cttccatcct gaaaatttat atgtttcaaa accacttgcc atcctgttag attgccagtt   180
cctgggacca ggcctcagac tgtgaagtat atatcctcca gcattcagtc caggggagc   240 cacggaaacc atgttttttgc ttaagccatt aaagtcagag a                      281
```

<210> SEQ ID NO 614
<211> LENGTH: 239
<212> TYPE: DNA
<213> ORGANISM: Homo sapiens

<400> SEQUENCE: 614

```
agatgcgctc gagacccacg ggccttccac ctccctcagc ttcctgcatg gacccacctt    60
actggccagt ctgcatcctt gcctagacca ttctcccctc cagggagccc acctgaccc    120
accccactg caccccctcc ccatgggttc tctccttcct ctgaacttct ttaggagtca    180
ctgcttgtgt ggttcctggg acacttaacc aatgccttct ggtactgcca ttcttttt    239
```

<210> SEQ ID NO 615
<211> LENGTH: 196
<212> TYPE: DNA
<213> ORGANISM: Homo sapiens

<400> SEQUENCE: 615

```
gcctttaaga taccttgatg aagacctgga ctattgaatg gagcagaaat tcacctctct    60
cactgactat tacagttgca tttttatgga gttcttcttc tcctaggatt cctaagactg    120
ctgctgaatt tataaaaatt aagtttgtga atgtgactac ttagtggtgt atatgagact    180
ttcaagggaa ttaaat                                                    196
```

<210> SEQ ID NO 616
<211> LENGTH: 38
<212> TYPE: DNA
<213> ORGANISM: Homo sapiens

<400> SEQUENCE: 616

```
agtctgccta tgatctttga atgagctttt taaggaag                            38
```

<210> SEQ ID NO 617
<211> LENGTH: 110
<212> TYPE: DNA
<213> ORGANISM: Homo sapiens

<400> SEQUENCE: 617

```
tttaacttga gggtgtagag gtcctccacg cttgtttgcc tgaaagtaat ataatgatgc    60
tgtctgaaca ggttttactg cttgctttcc aagtaaaggt taattatgat                110
```

<210> SEQ ID NO 618
<211> LENGTH: 173
<212> TYPE: DNA
<213> ORGANISM: Homo sapiens

<400> SEQUENCE: 618

```
tatttcccct ctttcgaaca aagacattgg tttgcccaag gactacaaat aaaccaacgg    60
gaaaaagaa aggttccagt tttgtctgaa aattctgatt aagcctctgg gccctacagc    120
ctggagaacc tggagaatcc tacacccaca gaacccggct tgtccccaa aga            173
```

<210> SEQ ID NO 619
<211> LENGTH: 82
<212> TYPE: DNA
<213> ORGANISM: Homo sapiens

<400> SEQUENCE: 619

```
gttatttaag atggctatcc agataatcct gaacactgtg tatttatttt atttagacta    60
ccagcaaaga ttaaagcatg aa                                              82
```

<210> SEQ ID NO 620
<211> LENGTH: 266
<212> TYPE: DNA
<213> ORGANISM: Homo sapiens

<400> SEQUENCE: 620

```
gcttggggaa caatgatggt gcacaaaggc ttagatttgc cttgtctcaa aataaggaat    60
tttgtagtgg ttttcaaaaa taattcaaca aagaaacaat acaaaagtg ggtagaatta    120
cctatcacat ttcccaatct tgactattca gaatgctgtt tatttagtga tgaggattag   180
cacttgattg aagattcttt taaaatacta tcagttaaac atttaatatg attatgatta   240
atgtattcat tatgctacag aactga                                         266
```

<210> SEQ ID NO 621
<211> LENGTH: 115
<212> TYPE: DNA
<213> ORGANISM: Homo sapiens

<400> SEQUENCE: 621

```
cagaaagcca agtggactca acggagaggc cagcaagttt caggaaatgg tgcatttggt   60
gaacaaggag tcgtcagaaa ctccagacca gtttatgaca gctgatgaga caagg        115
```

<210> SEQ ID NO 622
<211> LENGTH: 262
<212> TYPE: DNA
<213> ORGANISM: Homo sapiens

<400> SEQUENCE: 622

```
gttcacccgg tgaactattt atgagttctt ttggtgtgaa gaaagggctc atgttgcatt    60
tccagccatt gctacaaaga accttttattt gttcagtaac ggtagaaaat ccttcccgat   120
taaaaacttc agacttgctg aatatcctgc aatgtcaaga tgaccgatgt tgagttgggt   180
ggatttgcta acgagtcaga tttgaacatg aggctattgg aacccaatag gcgtcattga    240
tggcggcaag ccatagcttt ca                                             262
```

<210> SEQ ID NO 623
<211> LENGTH: 94
<212> TYPE: DNA
<213> ORGANISM: Homo sapiens

<400> SEQUENCE: 623

```
ggggagccag gcttccctca cgcagcctgt ggtggatgtg ggaaggagat caacttctcc    60
tcactctggg acagacgatg tatggaaact aaaa                                 94
```

<210> SEQ ID NO 624
<211> LENGTH: 114
<212> TYPE: DNA
<213> ORGANISM: Homo sapiens

<400> SEQUENCE: 624

```
ctgcacagct cagcacaaca ttccaagctc aaaatagaag ccttctcagt gagctccagc    60
acgcccagag gactgttaat aacgatgatc catgtgtttt actctaaagt gcta          114
```

<210> SEQ ID NO 625
<211> LENGTH: 37
<212> TYPE: DNA
<213> ORGANISM: Homo sapiens

```
<400> SEQUENCE: 625
cagggactgg ctatcccaag acctggcaga tgtggct                              37

<210> SEQ ID NO 626
<211> LENGTH: 74
<212> TYPE: DNA
<213> ORGANISM: Homo sapiens

<400> SEQUENCE: 626
gtgaaaggga agtagaaccg aaacaagatt agtcctgagt taacaatggc tgcaagctgg     60
atacatggaa ttca                                                      74

<210> SEQ ID NO 627
<211> LENGTH: 201
<212> TYPE: DNA
<213> ORGANISM: Homo sapiens

<400> SEQUENCE: 627
tggtgaatgc gtgctgccca ggaccagtga agacagacat ggatgggaaa gacagcatca    60
ggactgtgga ggaggggggct gagacccctg tctacttggc cctcttgcct ccagatgcca  120
ctgagccaca aggccagttg gtccatgaca agttgtgca aaactggtaa acgtctgctt    180
cggagcttgc tgcttaataa a                                             201

<210> SEQ ID NO 628
<211> LENGTH: 217
<212> TYPE: DNA
<213> ORGANISM: Homo sapiens

<400> SEQUENCE: 628
atgctgtggt tggatcaagg actcattcct gccttggaga aatacttca accagagcag     60 ggagcctggg ggtgtcgggg caggaggctg ggatgggggg tgggatatga gggtggcatg   120
cagctgaggg cagggccagg gctggtgtcc ctaaggttgt acagactctt gtgaatattt   180 gtatttttcca gatggaataa aaaggcccgt gtaatta                           217

<210> SEQ ID NO 629
<211> LENGTH: 33
<212> TYPE: DNA
<213> ORGANISM: Homo sapiens

<400> SEQUENCE: 629
ttctgtgcct cagccgttct tgacatcaag aat                                33

<210> SEQ ID NO 630
<211> LENGTH: 222
<212> TYPE: DNA
<213> ORGANISM: Homo sapiens

<400> SEQUENCE: 630
gacacagtcg ggttgaccca gggctgtctc cctccagagc ctccctccgg acaatgagtc    60
ccccctcttg tctcccaccc tgagattggg catggggtgc ggtgtggggg gcatgtgctg   120
cctgttgtta tgggtttttt ttgcgggggg ggttgctttt ttctggggtc tttgagctcc   180
aaaaaataaa cacttccttt gagggagagc acaccttccc aa                      222

<210> SEQ ID NO 631
<211> LENGTH: 278
<212> TYPE: DNA
<213> ORGANISM: Homo sapiens
```

<400> SEQUENCE: 631
tgagaggcaa gagttgttcc tgcccttccc tttgtgactt gaagaaccct gactttgttt    60
ctgcaaaggc acctgcatgt gtctgtgttc gtgtaggcat aatgtgagga ggtggggaga   120 gcacccacc cccatgtcca ccatgaccct cttcccacgc tgacctgtgc tccctctcca    180
atcatctttc ctgttccaga gaggtggggc tgaggtgtct ccatctctgt ctcaacttca   240
tggtgcactg agctgtaact tcttccttcc ctattaaa                            278

<210> SEQ ID NO 632
<211> LENGTH: 90
<212> TYPE: DNA
<213> ORGANISM: Homo sapiens

<400> SEQUENCE: 632
aaattaaagc taaagtatct gtattgcatt aaatataata tcgacacagt gctttccgtg    60
gcactgcata caatctgagg cctcctctct                                     90

<210> SEQ ID NO 633
<211> LENGTH: 198
<212> TYPE: DNA
<213> ORGANISM: Homo sapiens

<400> SEQUENCE: 633
accgcaggat cctttgctct gcacgagtta cctgttaaac tttggaacac ctaccaaaaa    60
ataagtttga taacatttaa aagatgggcg tttcccccaa tgaaatacac aagtaaacat   120
tccaacattg tctttaggag tgatttgcac cttgcaaaaa tggtcctgga gttggtagat   180
tgctgttgat cttttatc                                                  198

<210> SEQ ID NO 634
<211> LENGTH: 243
<212> TYPE: DNA
<213> ORGANISM: Homo sapiens

<400> SEQUENCE: 634
ttcatgctgg acctcaggta caaaaggtta agaacttctc agttcattat atgatcatca    60
ttggtgcctc cgagctctct ctctctccct tgatttattt ggtccctttt atctccagtc   120
cttactccca tatctaacct cttacccta cctcataggg aaacatttta atgaatttga    180
tgtttccttt tatttgcata gatcctctgt aatatgtagt agtgtccagt gtacatgtat   240
ttt                                                                  243

<210> SEQ ID NO 635
<211> LENGTH: 211
<212> TYPE: DNA
<213> ORGANISM: Homo sapiens
<220> FEATURE:
<221> NAME/KEY: misc_feature
<222> LOCATION: (140)..(140)
<223> OTHER INFORMATION: n is a, c, g, or t

<400> SEQUENCE: 635
ggtgagctac catactgctg acagtaatac actgcaaaat cttcaggctc cagtctgctg    60
atggtgagag tgaagtctgt cccagaccca ctgccactga acctgtctgg gatgccagtg   120
gccctgctgg atgcaccatn gatgaggagc ctgggagcct ggccaggttt ctgctggtac   180
caggctaagt agctgctgct aacactctga c                                   211

<210> SEQ ID NO 636
<211> LENGTH: 256
<212> TYPE: DNA
<213> ORGANISM: Homo sapiens

<400> SEQUENCE: 636
agagagtgga catttgtcgg gaaactccta acatatgccc ccattctgga gagaacacag    60
agtacgacac aatccctcac actaatagaa caatcctaaa ggaagatcca gcaaatacgg   120
tttactccac tgtggaaata ccgaaaaaga tggaaaatcc ccactcactg ctcacgatgc   180
cagacacacc aaggctattt gcctatgaga atgttatcta gacagcagtg cactgcccct   240
aagtctctgc tcaaaa                                                   256

<210> SEQ ID NO 637
<211> LENGTH: 239
<212> TYPE: DNA
<213> ORGANISM: Homo sapiens
<220> FEATURE:
<221> NAME/KEY: misc_feature
<222> LOCATION: (138)..(138)
<223> OTHER INFORMATION: n is a, c, g, or t

<400> SEQUENCE: 637
gaagggtaaa tgaagctatc gtagcttcac ttgggaaaag ggagagaaca gatgaccagc    60
accaaggata gaagagggat ttcttacttt aaaaaaaatg gtccaaagaa taaacaaact   120 gaaacagcc aaaagagnaa ggaagaattt gttagaatag ggcaagacta aaggacagag   180
taagggtgct ggccgccacc tgactcaagt tcaagtcgag ctgccactgt tgaaatttc    239

<210> SEQ ID NO 638
<211> LENGTH: 204
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, or t

<400> SEQUENCE: 638
attttatgac atttcgaagt ttctgtgtct taactctttt taattaattt tctgcacgtt    60
gcnttttttc tctttgtttt taattccata cagagtattc aattcttgaa acacattaaa   120
ataatttgct tgctagggta tggtttattt tataattaca ttcctagtct tgtgtggtta   180
ttgtaatgat gtctggtcct aatt                                          204

<210> SEQ ID NO 639
<211> LENGTH: 231
<212> TYPE: DNA
<213> ORGANISM: Homo sapiens

<400> SEQUENCE: 639
tgtctcccgg cctgatacca gatacaggtt gttgatttca tcgtgggtag caagctagta    60
ataaatttca aagtgctttc tcttttcatg ctttttgcca ataactgtta ccgccgttct   120
tattctctcc cttaactcat tgtctttggg ggagttagac accaggaggt gccttgtcgg   180
tcatattttt cagcacgtca tcaatcctat catcttcaat aacaacccgc t            231

<210> SEQ ID NO 640
<211> LENGTH: 237
<212> TYPE: DNA
<213> ORGANISM: Homo sapiens

<400> SEQUENCE: 640

```
gcatggcatc aaaaggtagg tcaacatatt aaataattcc atgtattgaa atatccagaa      60
aatatataga cagatctata gagatagaaa ctggtctgcc caggactagg ggttgtctaa     120
ggataaggag cttctttttt ggatggtgaa ataacctaaa atatattgtg ccattgtttg     180
cacaactttg tgaatatatt aaaaacctgt taattgtact cactaaatgt cctcctt       237
```

<210> SEQ ID NO 641
<211> LENGTH: 228
<212> TYPE: DNA
<213> ORGANISM: Homo sapiens

<400> SEQUENCE: 641

```
attgatagtg cttcttacca ggtgaaggga agggctactt tttcctaaag gagaaaaaag      60
cttttcagaca aagctcgtac caacccctga actgcaaatt tgctcaagtg accgtgcata   120
cttatattcc taatttaaat gattatttat gtcaaacgct cattgtgaaa cttgaaaatg   180
ttgtattaca ttacatcaaa taaagtttac ttgtagcaga cagaaaga                 228
```

<210> SEQ ID NO 642
<211> LENGTH: 188
<212> TYPE: DNA
<213> ORGANISM: Homo sapiens

<400> SEQUENCE: 642

```
gaagcagcca acaaaaacgt aattagtaac taggacttcc tcatgggata gaccaaataa      60
ggcaactgta taactgtgta actgtataac tgtaaccaat gaaatattat ctttgctttt    120
atctatttgt cctaaaaagc ctcctcctca tgttctctct ggggagctcc ctagccactt    180
ctggcttg                                                              188
```

<210> SEQ ID NO 643
<211> LENGTH: 259
<212> TYPE: DNA
<213> ORGANISM: Homo sapien

<400> SEQUENCE: 643

```
gactggacca aagagcatgt gaaaaaatgg gtaaatgaag accttaagat taatgagcaa      60
tacgggcaaa ttctgctcag tgaagaagta acaggattag tcctgcagga attaactgag    120
aaggaccttg tagaaatggg gctaccatgg ggtccagcac ttttgataaa acgttcatac    180
aacaaattga atagtaagtc ccctgaaagt gacaatcatg atccgggaca attagataat    240
tcaaaaccgt ccaaaacag                                                  259
```

<210> SEQ ID NO 644
<211> LENGTH: 242
<212> TYPE: DNA
<213> ORGANISM: Homo sapiens

<400> SEQUENCE: 644

```
tgttctagag agctcatgta caccatggtg accatagtta ataatactgg attgtatgct      60
taaaatttgc taagagagta gatcttaagt catcaccaaa aaaagtaact gtaagatgat    120
ggagatgtgt taattagctt gacggtggta atcacaatat atgtgtatat caaaacatca    180
cattatacac cttaaatgta tataatattt gtcaattata cctcagtaaa gccaaaaaga    240
aa                                                                    242
```

<210> SEQ ID NO 645
<211> LENGTH: 205
<212> TYPE: DNA
<213> ORGANISM: Homo sapiens

<400> SEQUENCE: 645
ataggcagga accaatttgc atttaagtag tatgggaagc ctcgagtatg ttttcttgtc      60
cagagtgaag caaccaagaa agtaagatgc tggagatatc ttagactcaa gagatagaaa     120
gcaagaccct aggggagata agtaggagca ggatttcaag gacggaatta gtattgcaca     180
gagattaggg acacttcttc cttgg                                           205

<210> SEQ ID NO 646
<211> LENGTH: 217
<212> TYPE: DNA
<213> ORGANISM: Homo sapiens

<400> SEQUENCE: 646
aaaggcaaaa cactccagga cctctcccgg atctgtctcc tcctctagcc agcagtatgg      60
acagctggac ccctgaactt cctctcctct tacctgggca gagtgttgtc tctccccaaa     120
tttataaaaa ctaaaatgca ttccattcct ctgaaagcaa aacaaattca taattgagtg     180
atattaaata gagaggtttt cggaagcaga tctgtga                              217

<210> SEQ ID NO 647
<211> LENGTH: 253
<212> TYPE: DNA
<213> ORGANISM: Homo sapiens
<220> FEATURE:
<221> NAME/KEY: misc_feature
<222> LOCATION: (208)..(208)
<223> OTHER INFORMATION: n is a, c, g, or t

<400> SEQUENCE: 647
aaagctgaac tgcaaatctc aacgaaggaa gaggccattt taaagaaact aaagtcaatt      60
gagcggacaa cagaagacat tataagatct gtgaaagtgg aaagagaaga aagagcagaa     120
gagtcaattg aggacatcta tgctaatatc cctgaccttc caaagtccta cataccttct     180
aggttaagga aggagataaa tgaagaanaa gaagatgatg aacaaaatag gaaagcttta     240
tatgccatgg aaa                                                        253

<210> SEQ ID NO 648
<211> LENGTH: 249
<212> TYPE: DNA
<213> ORGANISM: Homo sapiens

<400> SEQUENCE: 648
aggaggtaga ccctttagct cccttccaat taaaggagtc cccaattctg gcacctgaga      60
gtcccctggg tctaacagct atgatattta tgtagtgtgt tgcttaccta aatgaataca     120
atttccttcc agacacgtga cactgatatt aaagtgctaa tgagagggat ctatttcttc     180
ttgtacgcta aaagagaaac agcagttcag atttcccatc agaagtccga ggactttgtt     240
cttgataac                                                             249

<210> SEQ ID NO 649
<211> LENGTH: 185
<212> TYPE: DNA
<213> ORGANISM: Homo sapiens

<400> SEQUENCE: 649

```
ttgatattct cttttggttt tattgttgtg gttcattgaa aaaaaaagat aattttttt     60 tctgatccgg ggagctgtat ccccagtaga aaaacattt taatcactct aatataactc    120
tggatgaaac acccttttt ttttaataag aaaagagaat taactgcttc agaaatgact    180
aataa                                                               185

<210> SEQ ID NO 650
<211> LENGTH: 234
<212> TYPE: DNA
<213> ORGANISM: Homo sapiens

<400> SEQUENCE: 650
atcaacctgg ttgacctgtc atggccgcct gtgccctgcc tccacccca tcctacactc     60 ccccagggcg tgcggggctg tgcagactgg ggtgccaggc atctcctccc cacccggggt   120
gtccccacat gcagtactgt atacccccca tccctccctc ggtccactga acttcagagc   180
agttcccatt cctgccccgc ccatcttttt gtgtctcgct gtgatagatc aata         234

<210> SEQ ID NO 651
<211> LENGTH: 270
<212> TYPE: DNA
<213> ORGANISM: Homo sapiens

<400> SEQUENCE: 651
ggattttgat ccaagctggt ccactcagtc catagcagag aatgaaaggg cccagagagg     60
gtggtgacct ctgcctgaag tcacacagtg agtcgaggac agggaggtga ccccaggttt   120
ctatgtgtag ggcgggagga tgttctggga cacagttcaa ttctcatttg tcacacactt   180
tggctattag agatcaaccc cttcgctcct gtgtcttgca atggcagcct tggcaaacgc   240
taaatgaaaa tcgtgacaac acttgtgtta                                    270

<210> SEQ ID NO 652
<211> LENGTH: 37
<212> TYPE: DNA
<213> ORGANISM: Homo sapiens

<400> SEQUENCE: 652
cccaaattat ccccaattat ccccacacat aaaaaaa                             37

<210> SEQ ID NO 653
<211> LENGTH: 173
<212> TYPE: DNA
<213> ORGANISM: Homo sapiens

<400> SEQUENCE: 653
gttggtgttt catgacatgt ggacttcttt tgaaatagca agtcaaatgt agtgaccaaa     60
ttgtggaaga gatttctgtc aaataggaaa tgtgtaagtt cgtctaaaag ctgatggtta   120
tgtaagttgc tcagcactca gatgacagca gattctgggt tctgggagtg ttc          173

<210> SEQ ID NO 654
<211> LENGTH: 236
<212> TYPE: DNA
<213> ORGANISM: Homo sapiens

<400> SEQUENCE: 654
gaaaccatgg gcaggagtag gaattgagtg ataaacaatt gggctaatga agaaaacttc     60
tcttattgtt cagttcatcc agattataac ttcaatggga cactttagac cattagacaa   120
```

| | |
|---|---|
| ttgacactgg gattaaacaa attcacataa tgccaaatac acaatgtatt tatagcaacg | 180 |
| tataatttgc aaagatggac tttaaaagga tgctgtgtaa ctaaactgaa ataatt | 236 |

<210> SEQ ID NO 655
<211> LENGTH: 187
<212> TYPE: DNA
<213> ORGANISM: Homo sapiens

<400> SEQUENCE: 655

| | |
|---|---|
| taatccacta aactggtctt cttcaagaga gctaagtata cactatctgg tgaaacttgg | 60 |
| attctttcct ataaaagtgg gaccaagcaa tgatgatctt ctgtggtgct taaggaaact | 120 |
| tactagagct ccactaacag tctcataagg aggcagccat cataaccatt gaatagcatg | 180 |
| caagggt | 187 |

<210> SEQ ID NO 656
<211> LENGTH: 79
<212> TYPE: DNA
<213> ORGANISM: Homo sapiens

<400> SEQUENCE: 656

| | |
|---|---|
| ctcagttctg gtccttcaag cctgtatggt ttggattttc agtagggac agttgatgtg | 60 |
| gagtcaatct ctttggtac | 79 |

<210> SEQ ID NO 657
<211> LENGTH: 94
<212> TYPE: DNA
<213> ORGANISM: Homo sapiens

<400> SEQUENCE: 657

| | |
|---|---|
| taacaaatca tcaacttcca ctggtcaata tatagatttt gggtgtctga ggccccaaga | 60 |
| ttagatgcca ctaatctcca aagattccct ccaa | 94 |

<210> SEQ ID NO 658
<211> LENGTH: 246
<212> TYPE: DNA
<213> ORGANISM: Homo sapiens

<400> SEQUENCE: 658

| | |
|---|---|
| gaggcttggc cttctttgtg aggcagtgtg agcagaagct gatgccagca tgtcactggt | 60 |
| tttgaaggga tgagcccaga cttgatgttt tgggattgtc cttatttaa cctcaaggtc | 120 |
| tcgcatggtg gggcccctga ccaacctaca caagttccct cccacaagtg gacatcagtg | 180 |
| tcttctctgt gaggcatctg ggccattcgc actccctggt gtggtcagcc tctctcacac | 240 |
| aaggag | 246 |

<210> SEQ ID NO 659
<211> LENGTH: 270
<212> TYPE: DNA
<213> ORGANISM: Homo sapiens

<400> SEQUENCE: 659

| | |
|---|---|
| tttgtgccag gcctatagca gtgttgggag cgaaactcta gcaggatcct tcttacatgc | 60 |
| agaaaaggtt cattttacac ttgccaatag gaatgaaact atttcgctgc cacaatagct | 120 |
| aactgttttt ctaaatggcc tatttcgtca acaacaatca ggaaagtgta ggaaggtaca | 180 |
| atctctaatg attgtagccc gtgcttaagg tgaggaaaaa agtcaaaaaa ttacacatga | 240 |
| gaaacctgaa tccaggcaga tcttacccaa | 270 |

<210> SEQ ID NO 660
<211> LENGTH: 195
<212> TYPE: DNA
<213> ORGANISM: Homo sapiens

<400> SEQUENCE: 660
aagagtatga tacaacatta gagaaagaaa gatacaaagg ctttattcat gtgtgatagt      60
aaaaatcagg atgagtctta gatatacaaa agataaatgg atatttaaaa tagttatata     120 tgcttttta gcaaaatatt cacgtgttaa gtatttctgg atcttaaaat acaaaatcca      180
cttattttat tagtt                                                      195

<210> SEQ ID NO 661
<211> LENGTH: 147
<212> TYPE: DNA
<213> ORGANISM: Homo sapiens

<400> SEQUENCE: 661
gagaggccgc gctctcaggt gaaattaaaa ttggaggtca gttcccggat ccgattctct      60
cggttcattt tcttgagttt cattctgcga ttttgaaacc agattttgac ttgtctgtct     120
gtaaggttaa tggtcctgct tatctcc                                         147

<210> SEQ ID NO 662
<211> LENGTH: 106
<212> TYPE: DNA
<213> ORGANISM: Homo sapiens

<400> SEQUENCE: 662
gaaagatcca gtaagttcag tttctctatg aactaatcat tcaagtcaaa ggcacactga      60
tgcaaaatca gtatatggac cccggtgtct gattagcaag gtttc                     106

<210> SEQ ID NO 663
<211> LENGTH: 268
<212> TYPE: DNA
<213> ORGANISM: Homo sapiens

<400> SEQUENCE: 663
gataggattg atgacgtgct gaaaaatatg accgacaagg cacctcctgg tgtctaactc      60
ccccaaagac aatgagttaa gggagagaat aagaacggcg gtaacagtta ttggcaaaaa     120
gcatgaaaag agaaagcact ttgaaattta ttactagctt gctacccacg atgaaatcaa     180
caacctgtat ctggtatcag gccgggagac agatgaggcg agaggaggag gaggaggagg     240
agaaggctct gggctcctct gcaaaaaa                                        268

<210> SEQ ID NO 664
<211> LENGTH: 405
<212> TYPE: DNA
<213> ORGANISM: Homo sapiens

<400> SEQUENCE: 664
accagcaaag caatgcactc ctgaccaagt agattctttt aaaaattaga gtgcattact      60
ttgaatcaaa aatttattta tatttcaaga ataaagtact aagattgtgc tcaatacaca     120
gaaaagtttc aaacctacta atccagcgac aatttgaatc brrsatagtc ccgagactgg     180
gttcaagtag agggcagatc tagatggggg aggactagga ctgactccta tggggatgga     240
aaagggactc ctgggtgtct ttgtgactgt ttagtgtgtt ctgtgaatgt gcgggcaggt     300

```
atttttgccc acatctgtat atttgtctat taatgtgatg tatttgagta ttgttgtggg    360
ggcgggtatg tctgtatata aatctgtgca gccactagtc aacaa                   405
```

<210> SEQ ID NO 665
<211> LENGTH: 259
<212> TYPE: DNA
<213> ORGANISM: Homo sapiens

<400> SEQUENCE: 665

```
gaagaaagct ataccattac cataatacat ttttcatctc atggctacaa tggaattctt    60
gaaaaggaaa aaaaatccta tctacatata aaaacctgca tgaatgaatc actacatatg   120
cttataatga ggaagagtta tgggtcctga gtgtaatttt ttatccttc ttaaaaagtt    180 tctgtattat gcattttgat aacactactg atgatccttc cacttatatt tgaaatgtta   240
tgtaccacat ttgcacaat                                                259
```

<210> SEQ ID NO 666
<211> LENGTH: 234
<212> TYPE: DNA
<213> ORGANISM: Homo sapiens

<400> SEQUENCE: 666

```
ggctactctg aaatgttgca gtgtggaaca atggaaagag cctgggtgtt tgggtcagat    60
aaatgaagat caaactccag ctccagcctc atttgcttga ctttgtgt gtatggggga    120 cttgtatgta tgggagtgag gagtttcagg gccattgcaa acatagctgt gcccttgaag   180
agaatagtaa tgatgggaat ttagaggttt atgactgaat tcccttgac atta         234
```

<210> SEQ ID NO 667
<211> LENGTH: 294
<212> TYPE: DNA
<213> ORGANISM: Homo sapiens

<400> SEQUENCE: 667

```
ctcgattatt ccctgtacaa tatttaaaat ttattgcttg atacttttga caacaaatta    60
ggttttgtac aattgaactt aaataaatgt cattaaaata aataaatgca atatgtatta   120
atattcattg tataaaaata gaagaataca aacatatttg ttaaatattt acatatgaaa   180
tttaatatag ctattttat ggaatttttc attgatatga aaaatatgat attgcatatg   240
catagttccc atgttaaatc ccattcataa ctttcattaa agcatttact ttga        294
```

<210> SEQ ID NO 668
<211> LENGTH: 265
<212> TYPE: DNA
<213> ORGANISM: Homo sapiens

<400> SEQUENCE: 668

```
atatggctgt ggaaaaacga attaaaatgt tttgaggaga aagcttttt cacttctttg    60 ttgctttctt ttctattgag tctgggcttg tttgtgttac tgcatactgt gattagcata   120
ataattgttt ctttgaggtc atctaaatat ttttttccta aaggaataaa gggtgaggaa   180
agaaaaatat taaaaagct aatatttgat actgtgcttg ctgtcagtat gcattacatt   240
taaattattc tctattcaag tggga                                        265
```

<210> SEQ ID NO 669
<211> LENGTH: 190
<212> TYPE: DNA
<213> ORGANISM: Homo sapiens

<400> SEQUENCE: 669

```
ggaagatggt ttctatctca tgaccccac tccctgtgag agggaatggg ggaagcctga    60
tgaccctcag ctgttccaat ctagtatttt ttttcttttt taaaattact gtatttatta   120
tgacgatggt gactcccag tgcaaagggg ggccagattc tgtgtgtttc tctaacctct   180
ttgtaaataa                                                          190
```

<210> SEQ ID NO 670
<211> LENGTH: 138
<212> TYPE: DNA
<213> ORGANISM: Homo sapiens

<400> SEQUENCE: 670

```
aagaattaca gggatgtttt taatcccact atggactcag tctcctggaa ataggtctgt    60
ccactcctgg tcattggtgg atgttaaacc catattcctt tcaactgctg cctgctaggg   120
aaaactgctc ctcattat                                                 138
```

<210> SEQ ID NO 671
<211> LENGTH: 257
<212> TYPE: DNA
<213> ORGANISM: Homo sapiens

<400> SEQUENCE: 671

```
actctggctc cgaaaaactt tgttatatat atcaaggatg ttctggcttt acattttatt    60
tattagctgt aaatacatgt gtggatgtgt aatggagct tgtacatatt ggaaaggtca   120
ttgtggctat ctgcatttat aaatgtgtgg tgctaactgt atgtgtcttt atcagtgatg   180
gtctcacaga gccaactcac tcttatgaaa tgggctttaa caaaacaaga agaaacgta   240
cttaactgtg tgaagaa                                                 257
```

<210> SEQ ID NO 672
<211> LENGTH: 231
<212> TYPE: DNA
<213> ORGANISM: Homo sapiens

<400> SEQUENCE: 672

```
accatgtaca gagaaatttt aggccaaact taaaatatgt aaggaggcag ctttaggcta    60
aacttgattt aacagcacca ataccccta cctttagtga gcacatctgc acattccaat   120
tttaatgaca gctccttaga atttcttatc aacgaagaca ctaacaaaga atggcgcatt   180
cctccttctc ctttctgagg atgccctacc ctgtaacaaa gtcgtttcta a            231
```

<210> SEQ ID NO 673
<211> LENGTH: 132
<212> TYPE: DNA
<213> ORGANISM: Homo sapiens

<400> SEQUENCE: 673

```
gtgagcctgc cagcgtttgc gacgtccccg cacgacaggc tcatactttc tgaggatcgt    60
gcatagcata ggacgtctga acctttgtac aaatgtgtag atgacatctt gctacagctt   120
ttatttgtga at                                                       132
```

<210> SEQ ID NO 674
<211> LENGTH: 283
<212> TYPE: DNA
<213> ORGANISM: Homo sapiens

<400> SEQUENCE: 674

```
aattccagtg cttgtcctag taccttagca catggttgct gaatacatga atgaagagtg      60
agaaaccaga agctctgata tttaactgcc gtgataatga attcaatgtg caactatggg     120
caaattgtat ttaatagtaa ttgcatattg tacatatttt tcattcttat taacactgat     180
aaacttttca acttatactg actttaataa aattgtatta ctaggctatt aacatgatat     240
tttgtttccc attaaatgtg acatgcaaag acgtttatta aat                       283
```

<210> SEQ ID NO 675
<211> LENGTH: 229
<212> TYPE: DNA
<213> ORGANISM: Homo sapiens

<400> SEQUENCE: 675

```
actgtacaaa gtataagtct tagatgtata tatttcctat attgttttca gtgtacatgg      60
aataacatgt aattaagtac tatgtatcaa tgagtaacag gaaaatttta aaaatacaga    120
tagatatatg ctctgcatgt tacataagat aaatgtgctg aatggttttc aaataaaaat    180
gaggtactct cctggaaata ttaagaaaga ctatctaaat gttgaaaga                229
```

<210> SEQ ID NO 676
<211> LENGTH: 39
<212> TYPE: DNA
<213> ORGANISM: Homo sapiens

<400> SEQUENCE: 676

```
gttgctgacc tgctgtgctc gcagtagatt ccaaaaaaa                             39
```

<210> SEQ ID NO 677
<211> LENGTH: 259
<212> TYPE: DNA
<213> ORGANISM: Homo sapiens

<400> SEQUENCE: 677

```
gacatcccca ctcacgaata ttatgcccag tttctgcctc tgagggaaag cccagaaaag      60
gacagaaacg aagtagaaag gggcccagtc ctggcctggc ttctcctttg gaagtgaggc    120
attgcacggg gagacgtacg tatcagcggc cccttgactc tggggactcc gggtttgaga    180
tggacacact ggtgtggatt aacctgccag ggagacagag ctcacaataa aaatggctca    240
gatgccactt caaagaaaa                                                  259
```

<210> SEQ ID NO 678
<211> LENGTH: 236
<212> TYPE: DNA
<213> ORGANISM: Homo sapiens

<400> SEQUENCE: 678

```
gacagtccgt caaaacagat tgtttgcaaa ggggaggcat cagtgtcctt ggcaggctga      60
tttctaggta ggaaatgtgg tagcctcact tttaatgaac aaatggcctt tattaaaaac    120
tgagtgactc tatatagctg atcagttttt tcacctggaa gcatttgttt ctactttgat    180
atgactgttt ttcggacagt ttatttgttg agagtgtgac caaaagttac atgttt        236
```

<210> SEQ ID NO 679
<211> LENGTH: 280
<212> TYPE: DNA
<213> ORGANISM: Homo sapiens

<400> SEQUENCE: 679

```
tctgaactct caaaagtcta ttttttaac tgaaaatgta aatttataaa tatattcagg      60
agttggaatg ttgtagttac ctactgagta ggcggcgatt tttgtatgtt atgaacatgc    120
agttcattat tttgtggttc tattttactt tgtacttgtg tttgcttaaa caaagtgact    180
gtttggctta taaacacatt gaatgcgctt tattgcccat gggatatgtg gtgtatatcc    240
ttccaaaaaa ttaaaacgaa ataaagtag ctgcgattgg                            280
```

<210> SEQ ID NO 680
<211> LENGTH: 215
<212> TYPE: DNA
<213> ORGANISM: Homo sapiens

<400> SEQUENCE: 680

```
caaacttgga gcaggtgtcc atcccagccc tgtgtagtta gagcaggaat caagatctca     60
acacaaatgt ggctgccaag cactcagccc cggggcgagg ggtcaagttc ttctcagaga    120
aagaggaata agttggttct cagaagacat cacaagatac gtgtgtaccc aacaatctct    180
gatctctgct gatcttttgc ttagacgtta acttg                               215
```

<210> SEQ ID NO 681
<211> LENGTH: 258
<212> TYPE: DNA
<213> ORGANISM: Homo sapiens

<400> SEQUENCE: 681

```
aggcgcctgg agaagtgctc agctacttct cctgcacttt gaaagacccc tcccactcct     60
ggcctcacat ttctctgtgt gatcccccac ttctgggctc tgccacccca cagtgggaaa    120
ggccacccta gaaagaagtc cgctggcacc cataggaagg ggcctcagga gcaggaaggg    180
ccaggaccag aaccttgccc acggcaactg ccttcctgcc tctcccttc ctcctctgct    240 cttgatctgt gtttcaat                                                   258
```

<210> SEQ ID NO 682
<211> LENGTH: 248
<212> TYPE: DNA
<213> ORGANISM: Homo sapiens

<400> SEQUENCE: 682

```
gaaactccct agttccttca tgtaacttcc ctgaaaaatc taagtgtttc ataaatttga     60
gagtctgtga cccacttacc ttgcatctca caggtagaca gtatataact aacaaccaaa    120
gactacatat tgtcactgac acacgttaa taatcattta tcatatatat acatacatgc    180
atacactctc aaagcaaata atttttcact tcaaaacagt attgacttgt ataccttgta    240
atttgaaa                                                              248
```

<210> SEQ ID NO 683
<211> LENGTH: 39
<212> TYPE: DNA
<213> ORGANISM: Homo sapiens

<400> SEQUENCE: 683

```
ggtaggttga agggacctct ctcttaccag taccagaaa                             39
```

<210> SEQ ID NO 684
<211> LENGTH: 72
<212> TYPE: DNA
<213> ORGANISM: Homo sapiens

<400> SEQUENCE: 684

```
tctatttatt tattgaggac ccatggtaaa atgcaaatag atccggtgtc taaatgcatt    60
catattttta tg                                                       72
```

<210> SEQ ID NO 685
<211> LENGTH: 241
<212> TYPE: DNA
<213> ORGANISM: Homo sapiens

<400> SEQUENCE: 685

```
atgtgtgcaa aagcccaaag gttcctaagc ctggctgcaa agaagaatca acagggacac    60
tttttaaaaa cactcttatc agcctgggca acacagtgag actccatctc ttaaaaaaaa   120
aattagctgg gtatagtggt atgtgcctgt agtcccaggt actcaggagg ctgaggcagg   180
aggattgcct gagcccagga ggtggaaact gcagagagtc atgatcatgt ccttacactc   240
c                                                                  241
```

<210> SEQ ID NO 686
<211> LENGTH: 278
<212> TYPE: DNA
<213> ORGANISM: Homo sapiens

<400> SEQUENCE: 686

```
gtaataaact ctctagggcc aaaacctggt atggtcattg ggaaatgagt gctcagggag    60
atggagctta ggggaggtgg gtgcttccct cctagatgtc agcatacact ctttcttctt   120
ttgtcccagg tctaaaacat ctttcctaga gaaaacaaaa gggactaaac tagaaatata   180
aagagcccta tacatgacag gtgatcacgt actgaatgat tttgaagtag tacaaacaat   240
aaaaattctc attccgcatc atcatgcggt ccatgatg                          278
```

<210> SEQ ID NO 687
<211> LENGTH: 244
<212> TYPE: DNA
<213> ORGANISM: Homo sapiens

<400> SEQUENCE: 687

```
aaaagcttcc ccaactaaag cctagaagag cttctgaggc gctgctttgt caaaaggaag    60
tctctaggtt ctgagctctg gctttgcctt ggctttgcca gggctctgtg accaggaagg   120
aagtcagcat gcctctagag gcaaggaggg gaggaacact gcactcttaa gcttccgccg   180
tctcaacccc tcacaggagc ttactggcaa acatgaaaaa tcggcttacc attaaagttc   240
tcaa                                                              244
```

<210> SEQ ID NO 688
<211> LENGTH: 118
<212> TYPE: DNA
<213> ORGANISM: Homo sapiens

<400> SEQUENCE: 688

```
ccagcactct gaaactgaga aatgttcaga atgtacggaa agatgatcag ctattttcaa    60
cataactgaa ggcatatgct ggcccataaa caccctgtag gttcttgata tttataat    118
```

<210> SEQ ID NO 689
<211> LENGTH: 264
<212> TYPE: DNA
<213> ORGANISM: Homo sapiens

<400> SEQUENCE: 689

```
aatacccatt atattcctgt aagtaaatga ctattttcc cttaactcag tgattagaca      60
ggaaggaaga cattagtgat tagacaggag ggaagatatt agtgattaga cagcagggaa     120
gatattagtg gtaaagagtg aatgatagta gtgaatataa atgggctga ggaaacttta     180 agcataaaag attcctgaga tgactttaca agtctgtacg aatctgcctt gactgtatat    240
ttcatactgc ccaacaaaac aata                                           264
```

<210> SEQ ID NO 690
<211> LENGTH: 270
<212> TYPE: DNA
<213> ORGANISM: Homo sapiens

<400> SEQUENCE: 690

```
gttcctattc ttccattgta cgataatgtc tttaatatga atgctacat tatttataat      60 tggtagagtt attgtatctt tttatagttg taagtacaca gaggtggtat atttaaactt    120
ctgtaatata ctgtatttag aaatggaaat atatatagtg ttaggtttca cttcttttaa    180
ggtttacccc tgtggtgtgg tttaaaaatc tataggcctg ggaattccga tcctagctgc    240
agatcgcatc ccacaatgcg agaatgataa                                     270
```

<210> SEQ ID NO 691
<211> LENGTH: 187
<212> TYPE: DNA
<213> ORGANISM: Homo sapiens

<400> SEQUENCE: 691

```
aattcatagt aatttcactc tctgcattga cttatgagat aattaatgat taaactatta     60
atgataaaaa taatgcattt gtattgttca taatatcatg tgcacttcaa gaaaatggaa    120
tgctactctt ttgtggttta cgtgtattat tttcaatatc ttaatacct aataaagagt     180 ccataaa                                                              187
```

<210> SEQ ID NO 692
<211> LENGTH: 249
<212> TYPE: DNA
<213> ORGANISM: Homo sapiens

<400> SEQUENCE: 692

```
tcaccacaac agaacatgca gtactaaagc aatatatttg tgattcccca tgtaattctt     60
caatgttaaa cagtgcagtc ctctttcgaa agctaagatg accatgcgcc ctttcctctg    120
tacatatacc cttaagaacg cccctccac acactgcccc ccagtatatg ccgcattgta    180
ctgctgtgtt atatgctatg tacatgtcag aaaccattag cattgcatgc aggtttcata    240
ttctttccta                                                           249
```

<210> SEQ ID NO 693
<211> LENGTH: 199
<212> TYPE: DNA
<213> ORGANISM: Homo sapiens

<400> SEQUENCE: 693

```
gttgagccaa ctatagctct gtgttcctac tgggctttcc ctaatgtggt tgggagttat     60
gccctagact aactgtattg tcctagtcac agctccttgc tttgatttca tccttgataa    120
aatgaagatg aaacttacac tacttctcca agccttttgc tgtcttaaga ataagacctg    180
agattaacac taaccctag                                                 199
```

<210> SEQ ID NO 694
<211> LENGTH: 190
<212> TYPE: DNA
<213> ORGANISM: Homo sapiens

<400> SEQUENCE: 694

```
ttcacttaca agctctatga tcttaaataa tttacttaat gtattttggt gtattttcct      60
caaattaata ttggtgttca agactatatc taattcctct gatcactttg agaaacaaac     120
ttttattaaa tgtaaggcac ttttctatga attttaaata taaaaataaa tattgttctg     180
attattactg                                                            190
```

<210> SEQ ID NO 695
<211> LENGTH: 235
<212> TYPE: DNA
<213> ORGANISM: Homo sapiens

<400> SEQUENCE: 695

```
gttttgctgg agaaacatca ggtttgtagg agactgagtt gttagcaggt gtgcttagct      60
cttgatagtg aacgtgtacc ttgggaactg gctcacccac ctgctaatag caccatcgtc     120
actattaagc agacatttca gttggtagaa tccatgtaga agtcatggac ttttctggga     180
aatgactttt ctgggaaatg acagtttctt tgacatattt tctttgccca cttta          235
```

<210> SEQ ID NO 696
<211> LENGTH: 243
<212> TYPE: DNA
<213> ORGANISM: Homo sapiens

<400> SEQUENCE: 696

```
gactgaggga tcgtagattt ttacaatctg tatctttgac aattctgggt gcgagtgtga      60
gagtgtgagc agggcttgct cctgccaacc acaattcaat gaatccccga ccccctacc     120
ccatgctgta cttgtggttc tcttttttgta ttttgcatct gaccccgggg ggctgggaca    180
gattggcaat gggccgtccc ctctcccctt ggttctgcac tgttgccaat aaaaagctct     240
taa                                                                   243
```

<210> SEQ ID NO 697
<211> LENGTH: 192
<212> TYPE: DNA
<213> ORGANISM: Homo sapiens

<400> SEQUENCE: 697

```
gctgtttgtt ctcctggggc gctccctcca acttttgcag attcttgcaa cctcctcctg      60
agccgggatt gtccaattac taaaatgtaa ataatcacgt attgtgggga ggggagttcc     120
aagtgtgccc tcctctcttc tcctgcctgg attatttaaa aagccatgtg tggaaaccca     180
ctatttaata aa                                                         192
```

<210> SEQ ID NO 698
<211> LENGTH: 114
<212> TYPE: DNA
<213> ORGANISM: Homo sapiens

<400> SEQUENCE: 698

```
agcaagtgta gacaccttcg agggcagaga tcgggagatt taagatgtta cagcatattt      60
tttttcttg ttttacagta ttcaattttg tgttgattca gctaaattat gaaa            114
```

```
<210> SEQ ID NO 699
<211> LENGTH: 123
<212> TYPE: DNA
<213> ORGANISM: Homo sapiens

<400> SEQUENCE: 699
tgtggggagc caggcttccc tcacgcagcc tgtggtggat gtgggaagga gatcaacttc      60
tcctcactct gggacagacg atgtatggaa actaaaaaga acatgcggca ccttaaaaaa     120
aaa                                                                   123

<210> SEQ ID NO 700
<211> LENGTH: 158
<212> TYPE: DNA
<213> ORGANISM: Homo sapiens

<400> SEQUENCE: 700
cagccccacc cctgtaaatg gaatttacca gatgaaggga atgaagtccc tcactgagcc      60
tcagatttcc tcacctgtga atgggctga ggcaggaaat gggaaaaagt gttagtgctt     120
ccaggcggca ctgacagcct cagtaacaat aaaaacaa                             158

<210> SEQ ID NO 701
<211> LENGTH: 206
<212> TYPE: DNA
<213> ORGANISM: Homo sapiens

<400> SEQUENCE: 701
agtattatac aactgctgtg accagacttg tatactggct gaatatcagt gctgtttgta      60
atttttcact ttgagaacca acattaattc catatgaatc aagtgttttg taactgctat     120
tcatttattc agcaaatatt tattgatcat ctcttctcca taagatagtg tgataaacac     180
agtcatgaat aaagttattt tccaca                                          206

<210> SEQ ID NO 702
<211> LENGTH: 252
<212> TYPE: DNA
<213> ORGANISM: Homo sapiens

<400> SEQUENCE: 702
tggcagactc cttgttgctt aagagtggct ttctaggcag gccactggca tctgaattca      60
tcattgacaa taaatgtaag aaattggaat aaaaaagaga gacctgctgt tattcgcttt     120
tgttctccag tgatttgatt aactcagggc aaggctgaat atcagagtgt atcgcactga     180
agaataataa tccattcagt aatgttatag ttatcctcaa tctaaatatg tcaactgtca     240
ttttgctgct tt                                                         252

<210> SEQ ID NO 703
<211> LENGTH: 227
<212> TYPE: DNA
<213> ORGANISM: Homo sapiens

<400> SEQUENCE: 703
ctaaggtagc aacttatttc caaattaata tagatgaaaa atagatacca attagactaa      60
attgaaagct ttttgttcta tatttgcata gcctttgaaa tatttcttag tgcctaggag     120
gtctggggat tcctctttcg tggtggtcac taaccttact tgatgcagat aaaatcactt     180
gtcaatgcaa aatgtgttag aacttgataa agctttgagt ttgagaa                   227

<210> SEQ ID NO 704
```

```
<211> LENGTH: 262
<212> TYPE: DNA
<213> ORGANISM: Homo sapiens
<220> FEATURE:
<221> NAME/KEY: misc_feature
<222> LOCATION: (77)..(117)
<223> OTHER INFORMATION: n is a, c, g, or t

<400> SEQUENCE: 704
taaaaacgac cattacagtg ccaatatcgc taatatgatc cctggatgga attggttatt      60
ctgagctgtg acaaggnnnn nnnnnnnnnn nnnnnnnnnn nnnnnnnaag                120
ggcaagtgct gttttcctgt tttcttcctt atcttagttg taatgaatca cttttataac    180
ttgtacctgc tacactaagt attgtctcag caaagtcatt cattttactg gtaacaaaag    240
ccaggaataa cgtgctatgg aa                                             262

<210> SEQ ID NO 705
<211> LENGTH: 275
<212> TYPE: DNA
<213> ORGANISM: Homo sapiens

<400> SEQUENCE: 705
gcctggatag aggtatatga tcgtgtgcca agaatttatc ccagactccc ctgtgtgaca     60
gcttcataat aaagttactt aactgtgcct cttcctcctt cctctcccca cacaggatgg    120
atgggcatct ttctccttga ccaccctact ctcccttcct ccctgatca cctccctcc     180
ctgctcttcc ctggtgatgg acttctaaca tgagattttt ttaaaaaatt tctatttctt    240
ttataatttt gctgagtttt cagggtttct tctgt                                275

<210> SEQ ID NO 706
<211> LENGTH: 81
<212> TYPE: DNA
<213> ORGANISM: Homo sapiens

<400> SEQUENCE: 706
agctatctga gccttgacgc tgagcaagtg gaagtcccac agaagctaca agttgccagg     60
tcaacgcatg aagggagcca c                                               81

<210> SEQ ID NO 707
<211> LENGTH: 147
<212> TYPE: DNA
<213> ORGANISM: Homo sapiens

<400> SEQUENCE: 707
cagtatgtca tgtttgctgt agtgctcata tttattgttg ttttttgtttt agtactcact    60
tgtttcataa tatcaagatt actaaaaatg ggggaaagga cttctaatct ttttttcata    120
atatctttga cacatattac agaagaa                                        147

<210> SEQ ID NO 708
<211> LENGTH: 47
<212> TYPE: DNA
<213> ORGANISM: Homo sapiens

<400> SEQUENCE: 708
acacagtgct ttccgtggca ctgcatacaa tctgaggcct cctctct                   47

<210> SEQ ID NO 709
<211> LENGTH: 52
<212> TYPE: DNA
<213> ORGANISM: Homo sapiens
```

```
<400> SEQUENCE: 709
taaatatcca cagtactcac tttttccaaa tgatcctagt aattgcctag aa              52

<210> SEQ ID NO 710
<211> LENGTH: 222
<212> TYPE: DNA
<213> ORGANISM: Homo sapiens

<400> SEQUENCE: 710
ggtgttggca ctaacgctgc ttgtttggca aatcatcatc actgaggtat tccacccaga     60 gacttttttca aaaagtcaa ctaaagtgct aagtcataag aggagagcca ttatacccgt   120
tgtctttctg ggctccttga gtttatctgg attccaacag cacttggaaa gtaccgccct   180
ccactacctc aaatgcaaac acaatctctg ccagtagaca tt                      222

<210> SEQ ID NO 711
<211> LENGTH: 284
<212> TYPE: DNA
<213> ORGANISM: Homo sapiens
<220> FEATURE:
<221> NAME/KEY: misc_feature
<222> LOCATION: (33)..(33)
<223> OTHER INFORMATION: n is a, c, g, or t

<400> SEQUENCE: 711
acaagcccaa atttgatata cttttttatat ttnaaaaatt atattcactg cccccataag    60
agcaatcaag gcatgtcttt aaattctata catagatata gccaaaaata gtgcatttag   120
taacattctt ttccaaaact atattcttgg gaatgaatat ctgtttcttc taacagtttg   180
agtgataatc tatacctgta gatataagtt attttgcata taaaattaat cttaatcttt   240
tatggaatgt tctctgtctg tggcattaaa tgaaccttaa gaac                    284

<210> SEQ ID NO 712
<211> LENGTH: 224
<212> TYPE: DNA
<213> ORGANISM: Homo sapiens
<220> FEATURE:
<221> NAME/KEY: misc_feature
<222> LOCATION: (144)..(144)
<223> OTHER INFORMATION: n is a, c, g, or t

<400> SEQUENCE: 712
tgtgcccagc tgacatattc tcacttaata gaattataga gaaattttttc atgttttttct    60 ttttctctcc cacttttttca tattcctctt tttcattttt gcctttccgt ttctgtctat   120
gatgtaggct tctgaggaga accnagaagc ttggctttag tggtagaatg acagaactta   180 gggatcccctt gcaggctaga acaaagttct gacccttaga ccaa                    224

<210> SEQ ID NO 713
<211> LENGTH: 224
<212> TYPE: DNA
<213> ORGANISM: Homo sapiens

<400> SEQUENCE: 713
gaaattgcat caagcgtccg aacatgctgc ttacaacttt agaaacgcaa aatgcgttgt     60
tgtgggagtt gtgtaatttt tagtaggtgc tcaaatactt gctgaacttg gtgtctatttt  120 ttaagtcttg cccattgatg taaactgtcc ctaggtcacg tgtatcttga ggtctaaaag  180
attatttatg caataaattg aaattcccat agccaattaa agat                   224
```

<210> SEQ ID NO 714
<211> LENGTH: 194
<212> TYPE: DNA
<213> ORGANISM: Homo sapiens

<400> SEQUENCE: 714
tggtgggctg aggatgtctt cttcctgtcc aggatgcaat atggtcaagg atgaaaggaa     60
agagatgctg ggagcaagtc tgcattgaag atgtatttct gttgctttac taccaaccct    120
ggttataaat gatgaaacta taatgggtct gtaatagcta ctttcccata tagctcttgt    180
ctgtacatac ataa                                                      194

<210> SEQ ID NO 715
<211> LENGTH: 227
<212> TYPE: DNA
<213> ORGANISM: Homo sapiens
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (185)..(187)
<223> OTHER INFORMATION: n is a, c, g, or t
<220> FEATURE:
<221> NAME/KEY: misc_feature
<222> LOCATION: (189)..(191)
<223> OTHER INFORMATION: n is a, c, g, or t
<220> FEATURE:
<221> NAME/KEY: misc_feature
<222> LOCATION: (193)..(195)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (201)..(202)
<223> OTHER INFORMATION: n is a, c, g, or t

<400> SEQUENCE: 715
attgtgctta ggtgatttgt aactcaggta tagggtattt aaatagtagg cacccttttt     60
gcaccatgtg nnttttttttt tttatctagt tcttgtatac tacagataat atttgaactt   120
tgtcatctca ctgtaaaact tttgttcatt tctcattatg gtaataaata gctattataa    180
ccaannnann nannnaaana nnttatttcc ctaagtgtta ttttgac                   227

<210> SEQ ID NO 716
<211> LENGTH: 183
<212> TYPE: DNA
<213> ORGANISM: Homo sapiens
<220> FEATURE:
<221> NAME/KEY: misc_feature
<222> LOCATION: (126)..(127)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t

<400> SEQUENCE: 716
agtgccattt cattatttga ttatcaccaa attatctgga ataattggg acattgtaac      60 ttatctattt atagttatga gattaagact ggagtgccat caccgcgggt gatgatttag    120
cttttnntgt gtgtntgngt gtgtgccttc caaatcatgc cataattgta atgttgaatc  180
gga  183

<210> SEQ ID NO 717
<211> LENGTH: 288
<212> TYPE: DNA
<213> ORGANISM: Homo sapiens

<400> SEQUENCE: 717
tgtgcccaac cattgtaata tgcgtattga cgtatatgat aggagaaaac actagcattt  60
tgagttaata agtaggtcag tttggattaa tggaaagttt gaagcttaga gtgtttaaat  120
aatgatttta ttcttttcaa tacacaagtg gaaatgtttc tccagtctaa attccccta  180 gtattctcct gaaacaaaat ttttatatgc agatatttgc ttcttttgca agtttgagaa  240
tttcacagta acttctggtt accctgggtt gtgtcttgca gttaccaa  288

<210> SEQ ID NO 718
<211> LENGTH: 183
<212> TYPE: DNA
<213> ORGANISM: Homo sapiens

<400> SEQUENCE: 718
ttctgtgtct gaagtgtaag tgaacacaga agagtgacat gtttacaaac ctcaagccag  60
ccttgctcct ggctggggcc tgttgaagat gcttgtattt tacttttcca ttgtaattgc  120
tatcgccatc acagctgaac ttgttgagat ccccgtgtta ctgcctatca gcattttact  180
act  183

<210> SEQ ID NO 719
<211> LENGTH: 205
<212> TYPE: DNA
<213> ORGANISM: Homo sapiens

<400> SEQUENCE: 719
gctgcttcct cctggaaatt gacgaggggt gtcttgggca gagctggctc tgagcgcctc  60
catccaaggc caggttctcc gttagctcct gtggccccac cctgggccct gggctggaat  120
caggaatatt ttccaaagag tgatagtctt ttgcttttgg caaaactcta cttaatccaa  180
tgggtttttc cctgtacagt agatt  205

<210> SEQ ID NO 720
<211> LENGTH: 189
<212> TYPE: DNA
<213> ORGANISM: Homo sapiens

<400> SEQUENCE: 720
gcccacctga agcagcaagt gagcgggctg gagggtgtgc aggacgacct gttctggctg  60
accttcgagg ggaagcccct ggaggaccag ctcccgctgg gggagtacgg cctcaagccc  120
ctgagcaccg tgttcatgaa tctgcgcctg cggggaggcg gcacagagcc tggcgggcgg  180
agctaaggg  189

<210> SEQ ID NO 721
<211> LENGTH: 191
<212> TYPE: DNA
<213> ORGANISM: Homo sapiens

<400> SEQUENCE: 721

```
caaacagagt gaactttctg ccaagatgcg ggagtggttt tcagagacat ttcagaaagt    60
gaaggagaaa ctcaagattg actcatgagg acctgaaggg tgacatccca ggaggggcct   120
ctgaaatttc ccacacccca gcgcctgtgc tgaggactcc ctccatgtgg ccccaggtgc   180
caccaataaa a                                                        191

<210> SEQ ID NO 722
<211> LENGTH: 217
<212> TYPE: DNA
<213> ORGANISM: Homo sapiens

<400> SEQUENCE: 722
aggttagatt ctcattcacg ggactagtta gctttaagca ccctagagga ctagggtaat    60
ctgacttctc acttcctaag ttcccttcta tatcctcaag gtagaaatgt ctatgttttc   120
tactccaatt cataaatcta ttcataagtc tttggtacaa gtttacatga taaaagaaa    180 tgtgatttgt cttcccttct ttgcactttt gaaataa                            217

<210> SEQ ID NO 723
<211> LENGTH: 233
<212> TYPE: DNA
<213> ORGANISM: Homo sapiens

<400> SEQUENCE: 723
ggagagtaga acattttcc tcatttatc aaatcctctc ttgccctccc tcaattcccc      60
tgtaacattc ctgaagctgt tcccactccc agatggtttt atcaatagcc tagaggtaaa   120
gaactgtctt tttctctgat tctttaataa attatcttta tagaatatgc acaagttttt   180
ctacactcag tgttaaagta tttattaatg ggaagtcaac ttaatgtttt gaa           233

<210> SEQ ID NO 724
<211> LENGTH: 250
<212> TYPE: DNA
<213> ORGANISM: Homo sapiens

<400> SEQUENCE: 724
ttgcatttca tgtttaacct ccggctggaa atagaaagca ttcccttaga gatgaggata    60
aaagaaagtt tcagattcaa caggggggaag aaaatggaga tttaatccta aaactgtgac  120
ttggggaggt cagtcattta cagttagtcc tgtgtctttc gacttctgtg attattaacc   180
ccactcacta ccctgtttca gatgcatttg gaataccaaa gattaaatcc ttgacataag   240
atctcatttg                                                          250

<210> SEQ ID NO 725
<211> LENGTH: 183
<212> TYPE: DNA
<213> ORGANISM: Homo sapiens

<400> SEQUENCE: 725
ggagtggtgg cctctctgag atttcctaaa gttgctcaac agcccctgat caactaagtt    60
ttgtggtact tcaccctctt ctgccctcat ttcatgtgac agccattgtg agactgatgc   120
acaaactgtc acttggttaa tttaagcact tctgttttcg tgaatttact tgattgtttc   180
ttc                                                                 183

<210> SEQ ID NO 726
<211> LENGTH: 77
<212> TYPE: DNA
<213> ORGANISM: Homo sapiens
```

<400> SEQUENCE: 726
accaccacca gaatgcagtt ccagcttagg aagccacaaa caagccaccc aggaggaaca    60
aaacaccgcc agcgtgg                                                   77

<210> SEQ ID NO 727
<211> LENGTH: 231
<212> TYPE: DNA
<213> ORGANISM: Homo sapiens

<400> SEQUENCE: 727
aataattcct ttctactgca tacaaaggga cctgaagctt aaattcagtt agttttggag    60
aaatccaaaa tgagaaaaac agaaagcatg tagcattcca tgaagcaaga acagcgtgca   120
tatgctattc ctggaaatac tgaagtgtcc gaatttcatg cctaaaaagt ctggaaatca   180
cactgaatca gttgctggtt tctgatgtct ctgggatgtg ctattacaaa c            231

<210> SEQ ID NO 728
<211> LENGTH: 77
<212> TYPE: DNA
<213> ORGANISM: Homo sapiens

<400> SEQUENCE: 728
attcagcaaa aactcagcca gctctttcta tggggcagtt gctaatttag ttctaggcaa    60
acgtggacac attaaat                                                   77

<210> SEQ ID NO 729
<211> LENGTH: 269
<212> TYPE: DNA
<213> ORGANISM: Homo sapiens

<400> SEQUENCE: 729
ttccttcttg gcctaactct tccagttagg atctagaact ttgccttttt tttttttttt    60
ttttttttga gatgggttct cactatattg tccaggctag agtgcagtgg ctattcacag   120
atgcgaacat agtacactgc agcctccaac tcctagcctc aagtgatcct cctgtctcaa   180
cctcccaagt aggattacaa gcatgcgccg acgatgccca gaatccagaa ctttgtctat   240
cactctcccc aacaacctag atgtgaaaa                                     269

<210> SEQ ID NO 730
<211> LENGTH: 229
<212> TYPE: DNA
<213> ORGANISM: Homo sapiens

<400> SEQUENCE: 730
aaatatgttt acagaccaaa gtgtgatttc acactgtttt taaatctagc attattcatt    60
ttgcttcaat caaaagtggt ttcaatattt tttttagttg gttagaatac tttcttcata   120
gtcacattct ctcaacctat aatttggaat attgttgtgg tcttttgttt tttctcttag   180
tatagcattt ttaaaaaaat ataaaagcta ccaatctttg tacaatttg                229

<210> SEQ ID NO 731
<211> LENGTH: 216
<212> TYPE: DNA
<213> ORGANISM: Homo sapiens

<400> SEQUENCE: 731
gtgatctggc aatgctatcc agcatctttg gagaccaatg gtcagtcttt tcctggccag    60

```
aggaaagatt gatggccctc ccacttgaac tgacagcctg tgagcccctt gggggcatag    120
actgccttcc ttggacccctt ccaaagtgtg tggtacgggg ctcagtgcac agagtattca    180
cccagcatca tgaatcaact tgggaggagt caacca                               216

<210> SEQ ID NO 732
<211> LENGTH: 165
<212> TYPE: DNA
<213> ORGANISM: Homo sapiens

<400> SEQUENCE: 732
gggacatgaa gagcggcgca cgagtgggac tggcgcgcgc tcgccctcgc ggagcggacc     60
tgggaaggcg cgagaccgcg caggcgcagt accgcgggtg ccgcccaggt gatgcgcatg    120
cgcaccgggt agcagagcta gcgctactca gtaaaaatcc aatat                    165

<210> SEQ ID NO 733
<211> LENGTH: 124
<212> TYPE: DNA
<213> ORGANISM: Homo sapiens

<400> SEQUENCE: 733
gacctgggcc tgacgggccc ttctcagccc gttttgagga cagacagtcc cccgaggtag     60
gctacatccc cccacccccag ctggtctgct tggatttcct acagccccg tgggcatgga   120 ccac                                                                 124

<210> SEQ ID NO 734
<211> LENGTH: 156
<212> TYPE: DNA
<213> ORGANISM: Homo sapiens

<400> SEQUENCE: 734
gttataattt acactgaggg tttcaaaatt cgactagaag tggagatata ttatttattt     60
atgcactgta ctgtattttt atattgctgt ttaaaacttt taagctgtgc ctcacttatt    120
aaagcacaaa atgttttacc tactccttat ttacga                              156

<210> SEQ ID NO 735
<211> LENGTH: 276
<212> TYPE: DNA
<213> ORGANISM: Homo sapiens

<400> SEQUENCE: 735
gagtaagctc tagtccctct gtcctgtaga aagagccctg aagaatcagc aattttgttg     60
ctttattgtg gcatctgttc gaggtttgct tcctctttaa gtctgtttct tcattagcaa    120
tcatatcagt tttaatgcta ctactaacaa tgaacagtaa caataatatc cccctcaatt    180
aatagagtgc tttctatgtg caaggcactt ttcacgtgtc acctattta acctttccaa    240 ccacataaat aaaaaaggcc attattagtt gaatct                              276

<210> SEQ ID NO 736
<211> LENGTH: 257
<212> TYPE: DNA
<213> ORGANISM: Homo sapiens

<400> SEQUENCE: 736
gcctctggct tctcaggcct ctgctctccg acctctctcc tctgaaaccc tcctccacag     60
ctgcagccca tcctcccggc tccctcctag tctgtcctgc gtcctctgtc cccgggtttc    120
agagacaact tcccaaagca caaagcagtt tttcccccta ggggtgggag gaagcaaaag    180
```

```
actctgtacc tattttgtat gtgtataata atttgagatg ttttttaatta tttgattgc      240 tggaataaag catgtgg                                                     257

<210> SEQ ID NO 737
<211> LENGTH: 283
<212> TYPE: DNA
<213> ORGANISM: Homo sapiens

<400> SEQUENCE: 737
cgcatgttat ggtgctaatg tactttcact tttaaactct agatcagaat tgttgacttg       60
cattcagaac ataaatgcac aaaatctgta catgtctccc atcagaaaga ttcattggca      120
tgccacaggg gattctcctc cttcatcctg taaaggtcaa caataaaaac caaattatgg      180
ggctgctttt gtcacactag catagagaat gtgttgaaat ttaactttgt aagcttgtat      240
gtggttgttg atcttttttt tccttacaga cacccataat aaa                       283

<210> SEQ ID NO 738
<211> LENGTH: 254
<212> TYPE: DNA
<213> ORGANISM: Homo sapiens

<400> SEQUENCE: 738
aattcagtgg tgtgagtata ttcataagat ttatacttgg tgtctattca taagacttat       60
atccagcata ttcataacta gagccatatc acagatgcat tcatcataat aattccagac      120
attttcatca ccctaaaagg aaaccctgaa acccattagc agtcattccc cattcctcca      180
acccattctc tccctaatcc ctagaaacca ccaatctgct gtgtatttca tctattgcca      240
acatttcata taaa                                                        254

<210> SEQ ID NO 739
<211> LENGTH: 217
<212> TYPE: DNA
<213> ORGANISM: Homo sapiens

<400> SEQUENCE: 739 tattttttgag atatcccttt ggaagacctt gcttggaaga gcctggacac taacaattct      60
acaccaaatt gtctcttcaa atacgtatgg actggataac tctgagaaac acatctagta      120
taactgaata agcagagcat caaattaaac agacagaaac cgaaagctct atataaatgc      180
tcagagttct ttatgtattt cttattggca ttcaaca                               217

<210> SEQ ID NO 740
<211> LENGTH: 171
<212> TYPE: DNA
<213> ORGANISM: Homo sapiens

<400> SEQUENCE: 740
atcgctggtc accatggtga tcaaggtgct cctggctccg tgggtcctgc tggtcctagg       60
ggccctgctg gtccttctgg ccctgctgga aaagatggtc gcactggaca tcctggtaca      120
gttggacctg ctggcattcg aggccctcag ggtcaccaag gccctgctgg c               171

<210> SEQ ID NO 741
<211> LENGTH: 289
<212> TYPE: DNA
<213> ORGANISM: Homo sapiens

<400> SEQUENCE: 741
```

```
aaaccctcag gaaactccca gggtgatgct tggagaagct gtgagttgag ctgaagctgg      60
agaacttcct ccagagcaaa gggcttaaga aagaaagaag aactctaagc tgggtctgct     120
aacatcactc cagtttagat ggatcttggc agagagacat gcttgttcct ctggattgga     180
aagatgattt actctcggga atcttctctg tcagcctgta catctaaagg catgaagcac     240
tcaattgggc aattaacatt agtgtttgtt ctctgatggt atctctgag                 289

<210> SEQ ID NO 742
<211> LENGTH: 271
<212> TYPE: DNA
<213> ORGANISM: Homo sapiens

<400> SEQUENCE: 742
gtggtcatgc ggaacactct gttatttaag atggctatcc agataatcct gaacactgtg      60
tatttatttt atttagacta ccagcaaaga ttaaagcatg aaatgtaaaa catctgataa     120
aacttacagc cccctacacc aagagtgtat ctgtgaaaga gctcctacac tttgaaaact     180
taagaatccc ttatcatgaa gtttgcctgt tctagaattg taagattgtt aatttccttc     240
aatctctagt gacaacactt aatttctttt c                                    271

<210> SEQ ID NO 743
<211> LENGTH: 193
<212> TYPE: DNA
<213> ORGANISM: Homo sapiens

<400> SEQUENCE: 743
cacctggctt catgttcccg gtattagtac aatgccaaaa tatttaaaat tcttaaaggt      60
taactcaaat atcttaagtt ttacttcact tacaatttca ataatgctga aattttgatt     120
gaatattgtg tttgtagtgc tacctctttt tcgttcataa gaacaaaagc ctatcattct     180
cttagtttct aaa                                                        193

<210> SEQ ID NO 744
<211> LENGTH: 206
<212> TYPE: DNA
<213> ORGANISM: Homo sapiens

<400> SEQUENCE: 744
cctgtaactc tttaaaactt ggctataggc tgtttagcac agtacagatt aaagatacag      60
ttacgtaaac agcaaagtaa ttttatagtg cttcatccat ttatcatgct ttggtttgct     120
aattttttca ataccttttt tctatcacag tctgttgctt ttgtacacat ttctcatatt     180
ggggttcgac aggtaaacac aaactg                                          206

<210> SEQ ID NO 745
<211> LENGTH: 242
<212> TYPE: DNA
<213> ORGANISM: Homo sapiens

<400> SEQUENCE: 745
gtgctataat ccctatttag ttcaaaatta accagaattc ttccatgtga aatggaccaa      60
actcatatta ttgttatgta aatacagagt tttaatgcag tatgacatcc cacaggggaa     120
aagaatgtct gtagtgggtg actgttatca aatatttat agaatacaat gaacggtgaa     180
cagactggta acttgtttga gttcccatga cagatttgag acttgtcaat agcaaatcat     240
tt                                                                    242
```

```
<210> SEQ ID NO 746
<211> LENGTH: 266
<212> TYPE: DNA
<213> ORGANISM: Homo sapiens

<400> SEQUENCE: 746
ttatcaactg tgcacaagga aaaaaataga tatgtgaaag gttcacgtaa atttcctcac      60
atcacagaag attaaaattc agaaggaga aaacacagac caaagagaag tatctaagac     120
caaagggatg tgttttatta atgtctagga tgaagaaatg catagaacat tgtagtactt    180
gtaaataact agaaataaca tgatttagtc ataattgtga aaaataataa taatttttct    240
tggatttatg ttctgtatct gtgaaa                                          266

<210> SEQ ID NO 747
<211> LENGTH: 202
<212> TYPE: DNA
<213> ORGANISM: Homo sapiens

<400> SEQUENCE: 747
gtggaggata ttgcaactgg agttcagaca ctgtactcga agtggaagga ctttcatttt     60
gagaagatac catttgatcc agcagaaatg tccaaatgat atcaggtcct caatcttcag    120
ctacagggaa tgagtaactt tgagtggaga agaaacaaac atagtgggta taatcatgga    180
tcgcttgtac ccctgtgaaa at                                              202

<210> SEQ ID NO 748
<211> LENGTH: 208
<212> TYPE: DNA
<213> ORGANISM: Homo sapiens
<220> FEATURE:
<221> NAME/KEY: misc_feature
<222> LOCATION: (124)..(124)
<223> OTHER INFORMATION: n is a, c, g, or t

<400> SEQUENCE: 748
gaatatgtgg cagagctcct ggaaatgatg cagattaggt ggcattttg tcagctctgt      60 ggtttattgt tgggactatt ctttaaaata tccattgttc actacagtga agatctctga    120
tttnaccgtg tactatccac atgcattaca aacatttcgc agagctgctt agtatataag    180
cgtacaatgt atgtaataac catctcat                                        208

<210> SEQ ID NO 749
<211> LENGTH: 150
<212> TYPE: DNA
<213> ORGANISM: Homo sapiens

<400> SEQUENCE: 749
gctgataaat agcattaggg ttctttgcaa tgtggtatct agctgtatta ttggttttat     60
ttactttaaa cattttgaaa agcttatact ggcagcctag aaaaacaaac aattaatgta    120
tctttatgtc cctggcacat gaataaactt                                      150

<210> SEQ ID NO 750
<211> LENGTH: 97
<212> TYPE: DNA
<213> ORGANISM: Homo sapiens

<400> SEQUENCE: 750
caaattcaag tcactagact tcagagttca acacctggac atgagaagat attatattat     60
gtaccataaa tatttcctgt atctgactgc ctgaaca                              97
```

<210> SEQ ID NO 751
<211> LENGTH: 237
<212> TYPE: DNA
<213> ORGANISM: Homo sapiens

<400> SEQUENCE: 751

```
agcaagactt gctgcctaaa ggagcccacc attttacttt tcacatttaa tctgccacgt      60
tgaatcaatt ggaataaaac ctgactcgca ggtgactgga caggaaatcc caaagttcca     120
ccatttctat gcttaatttt aacgtccccc cgcttttttt tttgtagaaa ataaaaacaa     180
gaaaatcgtt ccaatgtaag atgtttgtta tagaaacttt aggcaataca ggtgtgt       237
```

<210> SEQ ID NO 752
<211> LENGTH: 292
<212> TYPE: DNA
<213> ORGANISM: Homo sapiens
<220> FEATURE:
<221> NAME/KEY: misc_feature
<222> LOCATION: (54)..(55)
<223> OTHER INFORMATION: n is a, c, g, or t

<400> SEQUENCE: 752

```
ttgcaagtca attaggtgtc ttgtgaacaa ggaaatacta atctctaagc tgcnngggtc      60
tttttgtgtg aatatttaat ggtgctccat gactgttgag ttttaaaaac ctcgttaaat     120
tttgccaaat cagttgcccc caaaagggaa tatgcttttc cttatttttt tttctaaaat     180
gctatttatc tctaaggaaa aaaaaaaaag actattactc atttaacatt gtttaagcag     240
gttgagctag ctgtgaaaat agcttttgtg agccttctaa ttcctaaacg tc            292
```

<210> SEQ ID NO 753
<211> LENGTH: 243
<212> TYPE: DNA
<213> ORGANISM: Homo sapiens

<400> SEQUENCE: 753

```
gttaacactg tggatcacct tcggccaagg gacacgactg gagattaaac gtaagtaatt      60
tttcactatt gtcttctgaa atttgggtct gatggccagt attgactttt agaggcttaa     120
ataggagttt ggtaaagatt ggtaaatgag ggcatttaag atttgccatg ggttgcaaaa     180
gttaaactca gcttcaaaaa tggatttgga gaaaaaaaga ttaaattgct ctaaactgaa     240
tga                                                                   243
```

<210> SEQ ID NO 754
<211> LENGTH: 120
<212> TYPE: DNA
<213> ORGANISM: Homo sapiens

<400> SEQUENCE: 754

```
tcattctcat ccatccagga tgtactaaaa cagtgtgttt aataaattgt aattattttg      60
tgtacagttc tatactgtta tctgtgtcca tttccaaaac ttgcacgtgt ccctgaattc     120
```

<210> SEQ ID NO 755
<211> LENGTH: 185
<212> TYPE: DNA
<213> ORGANISM: Homo sapiens

<400> SEQUENCE: 755

```
aaggtttggc agaaattgtt ttttgagtgg ctcaccagag tacccagaag aatcagtatg      60
gaattagagg acagtggcct accctaaata aagacatgag tgatgtataa agtctagtgt     120
```

-continued

```
caatttattc agaaaatatc aaaattattc tgggagctat gggtcaaagt tgataggcac      180
aaaca                                                                  185

<210> SEQ ID NO 756
<211> LENGTH: 130
<212> TYPE: DNA
<213> ORGANISM: Homo sapiens

<400> SEQUENCE: 756
atcccaatag atatccccct atgtgcatgc acacctgcac actcacggct gaaatctccc      60
taacccaggg ggaccttagc atgcctaagt gactaaacca ataaaaatgt tctggtctgg     120
cctgaaaaaa                                                            130

<210> SEQ ID NO 757
<211> LENGTH: 86
<212> TYPE: DNA
<213> ORGANISM: Homo sapiens

<400> SEQUENCE: 757
aagcagacta cgagaaacac aaagtctacg cctgcgaagt cacccatcag ggcctgagct      60
cgcccgtcac aaagagcttc aacagg                                          86

<210> SEQ ID NO 758
<211> LENGTH: 264
<212> TYPE: DNA
<213> ORGANISM: Homo sapiens

<400> SEQUENCE: 758
ggtacacaaa tctggttctc aatggtgagg tgggatcaga gatattctcc ctgttgttca      60
gaggaacaat aattcggatg tttctctcca caatgtcctc attaggatct tcggaagaac     120
ggatgatcct ggaagtaatc cgggcacact tacatttgtt gtcaacaaga acaatccttt     180
catcttcttg ggctttcaca tgaacagcct taataaaaac cgccaggact ccccagaaaa     240
gcaaatggtt cttcatcttg accc                                            264

<210> SEQ ID NO 759
<211> LENGTH: 101
<212> TYPE: DNA
<213> ORGANISM: Homo sapiens

<400> SEQUENCE: 759
ttgataggga tagcattgaa ctatttgctc aactcaacat tttaggaatt tatttctgct      60
gtctagtgct caaaacttgc agctagaatt gagggaagag a                         101

<210> SEQ ID NO 760
<211> LENGTH: 233
<212> TYPE: DNA
<213> ORGANISM: Homo sapiens

<400> SEQUENCE: 760
tgcttatccg ttagccgtgg tgatttagca ggaagctgtg agagcagttt ggtttctagc      60
atgaagacag agcccacccc tcagatgcac atgagctggc gggattgaaa gatgctgtct     120
tcgtactggg aaagggattt tcagccctca gaatcgctcc accttgcagc tctcccttc      180 tctgtattcc tagaaactga cacatgctga acatcacagc ttatttcctc att            233

<210> SEQ ID NO 761
```

```
<211> LENGTH: 256
<212> TYPE: DNA
<213> ORGANISM: Homo sapiens

<400> SEQUENCE: 761
ctgaggtgct atgttcttag tggatgttct gaccctgctt caaatatttc cctcacettt      60 cccatcttcc aagggtataa ggaatctttc tgctttgggg tttatcagaa ttctcagaat     120
ctcaaataac taaaaggtat gcaatcaaat ctgcttttta aagaatgctc tttacttcat     180
ggacttccac tgccatcctc ccaaggggcc caaattcttt cagtggctac ctacatacaa     240
ttccaaacac atacag                                                     256

<210> SEQ ID NO 762
<211> LENGTH: 259
<212> TYPE: DNA
<213> ORGANISM: Homo sapiens

<400> SEQUENCE: 762
acagaagcca ttgcctccct tgtttacctt gggtccacct ccaccaaaac ccaacagacc      60
accaaatgtt gacctgacga aattccacaa aacctcttct ggaaacagta ctagcaaagg     120
ccagacgtct tactcaacaa cttccctgcc accacctcca ccatcccatc cggccagcca     180
accaccattg ccagcatctc acccatcaca accaccagtc ccaagcctac ctcccagaaa     240
cattaaacct ccgtttgac                                                  259

<210> SEQ ID NO 763
<211> LENGTH: 114
<212> TYPE: DNA
<213> ORGANISM: Homo sapiens

<400> SEQUENCE: 763
ggacctgtac accacgagca gccagctgac cctgccggcc acacagtgcc tagccggcaa      60
gtccgtgaca tgccacgtga agcactacac gaatcccagc caggatgtga ctgt           114

<210> SEQ ID NO 764
<211> LENGTH: 265
<212> TYPE: DNA
<213> ORGANISM: Homo sapiens

<400> SEQUENCE: 764
ggatttctcc aaaactaact gaatttaagc ttcaggtccc tttgtatgca gtagaaagga      60
attattaaaa acaccaccaa agaaaataaa tatatcctac ttgaaattta ctctatggac     120
ttacccactg ctagaataaa tgtatcaaat cttatttgta aattctcaat tttgatatat     180
atatgtatat atgcatatac atatccacac ttgtctgcaa gaatattgat taaaattgct     240
aaatttgtac ttgttcacca gaaaa                                           265

<210> SEQ ID NO 765
<211> LENGTH: 198
<212> TYPE: DNA
<213> ORGANISM: Homo sapiens

<400> SEQUENCE: 765
gcacagctca gcacaacatt ccaagctcaa aatagaagcc ttctcagtga gctccagcac      60
gcccagagga ctgttaataa cgatgatcca tgtgttttac tctaaagtgc taaatatggg     120
agtttccttt ttttactctt tgtcactgat gacacaacag aaaagaaact gtagaccttg     180
ggacaatcaa catttaaa                                                   198
```

<210> SEQ ID NO 766
<211> LENGTH: 162
<212> TYPE: DNA
<213> ORGANISM: Homo sapiens

<400> SEQUENCE: 766

```
atgttcatac tctaagtatc aaaatcttcc aattatcatg ctcacctgaa agaggtatgc    60
tctcttagga atacagtttc tagcattaaa caaataaaca aggggagaaa ataaaactca   120
aggagtgaaa atcaggaggt gtaataaaat gttcctcgca tt                      162
```

<210> SEQ ID NO 767
<211> LENGTH: 256
<212> TYPE: DNA
<213> ORGANISM: Homo sapiens

<400> SEQUENCE: 767

```
tcctgtttac ccttcaagtt tcaagttcat gtcactgtct cagagaggtt ttcctgtgct    60
cgccctgttt ctctcaggaa gccttgctct tttccatcat gcctctaatc acagcttata   120
atcggatatt tatttctgtg tctacagtct tgccctgcca gactgtatgc cccatgtggg   180
caggcgctca tgattgtttc tgattgtttc acgcatgctg ctaacccaga gcctgggccc   240
aaagctagtt agtact                                                   256
```

<210> SEQ ID NO 768
<211> LENGTH: 294
<212> TYPE: DNA
<213> ORGANISM: Homo sapiens

<400> SEQUENCE: 768

```
caaagggtga gagggcttcc ttctcaccct tctctccata agtatcttga agatccatgg    60
tttgttttgc tctattgttt agttttttact tgggtgcaat gtgtacgtca aaagttttta   120
ttttgatatt tgaaagagac caaatcaggc ccagaccgcc tctctggaag gtgttgtagg   180
ccattcaaaa cgcctccgga gtgtcgcaaa ccaagtgcgg aggggccctg aggttgtact   240
gtaaacatca tagtgacttg tcttttcaaa tatattccca ctattttcgc agaa         294
```

<210> SEQ ID NO 769
<211> LENGTH: 221
<212> TYPE: DNA
<213> ORGANISM: Homo sapiens

<400> SEQUENCE: 769

```
tgctggactc cgacggctcc ttcttcctct acagcaagct caccgtggac aagagcaggt    60
ggcagcaggg gaacatcttc tcatgctccg tgatgcatga ggctctgcac aaccgcttca   120
cgcagaagag cctctccctg tctccgggta aatgagtgcg acggccggca agcccccgct   180
ccccgggctc tcggggtcgc gcgaggatgc ttggcacgta c                       221
```

<210> SEQ ID NO 770
<211> LENGTH: 239
<212> TYPE: DNA
<213> ORGANISM: Homo sapiens

<400> SEQUENCE: 770

```
ggagaggcag cattgcacag tgaaagaatt ctggatatct caggagcccc gaaattctag    60
ctctgacttt gctgtttcca gtggtatgac cttggagaag tcacttatcc tcttggagcc   120
```
tcagtttcct catctgcaga ataatgactg acttgtctaa ttcgtaggga tgtgaggttc    180
tgctgaggaa atgggtatga atgtgccttg aacacaaagc tctgtcaata agtgataca    239

<210> SEQ ID NO 771
<211> LENGTH: 181
<212> TYPE: DNA
<213> ORGANISM: Homo sapiens

<400> SEQUENCE: 771
gaggaccgag cacagaaatc ttagagattt cttgtcccct ctcaggtcat gtgtagatgc    60
gataaatcaa gtgattggtg tgcctgggtc tcactacaag cagcctatct gcttaagaga    120
ctctggagtt tcttatgtgc cctggtggac acttgcccac catcctgtga gtaaaagtga    180
a                                                                    181

<210> SEQ ID NO 772
<211> LENGTH: 228
<212> TYPE: DNA
<213> ORGANISM: Homo sapiens

<400> SEQUENCE: 772
gggatgacat gcactcagct cttggctcca ctgggatggg aggagaggac aagggaaatg    60 tcagggcgg ggagggtgac agtggccgcc caaggcccac gagcttgttc tttgttcttt    120
gtcacaggga ctgaaaacct ctcctcatgt tctgctttcg attcgttaag agagcaacat    180
tttacccaca cacagataaa gttttcccct gaggaaacaa cagcttta                 228

<210> SEQ ID NO 773
<211> LENGTH: 136
<212> TYPE: DNA
<213> ORGANISM: Homo sapiens

<400> SEQUENCE: 773
caggacccat cacgcctgtg cagtggcccc cacagaaaga ctgagctcaa ggtgggaacc    60
acgtctgcta acttggagcc ccagtgccaa gcacagtgcc tgcatgtatt tatccaataa    120
atgtgaaatt ctgtcc                                                    136

<210> SEQ ID NO 774
<211> LENGTH: 193
<212> TYPE: DNA
<213> ORGANISM: Homo sapiens

<400> SEQUENCE: 774
gcagtctact agattgtgat cccttgagat atggaaggat gccttttttt ctctgcattt    60
aaaaaaatcc cccagcactt cccacagtgc ctattgatac ttggggaggg tgcttggcac    120
ttattgaata tatgatcggc catcaaggga agaactattg tgctcagaga cactgttgat    180
aaaaactcag gca                                                       193

<210> SEQ ID NO 775
<211> LENGTH: 175
<212> TYPE: DNA
<213> ORGANISM: Homo sapiens

<400> SEQUENCE: 775
aaatttaatt ttctacgcct ctggggatat ctgctcagcc aatggaaaat ctgggttcaa    60
ccagcccctg ccatttctta agactttctg ctgcactcac aggatcctga gctgcactta    120
cctgtgagag tcttcaaact tttaaacctt gccagtcagg acttttgcta ttgca         175

<210> SEQ ID NO 776
<211> LENGTH: 183
<212> TYPE: DNA
<213> ORGANISM: Homo sapiens

<400> SEQUENCE: 776

```
taaatattga gcagatctat aggaagattg aacctgaata ttgccattat gcttgacatg      60
gtttccaaaa aatggtactc cacatacttc agtgagggta agtattttcc tgttgtcaag     120
aatagcattg taaaagcatt ttgtaataat aaagaatagc tttaatgata tgcttgtaac     180
taa                                                                   183
```

<210> SEQ ID NO 777
<211> LENGTH: 235
<212> TYPE: DNA
<213> ORGANISM: Homo sapiens

<400> SEQUENCE: 777

```
taacttttc tcaaagtcac tgatgtttgt tcctgttaaa tgtatagcat tgtaatgaga       60
gcccatcaaa tcctgagtgt cagtttgttg tccctattgt agatgaaata gtgatgtagc     120
aaaaacctag taaattctga atgcttttcc acgtagactt atctggaatg tgaacacaac     180
tctttggtta atagtaaatg cttaactgta gtcctgagta ggtgcatttc tgtct          235
```

<210> SEQ ID NO 778
<211> LENGTH: 154
<212> TYPE: DNA
<213> ORGANISM: Homo sapiens

<400> SEQUENCE: 778

```
agtatatttt ctatcttctg gtgacttgag cttgagctct gacaggcatg ggcctctccg      60
accttcatca ctattcttag gataatgctg gcgggcagag atgatcaatc atcatattaa     120
atcataatga gcttataatc ctcccactgg aaaa                                 154
```

<210> SEQ ID NO 779
<211> LENGTH: 280
<212> TYPE: DNA
<213> ORGANISM: Homo sapiens

<400> SEQUENCE: 779

```
atcagaaagg gcaacttact cttcctggca tcttattgta ttggagggtg accaccctgg      60
gcatggggtg ttggcagggg tcaaaaagct tatttctttt aatctcttac tcaacgaaca     120
catcttctga tgatttccca aaattaatga gaatgagatg agtagagtaa gatttgggtg     180
ggatgggtag gatgaagtat attgcccaac tctatgtttc tttgattcta acacaattaa     240
ttaagtgaca tgattttac taatgtatta ctgagactag                            280
```

<210> SEQ ID NO 780
<211> LENGTH: 206
<212> TYPE: DNA
<213> ORGANISM: Homo sapiens

<400> SEQUENCE: 780

```
tattcttcta taacactcta tatagagcta tgtgagtact aatcacattg aataatagtt      60
ataaaattat tgtatagaca tctgcttctt aaacagattg tgagttcttt gagaaacagc     120
gtggatttta cttatctgtg tattcacaga gcttagcaca gtgcctggta atgagcaagc     180
```

```
atacttgcca ttactttcc ttccca                                          206
```

<210> SEQ ID NO 781
<211> LENGTH: 247
<212> TYPE: DNA
<213> ORGANISM: Homo sapiens

<400> SEQUENCE: 781

```
gctgaaattg tatctctcag taattttaga tgtcttttaa aaaattgaaa aacaaagtgt     60
tagactgtgt gcgtgtgcgt tgatgggcac tcaagagtcc cgtgagtcat ccagccctgc   120 ctttccctg cgccccatc ctctcacgtc ccgccctgcc tccacttggg gaccctgcct    180
cgtgtcgtct ttatctgcct attactcagc taaggaaac aagtacactc cacacatgca    240
taaagga                                                              247
```

<210> SEQ ID NO 782
<211> LENGTH: 190
<212> TYPE: DNA
<213> ORGANISM: Homo sapiens

<400> SEQUENCE: 782

```
gtggagaacc acagctgcag agtaggcagc tgcctccagg atgagttact tgaaatttgc     60
cttgagtgtg ttacctcctt tccaagctcc tcgtgataat gcagacttcc tggagtacaa   120
acacaggatt tgtaattcct tactgtaacg gagtttagag ccagggctga tgctttggtg    180
tggccagcac                                                           190
```

<210> SEQ ID NO 783
<211> LENGTH: 165
<212> TYPE: DNA
<213> ORGANISM: Homo sapiens

<400> SEQUENCE: 783

```
cccattgaaa agaccgagcc ttgtatgtat gttatggata cataaaatgc acgcaagcca     60
ttatctctcc atgggaagct aagttataaa ataggtgct tggtgtacaa aacttttat     120 atcaaaaggc tttgccattt ctatatgagt gggtttactg gtaaa                   165
```

<210> SEQ ID NO 784
<211> LENGTH: 260
<212> TYPE: DNA
<213> ORGANISM: Homo sapiens

<400> SEQUENCE: 784

```
gaacagagag aaagtgctcc gtaaaagtga gctgcgatgc ggaggtgggc aagctcttcc     60
ctggaggggg aagagctctc aacccagagg gatctgacca ggaaggttca ccccccctcc   120
acccaggaag cccctgcaga cagtatgtgt tttaggcttt gctggccaaa tggtctctgc    180
cgtgactact cagctctgcc attgtggctg cagagtgacc atagaccttc tgaaagtgaa    240
tgagtatgac tgtgttccaa                                                260
```

<210> SEQ ID NO 785
<211> LENGTH: 197
<212> TYPE: DNA
<213> ORGANISM: Homo sapiens

<400> SEQUENCE: 785

```
aaatggtaaa catgagggtg ctcttgtgac ttaattttg ttcaagggac taaattgctt     60
atgtttattc cctgtcagcg gagtggagaa tgtcattcat caataaacca aagccaatag   120
```

```
ctggagaatt gagatctggt tgaaagtggt ttatggttta catgctgtac tatcctgagg    180
aattgcgaga tattgct                                                   197

<210> SEQ ID NO 786
<211> LENGTH: 187
<212> TYPE: DNA
<213> ORGANISM: Homo sapiens

<400> SEQUENCE: 786
aaaacatctg gttcaattac gctgaactct gactacatgt gggccagtaa taatatgaat    60
tggacttaag aataaacctt gtgtttaatc tcttttttc cttaaaattt taatgtgagt    120
tttctgttac gcaaattatc catgttagca catttggaac aaatgtataa atgtactttc    180
tgaataa                                                              187

<210> SEQ ID NO 787
<211> LENGTH: 228
<212> TYPE: DNA
<213> ORGANISM: Homo sapiens

<400> SEQUENCE: 787
gggatgacat gcactcagct cttggctcca ctgggatggg aggagaggac aagggaaatg    60 tcagggggcgg ggagggtgac agtggccgcc caaggcccac gagcttgttc tttgttcttt   120
gtcacaggga ctgaaaacct ctcctcatgt tctgctttcg attcgttaag agagcaacat    180
tttacccaca cacagataaa gttttcccctt gaggaaacaa cagcttta                228

<210> SEQ ID NO 788
<211> LENGTH: 213
<212> TYPE: DNA
<213> ORGANISM: Homo sapiens

<400> SEQUENCE: 788
actctccgga ttgaccaagt tcatcctggg ctccattggg tctgccattg cggctgtcat    60
tgcgaggttc tactagctcc ctgccccctcg ccctgcagag aagagaacca tgccagggga   120
gaaggcaccc agccatcctg acccagcgag gagccaacta tcccaaatat acctggggtg    180
aaatatacca aattctgcat ctccagagga aaa                                 213

<210> SEQ ID NO 789
<211> LENGTH: 104
<212> TYPE: DNA
<213> ORGANISM: Homo sapiens

<400> SEQUENCE: 789
gttggtgtgc tgaggtgtta gagagggacc atgtgtcact tgtgctttgc tcttgtccca    60
cgtgtcttcc actttgcata tgagccgtga actgtgcata gtgc                     104

<210> SEQ ID NO 790
<211> LENGTH: 132
<212> TYPE: DNA
<213> ORGANISM: Homo sapiens

<400> SEQUENCE: 790
acattgattc cccatcgctg aaggacagaa ttcattgtgt ggcatttgta tttgatgcca    60
gctctattca atacttctcc tctcagatga tagtaaagat caaaagaatt cgaagggagt    120
tggtaaacgc tg                                                        132
```

<210> SEQ ID NO 791
<211> LENGTH: 281
<212> TYPE: DNA
<213> ORGANISM: Homo sapiens

<400> SEQUENCE: 791

| | | | | | |
|---|---|---|---|---|---|
| gttattaaca | gtcctctggg | cgtgctggag | ctcactgaga | aggcttctat | tttgagcttg | 60 |
| gaatgttgtg | ctgagctgtg | cagcctgttc | ctgcatctgt | tgttcctgca | ttttctgttg | 120 |
| ctctgccagc | caattttgtt | tggctatctc | catttaactc | acttgttcct | gatggagtct | 180 |
| ctccctctcc | tgcatcattt | gctcgttctg | cctttgaatc | gccgccaacc | tttgcgcttc | 240 |
| agccttttca | gcttctgctt | tcacttgtgc | ctctgaggag | a | | 281 |

<210> SEQ ID NO 792
<211> LENGTH: 239
<212> TYPE: DNA
<213> ORGANISM: Homo sapiens

<400> SEQUENCE: 792

| | | | | | |
|---|---|---|---|---|---|
| gggagggtaa | cctcactctt | ctccaggcca | ggcctccttg | gactcccctg | ggggtgtccc | 60 |
| actcttcttc | cctctaaact | gccccacctc | ctaacctaat | cccccgccc | cgctgccttt | 120 |
| cccaggctcc | cctcacccca | gcgggtaatg | agcccttaat | cgctgcctct | aggggagctg | 180 |
| attgtagcag | cctcgttagt | gtcaccccct | cctccctgat | ctgtcagggc | cacttagtg | 239 |

<210> SEQ ID NO 793
<211> LENGTH: 174
<212> TYPE: DNA
<213> ORGANISM: Homo sapiens

<400> SEQUENCE: 793

| | | | | | |
|---|---|---|---|---|---|
| ggtcctgtag | ccctaagtgg | tactaacttt | ccttcattca | acccacctgc | gtctcatact | 60 |
| cacctcaccc | cactgtggct | gatttggaat | tttgtgcccc | catgtaagca | ccccttcatt | 120 |
| tggcattccc | cacttgagaa | ttaccctttt | gccccgaaca | tgttttttctt | ctcc | 174 |

<210> SEQ ID NO 794
<211> LENGTH: 270
<212> TYPE: DNA
<213> ORGANISM: Homo sapiens

<400> SEQUENCE: 794

| | | | | | |
|---|---|---|---|---|---|
| aaataaccac | tttttgttgg | gcaatatgaa | attttttaaag | gagtagaata | ccaaatgata | 60 |
| gaaacagact | gcctgaattg | agaattttga | tttcttaaag | tgtgtttctt | tctaaattgc | 120 |
| tgttccttaa | tttgattaat | ttaattcatg | tattatgatt | aaatctgagg | cagatgagct | 180 |
| tacaagtatt | gaaataatta | ctaattaatc | acaaatgtga | agttatgcat | gatgtaaaaa | 240 |
| atacaaacat | tctaattaaa | ggctttgcaa | | | | 270 |

<210> SEQ ID NO 795
<211> LENGTH: 276
<212> TYPE: DNA
<213> ORGANISM: Homo sapiens

<400> SEQUENCE: 795

| | | | | | |
|---|---|---|---|---|---|
| gagtaagctc | tagtccctct | gtcctgtaga | aagagccctg | aagaatcagc | aattttgttg | 60 |
| ctttattgtg | gcatctgttc | gaggtttgct | tcctctttaa | gtctgtttct | tcattagcaa | 120 |
| tcatatcagt | tttaatgcta | ctactaacaa | tgaacagtaa | caataatatc | cccctcaatt | 180 |

```
aatagagtgc tttctatgtg caaggcactt ttcacgtgtc acctatttta acctttccaa      240
ccacataaat aaaaaaggcc attattagtt gaatct                                276
```

<210> SEQ ID NO 796
<211> LENGTH: 264
<212> TYPE: DNA
<213> ORGANISM: Homo sapiens

<400> SEQUENCE: 796

```
taacttttc tcaaagtcac tgatgtttgt tcctgttaaa tgtatagcat tgtaatgaga       60
gcccatcaaa tcctgagtgt cagtttgttg tccctattgt agatgaaata gtgatgtagc     120
aaaaacctag taaattctga atgcttttcc acgtagactt atctggaatg tgaacacaac    180
tctttggtta atagtaaatg cttaactgta gtcctgagta ggtgcatttc tgtctgtctc    240
aataaatttt actttgtctg caaa                                            264
```

<210> SEQ ID NO 797
<211> LENGTH: 275
<212> TYPE: DNA
<213> ORGANISM: Homo sapiens

<400> SEQUENCE: 797

```
tattccatct actttctat cgccgtcccc ttttgcagcc ctctctgggg atggactggg       60
taaatgttga cagaggccct gccccgttca cagatcctgg ccctgagcca gcctgtgct     120 cctccctccc ccaacactcc ctaccaaccc cctaatcccc tactccctcc acccccctc    180 cactgtaggc cactggatgg tcatttgcat ctccgtaaat gtgctctgct cctcagctga    240
gagagaaaaa aataaactgt atttggctgc aagaa                                275
```

<210> SEQ ID NO 798
<211> LENGTH: 210
<212> TYPE: DNA
<213> ORGANISM: Homo sapiens

<400> SEQUENCE: 798

```
agaggctctt ctgcgtgtag tggttgtgca gagcctcatg catcacggag catgagaaga     60 cgttccctg ctgccacctg ctcttgtcca cggtgagctt gctatagagg aagaaggagc    120
cgtcggagtc cagcacggga ggcgtggtct tgtagttgtt ctccggctgc ccattgctct    180
cccactccac ggcgatgtcg ctgggataga                                      210
```

<210> SEQ ID NO 799
<211> LENGTH: 235
<212> TYPE: DNA
<213> ORGANISM: Homo sapiens

<400> SEQUENCE: 799

```
gagtgtctca gaagtgtgct cctctggcct cagttctcct cttttggaac aacataaaac      60
aaatttaatt ttctacgcct ctggggatat ctgctcagcc aatggaaaat ctgggttcaa    120
ccagcccctg ccatttctta agactttctg ctccactcac aggatcctga gctgcactta    180
cctgtgagag tcttcaaact tttaaaccct gccagtcagg acttttgcta ttgca          235
```

<210> SEQ ID NO 800
<211> LENGTH: 162
<212> TYPE: DNA
<213> ORGANISM: Homo sapiens

<400> SEQUENCE: 800

| | | | | | |
|---|---|---|---|---|---|
| ggacataaca | gacttggaag | cagatgatac | agacttcttt | ttttcataat | caggttagtg | 60 |
| taagaaattg | ccatttgaaa | caatccattt | tgtaactgaa | ccttatgaaa | tatatgtatt | 120 |
| tcatggtacg | tattctctag | cacagtctga | gcaattaaat | ag | | 162 |

<210> SEQ ID NO 801
<211> LENGTH: 249
<212> TYPE: DNA
<213> ORGANISM: Homo sapiens

<400> SEQUENCE: 801

| | | | | | |
|---|---|---|---|---|---|
| aggccctctt | gagagtctat | ccagggaccc | attgttttac | tttaacagac | cagaaaagat | 60 |
| gtttgttttc | catgtcatta | cccccagggg | ataccgaatg | tgtgggtaga | aatttctctg | 120 |
| tagattaaaa | atcagatttt | tacatggatt | caacaaagga | gcgtcacttg | gattttgtt | 180 |
| ttcatccatg | aatgtagctg | cttctgtgta | aatgccatt | ttgctattaa | aaatcaattc | 240 |
| acgctggaa | | | | | | 249 |

<210> SEQ ID NO 802
<211> LENGTH: 200
<212> TYPE: DNA
<213> ORGANISM: Homo sapiens

<400> SEQUENCE: 802

| | | | | | |
|---|---|---|---|---|---|
| aagtgtttgc | tgaggacatt | gctcctctga | ctcccatctc | actttgtcca | tcgcagcctt | 60 |
| ttgttgggag | atgacactgt | cagtcagccc | atgatgtctg | ttcacacgag | atgctttttt | 120 |
| aatagaattg | accaatgttt | tgctgccact | gattaaagta | ttatttatac | taattgttgc | 180 |
| ttgtagtttt | gatgtaattc | | | | | 200 |

<210> SEQ ID NO 803
<211> LENGTH: 150
<212> TYPE: DNA
<213> ORGANISM: Homo sapiens

<400> SEQUENCE: 803

| | | | | | |
|---|---|---|---|---|---|
| ctagttactg | tggtatggct | aatacctgtc | aacatttgga | ggcaatccta | ccttgctttt | 60 |
| gcttctagag | cttagcatat | ctgattgttg | tcaggccata | ttatcaatgt | ttactttttt | 120 |
| ggtactataa | aagctttctg | ccaccccta | | | | 150 |

<210> SEQ ID NO 804
<211> LENGTH: 142
<212> TYPE: DNA
<213> ORGANISM: Homo sapiens

<400> SEQUENCE: 804

| | | | | | |
|---|---|---|---|---|---|
| tgtggcatgc | ttttctgagc | cttcctactt | taaagcatgg | aacatgcagg | tgatttggga | 60 |
| agtgtagaaa | gacctgagaa | aacgagcctg | tttcagagga | acatcgtcac | aacgaatact | 120 |
| tctggaagct | taacaaaact | aa | | | | 142 |

<210> SEQ ID NO 805
<211> LENGTH: 224
<212> TYPE: DNA
<213> ORGANISM: Homo sapiens

<400> SEQUENCE: 805

| | | | | | |
|---|---|---|---|---|---|
| tgtagcagct | tgtgttgtca | cgcttcttct | tttgagcaac | tttcttacac | tgaagaaagg | 60 |

```
cagaatgagt gcttcagaat gtgatttcct actaacctgt tccttggata ggcttttttag    120 tatagtattt ttttttttgtc attttctcca tcagcaacca gggagactgc acctgatgga    180
aaagatatat gactgcttca tgacattcct aaactatctt tttt                      224
```

<210> SEQ ID NO 806
<211> LENGTH: 176
<212> TYPE: DNA
<213> ORGANISM: Homo sapiens

<400> SEQUENCE: 806

```
ggctgagcaa ggcacatagt ctactcagtc tattcctaag tcctaactcc tccttgtggt     60
gttggatttg taaggcactt tatccctttt gtctcatgtt tcatcgtaaa tggcataggc    120
agagatgata cctaattctg catttgattg tcactttttg tacctgcatt aattta        176
```

<210> SEQ ID NO 807
<211> LENGTH: 250
<212> TYPE: DNA
<213> ORGANISM: Homo sapiens
<220> FEATURE:
<221> NAME/KEY: misc_feature
<222> LOCATION: (221)..(221)
<223> OTHER INFORMATION: n is a, c, g, or t

<400> SEQUENCE: 807

```
tagaacagga tggagggcaa gacctgtgta agaagaagtc ttaaactgta aacatgggtg     60
tagtgagggt agtgtggcta agaggaaatg gatccagatg ggcttgatgg ggagcagatg    120
ggcaggcacg atggcagggg tgcatcggct cactggggct gcatctgagg taaatggaaa    180
taaaggaggt gaggaaatga ggaagagaag gaagtggcgg nactggctgt ggagttttgt    240
gggagccttc                                                           250
```

<210> SEQ ID NO 808
<211> LENGTH: 178
<212> TYPE: DNA
<213> ORGANISM: Homo sapiens

<400> SEQUENCE: 808

```
taccagaata ggagttttcc tctgtggacc tgaagccttg gctgaaaccc tgagtaaaca     60
aagcatctcc aactctgagt ctggccctcg gggagtgcat ttcattttca acaaggaaaa    120
cttctaactt gtctcttcca tgaggaaata aatgtgggtt gtgctgccaa atgctcaa     178
```

<210> SEQ ID NO 809
<211> LENGTH: 229
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, or t

<400> SEQUENCE: 809

```
gtagttagaa aaagcctcct aggtgatttt gatgaatccc agtctcanat ttcttcattt     60
ggaaatgata atgtaggcca cacgtattac tggagaaaaa tgtgctcccg agactttcca    120
gagcagcaga gctgggacta ggcaggtgag gcagctacgt gcaagtgtag ccctgagaat    180 gagcaccctct ttaagaatg taccttgcgt tagttctgtg cctgtttaa                229
```

<210> SEQ ID NO 810

```
<211> LENGTH: 278
<212> TYPE: DNA
<213> ORGANISM: Homo sapiens
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t

<400> SEQUENCE: 810
gaaagttggc tcgtaatatg atttaatatt caaagtagag tcatctacct attagcttgc      60
tggcgtggtc ctagtttatg cctgtttcag catgattgtt gagtaccctg tttcatcctt    120
agcattttct tgattttgtt gttaaatgat gtataccctt atttccattg aatctgtgct    180 tccaccccc caactgaagt tgtnttccct ttgcttggcc acccttacan cctnttggat     240
ggtgtatcct acagtgtaag cactaaactg aagaggca                              278

<210> SEQ ID NO 811
<211> LENGTH: 243
<212> TYPE: DNA
<213> ORGANISM: Homo sapiens

<400> SEQUENCE: 811
atcatagctc actgagattg ccaggttcga caaagaggaa tttataggat ggggatatag     60
ggtagacttg actctgcttt atccgggaaa gcttttaaaa ctctgagcca gttaactttg    120
agtaagcata aaacatactg tattggtgtt tgtattttc atgccacaat attaaaatgg     180
aattttaaat gtagattatt ataatctata aagataagt atgcatgtat taggatactg    240
gaa                                                                   243

<210> SEQ ID NO 812
<211> LENGTH: 151
<212> TYPE: DNA
<213> ORGANISM: Homo sapiens

<400> SEQUENCE: 812
aaatttgtaa atgggattga gtccctaaaa cctggaaaaa ctgacatggg ctagctattt     60
attcactcat cgagttactt attccttcgt aaaaaaaaaa aaaaaaaat catttgagat     120 gataaaaatg gtagggtata gtttaagatg a                                   151

<210> SEQ ID NO 813
<211> LENGTH: 84
<212> TYPE: DNA
<213> ORGANISM: Homo sapiens

<400> SEQUENCE: 813
cgcccgggca ggtactggat gtcaggtctg cgaaacttct tagattttga cctcagtcca     60
taaaccacac tatcacctcg gccg                                            84

<210> SEQ ID NO 814
<211> LENGTH: 252
<212> TYPE: DNA
<213> ORGANISM: Homo sapiens

<400> SEQUENCE: 814
```

```
tgagcttccc ttggacacta actcttccca gatgatgaca atgaaattag tgcctgtttt      60
cttgcaaatt tagcacttgg aacatttaaa gaaaggtcta tgctgtcata tggggtttat     120
tgggaactat cctcctggcc ccaccctgcc ccttcttttt ggttttgaca tcattcattt     180
ccacctggga atttctggtg ccatgccaga agaatgagg aacctgtatt cctcttcttc      240
gtgataatat aa                                                         252
```

<210> SEQ ID NO 815
<211> LENGTH: 272
<212> TYPE: DNA
<213> ORGANISM: Homo sapiens

<400> SEQUENCE: 815

```
aatgttgtgt gtggtgattg ttcaggtcga atctgttgta tccagtacag ctttaggtct      60
tcagctgccc ttctggcgag tacatgcaca ggattgtaaa tgagaaatgc agtcatattt     120
ccagtctgcc tctatgatga tgttaaatta ttgctgttta gctgtgaaca agggatgtac     180
cactggagga atagagtatc cttttgtaca cattttgaaa tgcttcttct gtagtgatag     240
aacaaataaa tgcaacgaat actctgtcaa aa                                   272
```

<210> SEQ ID NO 816
<211> LENGTH: 185
<212> TYPE: DNA
<213> ORGANISM: Homo sapiens

<400> SEQUENCE: 816

```
gccacaagct gtccagtcta atcgacagga ttccgattcc tgaacagtgt cattcgaatc      60
agaatgtcag agctgagtct gctgttctga cttaaggaac aacttgactc agtctcttga     120
tggctggaga atgcacatcc tagctgtcac tggggctaca ggcaggtcag tgagcacgct     180
aaaat                                                                 185
```

<210> SEQ ID NO 817
<211> LENGTH: 256
<212> TYPE: DNA
<213> ORGANISM: Homo sapiens

<400> SEQUENCE: 817

```
gcagcaagat ggtgttgcag acccaggtct tcatttctct gttgctctgg atctctggtg      60
cctacgggga catcgtgatg acccagtctc cagactccct ggctgtgtct ctgggcgaga     120
gggccaccat caagtgcaag tccagccaga gtattttata taggtccaac aacaagaact     180
acttagcttg gtaccagcag aaagcaggac agcctcctaa attgttcatt tactgggcat     240
ctacccggga atccgg                                                     256
```

<210> SEQ ID NO 818
<211> LENGTH: 146
<212> TYPE: DNA
<213> ORGANISM: Homo sapiens

<400> SEQUENCE: 818

```
aggtcggggc actctgagtc ccagttccca gtgcagctgt aggtcgtcat cacctaacca      60
cacgtgcaat aaagtcctcg tgcctgctgc tcacagcccc cgagagcccc tcctcctgga     120
gaataaaacc tttggcagct gccctt                                          146
```

<210> SEQ ID NO 819

```
<211> LENGTH: 122
<212> TYPE: DNA
<213> ORGANISM: Homo sapiens

<400> SEQUENCE: 819
ccagacgtca accaggaaca tgtaacttgg agagggacga agaaagggtc tgataaacac    60
agaggtttta aacagtccct accattggcc tgcatcatga caaagttaca aattcaagga   120
ga                                                                  122

<210> SEQ ID NO 820
<211> LENGTH: 225
<212> TYPE: DNA
<213> ORGANISM: Homo sapiens

<400> SEQUENCE: 820
gaagagtctg ttgccgagct ggactggaaa gccccaaaat cccaggattt cttcttcttt    60
tcttcttcca gctccttctc tctgaccttc tgcaatgcac ccctgtatac ctggtcctgg   120
cagtagacaa tctgttccat ctggaagtgg aggcggatca gcttctcacc ttctctctct   180
tgttctgctc taatgtcttc aattttggac ttggcggttc tgtgg                   225

<210> SEQ ID NO 821
<211> LENGTH: 274
<212> TYPE: DNA
<213> ORGANISM: Homo sapiens

<400> SEQUENCE: 821
ggattatacc cgtcttagtc tcgatcattg ctttcacttg tgccactgag ctggaccttc    60
gcacctggag gaggtgcctc tttgcctcat cacctgactc cacaagaaac aagggcagct   120
cctcatcact gggcttcacc actttcaggg taaggtggat ggtcttctct ttgtcaatgc   180
cataagatga gaggcttctc cgtggcttta agatcttgga gcccagcaaa gaacctggt    240 cctgcacagg aaccttggta gtagaccgga ccca                               274

<210> SEQ ID NO 822
<211> LENGTH: 256
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (221)..(221)
<223> OTHER INFORMATION: n is a, c, g, or t

<400> SEQUENCE: 822
ttgctgataa ttcaaattct gtactttggc aagcaaaaga ggtacaacat caccttggag    60
ttttacaatt taataatgca tactttaaaa ttcatgataa atcatggaac cccactatac   120
tcactaattc aactattgat ttcttttttga gcaactgact ttatgattta tccttaaaag  180
taaggaagta taccagaagg ncaaanggat aaatccaccc ntaaatacta gagtctaagt   240
tattttcctg aaaagg                                                   256

<210> SEQ ID NO 823
<211> LENGTH: 143
```

```
<212> TYPE: DNA
<213> ORGANISM: Homo sapiens

<400> SEQUENCE: 823
gttgtcccca cagtagacac atatgatggc cgaggtgata gtgtggttta tggactgagg    60
tcaaaatcta agaagtttcg cagacctgac atccagtacc ctgatgctac agacgaggac   120
atcacctcac acatggaaag cga                                           143

<210> SEQ ID NO 824
<211> LENGTH: 199
<212> TYPE: DNA
<213> ORGANISM: Homo sapiens

<400> SEQUENCE: 824
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt tttttactct ttgtcactga tgacacaaca gaaaagaaac tgtagacctt   180
gggacaatca acatttaaa                                                199

<210> SEQ ID NO 825
<211> LENGTH: 224
<212> TYPE: DNA
<213> ORGANISM: Homo sapiens

<400> SEQUENCE: 825
ccttgacccc agtacgaagt ctatgccctg aatccccaga gtagcccttc ctggtgccca    60
actggcctgg ggacaaacag cgtccactac atctaggact gccggctaag tggacacact   120
tcttgacctc ctaccaggaa ctttggtaaa agctagcttt ggggaagggg ttgggtgtaa   180
atatgagagg gtggagggag accagctggt agcaataaac atgg                    224

<210> SEQ ID NO 826
<211> LENGTH: 263
<212> TYPE: DNA
<213> ORGANISM: Homo sapiens

<400> SEQUENCE: 826
gagatcactt ggtaactggt ttcatgtgta tccaaaaatc agcatttgga tttaagcttt    60
ctgaatttgg tagtttaaga aacagattta gttttcaat ggttttaact catgtgaaat    120
aatgattttc caccagctct gatgcaaaga gatataattt taatgaacga tttatccagc   180
agtgtgttcc aggggttgcc tctccttatc tacggggatt actttgtaca tgcagataag   240
ttttcgcaaa cctatttcca ttt                                           263

<210> SEQ ID NO 827
<211> LENGTH: 252
<212> TYPE: DNA
<213> ORGANISM: Homo sapiens

<400> SEQUENCE: 827
cactgtgtat gactgaaatt tctggaataa ctgtaaatgg ttatgttaat ggaataaaac    60
acaaatgttg aaaaatgtaa aatatatata catagattca aatccttata tatgtatgct   120
tgttttgtgt acaggatttt gtttttttctt tttaagtaca ggttcctagt gttttactat   180
aactgtcact atgtatgtaa ctgacatata taaatagtca tttataaatg accgtattat   240
aacatttgaa aa                                                       252
```

<210> SEQ ID NO 828
<211> LENGTH: 226
<212> TYPE: DNA
<213> ORGANISM: Homo sapiens

<400> SEQUENCE: 828
agatccactg aacatctgtg tctttatttt gctgcttgta tttattgtag tcaaatgctt    60
tacatcagaa tgatgaaaat aggcttgcca ctttctctta ttttaattcc atggtagtca   120
atgaactggc tgccacttta ataactga aaattcattt tgagaccaag caggatcaag    180
tttgtagaat aaacactggt ttcctagcca tcctctgaaa acagta                  226

<210> SEQ ID NO 829
<211> LENGTH: 100
<212> TYPE: DNA
<213> ORGANISM: Homo sapiens

<400> SEQUENCE: 829
tagaattacc tatcacattt cccaatcttg actattcaga atgctgttta tttagtgatg    60
aggattagca cttgattgaa gattctttta aaatactatc                         100

<210> SEQ ID NO 830
<211> LENGTH: 239
<212> TYPE: DNA
<213> ORGANISM: Homo sapiens

<400> SEQUENCE: 830
ttctttgagg gctcgcatcc aaaagaatat aacactccaa gcatgaaaga gtggcagcaa    60
atttcatcac tgtatacttt caatccgaag ggccagtact acagcatgtt gcacaaatat   120
gtcaacagaa aagagaagac tcacagtatc aggtctactg aaggagatac ggtgattcct   180
gttcttggct ttgtagattc atctggtata aacagcactc ctgagttatg accttttga    239

<210> SEQ ID NO 831
<211> LENGTH: 292
<212> TYPE: DNA
<213> ORGANISM: Homo sapiens

<400> SEQUENCE: 831
catcttagtg cctttatctg tctttatgtc ttggggttgg ggtaggtaga taccaaatga    60
aacactttca ggaccttcct tcctcttgca gttgttcttt aatctccttt actagaggag   120
ataaatattt tgcatataat gaagaaattt ttctagtata taacgcaggc ctttttatttt   180 ctaaaatgat gatagtataa aaatgttagg ataacagaat gattttagat tttccagaga   240
atattataaa gtgctttagg tatgaaaata aatcatcttt gtctgattaa aa           292

<210> SEQ ID NO 832
<211> LENGTH: 207
<212> TYPE: DNA
<213> ORGANISM: Homo sapiens

<400> SEQUENCE: 832
atatttccgg tcatctctgg tggtgagagg ctggtgttct gttttgagga tatcccttta    60
aatctcccaa atgactgtct ctatcttcat gagtgtgact tgaggtgttg ggatgggtga   120
gggagcttct ctaaagagga aagtgagtgg attaacccct gcttctcttc ttgttccctg   180
ttatcattcc tccccaacat aataata                                       207

```
<210> SEQ ID NO 833
<211> LENGTH: 183
<212> TYPE: DNA
<213> ORGANISM: Homo sapiens

<400> SEQUENCE: 833
aaaatctgat tttgcagcga tcactttaa accctgtagt gatgtaagac taaaatataa      60
ttgctaagat tttgttggtt aatgtaaaga tatgactttt ctgcactgta ctctcttcat    120
aggattgtaa aggtgttcta atccaattgc atgatgtagt aagcctctta aatatgtgtg   180
tta                                                                  183

<210> SEQ ID NO 834
<211> LENGTH: 151
<212> TYPE: DNA
<213> ORGANISM: Homo sapiens

<400> SEQUENCE: 834
gtcttttgcg aaagggattg caggttcaga aggcatctta ccatggctgg ggaattgtct     60
ggtggtgggg ggcaggggac agaggccatg aaggagcaag ttttgtattt gtgacctcag   120
ctttgggaat aaaggatctt ttgaaggcca a                                   151

<210> SEQ ID NO 835
<211> LENGTH: 233
<212> TYPE: DNA
<213> ORGANISM: Homo sapiens

<400> SEQUENCE: 835
ttggcttcct tcctggcaag gaccaggcag tggggaagga ggaggtcctc cgtggtacat     60
actgggtcag gcactagcat ggaggagggt cacagagtgg ggcacgtgag gacccatgga   120
accgtcctgg tgcccaggcc ctcacaagta ccaaagccag caccaaagga gtcagggaag   180
gggttggctg agtcaaggga ccccagaggg caccaggaat aaaatcttct tga           233

<210> SEQ ID NO 836
<211> LENGTH: 211
<212> TYPE: DNA
<213> ORGANISM: Homo sapiens

<400> SEQUENCE: 836
aaatcggggt ccaggaaatc ctcaccagaa tctggcactg cagccaaagg cgatacttcc     60
agagttctag taggctgcta tggaatttct ggcatgaaaa ttcttgaccc ctcacacttt   120
accccctgta cagcacaggc ataccatgga gatattacag gatcagttcc agaccaccat   180
aataaagtgg atatcgcaat aaagtgagtc a                                   211

<210> SEQ ID NO 837
<211> LENGTH: 270
<212> TYPE: DNA
<213> ORGANISM: Homo sapiens

<400> SEQUENCE: 837
ctttaaaggt gggttttttgc tgtgataaat gaatacggta ctctgaagga gaaaaaagtt     60
tctcaaatga gcttaaactg caagtgattt aaaaattaga gaatataatt cttaaagcta   120
ttgaaagttt caaccagaaa acctcaagtg aattttgtat gtaaatgaaa tcttgaatgt   180
aagttctgtg attctttaag caaacaatta gctgaaaact tggtattgtt gtagtttatg   240
tagtaagtga cttggcaccc atcagaaaat                                     270
```

```
<210> SEQ ID NO 838
<211> LENGTH: 253
<212> TYPE: DNA
<213> ORGANISM: Homo sapiens

<400> SEQUENCE: 838
gctttgtaaa gtgcatgtgg aattaatggg acagtgtgcc ctttgtgtta gatgttagag      60
caaaagaaag ggcttatagt gttagtattg gagcactttg aagatagata ttttcagaaa     120
agatgtagga tttaaaagtt aaattttaaa ttttagaaaa agatatgatg gcaattggaa     180
atagtcacaa tgaagttctt catccagtag gtgtttaaca gtgttatttt gccactggta     240
atgtgtaaac tgt                                                        253

<210> SEQ ID NO 839
<211> LENGTH: 194
<212> TYPE: DNA
<213> ORGANISM: Homo sapiens

<400> SEQUENCE: 839
ctaggcctgg catggcacct gtcgcccagt gccctggggc tgatctcagg gaagcccagc      60
tccagggcca gatgagcaga agctctcgat ggacaatgaa cggccttgct ggggggccgcc    120 ctgtaccctc tttcaccttt ccctaaagac cctaaatctg aggaatcaac agggcagcag    180
atctgtatat tttt                                                      194

<210> SEQ ID NO 840
<211> LENGTH: 217
<212> TYPE: DNA
<213> ORGANISM: Homo sapiens

<400> SEQUENCE: 840
aaactggtgg tggaatgcgt catgaaaggc gtcacttcca cgagagttta tgagagagca      60
taagccaagg gacgttgacc tggactgaag ttcgcattga actctacaac attcgtgggg    120
atatattgtt caaaagata ttgttgtttt ccctgattta gcaagcaagt aattttctcc     180
caagctgatt ttattcaata tggttacgtt ggttaaa                              217

<210> SEQ ID NO 841
<211> LENGTH: 180
<212> TYPE: DNA
<213> ORGANISM: Homo sapiens

<400> SEQUENCE: 841
tcctgacttc taataacatt gatgtcaaga aaatgacggt cacagaccag gtgaactgcc      60
ccaagctctc gtaaccaggt tctacaggga ggctgcaccc actccatgtt acttctgctt    120
cgctttcccc taccccaccc cccccccata aagacaaacc aatcaaccac gacaaaggaa    180

<210> SEQ ID NO 842
<211> LENGTH: 262
<212> TYPE: DNA
<213> ORGANISM: Homo sapiens

<400> SEQUENCE: 842
gtattttcct tacatgtaca gtagacgttc tctattctat cagccttcta tggtacctttt      60 ttgtcaggac aattaggatt gtaatgctaa tgcaaaggca gcaattcaaa gatcttctag     120
tgcctcatga ataaagttga gatttaaaat ttgtaacatt gatggaacag ctgggaggtt     180
agaccaatca ttaaggaatg tatgccatag cttctctttgc taccataaac attttggagg    240
```

```
tgcatctgct atgtgacatg gt                                          262
```

<210> SEQ ID NO 843
<211> LENGTH: 274
<212> TYPE: DNA
<213> ORGANISM: Homo sapiens

<400> SEQUENCE: 843

```
ttccttttct tcgtggccaa tgccataatc cacctcttct gcttcagttg aggtgacacg   60
tctcagcctt agccctgtgc ccctgaaac agctgccacc atcactcgca agagaatccc   120
ctccatcttt gggaggggtt gatgccagac atcaccaggt tgtagaagtt gacaggcagt  180
gccatggggg caacagccaa aatagggggg taatgatgta ggggccaagc agtgcccagc  240
tgggggtcaa taaagttacc cttgtacttg caaa                              274
```

<210> SEQ ID NO 844
<211> LENGTH: 289
<212> TYPE: DNA
<213> ORGANISM: Homo sapiens

<400> SEQUENCE: 844

```
ttcatgtggc tgtagatccc aagatgactg ggtgggagg tcttgctaga atgggaaggg   60
tcatagaaag ggccttgaca tcagttcctt tgtgtgtact cactgaagcc tgcgttggtc  120
cagagcggag gctgtgtgcc tgggggagtt ttcctctata catctctccc caaccctagg  180
ttccctgttc ttcctccagc tgcaccagag caacctctca ctccccatgc cacgttccac  240
agttgccacc acctctgtgg cattgaaatg agcacctcca ttaaagtct              289
```

<210> SEQ ID NO 845
<211> LENGTH: 255
<212> TYPE: DNA
<213> ORGANISM: Homo sapiens

<400> SEQUENCE: 845

```
aaccagccgt attttacatg aagctgtata attaattgtc attatttttg ttagcaaaga   60
ttaaatgtgt cattggaagc catccctttt tttacatttc atacaacaga aaccagaaaa  120
gcaatactgt ttccatttta aggatatgat taatattatt aatataataa tgatgatgat  180
gatgatgaaa actaaggatt tttcaagaga tctttctttc caaaacatttt ctggacagta  240 cctgattgta tttttt                                                  255
```

<210> SEQ ID NO 846
<211> LENGTH: 166
<212> TYPE: DNA
<213> ORGANISM: Homo sapiens

<400> SEQUENCE: 846

```
attcctgtca ttacccattg taacagagcc acaaactaat actatgcaat gttttaccaa   60
taatgcaata caaaagacct caaaatacct gtgcatttct tgtaggaaaa caacaaaagg  120
taattatgtg taattatact agaagttttg taatctgtat cttatc                 166
```

<210> SEQ ID NO 847
<211> LENGTH: 198
<212> TYPE: DNA
<213> ORGANISM: Homo sapiens

<400> SEQUENCE: 847

```
gcactggcga ggagagggcg ctcctctctg cacacctact agtcaccaga gactttaggg      60
ggtgggattc cactcgtgtg tttctatttt ttgaaaagca gacattttaa aaaatggtca     120
cgtttggtgc ttctcagatt tctgaggaaa ttgctttgta ttgtatatta caatgatcac     180
cgactgaaaa tattgttt                                                   198

<210> SEQ ID NO 848
<211> LENGTH: 187
<212> TYPE: DNA
<213> ORGANISM: Homo sapiens

<400> SEQUENCE: 848
atccggagaa ttgcctctac ctggaccttt tgtctcacac agcagtaccc tgacctgctg      60
tgcaccttac attcctagag agcagaaata aaaagcatga ctatttccac catcaaatgc     120
tgtagaatgc ttggcactcc ctaaccaaat gctgtctcca taatgccact ggtgttaaga     180
tatattt                                                               187

<210> SEQ ID NO 849
<211> LENGTH: 93
<212> TYPE: DNA
<213> ORGANISM: Homo sapiens

<400> SEQUENCE: 849
atatcttgtt ttctgccaat agatttttta aaatgtagtc agcaaaatgg gggtggggaa      60
gcagagcatg tcctagttca atgttgactt ttt                                   93

<210> SEQ ID NO 850
<211> LENGTH: 257
<212> TYPE: DNA
<213> ORGANISM: Homo sapiens

<400> SEQUENCE: 850
aaaagcttcc ccaactaaag cctagaagag cttctgaggc gctgctttgt caaaaggaag      60
tctctaggtt ctgagctctg gctttgcctt ggctttgcca gggctctgtg accaggaagg     120
aagtcagcat gcctctagag gcaaggaggg gaggaacact gcactcttaa gcttccgccg     180
tctcaacccc tcacaggagc ttactggcaa acatgaaaaa tcggcttacc attaaagttc     240
tcaatgcaac cataaaa                                                    257

<210> SEQ ID NO 851
<211> LENGTH: 197
<212> TYPE: DNA
<213> ORGANISM: Homo sapiens

<400> SEQUENCE: 851
ccacagcagg ccaggtccag agagaccgag gagggagagt ctcccaggga gcatgagagg      60
aggcagcagg actgtcccct tgaaggagaa tcatcaggac cctggacctg atacggctcc     120
ccagtacacc ccacctcttc cttgtaaata tgatttatac ctaactgaat aaaaagctgt     180
tctgtcttcc cacccaa                                                    197

<210> SEQ ID NO 852
<211> LENGTH: 151
<212> TYPE: DNA
<213> ORGANISM: Homo sapiens

<400> SEQUENCE: 852
ataaaaaacc aacaaaggat ctcacatttt cttaaaaagt gaagattgct gtatactatt      60
```

```
tattcaactt ataatttatg ttactccttg atctttgtct tttgtcatga caaagcattt      120
atttaataaa gttatgcatt cagttaaaaa a                                     151

<210> SEQ ID NO 853
<211> LENGTH: 273
<212> TYPE: DNA
<213> ORGANISM: Homo sapiens

<400> SEQUENCE: 853
tgtctgacct ccgtgcctag tcgtggctct ccatcttgtc tcctcccgt gtccccaatg       60 tcttcagtgg ggggccccct cttgggtccc ctcctctgcc atcacctgaa gaccccacg      120 ccaaacactg aatgtcacct gtgcctgccg cctcggtcca ccttgcggcc cgtgtttgac    180
tcaactcaac tcctttaacg ctaatatttc cggcaaaatc ccatgcttgg gttttgtctt    240
taaccttgta acgcttgcaa tcccaataaa gca                                  273

<210> SEQ ID NO 854
<211> LENGTH: 284
<212> TYPE: DNA
<213> ORGANISM: Homo sapiens

<400> SEQUENCE: 854
catctctttg atgtcatatg gaagagttaa aacaggtgga gaaattcctt gattcacaat      60
gaaatgctct cctttcccct gccccccagac cttttatcca cttacctaga ttctacatat    120
tctttaaatt tcatctcagg cctccctcaa ccccaccact tcttttataa ctagtccttt    180
actaatccaa cccatgatga gctcctcttc ctggcttctt actgaaaggt taccctgtaa    240
catgcaattt tgcatttgaa taaagcctgc ttttttaagtg ttaa                     284

<210> SEQ ID NO 855
<211> LENGTH: 245
<212> TYPE: DNA
<213> ORGANISM: Homo sapiens

<400> SEQUENCE: 855
ggtgaaattc ttcaccaaca tttcatttgc tcctttgtca tattgtaatg ccaatataat      60
atagttaatg aaaacagcat ttttaaaaac cgaaatattg aaatggtgta atgttgtacc    120
atttgcactg tgagcaaatg ctaatacagt aaatatattg tgtttgctga caatcagccg    180
gcctataaat ctccttattt tatttcttgt ttttatagca taaagcttta gtttggcctg    240
aaaaa                                                                 245

<210> SEQ ID NO 856
<211> LENGTH: 268
<212> TYPE: DNA
<213> ORGANISM: Homo sapiens

<400> SEQUENCE: 856
attgccactc tgctccttgc tttgggagtc ttctgctttg ctggacatga gactggaagg      60
ctgtctgggg ctgccgacac acaagctctg ttgaggaatg accaggtcta tcagcccctc    120
cgagatcgag atgatgctca gtacagccac cttgaggaa actgggctcg gaacaagtga    180
acctgagact ggtggcttct agaagcagcc attccaact gtaccttccc ttcttgctca    240
gccaataaat atatcctctt tcactcag                                        268

<210> SEQ ID NO 857
```

```
<211> LENGTH: 251
<212> TYPE: DNA
<213> ORGANISM: Homo sapiens

<400> SEQUENCE: 857
tgggccatga ttatcttaaa ggcattattc tccagcctta agatcttagg acgtttcctt      60
tgctatgatt tgtacttgct tgagtcccat gactgtttct cttcctctct ttcttccttt     120
tggaatagta atatccatcc tatgtttgtc ccactattgt attttggaag cacataactt     180
gtttggtttc acaggttcac agttaagaag gaattttgcc tctgaataaa tagaatcttg     240
agtctcatgc a                                                          251

<210> SEQ ID NO 858
<211> LENGTH: 32
<212> TYPE: DNA
<213> ORGANISM: Homo sapiens

<400> SEQUENCE: 858
ctcagcccaa cttcttaccc gaaagcatca ct                                    32

<210> SEQ ID NO 859
<211> LENGTH: 268
<212> TYPE: DNA
<213> ORGANISM: Homo sapiens

<400> SEQUENCE: 859
aatggacatc attttagcac actagcggtt tatattttaa ggaccttcat tctctgttct      60
gcacctcttc tggaaattga gtaaattttg cttttttttt tttactcagt tgcaacttac     120
gcttggcatc ttcagaatgc ttttctagca ttaagagatg taaatgataa aggaattatt     180
gtatgaaata ttacaaagcg tagactatgc attgttattc attataatat tttttgctgt     240
cataatcgcc tcataaagac aggtttca                                        268

<210> SEQ ID NO 860
<211> LENGTH: 259
<212> TYPE: DNA
<213> ORGANISM: Homo sapiens

<400> SEQUENCE: 860
cttggagata gctcttaaag atataaatgt ttatggctga aatgttatgg catcttggat      60 ttgcttttaaa ataacccagc ttgctgcagg aggtgggtat tgtgtgtgtg ggaaggtggg    120
gaggctgcgg gaggaagaga tgacccaaga ttaggcagat gttgttaact gtggaagcag    180
ggtggtgagt gggggctcat gacattatgc tctctacttt gtgtacgtgt gaacatttcc    240
gtaataaaag atgccttca                                                 259

<210> SEQ ID NO 861
<211> LENGTH: 166
<212> TYPE: DNA
<213> ORGANISM: Homo sapiens

<400> SEQUENCE: 861
gattttgcaa ttgtggtaaa tagcaaataa caatcttgta ttctaacata atctgcagtt      60
gtctgtatgt gttttaacta ttacagtgca tgttagggag aaattccctg aatttcttta     120
gttttgtatt caaacaatta tgccactcga tgcaacaaac ataata                    166

<210> SEQ ID NO 862
<211> LENGTH: 158
```

```
<212> TYPE: DNA
<213> ORGANISM: Homo sapiens

<400> SEQUENCE: 862
aatctaacta actaactcat ttatttctat taaaaaggta ttgtccttta ggcggggaat    60
gggaatcctt gctgcactgt tgcagtcatt ctgaaaggac ctttccctgt acttaccttt   120
caacatgctt caatcttatc aacgctacat tttgtatt                           158

<210> SEQ ID NO 863
<211> LENGTH: 88
<212> TYPE: DNA
<213> ORGANISM: Homo sapiens

<400> SEQUENCE: 863
tgtgtgtcac tatctccgtt tgctctcggt tcccttcaat aacaatgaat ggtgctttct    60
tctgaaagac tcagcctaat taaaggat                                       88

<210> SEQ ID NO 864
<211> LENGTH: 168
<212> TYPE: DNA
<213> ORGANISM: Homo sapiens

<400> SEQUENCE: 864
gcaatgttta gtatattcag ctgtatctgt agaaactctt tgacgaacct caatttaacc    60
aatttgatga ataccccagtt ctcttctttt ctagagaaag atagttgcaa cctcacctcc  120
ctcactcaac actttgaata cttattgttt ggcaggtcat ccacacac                168

<210> SEQ ID NO 865
<211> LENGTH: 237
<212> TYPE: DNA
<213> ORGANISM: Homo sapiens

<400> SEQUENCE: 865
taagccacac agtgaatcct gtccttcaga gatggagagg tgataaaagt agaatgctca    60
ggtgtaattg gtttacggga attaaactgt tataaaaaca taaggtaaca ttcagaaatc   120
agagagcctc tgtttaaccc ttaaagacac aattaatgct tctaatactg taactactga   180
tctccctctt tctcctcagc tactcttttcc ccaaacagta gcacctcctc tttactt      237

<210> SEQ ID NO 866
<211> LENGTH: 277
<212> TYPE: DNA
<213> ORGANISM: Homo sapiens

<400> SEQUENCE: 866
gagaaaaagc ctttagggac cctgaaccaa tgaatctgaa attccccaac tgccagatgt    60
atcttcattt ttcattttcc gggagatgta atatgtccta aaaatcacag tcgctagatt   120
gaaatcaacc ttaaaaatca tctagtccaa tgtctactcc cagtccacta cttgaatccc   180
ctgtgtcccc tcccagtagt cgtcttgaca acctccactg aaaggcaatt tctacactcc   240 atccaccccca ccaaccc atggttcatg atctctt                              277

<210> SEQ ID NO 867
<211> LENGTH: 280
<212> TYPE: DNA
<213> ORGANISM: Homo sapiens
<220> FEATURE:
<221> NAME/KEY: misc_feature
<222> LOCATION: (55)..(63)
```

<223> OTHER INFORMATION: n is a, c, g, or t

<400> SEQUENCE: 867

```
gatcttcata agagcacctg gaggaggggg gtggggtgtt tgtgtttgtt taaannnnnn        60
nnngtgaaaa aaatgaagat aggcattttg tagacaatct ggaagttctg gaccggaatc       120
catgatgtag tcagggaaga aatgacccgt gtccagtaac cccaggcctc gagtgtgtgg       180
tgtattttc  tacataattg taatcattct atacatacaa attcatgtct tgaccatcat       240
attaatattt ggtaagtttc tctctcttta gagactccac                             280
```

<210> SEQ ID NO 868
<211> LENGTH: 89
<212> TYPE: DNA
<213> ORGANISM: Homo sapiens

<400> SEQUENCE: 868

```
ggttgctatg cgaaagcaag actgtggttt cattccaatt tcctgtatat cggaatcatc        60
accatctgtg tatgtgtgat tgaggtgtt                                          89
```

<210> SEQ ID NO 869
<211> LENGTH: 274
<212> TYPE: DNA
<213> ORGANISM: Homo sapiens

<400> SEQUENCE: 869

```
cccttactta catactagct tccaaggaca ggtggaggta gggccagcct ggcgggagtg        60
gagaagccca gtctgtccta gtaaggac   aaagccaggt ctaatggtac tgggtagggg       120
gcactgccaa gacaataagc taggctactg gtccagcta  ctactttggt gggattcagg       180
tgagtctcca tgcacttcac atgttaccca gtgttcttgt tacttccaag gagaaccaag       240
aatggctctg tcacactcga agccaggttt gatc                                   274
```

<210> SEQ ID NO 870
<211> LENGTH: 135
<212> TYPE: DNA
<213> ORGANISM: Homo sapiens

<400> SEQUENCE: 870

```
tggtatttgc cgctgtgttt ttaaataact ttgtctatct gtcttgactt cttagctttg        60
gattttgaga actgacttcc cgccctggtt gaggattcag ctttcttact gtgccttcct       120
catgcacatg tgcct                                                        135
```

<210> SEQ ID NO 871
<211> LENGTH: 221
<212> TYPE: DNA
<213> ORGANISM: Homo sapiens

<400> SEQUENCE: 871

```
gtaagccttc tataaccaag acattataaa tccaaggtag gtggttggtt gttttgggtg        60
tataattcag aggttcaaaa tggaaatgac cttgctctaa tgaaactctg ttcccatcac       120
ataattgata ggcaatgttt ctcaccattt atatgatacg gactaaaaca aggaatggaa       180
ttgatattga acccttggca aaataacat  tcatccatag g                           221
```

<210> SEQ ID NO 872
<211> LENGTH: 245
<212> TYPE: DNA
<213> ORGANISM: Homo sapiens

<400> SEQUENCE: 872

```
gctggtacca agctaagtag ttcttattgt tggagctgta taaaacactc tggctggact    60
tgcagttgat ggtggccctc tcgcccagag acacagccag ggagtctgga gactgggtca   120
tcacgatgtc cccgtaggca ccagagatcc agagcaacag agaaatgaag acctgggtct   180
gcaacaccat cttgctgccc ctgcctgcct gttgtagctc agttcacaat gcaaacggcc   240
cgttt                                                              245
```

<210> SEQ ID NO 873
<211> LENGTH: 292
<212> TYPE: DNA
<213> ORGANISM: Homo sapiens

<400> SEQUENCE: 873

```
atttccattt acctcagatg cagccccagt gagccgatgc acccctgcca tcgtgcctgc    60
ccatctgctc cccatcaagc ccatctggat ccatttcctc ttagccacac taccctcact   120
acacccatgt ttacagttta agacttcttc ttacacaggt cttgccctcc atcctgttct   180
acctttcctc ctctcttgct ctctaccttg cgtcttccaa acatgaagcc ctcatcccag   240
cacccgacac cctgaccctc tccaaactct gggcatactc tctcccactg gg           292
```

<210> SEQ ID NO 874
<211> LENGTH: 292
<212> TYPE: DNA
<213> ORGANISM: Homo sapiens

<400> SEQUENCE: 874

```
tctggaagtg actatgcctg agtcccaggg tgcggcaggt aggaaacatt cacagatgaa    60
gacagcagat tccccacatt ctcatctttg gcctgttcaa tgaaaccatt gtttgcccat   120
ctcttcttag tggaacttta ggtctctttt caagtctcct cagtcatcaa tagttcctgg   180
ggaaaaacag agctggtaga cttgaagagg agcattgatg ttgggtggct tttgttcttt   240
cactgagaaa ttcggaatac atttgtctca cccctgatat tggttcctga tg           292
```

<210> SEQ ID NO 875
<211> LENGTH: 90
<212> TYPE: DNA
<213> ORGANISM: Homo sapiens

<400> SEQUENCE: 875

```
actgtaggaa caagcatgat cttgttactg tgatatttta aatatccaca gtactcactt    60
tttccaaatg atcctagtaa ttgcctagaa                                     90
```

<210> SEQ ID NO 876
<211> LENGTH: 75
<212> TYPE: DNA
<213> ORGANISM: Homo sapiens

<400> SEQUENCE: 876

```
ctttatgaga attctcaggc tgaactatag gccattgttc ccaggcaaat caatacatca    60
atgcatcctc aaaaa                                                    75
```

<210> SEQ ID NO 877
<211> LENGTH: 208
<212> TYPE: DNA
<213> ORGANISM: Homo sapiens

```
<400> SEQUENCE: 877
tttccccatg tgctttagtg ggctttggtt ttcttttgt gcgagtgtgt gtgagaatgg      60
ctgtgtggtg agtgtgaact tgttctgtg atcatagaaa gggtatttta ggctgcaggg     120
gagggcaggg ctggggaccg aaggggacaa gttcccttt catcctttgg tgctgagttt    180
tctgtaaccc ttggttgcca gagataaa                                       208

<210> SEQ ID NO 878
<211> LENGTH: 148
<212> TYPE: DNA
<213> ORGANISM: Homo sapiens

<400> SEQUENCE: 878
accagaattt atggatgaac tgattgctta tattttagtc agggtttata aatgtagatg      60
gtcaaattta cattgcctag tgatggaaaa ttcaactttt tttgattttt tttccaata    120 ttaaaaaagg ctctgtatgc atggtggg                                        148

<210> SEQ ID NO 879
<211> LENGTH: 207
<212> TYPE: DNA
<213> ORGANISM: Homo sapiens
<220> FEATURE:
<221> NAME/KEY: misc_feature
<222> LOCATION: (182)..(182)
<223> OTHER INFORMATION: n is a, c, g, or t

<400> SEQUENCE: 879
ctgcaaaagc cgagatgggt tccatgcagt tctccagtgg gacatcagtg cttatccgaa      60
tgtcatcaat ggcaatctct ccggaacgtc ctttccctat cactccctcg aacacaatct    120
ggtactccat gtcgtagctg gcaggatga tccgcccgtg cttccactcg ccgccctggt    180
cntcacggat gacccacagc aacttgc                                         207

<210> SEQ ID NO 880
<211> LENGTH: 233
<212> TYPE: DNA
<213> ORGANISM: Homo sapiens

<400> SEQUENCE: 880
ggtggtttgg cctctaattt aattctgatt cagactctcc tgtcaggact caagaaaatt      60
taattaatta ccaaggatta agtcttctgg ttaaggtttc tgggaaaaaa aaatagcaaa    120
gatgttgatt tcttggaatc cttttacagg ttcataacag aaaaatcttc attccctgta    180
ggcatttaat taaacctagt tgagaagtgt gtgggattcc tcaattatga aca             233

<210> SEQ ID NO 881
<211> LENGTH: 254
<212> TYPE: DNA
<213> ORGANISM: Homo sapiens

<400> SEQUENCE: 881
gaagcaatgt gccaaaggtc atgattctta tcacggatgg gaaatcatca gatgctttca      60
gagatcctgc gataaaactg aggaattcag atgttgaaat ctttgcagtt ggtgtgaagg    120
atgccgttcg ctcagaattg gaagctattg cctctcctcc tgcagagacc catgtgttca    180
cagtggaaga ttttgatgct tttcagagga tatcttttga actcacacag tctatctgcc    240
ttagaattga gcaa                                                       254
```

```
<210> SEQ ID NO 882
<211> LENGTH: 244
<212> TYPE: DNA
<213> ORGANISM: Homo sapiens

<400> SEQUENCE: 882 aatgcccttta atgtgagggt ttgtaatggt gcttattaag accaaagact tgttaaatgt      60
atacaccaag tggtaatgaa atttcgtgac tggcccacac gtgcatagag gtctgggagg     120
accaggaaac agcctcagtg ccagaggat caccagtgca tccttcatca cagcatgtgc     180
aatatgccaa gattacccctc ggtcattcct gtcaacaagg ggtcaatgtc ataaatgtca     240
caat                                                                  244

<210> SEQ ID NO 883
<211> LENGTH: 291
<212> TYPE: DNA
<213> ORGANISM: Homo sapiens

<400> SEQUENCE: 883
gaagcatagc acctttcagt atctaaaata taaacaagaa tagtaagtcc atcccagctt      60
ctagagatga ggtagctcat gctaagaaat gttgggtcat ttttcctatg aaagttcaaa     120
ggccaaatgg tctaattcca atcatcacat ttgattagag tcagctccac aactcagttt     180
ctagatcttt ttcttcatta taggcttcag gatgatgaga ttgtacatgt ggaagagtct     240
caatttagag tccttggaca tatgtttgta aagttctata tgtcacctcg t              291

<210> SEQ ID NO 884
<211> LENGTH: 191
<212> TYPE: DNA
<213> ORGANISM: Homo sapiens

<400> SEQUENCE: 884
caaacagagt gaactttctg ccaagatgcg ggagtggttt tcagagacat ttcagaaagt      60
gaaggagaaa ctcaagattg actcatgagg acctgaaggg tgacatccca ggaggggcct     120
ctgaaatttc ccacacccca gcgcctgtgc tgaggactcc ctccatgtgg ccccaggtgc     180
caccaataaa a                                                          191

<210> SEQ ID NO 885
<211> LENGTH: 238
<212> TYPE: DNA
<213> ORGANISM: Homo sapiens
<220> FEATURE:
<221> NAME/KEY: misc_feature
<222> LOCATION: (194)..(206)
<223> OTHER INFORMATION: n is a, c, g, or t

<400> SEQUENCE: 885
aagatggcta gaatggtgcc tttctgagtg tctaaaactt gacacccctg gtaaatcttt      60
caacacactt ccactgcctg cgtaatgaag ttttgattca tttttaacca ctggaatttt     120
tcaatgccgt cattttcagt tagatgattt tgcactttga gattaaaatg ccatgtctat     180
ttgattagtc ttannnnnnn nnnnnnacag gcttatcatt ctcactgttg gctgtcat      238

<210> SEQ ID NO 886
<211> LENGTH: 188
<212> TYPE: DNA
<213> ORGANISM: Homo sapiens

<400> SEQUENCE: 886
```

```
gcacaccaga ttcagggaga ctgaccacca agggatagtg taaaaggaca tttttctcagt    60 tgggtccatc agcagttttt cttcctgcat ttattgttga aaactattgt ttcatttctt   120
cttttatagg ccttattact gcttaatcca aatgtgtacc attggtgaga cacatacaat   180
gctctgaa                                                            188
```

```
<210> SEQ ID NO 887
<211> LENGTH: 191
<212> TYPE: DNA
<213> ORGANISM: Homo sapiens
<220> FEATURE:
<221> NAME/KEY: misc_feature
<222> LOCATION: (38)..(51)
<223> OTHER INFORMATION: n is a, c, g, or t

<400> SEQUENCE: 887
```

```
gaggtgtcaa acagcagagt gtactttcca aagaacannn nnnnnnnnnn nacacagcaa    60
atcccaagcc ttcccagtct cacacctttc cacccattca taaaaaaaca cacgaatttc   120
tcgcaagttc caatatcact gtctctttat catctaaata gggccagttg gacacctcat   180
tgaaacaaaa a                                                        191
```

```
<210> SEQ ID NO 888
<211> LENGTH: 288
<212> TYPE: DNA
<213> ORGANISM: Homo sapiens
<220> FEATURE:
<221> NAME/KEY: misc_feature
<222> LOCATION: (114)..(145)
<223> OTHER INFORMATION: n is a, c, g, or t
<220> FEATURE:
<221> NAME/KEY: misc_feature
<222> LOCATION: (219)..(232)
<223> OTHER INFORMATION: n is a, c, g, or t

<400> SEQUENCE: 888
```

```
tatatttcca tgtctgctgt aatgtatcca agtcttgtaa agaccaataa tttattaatt    60
ttaataagac agaaagtatt tctccttcta gtctcatcgt ctgatttgaa aggnnnnnnn   120
nnnnnnnnnn nnnnnnnnnn nnnnngtgag ttccaggaag aaatgttttt ctttttttcat  180 ataaaatggt agctgtatgt atgtaactct gaattaaann nnnnnnnnnn nncagtcact   240
ctggttctaa atccttattg ggcaagctgg agttttgaag tgacccaa               288
```

```
<210> SEQ ID NO 889
<211> LENGTH: 189
<212> TYPE: DNA
<213> ORGANISM: Homo sapiens

<400> SEQUENCE: 889
```

```
accacacaag cagtgactcc taaagaagtt cagaggaagg agagaaccca tggggagggg    60
gtgcagtggg ggtgggtcag ggtgggctcc ctggagggga aattggtcta ggcaaggatg   120
cagactggcc agtaaggtgg gtccatgcag gaagctgagg gaggtggaag gcccgtgggt   180
ctcgagcgc                                                          189
```

```
<210> SEQ ID NO 890
<211> LENGTH: 269
<212> TYPE: DNA
<213> ORGANISM: Homo sapiens

<400> SEQUENCE: 890
```

```
ttccttcttg gcctaactct tccagttagg atctagaact ttgccttttt ttttttttt    60
```

```
tttttttttga gatgggttct cactatattg tccaggctag agtgcagtgg ctattcacag    120
atgcgaacat agtacactgc agcctccaac tcctagcctc aagtgatcct cctgtctcaa    180
cctcccaagt aggattacaa gcatgcgccg acgatgccca gaatccagaa ctttgtctat    240
cactctcccc aacaacctag atgtgaaaa                                      269

<210> SEQ ID NO 891
<211> LENGTH: 183
<212> TYPE: DNA
<213> ORGANISM: Homo sapiens

<400> SEQUENCE: 891
gagagttcaa ctaagaaagg tcacatatgt gaaagcccaa ggacactgtt tgatatacag     60
caggtattca atcagtgtta tttgaaacca aatctgaatt tgaagtttga atcttctgag    120
ttggaatgaa tttttttcta gctgagggaa actgtatttt tctttcccca aagaggaatg    180
taa                                                                  183

<210> SEQ ID NO 892
<211> LENGTH: 187
<212> TYPE: DNA
<213> ORGANISM: Homo sapiens

<400> SEQUENCE: 892
ccttcatgct gccttcaaag ctagatcatg tttgccttgc ttagagaatt actgcaaatc     60
agccccagtg cttggcgatg catttacaga tttctaggcc ctcagggttt tgtagagtgt    120
gagccctggt gggcagggtt ggggggtctg tcttctgctg gatgctgctt gtaatccatt    180
tggtgta                                                              187

<210> SEQ ID NO 893
<211> LENGTH: 183
<212> TYPE: DNA
<213> ORGANISM: Homo sapiens

<400> SEQUENCE: 893
ttctgtgtct gaagtgtaag tgaacacaga agagtgacat gtttacaaac ctcaagccag     60
ccttgctcct ggctggggcc tgttgaagat gcttgtattt tacttttcca ttgtaattgc    120
tatcgccatc acagctgaac ttgttgagat ccccgtgtta ctgcctatca gcattttact    180
act                                                                  183

<210> SEQ ID NO 894
<211> LENGTH: 272
<212> TYPE: DNA
<213> ORGANISM: Homo sapiens

<400> SEQUENCE: 894
tcctcacccc ggtatgaatg tgtttcctcc acattgtata tccttccacc ctctggctgc     60
ctagatcagt aaataaaatt gatgtaatat aatttataag taacactgtt gaaaccctga    120
tcccagtgga ggctgtaacc cacctgcccc cgcaccaccc ccctgacccc tgttaccgca    180
tttgtgtgta ttaatgctga agaattaaat gtttaaagag tttaaatttt gaaggcgttt    240
gctatataca gttgtcctgc attattataa ag                                  272

<210> SEQ ID NO 895
<211> LENGTH: 224
<212> TYPE: DNA
```

<213> ORGANISM: Homo sapiens

<400> SEQUENCE: 895

| | |
|---|---|
| aggccattct gagccacact gaaaaggaaa atgggaattt ataacccagt gagttcagcc | 60 |
| tttaagatac cttgatgaag acctggacta ttgaatggag cagaaattca cctctctcac | 120 |
| tgactattac agttgcattt ttatggagtt cttcttctcc taggattcct aagactgctg | 180 |
| ctgaatttat aaaaattaag tttgtgaatg tgactactta gtgg | 224 |

<210> SEQ ID NO 896
<211> LENGTH: 191
<212> TYPE: DNA
<213> ORGANISM: Homo sapiens

<400> SEQUENCE: 896

| | |
|---|---|
| caaacagagt gaactttctg ccaagatgcg ggagtggttt tcagagacat ttcagaaagt | 60 |
| gaaggagaaa ctcaagattg actcatgagg acctgaaggg tgacatccca ggagggcct | 120 |
| ctgaaatttc ccacacccca gcgcctgtgc tgaggactcc ctccatgtgg ccccaggtgc | 180 |
| caccaataaa a | 191 |

<210> SEQ ID NO 897
<211> LENGTH: 217
<212> TYPE: DNA
<213> ORGANISM: Homo sapiens

<400> SEQUENCE: 897

| | |
|---|---|
| aggttagatt ctcattcacg ggactagtta gctttaagca ccctagagga ctagggtaat | 60 |
| ctgacttctc acttcctaag ttccttcta tatcctcaag gtagaaatgt ctatgttttc | 120 |
| tactccaatt cataaatcta ttcataagtc tttggtacaa gtttacatga taaaaagaaa | 180 |
| tgtgatttgt cttcccttct ttgcactttt gaaataa | 217 |

<210> SEQ ID NO 898
<211> LENGTH: 174
<212> TYPE: DNA
<213> ORGANISM: Homo sapiens

<400> SEQUENCE: 898

| | |
|---|---|
| tccccagagt tcttgcaccc tcattccctc gggaccctcc cagtgagaag ggcctgctct | 60 |
| gcttttcctg tctgtatata acttatttgc cctaagaact ttgagaatcc caattattta | 120 |
| ttttaatgta ttttttagac cctctattta cctgcgaact tgtgtttata ataa | 174 |

<210> SEQ ID NO 899
<211> LENGTH: 269
<212> TYPE: DNA
<213> ORGANISM: Homo sapiens

<400> SEQUENCE: 899

| | |
|---|---|
| ttccttcttg gcctaactct tccagttagg atctagaact ttgccttttt tttttttttt | 60 |
| ttttttttga gatgggttct cactatattg tccaggctag agtgcagtgg ctattcacag | 120 |
| atgcgaacat agtacactgc agcctccaac tcctagcctc aagtgatcct cctgtctcaa | 180 |
| cctcccaagt aggattacaa gcatgcgccg acgatgccca gaatccagaa ctttgtctat | 240 |
| cactctcccc aacaacctag atgtgaaaa | 269 |

<210> SEQ ID NO 900
<211> LENGTH: 231

<212> TYPE: DNA
<213> ORGANISM: Homo sapiens

<400> SEQUENCE: 900

```
aaaacttggc acttttttcgt gtggatcttg ccacatttct gatcagaggt gtacactaac    60
atttcccccg agctcttggc ctttgcattt atttatacag tgccttgctc ggggcccacc   120
accccctcaa gccccagcag ccctcaacag gcccagggag ggaagtgtga gcgccttggt   180
atgacttaaa attggaaatg tcatctaacc attaagtcat gtgtgaacac a            231
```

<210> SEQ ID NO 901
<211> LENGTH: 186
<212> TYPE: DNA
<213> ORGANISM: Homo sapiens

<400> SEQUENCE: 901

```
taggtggtag atattgaggc caagaatatt gcaaaataca tgaagcttca tgcacttaaa    60
gaagtatttt tagaataaga atttgcatac ttacctagtg aaacttttct agaattattt   120
ttcactctaa gtcatgtatg tttctctttg attatttgca tgttatgttt aataagctac   180
tagcaa                                                              186
```

<210> SEQ ID NO 902
<211> LENGTH: 159
<212> TYPE: DNA
<213> ORGANISM: Homo sapiens

<400> SEQUENCE: 902

```
caccctcaga tgcacatgag ctggcgggat tgaaggatgc tgtcttcgta ctgggaaagg    60
gattttcagc cctcagaatc gctccacctt gcagctctcc ccttctctgt attcctagaa   120
actgacacat gctgaacatc acagcttatt tcctcattt                          159
```

<210> SEQ ID NO 903
<211> LENGTH: 295
<212> TYPE: DNA
<213> ORGANISM: Homo sapiens

<400> SEQUENCE: 903

```
aggatccatc ctattgtcaa tgagatgttc tcatccagaa gccatagaat cctgaataat    60
aattctaaaa gaaacttcta gagatcatct ggcaatcgct tttaaagact cggctcaccg   120
tgagaaagag tcactcacat ccattcttcc cttgatggtc cctattcctc cttcccttgc   180
ttcttggact tcttgaaatc aatcaagact gcaaaccctt tcataaagtc ttgccttgct   240
gaactccctc tctgcaggca gcctgccttt aaaaatagtt gctgtcatcc acttt        295
```

<210> SEQ ID NO 904
<211> LENGTH: 175
<212> TYPE: DNA
<213> ORGANISM: Homo sapiens

<400> SEQUENCE: 904

```
ccccacgtga cagtgcctgg gaatgtatta ttctgcagca tgacctgtga ccagcactgt    60
ctcagtttca ctttcacata gatgtccctt tcttggccag ttatcccttc cttttagcct   120
agttcatcca atcctcactg ggtggggtga ggaccactcc tgtacactga atatt        175
```

<210> SEQ ID NO 905
<211> LENGTH: 228
<212> TYPE: DNA

<213> ORGANISM: Homo sapiens

<400> SEQUENCE: 905

| | |
|---|---|
| gttgtggggt caaccgtaca atggtgtggg agtgacgatg atgtgaatat ttagaatgta | 60 |
| ccatattttt tgtaaattat ttatgttttt ctaaacaaat ttatcgtata ggttgatgaa | 120 |
| acgtcatgtg ttttgccaaa gactgtaaat atttatttat gtgttcacat ggtcaaaatt | 180 |
| tcaccactga aaccctgcac ttagctagaa cctcattttt aaagatta | 228 |

<210> SEQ ID NO 906
<211> LENGTH: 293
<212> TYPE: DNA
<213> ORGANISM: Homo sapiens

<400> SEQUENCE: 906

| | |
|---|---|
| agaggtcttt aatcattggt tcggctgctt ttatgtagtt taggctggaa atggtttcac | 60 |
| ttgctctttg actgtcagca agactgaaga tggcttttcc tggacagcta gaaaacacaa | 120 |
| aatcttgtag gtcattgcac ctatctcagc cataggtgca gtttgcttct acatgatgct | 180 |
| aaaggctgcg aatgggatcc tgatggaact aaggactcca atgtcgaact cttctttgct | 240 |
| gcattccttt tcttcactt acaagaaagg cctgaatgga ggacttttct gta | 293 |

<210> SEQ ID NO 907
<211> LENGTH: 137
<212> TYPE: DNA
<213> ORGANISM: Homo sapiens

<400> SEQUENCE: 907

| | |
|---|---|
| gtcagacaga tgtggttgca tcctaactcc atgtctctga gcattagatt tctcatttgc | 60 |
| caataataat acctccctta gaagtttgtt gtgaggatta ataatgtaa ataaagaact | 120 |
| agcataacac tcaaaaa | 137 |

<210> SEQ ID NO 908
<211> LENGTH: 267
<212> TYPE: DNA
<213> ORGANISM: Homo sapiens

<400> SEQUENCE: 908

| | |
|---|---|
| gccttctggc tgacaatcct ggaaatctgt tctccagaat ccaggccaaa aagttcacag | 60 |
| tcaaatgggg aggggtattc ttcatgcagg agaccccagg ccctggaggc tgcaacatac | 120 |
| ctcaatcctg tcccaggccg gatcctcctg aagcccttt cgcagcactg ctatcctcca | 180 |
| aagccattgt aaatgtgtgt acagtgtgta taaaccttct tcttcttttt tttttttaa | 240 |
| actgaggatt gtcattaaac acagttg | 267 |

<210> SEQ ID NO 909
<211> LENGTH: 254
<212> TYPE: DNA
<213> ORGANISM: Homo sapiens

<400> SEQUENCE: 909

| | |
|---|---|
| aattcagtgg tgtgagtata ttcataagat ttatacttgg tgtctattca taagacttat | 60 |
| atccagcata ttcataacta gagccatatc acagatgcat tcatcataat aattccagac | 120 |
| attttcatca ccctaaaagg aaaccctgaa acccattagc agtcattccc cattcctcca | 180 |
| acccattctc tccctaatcc ctagaaacca ccaatctgct gtgtatttca tctattgcca | 240 |
| acatttcata taaa | 254 |

<210> SEQ ID NO 910
<211> LENGTH: 162
<212> TYPE: DNA
<213> ORGANISM: Homo sapiens

<400> SEQUENCE: 910

```
tacgttatgt atttgacaag tggtggtgaa acaaaatcaa aacagatttg atttgtgttt      60
ttgaaatgtc agtacatttt gtgccactaa cactgtgatg tataaaagag ctgtttgaat     120
gccttttaat gttgtgtttt gtactctgga atcatatgga aa                        162
```

<210> SEQ ID NO 911
<211> LENGTH: 254
<212> TYPE: DNA
<213> ORGANISM: Homo sapiens

<400> SEQUENCE: 911

```
aaagattaaa ttgctattgc tgtagtaaga gaagctcttt gtatctgaac atagttgtat      60
ttgaaatttg tggttttta atttatttaa aattgggggg agggcatggg aaggatttaa     120
caccgatata ttgttaccgc tgaaaatgaa ctttatgaac cttttccaag ttgatctatc     180
cagtgacgtg gcctggtggg cgtttcttct tgtacttatg tggttttttg gcttttaata     240
cagacatttt cctc                                                        254
```

<210> SEQ ID NO 912
<211> LENGTH: 83
<212> TYPE: DNA
<213> ORGANISM: Homo sapiens

<400> SEQUENCE: 912

```
tctgctgaac atgagcttca gttgctactc ggagcattga gagggaggcc taagaataat      60
aacaatccag tgcttaagag tca                                              83
```

<210> SEQ ID NO 913
<211> LENGTH: 296
<212> TYPE: DNA
<213> ORGANISM: Homo sapiens

<400> SEQUENCE: 913

```
gccacaagag aagagctcta gtcctggact ctaccctcct ctgaaagaag ctggggcttg      60
ctctgacggt ctccactccc gtctgcaggc agccaggagg caggaagcc cttgctctgt      120
gctgccatcc tgcctccctc ctccagcctc agggcactcg ggcctgggtg ggagtcaacg     180
ccttcccctc tggactcaaa taaaacccag tgacctcact tctttctct gcaaaggtg      240
cttgtgggc tggagtgca gacattggtg tttctgctga tgtcccttgt gaaaaa           296
```

<210> SEQ ID NO 914
<211> LENGTH: 244
<212> TYPE: DNA
<213> ORGANISM: Homo sapiens

<400> SEQUENCE: 914

```
atttacctat atagcaagcc tacacatgtg cccctgaacc taaaaaaaaa gttaaagaa       60
aaacgtttgg attattttcc ctctttcgaa caaagacatt ggtttgccca aggactacaa     120
ataaaccaac gggaaaaaag aaaggttcca gttttgtctg aaaattctga ttaagcctct     180
gggccctaca gcctggagaa cctggagaat cctacaccca cagaaccccgg ctttgtcccc   240
```

| aaag | 244 |

<210> SEQ ID NO 915
<211> LENGTH: 253
<212> TYPE: DNA
<213> ORGANISM: Homo sapiens

<400> SEQUENCE: 915

| gaaacaagat tagtcctgag ttaacaatgg ctgcaagctg gatacatgga attcagcaca | 60 |
| cttttctccc tcttactgat tatgcttttg aaattttctc ttgtaaaaca tttagaaaac | 120 |
| aaaaacaaaa aaaatgtgat tgtttctgt cttcaaaatc tcattagaat tttttcactg | 180 |
| gaggaagatt ttcccttgct tctgcataaa attttaactc cataacttat aagctcactc | 240 |
| tttattgtta ctt | 253 |

<210> SEQ ID NO 916
<211> LENGTH: 74
<212> TYPE: DNA
<213> ORGANISM: Homo sapiens

<400> SEQUENCE: 916

| aaaaatttaa ctcccatatg tgttcctctt gttcctaatc ttgtcaaccc agtgcaagtg | 60 |
| accgacaaaa ttcc | 74 |

<210> SEQ ID NO 917
<211> LENGTH: 294
<212> TYPE: DNA
<213> ORGANISM: Homo sapiens

<400> SEQUENCE: 917

| actccacagt ttccattgtg aatggcttct ttggtgcaga gttccaaaaa ttatgtagcc | 60 |
| cagctctta attttgtaac atctaatgat atcaccgcct tgaagtgatt aaagtagatt | 120 |
| gcttaaagaa ttaaagcttt aaagatgaaa gatgttattg cttttgctgg acatgaggaa | 180 |
| cagttgtaaa gtttccaggt ctacaataac tttctggaac cctctcagtg aactgtttct | 240 |
| tgtaaaagtt ttccctaaga taaaagctca atcccattgt ttccacactc aaaa | 294 |

<210> SEQ ID NO 918
<211> LENGTH: 153
<212> TYPE: DNA
<213> ORGANISM: Homo sapiens

<400> SEQUENCE: 918

| gggcatgtgg gctgttgtga gtgaagccac ttcagacgtt tgcgtgcagg tttggtgggg | 60 |
| acgtgcagtt tcatttcttt tgagagtggg attgctggag cctatgttaa gggtacgttc | 120 |
| aactcatcag ctcaactgtc ttccaaatgg cag | 153 |

<210> SEQ ID NO 919
<211> LENGTH: 266
<212> TYPE: DNA
<213> ORGANISM: Homo sapiens

<400> SEQUENCE: 919

| ttatcaactg tgcacaagga aaaaatagga tatgtgaaag gttcacgtaa atttcctcac | 60 |
| atcacagaag attaaaattc agaaggaga aaacacagac caaagagaag tatctaagac | 120 |
| caaagggatg tgtttatta atgtctagga tgaagaaatg catagaacat tgtagtactt | 180 |
| gtaaataact agaaataaca tgatttagtc ataattgtga aaaataataa taatttttct | 240 |

```
tggatttatg ttctgtatct gtgaaa                                          266
```

<210> SEQ ID NO 920
<211> LENGTH: 202
<212> TYPE: DNA
<213> ORGANISM: Homo sapiens

<400> SEQUENCE: 920

```
gtggaggata ttgcaactgg agttcagaca ctgtactcga agtggaagga ctttcatttt    60
gagaagatac catttgatcc agcagaaatg tccaaatgat atcaggtcct caatcttcag   120
ctacagggaa tgagtaactt tgagtggaga agaaacaaac atagtgggta taatcatgga   180
tcgcttgtac ccctgtgaaa at                                            202
```

<210> SEQ ID NO 921
<211> LENGTH: 208
<212> TYPE: DNA
<213> ORGANISM: Homo sapiens
<220> FEATURE:
<221> NAME/KEY: misc_feature
<222> LOCATION: (124)..(124)
<223> OTHER INFORMATION: n is a, c, g, or t

<400> SEQUENCE: 921

```
gaatatgtgg cagagctcct ggaaatgatg cagattaggt ggcattttttg tcagctctgt    60 ggtttattgt tgggactatt cttttaaaata tccattgttc actacagtga agatctctga   120
tttnaccgtg tactatccac atgcattaca aacatttcgc agagctgctt agtatataag   180
cgtacaatgt atgtaataac catctcat                                       208
```

<210> SEQ ID NO 922
<211> LENGTH: 150
<212> TYPE: DNA
<213> ORGANISM: Homo sapiens

<400> SEQUENCE: 922

```
gctgataaat agcattaggg ttcttttgcaa tgtggtatct agctgtatta ttggttttat    60
ttactttaaa cattttgaaa agcttatact ggcagcctag aaaaacaaac aattaatgta   120
tctttatgtc cctggcacat gaataaactt                                    150
```

<210> SEQ ID NO 923
<211> LENGTH: 97
<212> TYPE: DNA
<213> ORGANISM: Homo sapiens

<400> SEQUENCE: 923

```
caaattcaag tcactagact tcagagttca acacctggac atgagaagat attatattat    60
gtaccataaa tatttcctgt atctgactgc ctgaaca                             97
```

<210> SEQ ID NO 924
<211> LENGTH: 237
<212> TYPE: DNA
<213> ORGANISM: Homo sapiens

<400> SEQUENCE: 924

```
agcaagactt gctgcctaaa ggagcccacc attttactttt tcacatttaa tctgccacgt    60
tgaatcaatt ggaataaaac ctgactcgca ggtgactgga caggaaatcc caaagttcca   120
ccatttctat gcttaatttt aacgtccccc cgctttttt tttgtagaaa ataaaaacaa   180
```
gaaaatcgtt ccaatgtaag atgtttgtta tagaaacttt aggcaataca ggtgtgt     237

<210> SEQ ID NO 925
<211> LENGTH: 292
<212> TYPE: DNA
<213> ORGANISM: Homo sapiens
<220> FEATURE:
<221> NAME/KEY: misc_feature
<222> LOCATION: (54)..(55)
<223> OTHER INFORMATION: n is a, c, g, or t

<400> SEQUENCE: 925
ttgcaagtca attaggtgtc ttgtgaacaa ggaaatacta atctctaagc tgcnnggggtc    60 tttttgtgtg aatatttaat ggtgctccat gactgttgag ttttaaaaac ctcgttaaat   120
tttgccaaat cagttgcccc caaaagggaa tatgcttttc cttattttt ttttctaaaat   180 gctatttatc tctaaggaaa aaaaaaaaag actattactc atttaacatt gtttaagcag   240
gttgagctag ctgtgaaaat agcttttgtg agccttctaa ttcctaaacg tc           292

<210> SEQ ID NO 926
<211> LENGTH: 243
<212> TYPE: DNA
<213> ORGANISM: Homo sapiens

<400> SEQUENCE: 926
gttaacactg tggatcacct tcggccaagg gacacgactg gagattaaac gtaagtaatt    60
tttcactatt gtcttctgaa atttgggtct gatggccagt attgactttt agaggcttaa   120
ataggagttt ggtaaagatt ggtaaatgag ggcatttaag atttgccatg ggttgcaaaa   180
gttaaactca gcttcaaaaa tggatttgga gaaaaaaaga ttaaattgct ctaaactgaa   240
tga                                                                  243

<210> SEQ ID NO 927
<211> LENGTH: 120
<212> TYPE: DNA
<213> ORGANISM: Homo sapiens

<400> SEQUENCE: 927
tcattctcat ccatccagga tgtactaaaa cagtgtgttt aataaattgt aattattttg    60
tgtacagttc tatactgtta tctgtgtcca tttccaaaac ttgcacgtgt ccctgaattc   120

<210> SEQ ID NO 928
<211> LENGTH: 185
<212> TYPE: DNA
<213> ORGANISM: Homo sapiens

<400> SEQUENCE: 928
aaggtttggc agaaattgtt ttttgagtgg ctcaccagag tacccagaag aatcagtatg    60
gaattagagg acagtggcct accctaaata aagacatgag tgatgtataa agtctagtgt   120
caatttattc agaaaatatc aaaattattc tgggagctat gggtcaaagt tgataggcac   180
aaaca                                                                185

<210> SEQ ID NO 929
<211> LENGTH: 130
<212> TYPE: DNA
<213> ORGANISM: Homo sapiens

<400> SEQUENCE: 929
atcccaatag atatccccct atgtgcatgc acacctgcac actcacggct gaaatctccc    60

```
taacccaggg ggaccttagc atgcctaagt gactaaacca ataaaaatgt tctggtctgg        120
cctgaaaaaa                                                              130

<210> SEQ ID NO 930
<211> LENGTH: 86
<212> TYPE: DNA
<213> ORGANISM: Homo sapiens

<400> SEQUENCE: 930
aagcagacta cgagaaacac aaagtctacg cctgcgaagt cacccatcag ggcctgagct         60
cgcccgtcac aaagagcttc aacagg                                             86

<210> SEQ ID NO 931
<211> LENGTH: 264
<212> TYPE: DNA
<213> ORGANISM: Homo sapiens

<400> SEQUENCE: 931
ggtacacaaa tctggttctc aatggtgagg tgggatcaga gatattctcc ctgttgttca         60
gaggaacaat aattcggatg tttctctcca caatgtcctc attaggatct tcggaagaac        120
ggatgatcct ggaagtaatc cgggcacact tacatttgtt gtcaacaaga acaatccttt        180
catcttcttg ggctttcaca tgaacagcct taataaaaac cgccaggact ccccagaaaa        240
gcaaatggtt cttcatcttg accc                                              264

<210> SEQ ID NO 932
<211> LENGTH: 101
<212> TYPE: DNA
<213> ORGANISM: Homo sapiens

<400> SEQUENCE: 932
ttgataggga tagcattgaa ctatttgctc aactcaacat tttaggaatt tatttctgct         60
gtctagtgct caaaacttgc agctagaatt gagggaagag a                           101

<210> SEQ ID NO 933
<211> LENGTH: 233
<212> TYPE: DNA
<213> ORGANISM: Homo sapiens

<400> SEQUENCE: 933
tgcttatccg ttagccgtgg tgatttagca ggaagctgtg agagcagttt ggtttctagc         60
atgaagacag agcccaccc tcagatgcac atgagctggc gggattgaaa gatgctgtct        120
tcgtactggg aaagggattt tcagccctca gaatcgctcc accttgcagc tctcccttc        180 tctgtattcc tagaaactga cacatgctga acatcacagc ttatttcctc att              233

<210> SEQ ID NO 934
<211> LENGTH: 256
<212> TYPE: DNA
<213> ORGANISM: Homo sapiens

<400> SEQUENCE: 934
ctgaggtgct atgttcttag tggatgttct gaccctgctt caaatatttc cctcacctt         60 cccatcttcc aagggtataa ggaatctttc tgctttgggg tttatcagaa ttctcagaat        120
ctcaaataac taaaggtat gcaatcaaat ctgcttttta aagaatgctc tttacttcat        180
ggacttccac tgccatcctc ccaagggcc caaattcttt cagtggctac ctacatacaa        240
```

```
ttccaaacac atacag                                              256
```

<210> SEQ ID NO 935
<211> LENGTH: 259
<212> TYPE: DNA
<213> ORGANISM: Homo sapiens

<400> SEQUENCE: 935

```
acagaagcca ttgcctccct tgtttacctt gggtccacct ccaccaaaac ccaacagacc    60
accaaatgtt gacctgacga aattccacaa aacctcttct ggaaacagta ctagcaaagg   120
ccagacgtct tactcaacaa cttccctgcc accacctcca ccatcccatc cggccagcca   180
accaccattg ccagcatctc acccatcaca accaccagtc ccaagcctac ctcccagaaa   240
cattaaacct ccgtttgac                                               259
```

<210> SEQ ID NO 936
<211> LENGTH: 114
<212> TYPE: DNA
<213> ORGANISM: Homo sapiens

<400> SEQUENCE: 936

```
ggacctgtac accacgagca gccagctgac cctgccggcc acacagtgcc tagccggcaa    60
gtccgtgaca tgccacgtga agcactacac gaatcccagc caggatgtga ctgt         114
```

<210> SEQ ID NO 937
<211> LENGTH: 265
<212> TYPE: DNA
<213> ORGANISM: Homo sapiens

<400> SEQUENCE: 937

```
ggatttctcc aaaactaact gaatttaagc ttcaggtccc tttgtatgca gtagaaagga    60
attattaaaa acaccaccaa agaaaataaa tatatcctac ttgaaattta ctctatggac   120
ttacccactg ctagaataaa tgtatcaaat cttatttgta aattctcaat tttgatatat   180
atatgtatat atgcatatac atatccacac ttgtctgcaa gaatattgat taaaattgct   240
aaatttgtac ttgttcacca gaaaa                                         265
```

<210> SEQ ID NO 938
<211> LENGTH: 198
<212> TYPE: DNA
<213> ORGANISM: Homo sapiens

<400> SEQUENCE: 938

```
gcacagctca gcacaacatt ccaagctcaa aatagaagcc ttctcagtga gctccagcac    60
gcccagagga ctgttaataa cgatgatcca tgtgttttac tctaaagtgc taaatatggg   120
agtttccttt ttttactctt tgtcactgat gacacaacag aaaagaaact gtagaccttg   180
ggacaatcaa catttaaa                                                198
```

<210> SEQ ID NO 939
<211> LENGTH: 162
<212> TYPE: DNA
<213> ORGANISM: Homo sapiens

<400> SEQUENCE: 939

```
atgttcatac tctaagtatc aaaatcttcc aattatcatg ctcacctgaa agaggtatgc    60
tctcttagga atacagtttc tagcattaaa caaataaaca aggggagaaa ataaaactca   120
aggagtgaaa atcaggaggt gtaataaaat gttcctcgca tt                     162
```

<210> SEQ ID NO 940
<211> LENGTH: 256
<212> TYPE: DNA
<213> ORGANISM: Homo sapiens

<400> SEQUENCE: 940
tcctgtttac ccttcaagtt tcaagttcat gtcactgtct cagagaggtt ttcctgtgct    60
cgccctgttt ctctcaggaa gccttgctct tttccatcat gcctctaatc acagcttata   120
atcggatatt tatttctgtg tctacagtct tgccctgcca gactgtatgc cccatgtggg   180
caggcgctca tgattgtttc tgattgtttc acgcatgctg ctaacccaga gcctgggccc   240
aaagctagtt agtact                                                   256

<210> SEQ ID NO 941
<211> LENGTH: 294
<212> TYPE: DNA
<213> ORGANISM: Homo sapiens

<400> SEQUENCE: 941
caaagggtga gagggcttcc ttctcaccct tctctccata agtatcttga agatccatgg    60
tttgttttgc tctattgttt agttttttact tgggtgcaat gtgtacgtca aaagttttta   120
ttttgatatt tgaaagagac caaatcaggc ccagaccgcc tctctggaag gtgttgtagg   180
ccattcaaaa cgcctccgga gtgtcgcaaa ccaagtgcgg aggggccctg aggttgtact   240
gtaaacatca tagtgacttg tcttttcaaa tatattccca ctattttcgc agaa          294

<210> SEQ ID NO 942
<211> LENGTH: 221
<212> TYPE: DNA
<213> ORGANISM: Homo sapiens

<400> SEQUENCE: 942
tgctggactc cgacggctcc ttcttcctct acagcaagct caccgtggac aagagcaggt    60
ggcagcaggg gaacatcttc tcatgctccg tgatgcatga ggctctgcac aaccgcttca   120
cgcagaagag cctctccctg tctccgggta atgagtgcg acggccggca agcccccgct   180
ccccgggctc tcggggtcgc gcgaggatgc ttggcacgta c                       221

<210> SEQ ID NO 943
<211> LENGTH: 239
<212> TYPE: DNA
<213> ORGANISM: Homo sapiens

<400> SEQUENCE: 943
ggagaggcag cattgcacag tgaaagaatt ctggatatct caggagcccc gaaattctag    60
ctctgacttt gctgtttcca gtggtatgac cttggagaag tcacttatcc tcttggagcc   120
tcagtttcct catctgcaga ataatgactg acttgtctaa ttcgtaggga tgtgaggttc   180
tgctgaggaa atgggtatga atgtgccttg aacacaaagc tctgtcaata agtgataca    239

<210> SEQ ID NO 944
<211> LENGTH: 181
<212> TYPE: DNA
<213> ORGANISM: Homo sapiens

<400> SEQUENCE: 944
gaggaccgag cacagaaatc ttagagattt cttgtcccct ctcaggtcat gtgtagatgc    60

```
gataaatcaa gtgattggtg tgcctgggtc tcactacaag cagcctatct gcttaagaga      120
ctctggagtt tcttatgtgc cctggtggac acttgcccac catcctgtga gtaaaagtga      180
a                                                                      181

<210> SEQ ID NO 945
<211> LENGTH: 228
<212> TYPE: DNA
<213> ORGANISM: Homo sapiens

<400> SEQUENCE: 945
gggatgacat gcactcagct cttggctcca ctgggatggg aggagaggac aagggaaatg       60 tcagggcgg ggagggtgac agtggccgcc caaggcccac gagcttgttc tttgttcttt      120
gtcacaggga ctgaaaacct ctcctcatgt tctgctttcg attcgttaag agagcaacat      180
tttacccaca cacagataaa gttttcccTT gaggaaacaa cagcttta                   228

<210> SEQ ID NO 946
<211> LENGTH: 136
<212> TYPE: DNA
<213> ORGANISM: Homo sapiens

<400> SEQUENCE: 946
caggacccat cacgcctgtg cagtggcccc cacagaaaga ctgagctcaa ggtgggaacc       60
acgtctgcta acttggagcc ccagtgccaa gcacagtgcc tgcatgtatt tatccaataa      120
atgtgaaatt ctgtcc                                                      136

<210> SEQ ID NO 947
<211> LENGTH: 193
<212> TYPE: DNA
<213> ORGANISM: Homo sapiens

<400> SEQUENCE: 947
gcagtctact agattgtgat cccttgagat atggaaggat gccttttttt ctctgcattt       60
aaaaaaatcc cccagcactt cccacagtgc ctattgatac ttggggaggg tgcttggcac      120
ttattgaata tatgatcggc catcaaggga agaactattg tgctcagaga cactgttgat      180
aaaaactcag gca                                                         193

<210> SEQ ID NO 948
<211> LENGTH: 175
<212> TYPE: DNA
<213> ORGANISM: Homo sapiens

<400> SEQUENCE: 948
aaatttaatt ttctacgcct ctggggatat ctgctcagcc aatggaaaat ctgggttcaa       60
ccagcccctg ccatttctta agactttctg ctgcactcac aggatcctga gctgcactta      120
cctgtgagag tcttcaaact tttaaacctt gccagtcagg acttttgcta ttgca           175

<210> SEQ ID NO 949
<211> LENGTH: 183
<212> TYPE: DNA
<213> ORGANISM: Homo sapiens

<400> SEQUENCE: 949
taaatattga gcagatctat aggaagattg aacctgaata ttgccattat gcttgacatg       60
gtttccaaaa aatggtactc cacatacttc agtgagggta agtattttcc tgttgtcaag      120
aatagcattg taaaagcatt ttgtaataat aaagaatagc tttaatgata tgcttgtaac      180
```

```
taa                                                                     183
```

<210> SEQ ID NO 950
<211> LENGTH: 235
<212> TYPE: DNA
<213> ORGANISM: Homo sapiens

<400> SEQUENCE: 950

```
taacttttc  tcaaagtcac  tgatgtttgt  tcctgttaaa  tgtatagcat  tgtaatgaga    60
gcccatcaaa  tcctgagtgt  cagtttgttg  tccctattgt  agatgaaata  gtgatgtagc  120
aaaaacctag  taaattctga  atgcttttcc  acgtagactt  atctggaatg  tgaacacaac  180
tctttggtta  atagtaaatg  cttaactgta  gtcctgagta  ggtgcatttc  tgtct       235
```

<210> SEQ ID NO 951
<211> LENGTH: 154
<212> TYPE: DNA
<213> ORGANISM: Homo sapiens

<400> SEQUENCE: 951

```
agtatatttt  ctatcttctg  gtgacttgag  cttgagctct  gacaggcatg  ggcctctccg    60
accttcatca  ctattcttag  gataatgctg  gcgggcagag  atgatcaatc  atcatattaa  120
atcataatga  gcttataatc  ctcccactgg  aaaa                                154
```

<210> SEQ ID NO 952
<211> LENGTH: 280
<212> TYPE: DNA
<213> ORGANISM: Homo sapiens

<400> SEQUENCE: 952

```
atcagaaagg  gcaacttact  cttcctggca  tcttattgta  ttggagggtg  accaccctgg    60
gcatggggtg  ttggcagggg  tcaaaaagct  tatttctttt  aatctcttac  tcaacgaaca  120
catcttctga  tgatttccca  aaattaatga  gaatgagatg  agtagagtaa  gatttgggtg  180
ggatgggtag  gatgaagtat  attgcccaac  tctatgtttc  tttgattcta  acacaattaa  240
ttaagtgaca  tgattttac   taatgtatta  ctgagactag                          280
```

<210> SEQ ID NO 953
<211> LENGTH: 206
<212> TYPE: DNA
<213> ORGANISM: Homo sapiens

<400> SEQUENCE: 953

```
tattcttcta  taacactcta  tatagagcta  tgtgagtact  aatcacattg  aataatagtt    60
ataaaattat  tgtatagaca  tctgcttctt  aaacagattg  tgagttcttt  gagaaacagc  120
gtggatttta  cttatctgtg  tattcacaga  gcttagcaca  gtgcctggta  atgagcaagc  180
atacttgcca  ttacttttcc  ttccca                                         206
```

<210> SEQ ID NO 954
<211> LENGTH: 247
<212> TYPE: DNA
<213> ORGANISM: Homo sapiens

<400> SEQUENCE: 954

```
gctgaaattg  tatctctcag  taattttaga  tgtcttttaa  aaaattgaaa  acaaagtgt     60
tagactgtgt  gcgtgtgcgt  tgatgggcac  tcaagagtcc  cgtgagtcat  ccagccctgc  120
```

```
ctttcccctg cgcccccatc ctctcacgtc ccgccctgcc tccacttggg gaccctgcct    180
cgtgtcgtct ttatctgcct attactcagc ctaaggaaac aagtacactc cacacatgca    240
taaagga                                                              247
```

<210> SEQ ID NO 955
<211> LENGTH: 190
<212> TYPE: DNA
<213> ORGANISM: Homo sapiens

<400> SEQUENCE: 955

```
gtggagaacc acagctgcag agtaggcagc tgcctccagg atgagttact tgaaatttgc     60
cttgagtgtg ttacctcctt tccaagctcc tcgtgataat gcagacttcc tggagtacaa    120
acacaggatt tgtaattcct tactgtaacg gagtttagag ccagggctga tgctttggtg    180
tggccagcac                                                           190
```

<210> SEQ ID NO 956
<211> LENGTH: 165
<212> TYPE: DNA
<213> ORGANISM: Homo sapiens

<400> SEQUENCE: 956

```
cccattgaaa agaccgagcc ttgtatgtat gttatggata cataaaatgc acgcaagcca     60
ttatctctcc atgggaagct aagttataaa ataggtgct  tggtgtacaa aactttttat    120
atcaaaaggc tttgccattt ctatatgagt gggtttactg gtaaa                    165
```

<210> SEQ ID NO 957
<211> LENGTH: 260
<212> TYPE: DNA
<213> ORGANISM: Homo sapiens

<400> SEQUENCE: 957

```
gaacagagag aaagtgctcc gtaaaagtga gctgcgatgc ggaggtgggc aagctcttcc     60
ctggaggggg aagagctctc aacccagagg gatctgacca ggaaggttca ccccccctcc    120
acccaggaag cccctgcaga cagtatgtgt tttaggcttt gctggccaaa tggtctctgc    180
cgtgactact cagctctgcc attgtggctg cagagtgacc atagaccttc tgaaagtgaa    240
tgagtatgac tgtgttccaa                                                260
```

<210> SEQ ID NO 958
<211> LENGTH: 197
<212> TYPE: DNA
<213> ORGANISM: Homo sapiens

<400> SEQUENCE: 958

```
aaatggtaaa catgagggtg ctcttgtgac ttaattttg ttcaagggac taaattgctt      60
atgtttattc cctgtcagcg gagtggagaa tgtcattcat caataaacca aagccaatag    120
ctggagaatt gagatctggt tgaaagtggt ttatggttta catgctgtac tatcctgagg    180
aattgcgaga tattgct                                                   197
```

<210> SEQ ID NO 959
<211> LENGTH: 187
<212> TYPE: DNA
<213> ORGANISM: Homo sapiens

<400> SEQUENCE: 959

```
aaaacatctg gttcaattac gctgaactct gactacatgt gggccagtaa taatatgaat     60
```
tggacttaag aataaacctt gtgtttaatc tcttttttc cttaaaattt taatgtgagt    120
tttctgttac gcaaattatc catgttagca catttggaac aaatgtataa atgtactttc    180
tgaataa                                                              187

<210> SEQ ID NO 960
<211> LENGTH: 228
<212> TYPE: DNA
<213> ORGANISM: Homo sapiens

<400> SEQUENCE: 960
gggatgacat gcactcagct cttggctcca ctgggatggg aggagaggac aagggaaatg    60 tcagggcgg ggagggtgac agtggccgcc caaggcccac gagcttgttc tttgttcttt    120
gtcacaggga ctgaaaacct tcctcatgt tctgctttcg attcgttaag agagcaacat    180
tttacccaca cacagataaa gttttcccctt gaggaaacaa cagcttta              228

<210> SEQ ID NO 961
<211> LENGTH: 213
<212> TYPE: DNA
<213> ORGANISM: Homo sapiens

<400> SEQUENCE: 961
actctccgga ttgaccaagt tcatcctggg ctccattggg tctgccattg cggctgtcat    60
tgcgaggttc tactagctcc ctgcccctcg ccctgcagag aagagaacca tgccagggga   120
gaaggcaccc agccatcctg acccagcgag gagccaacta tcccaaatat acctgggtg    180 aaatatacca aattctgcat ctccagagga aaa                                 213

<210> SEQ ID NO 962
<211> LENGTH: 104
<212> TYPE: DNA
<213> ORGANISM: Homo sapiens

<400> SEQUENCE: 962
gttggtgtgc tgaggtgtta gagagggacc atgtgtcact tgtgctttgc tcttgtccca    60
cgtgtcttcc actttgcata tgagccgtga actgtgcata gtgc                    104

<210> SEQ ID NO 963
<211> LENGTH: 132
<212> TYPE: DNA
<213> ORGANISM: Homo sapiens

<400> SEQUENCE: 963
acattgattc cccatcgctg aaggacagaa ttcattgtgt ggcatttgta tttgatgcca    60
gctctattca atacttctcc ctcagatga tagtaaagat caaaagaatt cgaagggagt   120
tggtaaacgc tg                                                        132

<210> SEQ ID NO 964
<211> LENGTH: 281
<212> TYPE: DNA
<213> ORGANISM: Homo sapiens

<400> SEQUENCE: 964
gttattaaca gtcctctggg cgtgctggag ctcactgaga aggcttctat tttgagcttg    60
gaatgttgtg ctgagctgtg cagcctgttc ctgcatctgt tgttcctgca ttttctgttg   120
ctctgccagc caattttgtt tggctatctc catttaactc acttgttcct gatggagtct   180
ctccctctcc tgcatcattt gctcgttctg cctttgaatc gccgccaacc tttgcgcttc    240
agccttttca gcttctgctt tcacttgtgc ctctgaggag a    281

<210> SEQ ID NO 965
<211> LENGTH: 239
<212> TYPE: DNA
<213> ORGANISM: Homo sapiens

<400> SEQUENCE: 965
gggagggtaa cctcactctt ctccaggcca ggcctccttg gactcccctg ggggtgtccc    60
actcttcttc cctctaaact gccccactc ctaacctaat cccccgccc cgctgccttt    120 cccaggctcc cctcacccca gcgggtaatg agcccttaat cgctgcctct aggggagctg    180
attgtagcag cctcgttagt gtcaccccct cctccctgat ctgtcagggc acttagtg    239

<210> SEQ ID NO 966
<211> LENGTH: 174
<212> TYPE: DNA
<213> ORGANISM: Homo sapiens

<400> SEQUENCE: 966
ggtcctgtag ccctaagtgg tactaacttt ccttcattca acccacctgc gtctcatact    60 caccttcaccc cactgtggct gatttggaat tttgtgcccc catgtaagca ccccttcatt    120
tggcattccc cacttgagaa ttacccttttt gccccgaaca tgttttttctt ctcc    174

<210> SEQ ID NO 967
<211> LENGTH: 270
<212> TYPE: DNA
<213> ORGANISM: Homo sapiens

<400> SEQUENCE: 967
aaataaccac tttttgttgg gcaatatgaa attttttaaag gagtagaata ccaaatgata    60
gaaacagact gcctgaattg agaatttttga tttcttaaag tgtgtttctt tctaaattgc    120
tgttccttaa tttgattaat ttaattcatg tattatgatt aaatctgagg cagatgagct    180
tacaagtatt gaataattta ctaattaatc acaaatgtga agttatgcat gatgtaaaaa    240
atacaaacat tctaattaaa ggctttgcaa    270

<210> SEQ ID NO 968
<211> LENGTH: 276
<212> TYPE: DNA
<213> ORGANISM: Homo sapiens

<400> SEQUENCE: 968
gagtaagctc tagtccctct gtcctgtaga aagagccctg aagaatcagc aattttgttg    60
ctttattgtg gcatctgttc gaggtttgct tcctctttaa gtctgtttct tcattagcaa    120
tcatatcagt tttaatgcta ctactaacaa tgaacagtaa caataatatc cccctcaatt    180
aatagagtgc tttctatgtg caaggcactt ttcacgtgtc acctatttta accttccaa    240 ccacataaat aaaaaaggcc attattagtt gaatct    276

<210> SEQ ID NO 969
<211> LENGTH: 264
<212> TYPE: DNA
<213> ORGANISM: Homo sapiens

<400> SEQUENCE: 969
taactttttc tcaaagtcac tgatgtttgt tcctgttaaa tgtatagcat tgtaatgaga    60

```
gcccatcaaa tcctgagtgt cagtttgttg tccctattgt agatgaaata gtgatgtagc    120
aaaaacctag taaattctga atgcttttcc acgtagactt atctggaatg tgaacacaac    180
tctttggtta atagtaaatg cttaactgta gtcctgagta ggtgcatttc tgtctgtctc    240
aataaatttt actttgtctg caaa                                           264
```

<210> SEQ ID NO 970
<211> LENGTH: 275
<212> TYPE: DNA
<213> ORGANISM: Homo sapiens

<400> SEQUENCE: 970

```
tattccatct acttttctat cgccgtcccc ttttgcagcc ctctctgggg atggactggg     60
taaatgttga cagaggccct gccccgttca cagatcctgg ccctgagcca gccctgtgct    120
cctccctccc ccaacactcc ctaccaaccc cctaatcccc tactccctcc acccccctc    180 cactgtaggc cactgatgg tcatttgcat ctccgtaaat gtgctctgct cctcagctga    240
gagagaaaaa aataaactgt atttggctgc aagaa                               275
```

<210> SEQ ID NO 971
<211> LENGTH: 210
<212> TYPE: DNA
<213> ORGANISM: Homo sapiens

<400> SEQUENCE: 971

```
agaggctctt ctgcgtgtag tggttgtgca gagcctcatg catcacggag catgagaaga     60
cgttcccctg ctgccacctg ctcttgtcca cggtgagctt gctatagagg aagaaggagc    120
cgtcggagtc cagcacggga ggcgtggtct tgtagttgtt ctccggctgc ccattgctct    180
cccactccac ggcgatgtcg ctgggataga                                     210
```

<210> SEQ ID NO 972
<211> LENGTH: 235
<212> TYPE: DNA
<213> ORGANISM: Homo sapiens

<400> SEQUENCE: 972

```
gagtgtctca gaagtgtgct cctctggcct cagttctcct cttttggaac aacataaaac     60
aaatttaatt ttctacgcct ctggggtatat ctgctcagcc aatggaaaat ctgggttcaa    120
ccagcccctg ccatttctta agactttctg ctccactcac aggatcctga gctgcactta    180
cctgtgagag tcttcaaact tttaaacctt gccagtcagg acttttgcta ttgca         235
```

<210> SEQ ID NO 973
<211> LENGTH: 162
<212> TYPE: DNA
<213> ORGANISM: Homo sapiens

<400> SEQUENCE: 973

```
ggacataaca gacttggaag cagatgatac agacttcttt ttttcataat caggttagtg     60
taagaaattg ccatttgaaa caatccattt tgtaactgaa ccttatgaaa tatatgtatt    120
tcatggtacg tattctctag cacagtctga gcaattaaat ag                       162
```

<210> SEQ ID NO 974
<211> LENGTH: 249
<212> TYPE: DNA
<213> ORGANISM: Homo sapiens

```
<400> SEQUENCE: 974
aggccctctt gagagtctat ccagggaccc attgttttac tttaacagac cagaaaagat      60
gtttgttttc catgtcatta cccccagggg ataccgaatg tgtgggtaga aatttctctg     120
tagattaaaa atcagatttt tacatggatt caacaaagga gcgtcacttg gatttttgtt    180
ttcatccatg aatgtagctg cttctgtgta aaatgccatt ttgctattaa aaatcaattc     240
acgctggaa                                                             249
```